United States Patent
Kraynov et al.

(10) Patent No.: US 11,439,710 B2
(45) Date of Patent: *Sep. 13, 2022

(54) NUCLEIC ACIDS ENCODING MODIFIED RELAXIN POLYPEPTIDES

(71) Applicant: AMBRX, INC., La Jolla, CA (US)

(72) Inventors: Vadim Kraynov, San Diego, CA (US);
Nick Knudsen, Escondido, CA (US);
Amha Hewet, San Diego, CA (US);
Kristine De Dios, San Diego, CA (US);
Jason Pinkstaff, Carlsbad, CA (US);
Lorraine Sullivan, San Diego, CA (US)

(73) Assignee: AMBRX, INC., La Jolla, CA (US)

( * ) Notice: Subject to any disclaimer, the term of this patent is extended or adjusted under 35 U.S.C. 154(b) by 43 days.

This patent is subject to a terminal disclaimer.

(21) Appl. No.: 16/885,631

(22) Filed: May 28, 2020

(65) Prior Publication Data

US 2020/0360525 A1 Nov. 19, 2020

Related U.S. Application Data

(62) Division of application No. 15/941,033, filed on Mar. 30, 2018, now Pat. No. 10,702,588, which is a division of application No. 15/239,277, filed on Aug. 17, 2016, now Pat. No. 9,962,450, which is a division of application No. 14/152,302, filed on Jan. 10, 2014, now Pat. No. 9,452,222, which is a division of application No. 13/212,101, filed on Aug. 17, 2011, now Pat. No. 8,735,539.

(60) Provisional application No. 61/374,582, filed on Aug. 17, 2010.

(51) Int. Cl.
| | | |
|---|---|---|
| *A61K 38/18* | (2006.01) | |
| *A61K 47/60* | (2017.01) | |
| *C07K 14/64* | (2006.01) | |
| *A61K 38/22* | (2006.01) | |
| *A61K 38/00* | (2006.01) | |

(52) U.S. Cl.
CPC .......... *A61K 47/60* (2017.08); *A61K 38/2221* (2013.01); *C07K 14/64* (2013.01); *A61K 38/00* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,289,872 A | 9/1981 | Denkewalter et al. |
| 4,412,989 A | 11/1983 | Iwashita et al. |
| 4,414,148 A | 11/1983 | Jansen et al. |
| 4,485,045 A | 11/1984 | Regen |
| 4,511,502 A | 4/1985 | Builder et al. |
| 4,511,503 A | 4/1985 | Olson et al. |
| 4,512,922 A | 4/1985 | Jones et al. |
| 4,544,545 A | 10/1985 | Ryan et al. |
| 4,551,433 A | 11/1985 | Deboer |
| 4,569,789 A | 2/1986 | Blattler et al. |
| 4,619,794 A | 10/1986 | Hauser |
| 4,659,839 A | 4/1987 | Nicolotti et al. |
| 4,670,417 A | 6/1987 | Iwasaki et al. |
| 4,671,958 A | 6/1987 | Rodwell et al. |
| 4,680,338 A | 7/1987 | Sundoro |
| 4,689,406 A | 8/1987 | Banks et al. |
| 4,699,784 A | 10/1987 | Shih et al. |
| 4,738,921 A | 4/1988 | Belagaje et al. |
| 4,755,465 A | 7/1988 | Gray et al. |
| 4,837,148 A | 6/1989 | Cregg |
| 4,859,600 A | 8/1989 | Gray et al. |
| 4,876,197 A | 10/1989 | Burke et al. |
| 4,880,734 A | 11/1989 | Burke et al. |
| 4,902,502 A | 2/1990 | Nitecki et al. |
| 4,904,584 A | 2/1990 | Shaw |
| 4,929,555 A | 5/1990 | Cregg et al. |
| 5,021,234 A | 6/1991 | Ehrenfeld |
| 5,089,398 A | 2/1992 | Rosenberg et al. |
| 5,122,614 A | 6/1992 | Zalipsky |
| 5,145,962 A | 9/1992 | Hudson et al. |
| 5,162,601 A | 11/1992 | Slightom |
| 5,219,564 A | 6/1993 | Zalipsky et al. |
| 5,229,490 A | 7/1993 | Tam |
| 5,231,178 A | 7/1993 | Holtz et al. |
| 5,252,714 A | 10/1993 | Harris et al. |
| 5,281,698 A | 1/1994 | Nitecki |
| 5,290,686 A | 1/1994 | Kendal et al. |
| 5,324,639 A | 6/1994 | Brierley et al. |
| 5,324,844 A | 6/1994 | Zalipsky |
| 5,382,657 A | 1/1995 | Karasiewicz et al. |
| 5,446,090 A | 8/1995 | Harris |
| 5,468,478 A | 11/1995 | Saifer et al. |

(Continued)

FOREIGN PATENT DOCUMENTS

| | | |
|---|---|---|
| CA | 2707840 | 2/2009 |
| DE | 3218121 | 11/1983 |

(Continued)

OTHER PUBLICATIONS

Aebersold, P. and Sample, S., "A Simplified Antigrowth Assay Based on Color Change of the Medium", Methods in Enzymology, 1986. 119: 579-582.

(Continued)

*Primary Examiner* — Christine J Saoud

(74) *Attorney, Agent, or Firm* — Robin L. Teskin; Baker, Donelson, Bearman, Caldwell & Berkowitz PC

(57) ABSTRACT

Modified relaxin polypeptides and their uses thereof are provided.

20 Claims, 26 Drawing Sheets

Specification includes a Sequence Listing.

(56) References Cited

U.S. PATENT DOCUMENTS

| | | |
|---|---|---|
| 5,473,034 A | 12/1995 | Yasui et al. |
| 5,476,653 A | 12/1995 | Pitt et al. |
| 5,516,657 A | 5/1996 | Murphy et al. |
| 5,516,673 A | 5/1996 | Margel et al. |
| 5,532,142 A | 7/1996 | Johnston et al. |
| 5,559,213 A | 9/1996 | Hakimi et al. |
| 5,571,709 A | 11/1996 | Devauchelle et al. |
| 5,580,723 A | 12/1996 | Wells et al. |
| 5,583,023 A | 12/1996 | Cerutti et al. |
| 5,602,034 A | 2/1997 | Tekamp-Olson |
| 5,605,827 A | 2/1997 | Ack et al. |
| 5,612,460 A | 3/1997 | Zalipsky |
| 5,629,203 A | 5/1997 | Shuster |
| 5,629,384 A | 5/1997 | Veronese et al. |
| 5,643,575 A | 7/1997 | Martinez et al. |
| 5,650,234 A | 7/1997 | Dolence et al. |
| 5,672,662 A | 9/1997 | Harris et al. |
| 5,674,706 A | 10/1997 | Shuster |
| RE35,749 E | 3/1998 | Rosenberg et al. |
| 5,736,625 A | 4/1998 | Callstrom et al. |
| 5,739,208 A | 4/1998 | Harris |
| 5,747,646 A | 5/1998 | Hakimi et al. |
| 5,750,373 A | 5/1998 | Garrard et al. |
| 5,753,220 A | 5/1998 | Suzuki et al. |
| 5,762,939 A | 6/1998 | Smith et al. |
| 5,766,885 A | 6/1998 | Carrington et al. |
| 5,808,096 A | 9/1998 | Zalipsky |
| 5,824,778 A | 10/1998 | Ishikawa et al. |
| 5,824,784 A | 10/1998 | Kinstler et al. |
| 5,834,250 A | 11/1998 | Wells et al. |
| 5,834,594 A | 11/1998 | Hakimi et al. |
| 5,843,733 A | 12/1998 | Estes |
| 5,849,860 A | 12/1998 | Hakimi et al. |
| 5,858,368 A | 1/1999 | Smith et al. |
| 5,861,279 A | 1/1999 | Zhang et al. |
| 5,871,986 A | 2/1999 | Boyce |
| 5,891,676 A | 4/1999 | Estes |
| 5,900,461 A | 5/1999 | Harris |
| 5,911,997 A | 6/1999 | Schwabe et al. |
| 5,932,462 A | 8/1999 | Harris et al. |
| 5,939,285 A | 8/1999 | Devauchelle et al. |
| 5,965,393 A | 10/1999 | Hasnain et al. |
| 5,980,948 A | 11/1999 | Goedemoed et al. |
| 5,989,868 A | 11/1999 | Harrison et al. |
| 5,990,237 A | 11/1999 | Bentley et al. |
| 6,004,573 A | 12/1999 | Rathi et al. |
| 6,013,433 A | 1/2000 | Pellett et al. |
| 6,013,478 A | 1/2000 | Wells et al. |
| 6,017,731 A | 1/2000 | Tekamp-Olson et al. |
| 6,083,723 A | 7/2000 | Tekamp-Olson |
| 6,096,304 A | 8/2000 | McCutchen |
| 6,126,944 A | 10/2000 | Pellett et al. |
| 6,129,912 A | 10/2000 | Hortin et al. |
| 6,168,932 B1 | 1/2001 | Uckun et al. |
| 6,183,985 B1 | 2/2001 | Shuster |
| 6,183,987 B1 | 2/2001 | van de Wiel et al. |
| 6,201,072 B1 | 3/2001 | Rathi et al. |
| 6,214,966 B1 | 4/2001 | Harris |
| 6,225,060 B1 | 5/2001 | Clark et al. |
| 6,245,528 B1 | 6/2001 | Chao |
| 6,261,805 B1 | 7/2001 | Wood |
| RE37,343 E | 8/2001 | Tekamp-Olson |
| 6,281,211 B1 | 8/2001 | Cai et al. |
| 6,306,821 B1 | 10/2001 | Mikos et al. |
| 6,312,923 B1 | 11/2001 | Tekamp-Olson |
| 6,337,191 B1 | 1/2002 | Swartz et al. |
| 6,338,846 B1 | 1/2002 | Kang et al. |
| 6,342,216 B1 | 1/2002 | Fidler et al. |
| 6,361,969 B1 | 3/2002 | Galeotti |
| 6,368,825 B1 | 4/2002 | Chao |
| 6,420,339 B1 | 7/2002 | Gegg et al. |
| 6,423,685 B1 | 7/2002 | Drummond et al. |
| 6,428,954 B1 | 8/2002 | Wells et al. |
| 6,436,386 B1 | 8/2002 | Roberts et al. |
| 6,451,346 B1 | 9/2002 | Shah et al. |
| 6,451,561 B1 | 9/2002 | Wells et al. |
| 6,461,603 B2 | 10/2002 | Bentley et al. |
| 6,515,100 B2 | 2/2003 | Harris |
| 6,521,427 B1 | 2/2003 | Evans |
| 6,552,167 B1 | 4/2003 | Rose |
| 6,586,207 B2 | 7/2003 | Tirrell et al. |
| 6,602,498 B2 | 8/2003 | Shen |
| 6,608,183 B1 | 8/2003 | Cox, III |
| 6,610,281 B2 | 8/2003 | Harris |
| 6,646,110 B2 | 11/2003 | Nissen et al. |
| 6,927,042 B2 | 8/2005 | Schultz et al. |
| 7,045,337 B2 | 5/2006 | Schultz et al. |
| 7,083,970 B2 | 8/2006 | Schultz et al. |
| 7,230,068 B2 | 6/2007 | Wilson |
| 7,332,571 B2 | 2/2008 | Miao |
| 7,385,028 B2 | 6/2008 | Miao |
| 7,632,823 B2 | 12/2009 | Tian |
| 7,632,924 B2 | 12/2009 | Cho |
| 7,638,299 B2 | 12/2009 | Cho |
| 7,638,491 B2 | 12/2009 | Miao |
| 7,696,312 B2 | 4/2010 | Miao |
| 7,736,872 B2 | 6/2010 | Paulsel |
| 7,737,226 B2 | 6/2010 | Wilson |
| 7,816,320 B2 | 10/2010 | Hays |
| 7,820,766 B2 | 10/2010 | Wilson |
| 7,829,310 B2 | 11/2010 | Paulsel |
| 7,838,265 B2 | 11/2010 | Paulsel |
| 7,846,689 B2 | 12/2010 | Paulsel |
| 7,858,344 B2 | 12/2010 | Paulsel |
| 7,883,866 B2 | 2/2011 | Paulsel |
| 7,888,533 B2 | 2/2011 | Tian |
| 7,919,591 B2 | 4/2011 | Sheffer |
| 7,928,163 B2 | 4/2011 | Miao |
| 7,939,496 B2 | 5/2011 | Cho |
| 7,947,473 B2 | 5/2011 | Buechler |
| 7,959,926 B2 | 6/2011 | Buechler |
| 8,008,428 B2 | 8/2011 | Wilson |
| 8,008,456 B2 | 8/2011 | Miao |
| 8,012,931 B2 | 9/2011 | Cujec |
| 8,022,186 B2 | 9/2011 | Sheffer |
| 8,048,988 B2 | 11/2011 | Miao |
| 8,053,560 B2 | 11/2011 | Sheffer |
| 8,071,809 B2 | 12/2011 | Tian |
| 8,080,391 B2 | 12/2011 | Buechler |
| 8,093,356 B2 | 1/2012 | Hays |
| 8,097,702 B2 | 1/2012 | Cho |
| 8,114,630 B2 | 2/2012 | Kraynov |
| 8,119,603 B2 | 2/2012 | Cho |
| 8,143,216 B2 | 3/2012 | Cho |
| 8,153,758 B2 | 4/2012 | Miao |
| 8,163,695 B2 | 4/2012 | Hays |
| 8,178,108 B2 | 5/2012 | Buechler |
| 8,178,494 B2 | 5/2012 | Hays |
| 8,232,371 B2 | 7/2012 | Cho |
| 8,263,740 B2 | 9/2012 | Miao |
| 8,278,418 B2 | 10/2012 | Tian |
| 8,329,869 B2 | 12/2012 | Kraynov |
| 8,367,612 B2 | 2/2013 | Miao |
| 8,383,365 B2 | 2/2013 | Cujec |
| 8,399,614 B2 | 3/2013 | Miao |
| 8,420,792 B2 | 4/2013 | Tian |
| 8,476,411 B2 | 7/2013 | Miao |
| 8,557,781 B2 | 10/2013 | Miao |
| 8,569,233 B2 | 10/2013 | Tian |
| 8,618,257 B2 | 12/2013 | Sheffer |
| 8,735,539 B2 | 5/2014 | Kraynov et al. |
| 8,778,880 B2 | 7/2014 | Cho |
| 8,791,231 B2 | 7/2014 | Miao |
| 8,809,511 B2 | 8/2014 | Miao |
| 9,452,222 B2 | 9/2016 | Kraynov et al. |
| 9,567,386 B2 | 2/2017 | Kraynov |
| 9,962,450 B2 | 5/2018 | Kraynov et al. |
| 10,253,083 B2 | 4/2019 | Kraynov et al. |
| 10,702,588 B2 | 7/2020 | Kraynov et al. |
| 2001/0021763 A1 | 9/2001 | Harris |
| 2001/0044526 A1 | 11/2001 | Shen |
| 2001/0056171 A1 | 12/2001 | Kozlowski |
| 2002/0002250 A1 | 1/2002 | Bentley et al. |
| 2002/0037949 A1 | 3/2002 | Harris et al. |

(56) References Cited

U.S. PATENT DOCUMENTS

| | | |
|---|---|---|
| 2002/0040076 A1 | 4/2002 | Harris et al. |
| 2002/0042097 A1 | 4/2002 | Tirrell et al. |
| 2002/0052009 A1 | 5/2002 | Hornauer et al. |
| 2002/0052430 A1 | 5/2002 | Harris et al. |
| 2002/0055169 A1 | 5/2002 | Tekamp-Olson |
| 2002/0072573 A1 | 6/2002 | Bentley et al. |
| 2002/0081660 A1 | 6/2002 | Swartz et al. |
| 2002/0082345 A1 | 6/2002 | Kozlowski et al. |
| 2002/0086939 A1 | 7/2002 | Kozlowski |
| 2002/0099133 A1 | 7/2002 | Kozlowski |
| 2002/0156047 A1 | 10/2002 | Zhao |
| 2003/0023023 A1 | 1/2003 | Harris et al. |
| 2003/0082575 A1 | 5/2003 | Schultz et al. |
| 2003/0105224 A1 | 6/2003 | Roberts et al. |
| 2003/0105275 A1 | 6/2003 | Bentley et al. |
| 2003/0108885 A1 | 6/2003 | Schultz et al. |
| 2003/0114647 A1 | 6/2003 | Harris et al. |
| 2003/0143596 A1 | 7/2003 | Bentley et al. |
| 2003/0158333 A1 | 8/2003 | Roberts et al. |
| 2003/0162949 A1 | 8/2003 | Cox |
| 2003/0228274 A1 | 12/2003 | Rose |
| 2004/0001838 A1 | 1/2004 | Zhao et al. |
| 2004/0013637 A1 | 1/2004 | Bentley et al. |
| 2004/0198637 A1 | 10/2004 | Schultz et al. |
| 2005/0009049 A1 | 1/2005 | Chin et al. |
| 2005/0085619 A1 | 4/2005 | Wilson |
| 2005/0170404 A1 | 8/2005 | Cho |
| 2005/0220762 A1 | 10/2005 | Cho |
| 2006/0019347 A1 | 1/2006 | Cho |
| 2006/0135427 A1 | 6/2006 | Hays |
| 2006/0153860 A1 | 7/2006 | Cho |
| 2006/0183198 A1 | 8/2006 | Buechler |
| 2006/0189529 A1 | 8/2006 | Cho |
| 2006/0194256 A1 | 8/2006 | Miao |
| 2006/0217289 A1 | 9/2006 | Miao |
| 2006/0217532 A1 | 9/2006 | Miao |
| 2007/0004619 A1 | 1/2007 | Del Borgo et al. |
| 2007/0123691 A1 | 5/2007 | Wilson |
| 2007/0123693 A1 | 5/2007 | Wilson |
| 2008/0050374 A1 | 2/2008 | Cho |
| 2008/0050777 A1 | 2/2008 | Buechler |
| 2008/0081038 A1 | 4/2008 | Cho |
| 2008/0085277 A1 | 4/2008 | Cho |
| 2008/0085538 A1 | 4/2008 | Buechler |
| 2008/0097083 A1 | 4/2008 | Cho |
| 2008/0102124 A1 | 5/2008 | Cho |
| 2008/0102125 A1 | 5/2008 | Cho |
| 2008/0103293 A1 | 5/2008 | Cho |
| 2008/0103294 A1 | 5/2008 | Cho |
| 2008/0107680 A1 | 5/2008 | Cho |
| 2008/0108791 A1 | 5/2008 | Cho |
| 2008/0108792 A1 | 5/2008 | Hays |
| 2008/0108797 A1 | 5/2008 | Cho |
| 2008/0112943 A1 | 5/2008 | Mariani |
| 2008/0113408 A1 | 5/2008 | Mariani |
| 2008/0113411 A1 | 5/2008 | Sheffer |
| 2008/0113412 A1 | 5/2008 | Sheffer |
| 2008/0113912 A1 | 5/2008 | Hays |
| 2008/0113913 A1 | 5/2008 | Hays |
| 2008/0113914 A1 | 5/2008 | Hays |
| 2008/0114154 A1 | 5/2008 | Cho |
| 2008/0114155 A1 | 5/2008 | Cho |
| 2008/0118464 A1 | 5/2008 | Miao |
| 2008/0119640 A1 | 5/2008 | Hays |
| 2008/0125574 A1 | 5/2008 | Sheffer |
| 2008/0132681 A1 | 6/2008 | Hays |
| 2008/0139793 A1 | 6/2008 | Tian |
| 2008/0139794 A1 | 6/2008 | Tian |
| 2008/0146781 A1 | 6/2008 | Cho |
| 2008/0153745 A1 | 6/2008 | Tian |
| 2008/0153979 A1 | 6/2008 | Miao |
| 2008/0154058 A1 | 6/2008 | Tian |
| 2008/0161539 A1 | 7/2008 | Cho |
| 2008/0177027 A1 | 7/2008 | Miao |
| 2008/0177038 A1 | 7/2008 | Miao |
| 2008/0182968 A1 | 7/2008 | Miao |
| 2008/0182969 A1 | 7/2008 | Miao |
| 2008/0187491 A1 | 8/2008 | Miao |
| 2008/0194459 A1 | 8/2008 | Miao |
| 2008/0199909 A1 | 8/2008 | Buechler |
| 2008/0207877 A1 | 8/2008 | Cho |
| 2008/0213840 A1 | 9/2008 | Miao |
| 2008/0227205 A1 | 9/2008 | Cho |
| 2008/0255045 A1 | 10/2008 | Cujec |
| 2008/0268518 A1 | 10/2008 | Miao |
| 2008/0268519 A1 | 10/2008 | Miao |
| 2008/0300163 A1 | 12/2008 | Cho |
| 2008/0317670 A1 | 12/2008 | Miao |
| 2009/0018029 A1 | 1/2009 | Miao |
| 2009/0093405 A1 | 4/2009 | Wallen, III et al. |
| 2009/0111147 A1 | 4/2009 | Miao |
| 2009/0123968 A1 | 5/2009 | Miao |
| 2009/0123971 A1 | 5/2009 | Paulsel |
| 2009/0137736 A1 | 5/2009 | Tian |
| 2009/0163368 A1 | 6/2009 | Liu |
| 2009/0208454 A1 | 8/2009 | Kraynov |
| 2009/0240029 A1 | 9/2009 | Miao |
| 2010/0035812 A1 | 2/2010 | Hay |
| 2010/0048871 A1 | 2/2010 | Cho |
| 2010/0075866 A1 | 3/2010 | Hood et al. |
| 2010/0087677 A1 | 4/2010 | Tian |
| 2010/0093082 A1 | 4/2010 | Tian |
| 2010/0093608 A1 | 4/2010 | Tian |
| 2010/0098630 A1 | 4/2010 | Miao |
| 2010/0120686 A1 | 5/2010 | Miao |
| 2010/0135959 A1 | 6/2010 | Hay |
| 2010/0159585 A1 | 6/2010 | Tian |
| 2010/0159586 A1 | 6/2010 | Tian |
| 2010/0160212 A1 | 6/2010 | Sheffer |
| 2010/0167347 A1 | 7/2010 | Paulsel |
| 2010/0173379 A1 | 7/2010 | Paulsel |
| 2010/0173380 A1 | 7/2010 | Paulsel |
| 2010/0174054 A1 | 7/2010 | Paulsel |
| 2010/0184140 A1 | 7/2010 | Paulsel |
| 2010/0217050 A1 | 8/2010 | Wilson |
| 2010/0298212 A1 | 11/2010 | Miao |
| 2011/0015345 A1 | 1/2011 | Pinkstaff |
| 2011/0065596 A1 | 3/2011 | Liu |
| 2011/0118450 A1 | 5/2011 | Tian |
| 2011/0118451 A1 | 5/2011 | Miao |
| 2011/0118501 A1 | 5/2011 | Miao |
| 2011/0124880 A1 | 5/2011 | Miao |
| 2011/0144307 A1 | 6/2011 | Miao |
| 2011/0172401 A1 | 7/2011 | Cujec |
| 2011/0178029 A1 | 7/2011 | Knudsen |
| 2011/0195483 A1 | 8/2011 | Tian |
| 2011/0195899 A1 | 8/2011 | Hay |
| 2011/0207914 A1 | 8/2011 | Sheffer |
| 2011/0269974 A1 | 11/2011 | Wilson |
| 2011/0288279 A1 | 11/2011 | Miao |
| 2011/0294161 A1 | 12/2011 | Cho |
| 2012/0041180 A1 | 2/2012 | Sheffer |
| 2012/0046229 A1 | 2/2012 | Kraynov |
| 2012/0142890 A1 | 6/2012 | Mariani |
| 2012/0142896 A1 | 6/2012 | Cho |
| 2012/0149636 A1 | 6/2012 | Kraynov |
| 2012/0190827 A1 | 7/2012 | Sheffer |
| 2012/0197006 A1 | 8/2012 | Kraynov |
| 2012/0283171 A1 | 11/2012 | Putman |
| 2012/0283172 A1 | 11/2012 | Wallen |
| 2012/0315686 A1 | 12/2012 | Miao |
| 2013/0017995 A1 | 1/2013 | Tian |
| 2013/0030160 A1 | 1/2013 | Miao |
| 2013/0150564 A1 | 6/2013 | Cujec |
| 2013/0237474 A1 | 9/2013 | Mariani |
| 2013/0237481 A1 | 9/2013 | Kraynov |
| 2013/0280301 A1 | 10/2013 | Tian |
| 2013/0323821 A1 | 12/2013 | Tian |
| 2014/0011740 A1 | 1/2014 | Tian |
| 2014/0045259 A1 | 2/2014 | Tian |

(56) References Cited

U.S. PATENT DOCUMENTS

2014/0100357 A1  4/2014  Miao
2014/0194357 A1  7/2014  Kraynov et al.

FOREIGN PATENT DOCUMENTS

| | | |
|---|---|---|
| EP | 0 036 776 | 9/1981 |
| EP | 036 676 | 9/1981 |
| EP | 0 052 322 | 5/1982 |
| EP | 0 058 481 | 8/1982 |
| EP | 0 073 657 | 3/1983 |
| EP | 0 102 324 | 3/1984 |
| EP | 0 121 775 | 10/1984 |
| EP | 0 127 839 | 12/1984 |
| EP | 0 133 988 | 3/1985 |
| EP | 0 143 949 | 6/1985 |
| EP | 0 154 316 | 9/1985 |
| EP | 0 155 476 | 9/1985 |
| EP | 0 164 556 | 12/1985 |
| EP | 0 183 503 | 6/1986 |
| EP | 0 188 256 | 7/1986 |
| EP | 0 229 108 | 7/1987 |
| EP | 0 244 234 | 11/1987 |
| EP | 0 267 851 | 5/1988 |
| EP | 0 284 044 | 9/1988 |
| EP | 0 324 274 | 7/1989 |
| EP | 0 329 203 | 8/1989 |
| EP | 0 340 986 | 11/1989 |
| EP | 0 400 472 | 12/1990 |
| EP | 0 402 378 | 12/1990 |
| EP | 0 439 508 | 8/1991 |
| EP | 0 480 480 | 4/1992 |
| EP | 0 510 356 | 10/1992 |
| EP | 0 605 963 | 7/1994 |
| EP | 0 732 403 | 9/1996 |
| EP | 0 809 996 | 12/1997 |
| EP | 0 921 131 | 6/1999 |
| EP | 0 946 736 | 10/1999 |
| JP | 83-118008 | 1/1985 |
| JP | 2010-152800 A | 4/2010 |
| WO | WO 88/07082 | 9/1988 |
| WO | WO 89/01037 | 2/1989 |
| WO | WO 89/01038 | 2/1989 |
| WO | WO 90/01556 | 2/1990 |
| WO | WO 90/02186 | 3/1990 |
| WO | WO 90/02566 | 3/1990 |
| WO | WO 90/05785 | 5/1990 |
| WO | WO 90/10078 | 9/1990 |
| WO | WO 90/10277 | 9/1990 |
| WO | WO 90/13540 | 11/1990 |
| WO | WO 90/14428 | 11/1990 |
| WO | WO 91/00357 | 1/1991 |
| WO | WO 92/01801 | 2/1992 |
| WO | WO 92/02628 | 2/1992 |
| WO | WO 92/16555 | 10/1992 |
| WO | WO 92/16619 | 10/1992 |
| WO | WO 93/15189 | 8/1993 |
| WO | WO 93/21259 | 10/1993 |
| WO | WO 94/04193 | 3/1994 |
| WO | WO 94/09027 | 4/1994 |
| WO | WO 94/14758 | 7/1994 |
| WO | WO 94/15625 | 7/1994 |
| WO | WO 94/17039 | 8/1994 |
| WO | WO 94/18247 | 8/1994 |
| WO | WO 94/28024 | 12/1994 |
| WO | WO 95/00162 | 1/1995 |
| WO | WO 95/06058 | 3/1995 |
| WO | WO 95/11924 | 5/1995 |
| WO | WO 95/13090 | 5/1995 |
| WO | WO 95/13312 | 5/1995 |
| WO | WO 95/20672 | 8/1995 |
| WO | WO 95/33490 | 12/1995 |
| WO | WO 96/00080 | 1/1996 |
| WO | WO 96/06161 | 2/1996 |
| WO | WO 96/07670 | 3/1996 |
| WO | WO 96/21469 | 7/1996 |
| WO | WO 96/25496 | 8/1996 |
| WO | WO 96/29400 | 9/1996 |
| WO | WO 96/40791 | 12/1996 |
| WO | WO 96/41813 | 12/1996 |
| WO | WO 97/03106 | 1/1997 |
| WO | WO 97/18832 | 5/1997 |
| WO | WO 97/26332 | 7/1997 |
| WO | WO 97/32607 | 9/1997 |
| WO | WO 98/05363 | 2/1998 |
| WO | WO 98/26080 | 6/1998 |
| WO | WO 98/32466 | 7/1998 |
| WO | WO 98/37208 | 8/1998 |
| WO | WO 98/41562 | 9/1998 |
| WO | WO 98/48837 | 11/1998 |
| WO | WO 99/03887 | 1/1999 |
| WO | WO 99/05297 | 2/1999 |
| WO | WO 99/09193 | 2/1999 |
| WO | WO 99/10515 | 3/1999 |
| WO | WO 99/31257 | 6/1999 |
| WO | WO 99/32134 | 7/1999 |
| WO | WO 99/32139 | 7/1999 |
| WO | WO 99/32140 | 7/1999 |
| WO | WO 99/45130 | 9/1999 |
| WO | WO 99/51721 | 10/1999 |
| WO | WO 99/67291 | 12/1999 |
| WO | WO 00/20032 | 4/2000 |
| WO | WO 00/26354 | 5/2000 |
| WO | WO 00/55345 | 9/2000 |
| WO | WO 00/55353 | 9/2000 |
| WO | WO 01/05956 | 1/2001 |
| WO | WO 01/27301 | 4/2001 |
| WO | WO 01/90390 | 11/2001 |
| WO | WO 02/06305 | 1/2002 |
| WO | WO 02/085923 | 10/2002 |
| WO | WO 02/086075 | 10/2002 |
| WO | WO 03/101972 | 12/2003 |
| WO | WO 04/035605 | 4/2004 |
| WO | WO 04/035743 | 4/2004 |
| WO | WO 04/058946 | 7/2004 |
| WO | WO 04/094593 | 11/2004 |
| WO | WO 05/007624 | 1/2005 |
| WO | WO 05/007870 | 1/2005 |
| WO | WO 05/019415 | 3/2005 |
| WO | WO 05/035727 | 4/2005 |
| WO | WO 05/074524 | 8/2005 |
| WO | WO 05/074546 | 8/2005 |
| WO | WO 05/074650 | 8/2005 |
| WO | 2006009901 | 1/2006 |
| WO | 2006068802 | 6/2006 |
| WO | 2006069220 | 6/2006 |
| WO | 2006069246 | 6/2006 |
| WO | 2006071840 | 7/2006 |
| WO | 2006073846 | 7/2006 |
| WO | 2006091231 | 8/2006 |
| WO | 2006132969 | 12/2006 |
| WO | 2006133088 | 12/2006 |
| WO | 2006133089 | 12/2006 |
| WO | 2007021297 | 2/2007 |
| WO | 2007056083 | 5/2007 |
| WO | 2007056448 | 5/2007 |
| WO | 2007059312 | 5/2007 |
| WO | 2007070659 | 6/2007 |
| WO | 2007079130 | 7/2007 |
| WO | 2007094916 | 8/2007 |
| WO | 2008030558 | 3/2008 |
| WO | 2008030612 | 3/2008 |
| WO | 2008030613 | 3/2008 |
| WO | 2008030614 | 3/2008 |
| WO | 2008077079 | 6/2008 |
| WO | 2008083346 | 7/2008 |
| WO | 2008121563 | 10/2008 |
| WO | 2008137471 | 11/2008 |
| WO | 2008148839 | 12/2008 |
| WO | 2009036460 | 3/2009 |
| WO | 2009052435 | 4/2009 |
| WO | 2009061369 | 5/2009 |
| WO | 2009067636 | 5/2009 |
| WO | 2009100255 | 8/2009 |
| WO | 2009117622 | 9/2009 |

(56) References Cited

FOREIGN PATENT DOCUMENTS

| | | |
|---|---|---|
| WO | 2009/140659 A2 | 11/2009 |
| WO | 2010006214 | 1/2010 |
| WO | 2010011735 | 1/2010 |
| WO | 2010036964 | 4/2010 |
| WO | 2010037062 | 4/2010 |
| WO | 2010051056 | 5/2010 |
| WO | 2011028195 | 3/2011 |
| WO | 2011079293 | 6/2011 |
| WO | 2011087808 | 7/2011 |
| WO | 2011087810 | 7/2011 |
| WO | 2012024452 | 2/2012 |
| WO | 2012166559 | 12/2012 |
| WO | 2012166560 | 12/2012 |
| WO | 2013068874 | 5/2013 |
| WO | 2013130676 | 9/2013 |
| WO | 2013130814 | 9/2013 |
| WO | 2013130913 | 9/2013 |
| WO | 2013130917 | 9/2013 |
| WO | 2013185117 | 12/2013 |
| WO | 2013188740 | 12/2013 |
| WO | 2013192360 | 12/2013 |

OTHER PUBLICATIONS

Weitkamp, L.R. et al., "Additional data on the population distribution of human serum albumin genes; three new variants", Ann. Hum. Genet., Lond. 1973. 37: 219-226.

Strausberg, R.L. et al., Database GeneBank[online], Accession No. AAI26416, <http://www.ncbi.nlm.nih.gov/protein/116497221?sat=15&satkey=6070787>, Mar. 10, 2010 uploaded, Jul. 24, 2015 retrieved, Definition: Relaxin 2 [*Homo sapiens*].

Hossain MA, et al. "The A-chain of human relaxin family peptides has distinct roles in the binding and activation of the different relaxin family peptide receptors." J Biol Chem. Jun. 20, 2008;283(25):17287-97.

Adams et al., "Molecular cloning of mouse immunoglobulin heavy chain messenger ribonucleic acids coding for mu, alpha, gamma 1, gamma 2a, and gamma 3 chains", Biochemistry (1980) 19(12):2711-2719.

Aebersold et al., "A simplified antigrowth assay based on color change of the medium", Meth. Enzvmol. 119:579-582, 1986.

Bain et al., "Ribosome-mediated incorporation of a non-standard amino acid into a peptide through expansion of the genetic code", Nature (1992) 356(6369):537-9.

Beaucage et al., "Deoxynucleoside Phosphoramidites—A New Class of Key Intermediates for Deoxypolynucleotide Synthesis", Tetrahedron Letts. (1981) 22(20):1859-1862.

Bowie et al., "A method to identify protein sequences that fold into a known three-dimensional structure", Science (1991) 253(5016):164-170.

Brange, J. J. V., et al., Current Opinion in Structural Biology, 1, 934-940 (1991).

Brems et al., "Altering the association properties of insulin by amino acid replacement", Protein Engineering, (1992) 5(6):527-533.

Bryant-Greenwood, "Relaxin as a new hormone", Endocrine Reviews, (1982) 3(1):62-90.

Cate et al., "Isolation of the Bovine and Human Genes for Mullerian Inhibiting Substance and Expression of the Human Gene in Animal Cells", Cell, 45, pp. 685-698 (1986).

Cech, "The Chemistry of Self-Splicing RNA and RNA Enzymes", Science, (1987) 236:1532-1539.

Coloma, "Novel vectors for the expression of antibody molecules using variable regions generated by polymerase chain reaction", J Immunol Methods. (1992) 152(1):89-104.

Dahiyat et al., "Protein design automation", Protein Sci May 1996;5(5):895-903.

Dahiyat et al., "De novo protein design: fully automated sequence selection", Science (1997) 278(5335):82-7.

Desjarlais et al., "De novo design of the hydrophobic cores of proteins", Protein Science (1995) 4(10):2006-18.

Dolby et al., "Cloning and partial nucleotide sequence of human immunoglobulin mu chain eDNA from B cells and mouse-human hybridomas", Proc. NatL Acad. Sci. USA (1980) 77(10):6027-6031.

Edwards et al., "A bacterial amber suppressor in *Saccharomyces cerevisiae* is selectively recognized by a bacterial aminoacyl-tRNA synthetase", Mol. Cell. Bioi. (1990) 10(4):1633-1641.

Egel-Mitani et al., "A novel aspartyl protease allowing KEX2-independent MF alpha propheromone processing in yeast", Yeast (1990) 6(2): 127-137.

Falkner et al., "Expression of mouse immunoglobulin genes in monkey cells", Nature (1982) 298(5871):286-288.

Familletti et al., "A convenient and rapid cytopathic effect inhibition assay for interferon", Meth. Enzymol. (1981) 78(Pt A):387-394.

Friesen et al., "The Regulation of Baculovirus Gene Expression", Current Topics in Microbiology and Immunology, (1986) 131:31-49.

Gough et al., "Molecular Cloning of Seven Mouse Immunoglobulin k Chain Messenger Ribonucleic Acids", Biochemistry (1980) 19(12):2702-2710.

Hagenbuchle et al., "Mouse liver and salivary gland alpha-amylase mRNAs differ only in 5' non-translated sequences", Nature (1981) 289(5799):643-646.

Hakola et al., "Recombinant rat follicle-stimulating hormone; production by Chinese hamster ovary cells, purification and functional characterization", Molecular and Cellular Endocrinology, (1997) 127(1):59-69.

Harbury et al., "Repacking protein cores with backbone freedom: structure prediction for coiled coils", PNAS USA (1995) 92(18):8408-12.

Hecht, "Probing the Synthetic Capabilities of a Center of Biochemical Catalysis", Ace. Chern. Res. (1992) 25(12):545-552.

Hecht et al., "Chemical Aminoacylation of tRNA's", J. Bioi. Chem. (1978) 253(13):4517-4520.

Heckler et al., "Ribosomal binding and dipeptide formation by misacylated tRNA(Phe),S", Biochemistry (1988) 27(19):7254-7262.

Hellinga et al., "Optimal sequence selection in proteins of known structure by simulated evolution", PNAS USA (1994) 91(13):5803-5807.

Hokland et al., "Measurements of changes in histocompatibility antigens induced by interferons", Meth. EnzvmoL (1986) 119:688-693.

Hudson et al., "Structure of a genomic clone encoding biologically active human relaxin", Nature, (1983) 301 (5901 ):628-31.

Hudson et al., "Relaxin gene expression in human ovaries and the predicted structure of a human preprorelaxin by analysis of eDNA clones", The EMBO Journal, (1984) 3(10):2333-9.

Illangakekare et al., "Aminoacyl-RNA Synthesis Catalyzed by an RNA", Science (1995) 267(5198):643-647.

James et al., "Primary structure of porcine relaxin: homology with insulin and related growth factors", Nature, (1977) 267(5611):544-6.

Johnston et al., in Peptides: Structure and Function, Proc. Ninth American Peptide Symposium, Deber, C. M., et al. (eds.) (Pierce Chern. Co. 1985).

Jones, "De novo protein design using pairwise potentials and a genetic algorithm", Protein Science (1994) 3(4):567-74.

Kono et al., "Energy minimization method using automata network for sequence and side-chain conformation prediction from given backbone geometry", Proteins (1994) 19(3):244-255.

Kourouklis et al., "Programmable ribozymes for mischarging tRNA with nonnatural amino acids and the applications to translation", Methods (2005) 36:239-744.

Kowal et al., "Exploiting unassigned codons in Micrococcus Itueus for tRNA-based amino acid mutagenesis", Nucl. Acid. Res., (1997) 25(22):4685-4689.

Kowal et al., "Twenty-first aminoacyl synthetase-suppressor tRNA pairs for possible use in site-specific incorporation of amino acid analogues into proteins in eukaryotes and in eubacteria", Proc. Natl. Acad. Sci. U. s. A. (2001) 98(5):2268-2273.

(56) References Cited

OTHER PUBLICATIONS

Lawn et al., "The sequence of human serum albumin eDNA and its expression in *E. coli*", Nucleic Acids Research (1981) 9(22):6102-6114.
Lohse et al., "Ribozyme-catalysed amino-acid transfer reactions", Nature (1996) 381:442-444.
Lu et al., "Site-specific incorporation of a Phosephotyrosine Mimetic Reveals a Role for Tyrosine Phosphorylation of SHP-2 in Cell Signalling", Mol Cell. (2001) 8(4):759-69.
Mccorkle et al., "RNA's as Catalysts: A New Class of Enzymes", Concepts Biochem. (1987) 64(3):221-226.
Meloun et al., "Complete amino acid sequence of human serum albumin", FEBS Letters (1975) 58(1):136-7.
Behrens et al., "Structure of Human Serum Albumin", Fed. Proc. (1975) Biochemistry 2106:591.
Minghetti et al., "Molecular structure of the human albumin gene is revealed by nucleotide sequence within q11-22 of chromosome 4", J Bioi Chern. (1986) 261(15):6747-57.
MmTison et al., "Transfer and expression of immunoglobulin genes", Ann. Rev. Immunol. (1984) 2:239-256.
Needham-Vandevanter et al., "Characterization of an adduct between CC-1065 and a Defined Oligodeoxynucleotide Duplex", Nucleic Acids Res., (1984) 12(15):6159-6168.
Nicol et al., "Amino-acid sequence of human insulin", Nature, (1960) 187:483-5.
Offord, R.E. Protein engineering by chemical means? Protein Eng., 1(3):151-157 (1987).
Ohno et al., "Co-Expression of Yeast Amber Suppressor tRNATyr and Tyrosyl-tRNA Synthetase in *Escherichia coli*: Possibility to Expand the Genetic Code", J. Biochem. (1998) 124:1065-1068.
Pastrnak et al., "A new orthogonal suppressor tRNA/Aminoacyl-tRNA Synthetase Pair for Evolving an Organism with an Expanded Genetic Code", Helv. Chim. Acta (2000) 83:2277-2286.
Pearson et al., "The Importance of Silica Type for Reverse-Phase Protein Separations", Anal Biochem. (1982) 124:217-230.
Peng et al., "Rapid Purification of Recombinant Caculovirus Using Fluorescence-Activated Cell Sorting", BioTechniques (1993) 14(2):274-277.
Rice et al., "Regulated expression of an immunoglobulin kappa gene introduced into a mouse lymphoid cell line", Proc. Natl. Acad. Sci. USA (1982) 79(24):7862-7862.
Robertson et al., "A General and Efficient Route for Chemical Aminoacylation of Transfer RNAs", J. Am. Chern. Soc. (1991) 113:2722-2729.
Sakamoto et al., "Site-specific incorporation on unnatural amino acid into proteins in mammalian cells", Nucleic Acids Res. (2002) 30(21):4692-4699.
Saks et al., "An Engineered Tetrahymena tRNAGIn for in Vivo Incorporation of Unnatural Amino Acids into Proteins by Nonsense Suppression", J. Bioi. Chern. K1996) 271(38):23169-23175.
Schwabe et al., "Primary structure of the B-chain of porcine relaxin", Biochem. Biophys. Res. Comm., (1977) 75(2): 503-570.
Sherwood, The Physiology of Reproduction, Chapter 16, "Relaxin", Knobil, E. and Neill, J., et al. (eds.), (Raven Press Ltd., New York), pp. 585-673 (1988).
Stephan, "Give Your Protein a Tune-Up", Scientist (Oct. 2005) 30-33.
Taylor, M.D. et al., Annual Repmts in Med. Chern. 22, 85-94 (1987).
Valls et al., "Protein smting in yeast: the localization determinant of yeast vacuolar carboxypeptidase Y resides in the propeptide", Cell (1987) 48(5):887-897.
Weiss, "Relaxin", Ann. Rev. Physiol., (1984) 46:43-52.
Weitkamp et al., "Additional Data on the Population Distribution of Human Serum Albumin Genes; Three New Variants". Ann. Hum. Genet. 0973) 37:2191, 1973.
Wu, et al., "Enzymatic Phosphorylation of Unnatural Nucelosides", J. Am. Chern. Soc. (2002) 124(49):14626-14630.
Zalipsky, S., et al., "Use of Functionalized Poly(Ethylene Glycols) for Modification of Polypeptides" in Polyethylene Glycol Chemistry: Biotechnical and Biomedical Applications, Hanis, Plenus Press, New York (1992), and in Advanced Drug Reviews, 16:157-182 (1995).
Holland, MJ et JP Holland., "Isolation and identification of yeast messenger ribonucleic acids coding for enolase, glyceraldehyde-3-phosphate dehydrogenase, and phosphoglycerate kinase," Biochemistry. Nov. 14, 1978; 17 (23):4900-7.
Holland, MJ et al., "The primary structures of two yeast enolase genes. Homology between the 5' noncoding flanking regions of yeast enolase and glyceraldehyde-3-phosphate dehydrogenase genes," J Bioi Chern. Feb. 10, 1981;256(3):1385-95.
Hsiao, CL et J Carbon, High-frequency transformation of yeast by plasmids containing the cloned yeast ARG4 gene, Proc Nail Acad Sci US A. Aug. 1979;76(8):3829-33.
Huisgen, R. in 1,3-Dipolar Cycloaddilion Chemistry, val. 1, 1984; Ed. Padwa A.; John Wiley and Sons, New York, p. 1 -176.
Hwang, KJ et al., "Hepatic uptake and degradation of unilamellar sphingomyelin/cholesterol liposomes: a kinetic study," Proc Nail Acad Sci U SA. Jul. 1980;77(7):4030-4.
Ibba, Metal., "Substrate specificity is determined by amino acid binding pocket size in *Escherichia coli* phenylalanyi lRNA synthetase," Biochemistry. Jun. 14, 1994;33(23):7107-12.
Ibba, M and H Hennecke, "Relaxing the substrate specificity of an aminoacyi-lRNA synthetase allows in vitro and in vivo synthesis of proteins containing unnatural amino acids," FEBS Lett. May 15, 1995;364(3):272-5.
Ito, H. et al., "Transformation of intact yeast cells treated with alkali cations," J. Bacteriol. 1983; 153(1):163-8.
Jackson, DY et al. "A designed peptide ligase for total synthesis of ribonuclease A with unnatural catalytic residues," Science. Oct. 14, 1994;266(5183):243-7.
Jakobsson, PJ et al., "Identification and characterization of a novel human microsomal glutathione S-transferase with leukotriene C4 synthase activity and significant sequence identity to 5-lipoxygenase-activating protein and leukotriene C4 synthase," J Bioi Chern. Sep. 6, 1996;271(36):22203-10.
Jencks, W.P., "Studies on the Mechanism of Oxime and Semicarbazone Formation," J. Am. Chern. Soc.; 1959; 81 (2);475-481.
Joppich, M. et al. "Peptides Flanked by Two Polymer Chains, 1; Synthesis of Glycyi-L-tryptophylglycine Substituted by Poly(ethylene oxide) at both the Carboxy and the Amino End Groups," Makromol. Chern. 1979;180:1381-4.
Kaiser, ET. "Synthetic approaches to biologically active peptides and proteins including enzymes," Ace Chern Res, (1989); 22(2):47-54.
Kaiser, ET et al. "The chemical modification of enzymatic specificity," Annu Rev Biochem. 1985;54:565-95.
Kaiser, ET and OS Lawrence. "Chemical mutation of enzyme active sites," Science. Nov. 2, 1984;226(4674):505-11.
Karlin, Sand SF Altschul "Applications and statistics for multiple high-scoring segments in molecular sequences," Proc Natl Acad Sci US A. Jun. 15, 1993;90(12):5873-7.
Kayser, B., et al., "Aikyne bridged alpha- amino acids by palladium mediated coupling of alkynes with N-t-Boc-4- iodo-phenylalanine methyl ester," Tetrahedron (1997); 53(7): 2475-2484.
Kelly, JM and MJ Hynes, "Transformation of Aspergillus niger by the amdS gene of Aspergillus nidulans," EMBO J. 1985; 4(2):475-479.
Kiick, K. L. and D. A. Tirrell, "Protein Engineering by In Vivo Incorporation of Non-Natural Amino Acids: Control of Incorporation of Methionine Analogues by Methionyl-tRNA Synthetase," Tetrahedron (2000), 56:9487-9493.
Kiick, KL et al., "Incorporation of azides into recombinant proteins for chemoselective modification by the Staudinger ligation," Proc Natl Acad Sci US A. Jan. 8, 2002;99(1):19-24. Epub Dec. 18, 2001.
Kim, Om and JR Swartz, "Regeneration of adenosine triphosphate from glycolyl ic • intermediates for cell-free protein synthesis," Biotechnol Bioeng. Aug. 2, 20010;74(4):309-16.
Kim, OM and JR Swartz, "Oxalate improves protein synthesis by enhancing ATP supply in a cell-free system derived from *Escherichia coli*," Biotechnology Letters, 2000; 22:1537-1542.

(56) References Cited

OTHER PUBLICATIONS

Kim, OM, and JR Swartz, "Prolonging cell-free protein synthesis by selective reagent additions," Biotechnol Prog. May-Jun. 2000;16(3):385-90.
Kim, OM, and JR Swartz, "Prolonging cell-free protein synthesis with a novel ATP regeneration system," Biotechnol Bioeng. 1999;66(3):180-8.
King, F.E. & Kidd, D.AA "A New Synthesis of Glutamine and of gamma-Dipeplides of Glutamic Acid from Phthylaled Intermediates," J. Chern. Soc. 1949; 3315-3319.
Kingsman, AJ et al., "Replication in Saccharomyces cerevisiae of plasmid pBR313 carrying DNA from the yeast trpl region," Gene. Oct. 1979;7(2):141-52.
Kitis, PA et al. "Linearization of baculovirus DNA enhances the recovery of recombinant virus expression vectors," Nucleic Acids Res. Oct. 11, 1990;18(19):5667-72.
Klein, TM et al., "High-velocity microprojectiles for delivering nucleic acids into living cells," Nature 1987; 327 (6117):70-73.
Kobayashi, T. et al., "Structural basis for orthogonal !RNA specificities of tyrosyi-IRNA synthetases for genetic code expansion," Nature Structural Biology (2003) 10(6):425-432.
Kogan, TP. "The synthesis of substituted methoxy-poly(elhyleneglycol) derivatives suitable for selective protein modification," Synthetic Comm. 1992; 22(16):2417-24.
Kool, ET. "Synthetically modified DNAs as substrates for polymerases," Curr Opin Chern Bioi. Dec. 2000;4(6):602-8.
Koskinen, A.M.P. & Rapoport, H. "Synthesis of 4-Subslituted Pralines as Conformationally Constrained Amino Acid Analogues," J. Org. Chern. (1989) 54(8):1859-1866.
Kost, TA et al., "Production of a urokinase plasminogen activator-igG fusion protein (uPA-IgG) in the baculovirus expression system," Gene. Apr. 29, 1997;190(1):139-44.
Kramer, W et al., "The gapped duplex DNA approach to oligonucleotide-directed mutation construction," Nucleic Acids Res. Dec. 21, 1984;12(24):9441-56.
Kramer, W & Fritz HJ. "Oligonucleotide-directed construction of mutations via n gapped duplex DNA" Methods Enzymol. 1987;154:350-67.
Kramer, W. et al., "Improved enzymatic in vitro reactions in the gapped duplex DNA approach to oligonucleotidedirected construction of mutations," Nucleic Acids Res. Jul. 25, 1988;16(14B):7207.
Kramer, B. et al., "Different base/base mismatches are corrected with different efficiencies by the methyl-directed DNA mismatch-repair system of *E. coli*," Cell. Oct. 1984;38(3):879-87.
Kreitman, RJ and I. Pastan "Purification and characterization of IL6-PE4E, a recombinant fusion of interleukin 6 with Pseudomonas exotoxin," Bioconjug Chern. Nov.-Dec. 1993;4(6):581-5.
Krieg, UC, et al. "Photocrosslinking of the signal sequence of nascent preprolactin to the 54-kilodalton polypeptide of the signal recognition particle," Proc Nail Acad Sci U SA. Nov. 1986;83(22):8604-8.
Kunitani, M. et al., "Reversed-phase chromatography of interleukin-2 muteins," J Chromatogr. May 30, 1986;359:391-402.
Kunkel, "The efficiency of oligonucleotide directed mutagenesis," in Nucleic Acids & Molecular Biology 1987; Eckstein, F. and Lilley, D.M.J. eds.; Springer Verlag, Berlin; 124-135.
Kunkel, TA "Rapid and efficient site-specific mutagenesis without phenotypic selection," Proc Nail Acad Sci USA. Jan. 1985;82(2):488-92.
Kunkel, TA et al., "Rapid and efficient site-specific mutagenesis without phenotypic selection," Methods Enzymol. 1987;154:367-82.
Kunze, Get al., "Transformation of the industrially important yeasts Candida maltosa and Pichia guilliermondii," J. Basic Microbiol. 1985; 25:141-4.
Kurtz et al., "Integrative transformation of Candida albicans, using a cloned Candida ADE2 gene," Mol Cell Bioi. Jan. 1986;6(1):142-9.
Kurtzhals, Pet al., "Albumin binding of insulins acylated with fatty acids: characterization of the ligand-protein interaction and correlation between binding affinity and timing of the insulin effect in vivo," Biochem J. Dec. 15, 1995;312 (Pt 3):725-31.
Langer, R et al., "Biocompatibility of polymeric delivery systems for • macromolecules," J Biomed Mater Res. Mar. 1981;15(2):267-77.
Langer, R. "Controlled release of macromolecules," Chern. Tech. 1982; 12:98-105.
Liebman, JM et al., "When less is more: enhanced baculovirus production of recombinant proteins at very low multiplicities of infection," Biotechniques. Jan. 1999;26(1):36-8, 40, 42.
Ling, MM et BH Robinson, "Approaches to DNA mutagenesis: an overview" Anal Biochem. Dec. 1, 19975;254 (2):157-78.
Wang, L & PG Schultz, "Expanding the genetic code," Chern Commun (Camb). Jan. 7, 2002;1:1-11.
Weissmann, C. "The cloning of interferon and other mistakes." in Interferon 3 1981; ed. I. Gresser; Academic Press, London, 101-134.
Wells, JA et al., "Importance of hydrogen-bond formation in stabilizing the transition state of subtilisin," Phil. Trans.R. Soc. Lond. A 1986; 317:415-423.
Wells, JA et al., "Cassette mutagenesis: an efficient method for generation of multiple mutations at defined sites," Gene. 1985;34(2-3):315-23.
Woghiren, C et al. "Protected thiol-polyethylene glycol: a new activated polymer for reversible protein modification," Bioconjug Chern. Sep.-Oct. 1993; 4(5):314-8.
Wong, SS et LJ Wong, "Chemical crosslinking and the stabilization of proteins and enzymes," Enzyme Microb Technol. Nov. 1992;14(11):866-74.
Wright, K. "Biotechnology: Insect virus as super-vector?," Nature (1986)321 (6072):718.
Liu, H. et al. "A Method for the Generation of Glycoprotein Mimetics," J. Am. Chern. Soc. 2003 125(7): 1702-1703.
Liu, D.R. & Schultz, P.G. "Progress toward the evolution of an organism with an expanded genetic code," Proc Natl Acad Sci US A. Apr. 27, 1999;96(9):4780-5.
Lorimer, I. A. et I. Pastan, "Random recombination of antibody single chain Fv sequences after fragmentation with DNaseI in the presence of Mn2+," Nucleic Acids Res. Aug. 1, 19951;23(15):3067-8.
Lu, T. et al. "Probing ion permeation and gating in a K +channel with backbone mutations in the selectivity filter," Nature Neurosci. Mar. 2001;4(3):239-246.
Luckow, VA and MD Summers, "High level expression of nonfused foreign genes with Autographa californica nuclear polyhedrosis virus expression vectors," Virology. May 1989;170(1):31-9.
Ma, C et al., "In vitro protein engineering using synthetic tRNA(Aia) with different anticodons," Biochemistry. Aug. 10, 1993;32(31):7939-45.
Magliery, TJ et al. "Expanding the Genetic Code: Selection of Efficient Suppressors of Four-base Codons and Identification of "Shifty" Four-base Codons with a Library Approach in *Escherichia coli*," J Mol Bioi. Mar. 30, 2001;307 (3):755-69.
Mahal, L. K., et al., "Engineering chemical reactivity on cell surfaces through oligosaccharide biosynthesis," Science. May 16, 1997;276(5315):1125-8.
Makrides, SC et al., "Extended in vivo half-life of human soluble complement receptor type 1 fused to a serum albumin-binding receptor," J Pharmacol Exp Ther. Apr. 1996;277(1):534-42.
Mamot, C, et al., "Epidermal growth factor receptor (EGFR)-targeted immunoliposomes mediate specific and efficient drug delivery to EGFR- and EGFRvIII-overexpressing tumor cells," Cancer Res. Jun. 15, 2003;63(12):3154-61.
Mandecki, W. Oligonucleotide-directed double-strand break repair in plasmids of *Escherichia coli*: a method for sitespecific mutagenesis, Proc Natl Acad Sci US A. Oct. 1986;83(19):7177-81.
Mann, SG and LA King, "Efficient transfection of insect cells with baculovirus DNA using electroporation," J Gen Virol. Dec. 1989;70 (PI12):3501-5.
Matsoukas, JM et al., "Differences in backbone structure between angiotensin II agonists and type I antagonists," J Med Chern. Nov. 10, 1995;38(23):4660-9.

(56) References Cited

OTHER PUBLICATIONS

McMinn, DL et al., "Efforts toward Expansion of the Genetic Alphabet: DNA Polymerase Recognition of a Highly Stable, Self-Pairing Hydrophobic Base," J. Am. Chem. Soc. 1999; 121(49):11585-6.

Meggers, E et al., "A Novel Copper-Mediated DNA Base Pair," J. Am. Chem. Soc. 2000; 122(43):10714-10715.

Mehvar, R.,"Modulation of the pharmacokinetics and pharmacodynamics of proteins by polyethylene glycol conjugation" J Pharm Pharm Sci. Jan.-Apr. 2000;3(1):125-36.

Mendel, D, et al. "Site-directed mutagenesis with an expanded genetic code," Annu Rev Biophys Biomol Struct. 1995;24:435-62.

Miller, Lk, "Baculoviruses as gene expression vectors," Ann. Rev. Microbiol. 1988; 42:177-99.

Miller, LK. "Insect baculoviruses: powerful gene expression vectors," Bioessays. Oct. 1989;11(4):91-5.

Miller, JC et al. "Flash decaging of tyrosine sidechains in an ion channel," Neuron. Apr. 1998;20(4):619-24.

Minks, C. et al., Noninvasive tracing of recombinant proteins with "fluorophenylalanine-fingers,"Anal Biochem. Aug. 15, 2000;284(1):29-34.

Miyanohara, A et al., "Expression of hepatitis B surface antigen gene in yeast," Proc Nail Acad Sci US A. Jan. 1983;80(1):1-5.

Moore, B. et al., "Quadruplet codons: implications for code expansion and the specification of translation step size," J. Mol. Bioi. 2000; 298(2):195-209.

Mosbach, K. et al., "Formation of proinsulin by immobilized Bacillus subtilis," Nature Apr. 1983; 302:543-545.

Nakamaye, KL & Eckstein F, "Inhibition of restriction endonuclease Nci I cleavage by phosphorothioate groups and its application to oligonucleotide-directed mutagenesis" Nucleic Acids Res. Dec. 22, 1986;14(24):9679-98.

Nakatsuka, T., et al. "Peptide segment coupling catalyzed by the semisynthetic enzyme thiosubtilisin," JAm Chem Soc, 1987; 109(12): 3808-3810.

Nambiar, KP et al., "Total synthesis and cloning of a gene coding for the ribonuclease S protein," Science (1984) 223: 1299-1301.

Needleman, SB and Wunsch CD, "A general method applicable to the search for similarities in the amino acid sequence of two proteins," J Mol Bioi. Mar. 1970;48(3):443-53.

Neet, KE et al. "Properties of thiol-subtilisin. The consequences of converting the active serine residue to cysteine in a serine protease," J Bioi Chem. Dec. 25, 1968;243(24):6392-401.

Nielsen, UB, et al., "Therapeutic efficacy of anti-ErbB2 immunoliposomes targeted by a phage antibody selected for cellular endocytosis," Biochim Biophys Acta. Aug. 19, 2002;1591(1-3):109-118.

Nomura, T, et al., "Purification, eDNA Cloning, and Expression of UDP-Gal: Glucosylceramide -1,4- Galactosyltransferase from Rat Brain," J. Biol. Chem. 1998; 273(22):13570-7.

Noren, CJ et al. "A general method for site-specific incorporation of unnatural amino acids into proteins," Science. Apr. 14, 1989;244(4901):182-8.

Nowak, MW et al., "Nicotinic receptor binding site probed with unnatural amino acid incorporation in intact cells," Science. Apr. 21, 1995;268(5209):439-42.

Ogawa, AK et al., "Efforts toward the Expansion of the Genetic Alphabet: Information Storage and Replication with Unnatural Hydrophobic Base Pairs," J. Am. Chem. Soc. 2000; 122(14):3274-3287.

Ogawa, AK et al., "Rational Design of an Unnatural Base Pair with Increased Kinetic Selectivity," J. Am. Chem. Soc. 2000; 122(36); 8803-8804.

Ohtsuka, E et al., "An alternative approach to deoxyoligonucleolides as hybridization probes by insertion of deoxyinosine at ambiguous codon positions," J Bioi Chem. Mar. 10, 1985;260(5):2605-8.

Olson et al. "Preparation and Characterization of Poly(ethylene glycol)yated Human Growth Hormone Antagonist," in Poly(ethylene glycol) Chemistry & Biological Applications, 1997; Eds. JM Harris & S. Zalipsky; ACS, Washington, D.C., 170-181.

Padwa, A. "Intenmolecular 1,3-Dipolar Cycloaddilions," in Comprehensive Organic Synthesis, vol. 4, (1991) Ed. Trost, B. M.; Pergamon, Oxford, 1069-1109.

Palva, I et al., "Secretion of interferon by Bacillus sublilis," Gene. May-Jun. 1983;22(2-3):229-35.

Park, JW, et al., "Development of anti-p185HER2 immunoliposomes for cancer therapy," Proc Nail Acad Sci U SA. Feb. 28, 1995;92(5):1327-31.

Park, JW, et al., "Anti-HER2 immunoliposomes: enhanced efficacy attributable to targeted delivery," Clin Cancer Res. Apr. 2002;8(4):1172-81.

Patnaik, R. and JR Swartz, "*E. coli*-based in vitro transcription/translation: in vivo-specific synthesis rates and high yields in a balch system," Biotechniques. May 1998;24(5):862-8.

Pearson, WR and DJ Lipman, "Improved tools for biological sequence comparison," Proc Nail Acad Sci U SA. Apr. 1988;85(8):2444-8.

Pepinsky, RB., et al., "Improved pharmacokinetic properties of a polyethylene glyco I-modified form of inlerferonbela-1a with preserved in vitro bioactivity," J Pharmacal Exp Ther. Jun. 2001;297(3):1059-66.

Piccirilli, JA et al., "Enzymatic incorporation of a new base pair into DNA and RNA extends the genetic alphabet," Nature 1990; 343:33-37.

Pintar, A et al. "CX, an algorithm that identifies protruding atoms in proteins," Bioinformatics. Jul. 2002;18(7):980-4.

Pitha, J et al. "Detergents linked to polysaccharides: preparation and effects on membranes and cells," Eur J Biochem. Feb. 15, 1979;94(1):11-8.

Polgar, L. and ML Bender. "A new enzyme containing a synthetically formed active site. Thiol-subtilisin." J. Am Chem Soc., 1966; 88(13): 3153-3154.

Pollack, SJ et al. "Introduction of nucleophiles and spectroscopic probes into antibody combining sites," Science. Nov. 18, 1988;242(4881):1038-40.

Preneta, AZ. "Separation on the basis of size: gel permeation chromatography," in Protein Purification Methods, a practical approach, 1989; Eds. Harris & Angal IRL Press, Oxford; 293-306.

Yelton, MM et al., "Transformation of Aspergillus nidulans by using a trpC plasmid," Proc Natl Acad Sci U SA. Mar. 1984;81 (5):1470-4.

Yelverton, E et al., "Bacterial synthesis of a novel human leukocyte interferon," Nucleic Acids Res. Feb. 11, 1981;9 (3);731-41.

Zalipsky, Setal. "Attachment of drugs to polyethylene glycols," Eur. Polymer Journal. 1983 19(12): 1177-83.

Zalipsky, S. "Functionalized poly(ethylene glycol) for preparation of biologically relevant conjugates," Bioconjug Chem. Mar.-Apr. 1995;6(2):150-65.

Zhang, Z., et al. "A new strategy for the site-specific modification of proteins in vivo," Biochemistry. Jun. 10, 2003;42 (22):6735-46.

Zoller, MJ & M Smith, "Oligonucleotide-directed mutagenesis using M13-derived vectors: an efficient and general procedure for the production of point mutations in any fragment of DNA" Nucleic Acids Res. Oct. 25, 1982;10 (20):6487-500.

Zoller, MJ & M. Smith, "Oligonucleotide-directed mutagenesis of DNA fragments cloned into M13 vectors" Methods Enzymol. 1983;100:468-500.

Raibaud, 0 et M Schwartz. "Positive control of transcription initiation in bacteria," Annu Rev Genet. 1984;18:173-206.

Reverey, H. et al., "Differential Fatty Acid Selection during Biosynthetic S- Acylation of a Transmembrane Protein (HEF) and Other Proteins in Insect Cells (Sf9) and in Mammalian Cells (CV1)," J. Biol. Chem. 1996; 271 (39):23607-10.

Rivier, Jet R McClintock, "Reversed-phase high-performance liquid chromatography of insulins from different species," J Chromatogr. Sep. 23, 1983;268(1):112-9.

Roberts, et al., "Generation of an antibody with enhanced affinity and specificity for its antigen by protein engineering," Nature 1987;328:731-734.

Roberts, RW and JW Szostak, "RNA-peptide fusions for the in vitro selection of 1peplides and proteins," Proc Nail Acad Sci US A. Nov. 11, 1997;94(23):12297-302.

(56) References Cited

OTHER PUBLICATIONS

Roggenkamp, R. et al., "Transformation of the methylotrophic yeast Hansenula polymorpha by autonomous replication and integration vectors," Mol. Genetics and Genomics 1986;202(2):302-8.

Romani et al. "Synthesis of unsymmetrical cystine peplides: directed disulfide pairing with the sulfenohydrazide method," in Chemistry of Peplides and Proteins 1984; eds. Voeller, W. et al.; Walter de Gruyler et al., Berlin; vol. 2:29-33.

Romanos, MA et al., "Foreign gene expression in yeast: a review," Yeast. Jun. 1992;8(6):423-88.

Rosenthal, GA. "L-canaline: a potent antimetabolite and anti-cancer agent from leguminous plants," Life Sci.1997;60(19):1635-41.

Rossolini, GM et al., "Use of deoxyinosine-conlaining primers vs degenerate primers for polymerase chain reaction based on ambiguous sequence information," Mol. Cell. Probes 1994; 8:91-98.

Rostovtsev, VV et al., "A stepwise huisgen cycloaddilion process: copper(I)-catalyzed regioselective "ligation" of azides and terminal alkynes," Angew Chern In!Ed EnglJul. 15, 2002;41(14):2596-9.

Rowles, Jet al., "Cloning and characterization of PDK4 on 7q21.3 encoding a fourth pyruvate dehydrogenase kinase isoenzyme in human," J Bioi Chern. Sep. 13, 1996;271(37):22376-82.

Sakmar, TP and Khorana HG, "Total synthesis and expression of a gene for the alpha-subunit of bovine rod outer segment guanine nucleotide-binding protein (transducin)" Nucleic Acids Res. Jul. 25, 1988;16(14A):6361-72.

Sandler and Karo, "Polyoxyalkylation of hydroxyl compounds," in Polymer Synthesis, vol. 3, 1980; Academic Press, New York, 138-161.

Sartore, Let al., "Enzyme modification by MPEG with an amino acid or peptide asspacer arms," Appl Biochem Biotechnol. Jan. 1991;27(1):45-54.

Sawhney, AS et al., "Bioerodible Hydrogels Based on Photopolymerized Poly(ethylene glycol)-co-poly(alpha-hydroxy acid) Diacrylate Macromers," Macromolecules 1993; 26(4):581-7.

Saxon, E and C. Bertozzi, "Cell Surface Engineering by a Modified Staudinger Reaction," Science (2000); 287 (5460):2007-2010.

Sayers, JR et al., "Strand specific cleavage of phosphorothioate-containing DNA by reaction with restriction endonucleases in the presence of ethidium bromide" Nucleic Acids Res. Feb. 11, 1988;16(3):803-14.

Sayers, JR, et al. "5'-3' exonucleases in phosphorothioate-based oligonucleotide-directed mutagenesis," Nucleic Acids Res. Feb. 11, 1988;16(3):791-802.

Schanbacher, FL et al. "Galactosyltransferase Acceptor Specificity of the Lactose Synthetase A Protein," J. Bioi. Chem. 1970; 245(19):5057-5061.

Schmidt, Metal., "Baculovirus-mediated large-scale expression and purification of a polyhistidine-tagged rubella virus capsid protein," Protein Expr Purif. Apr. 1998;12(3):323-30.

Schneider, E., et al., "Functional Purification of a Bacterial ATP-Binding Cassette Transporter Protein (MaiK) from the Cytoplasmic Fraction of an Overproducing Strain," Protein Expr. Purif. 1995; 6(1):10-14.

Schnolzer, M. and SBH Kent. "Constructing proteins by dovetailing unprotected synthetic peptides: backboneengineered HIV protease," Science. Apr. 10, 1992;256(5054):221-5.

Scouten, WH. "A survey of enzyme coupling techniques," Methods Enzymol. 1987;135:30-65.

Shao, J and JP Tam, "Unprotected Peptides as Building Blocks for the Synthesis of Peptide Dendrimers with Oxime, Hydrazone, and Thiazolidine Linkages," J. Am. Chern. Soc. 1995; 117(14):3893-3899.

Sharma, N et al., "Efficient introduction of aryl bromide functionality into proteins in vivo," FEBS Lett. Feb. 4, 2000;467 (1):37-40.

Shimatake, H et M Rosenberg, "Purified gamma regulatory protein ell positively activates promoters for lysogenic development," Nature Jul. 1981; 292:128-132.

Shine, J and L Dalgarno, "Determinant of cistron specificity in bacterial ribosomes," Nature. Mar. 6, 1975;254 (5495):34-8.

Sidman, KR et al., "Controlled release of macromolecules and pharmaceuticals from synthetic polypeptides based on glutamic acid," Biopolymers. Jan. 1983;22(1):547-56.

Sieber, V. et al., "Libraries of hybrid proteins from distantly related sequences", Nature Biotechnology, May 2001;19:456-460.

Siffert, Wet al., "Association of a human G-protein beta3 subunit variant with 1 hypertension," Nat Genet. Jan. 1998;18(1):45-8.

Sikorski, RS et al., "A System of Shuttle Vectors and Yeast Host Strains Designed for Efficient Manipulation of DNA in *Saccharomyces cerevisiae*," Genetics (1989) 122:19-27.

Sisk, WP et al., "High-level expression and purification of secreted forms of herpes simplex virus type 1 glycoprotein gO synthesized by baculovirus-infected insect cells," J Viral. Feb. 1994;68(2):766-75.

Sjolander, A et al., "The serum albumin-binding region of streptococcal protein G: a bacterial fusion partner with carrier-related properties," J Immunol Methods. Feb. 14, 1997;201(1):115-23.

Smith, M. "In vitro mutagenesis" Ann. Rev. Genet. 1985; 19:423-462.

Smith, GE et al., "Production of human bela interferon in insect cells infected with a baculovirus expression vector," Mol Cell Bioi. Dec. 1983;3(12):2156-65.

Stanley, SL et al., "The serine-rich Entamoeba hislolytica protein is a phosphorylated membrane protein containing 0-linked terminal N-acetylglucosamine residues," J Bioi Chern. Feb. 24, 1995;270(8):4121-6.

Steitz, JA et al. "Genetic signals and nucleotide sequences in messenger RNA," in Biological Regulation and Development: Gene Expression 1979; ed. R. F. Goldberger; Plenum Press, New York; 349-399.

Stemmer, WPC, "Rapid evolution of a protein in vitro by DNA shuffling," Nature 1994;370(4):389-391.

Stemmer, WP "DNA shuffling by random fragmentation and reassembly: In vitro recombination for molecular evolution," Proc Nail Acad Sci US A. Oct. 25, 1994;91(22):10747-51.

Studier, FW et BA Moffatt, "Use of bacteriophage T7 RNA polymerase to direct selective high-level expression of cloned genes," J. Mol Bioi. May 5, 1986;189(1):113-30.

Subasinghe, N. et al., "Quisqualic acid analogues: synthesis of bela-heterocyclic 2-aminopropanoic acid derivatives and their activity at a novel quisqualate-sensitized site," J Med Chern. Nov. 27, 1992;35(24):4602-7.

Switzer, C et al., "Enzymatic incorporation of a new base pair into DNA and RNA," J. Am. Chern. Soc. 1989; 111 (21):8322-8323.

Tabor, Set CC Richardson, "A bacteriophage T7 RNA polymerase/promoter system for controlled exclusive expression of specific genes," Proc Nail Acad Sci US A. Feb. 1985;82(4):1074-8.

Tae, EL et al., "Efforts toward Expansion of the Genetic Alphabet: Replication of DNA with Three Base Pairs," J. Am. Chern. Soc. 2001; 123(30):7439-7440.

Tang, Yet al., "Fluorinated Coiled-Coil Proteins Prepared In Vivo Display Enhanced Thermal and Chemical Stability," Angew Chern Int Ed Engl. Apr. 17, 2001;40(8):1494-1496.

Taylor, JW et al., "The use of phosphorothioate-modified DNA in restriction enzyme reactions to prepare nicked DNA," Nucleic Acids Res. Dec. 20, 1985;13(24):8749-64.

Taylor, JW et al., "The rapid generation of oligonucleotide-directed mutations at high frequency using phosphorothioate-modified DNA," Nucleic Acids Res. Dec. 20, 1985;13(24):8765-85.

Tijssen, P. "Overview of principles of hybridization and the strategy of nucleic acid assays," in Laboratory Techniques in Biochemistry and Molecular Biology—Hybridization with Nucleic Probes, Part I, 1993; Elsevier Science Publishers, Amsterdam, 19-78.

Tilburn, J. et al., "Transformation by integration in Aspergillus nidulans," Gene. Dec. 1983;26(2-3):205-21.

Zoller, MJ & Smith M, "Oligonucleotide-directed mutagenesis: a simple method using two oligonucleotide primers and a single-stranded DNA template," Methods Enzymol. 1987;154:329-50.

Mehl, RA et al. "Generation of a bacterium with a 21 amino acid genetic code," JAm Chern Soc. Jan. 29, 2003;125 (4):935-9.

Santoro, SW et al. "An efficient system for the evolution of aminoacyl-tRNA synthetase specificity," Nat Biotechnol. Oct. 2002;20(10):1044-8. Epub Sep. 16, 2002.

(56) References Cited

OTHER PUBLICATIONS

Caliceti, Pet FM Veronese. "Pharmacokinetic and biodistribution properties of poly(ethylene glycol)-protein conjugates," Adv Drug Deliv Rev. Sep. 26, 2003;55(10):1261-77.
Clark, EDB, "Refolding of recombinant proteins," Curr Opin Biotechnol Apr. 1, 1998;9(2):157-63.
Clark, EDB, "Protein refolding for industrial processes," Curr Opin BiotechnolApr. 2001;12(2):202-7.
Davis, GD et al., "New fusion protein systems designed to give soluble expression in *Escherichia coli*," Biotechnol Bioeng Nov. 20, 1999;65(4);382-8.
Duncan, R. "The dawning era of polymer therapeutics," Nat Rev Drug Discov May 2003;2(5):347-60.
Gaertner, HF et RE Offord. "Site-specific attachment offunctionalized poly(ethylene glycol) to the amino terminus of proteins," Bioconjug Chern Jan.-Feb. 1996;7(1):38-44.
Gu, Z et al. "Chromatographic methods for the isolation of, and refolding of proteins from, *Escherichia coli* inclusion bodies," Protein Expr Purif. Jun. 2002;25(1):174-9.
Hohsaka, T et M Sisido. "Incorporation of non-naturaf amino acids into proteins," Curr Opin Chern Bioi. Dec. 2002;6 (6):809-15.
Lilie, H et al. "Advances in refolding of proteins produced in *E. coli*," Curr Opin Biotechnol. 1998 Ocl;9(5):497-501.
Tsumoto, Ketal. "Practical considerations in refolding proteins from inclusion bodies," Protein Expr Purif. Mar. 2003;28(1):1-8.
Wang, W. "Instability, stabilization, and formulation of liquid protein pharmaceuticals," In!J Pharm. Aug. 20, 1999;185 (2):129-88.
Abuchowski, A. et al. "Cancer therapy with chemically modified enzymes. I. Antitumor properties of polyethylene glycol-asparaginase conjugates," Cancer Biochem Biophys. Jun. 1984;7(2):175-86.
Altschul, SF et al. "Gapped BLAST and PSI-BLAST: a new generation of protein database search programs," Nucleic Acids Res. Sep. 1, 1997;25(17):3389-402.
Altschul, SF et al. "Basic local alignment search tool," J Mol Bioi. Oct. 5, 1990;215(3):403-10.
Amann, E et al., "Vectors bearing a hybrid trp-lac promoter useful for regulated expression of cloned genes in *Escherichia coli*," Gene. Nov. 1983;25(2-3):167-78.
Anderson, JC et al., "Exploring the limits of codon and anticodon size," Chern Bioi. Feb. 2002;9(2):237-44.
Andresz, H et al. Abstract of "Chemische Synthese verzweigter Polysaccharide, 5; Kopplung von Oligosacchariden und Amylose an verschiedene Trager durch Hydrazonbindung," Makromol. Chern. 1978;179:301 Abstract.
Arnold, FH. "Protein engineering for unusual environments," Curr Opin Biotechnol. Aug. 1993;4(4):450-5.
Azoulay, M., et al. "Glutamine analogues as Potential Antimalarials," Eur. J. Med. • Chern. (1991); 26(2):201-5.
Bain, JD, et al. "Biosynthetic site-specific incorporation of a non-natural amino acid into a polypeptide," J. Am Chern Soc 1989;111 (20):8013-8014.
Ballance, DJ et al., "Transformation of Aspergillus nidulans by the orotidine-5'-phosphate decarboxylase gene of Neurospora crassa," Biochem Biophys Res Common. Apr. 15, 1983;112(1):284-9.
Barany, F. et al., "Genetic disease detection and DNA amplification using cloned thermostable ligase," Proc Natl Acad Sci US A, Jan. 1, 1991;88(1):189-93.
Barton, Dhr et al., "Synthesis of Novel alpha-Amino-Acids and Derivatives Using Radical Chemistry: Synthesis of L-and D-alpha-Amino-Adipic Acids, L-alpha-aminopimelic Acid and Appropriate Unsaturated Derivatives," Tetrahedron (1987) 43:4297-4308.
Bass, Setal., "Mutant Trp repressors with new DNA-binding specificities," Science (1988) 242:240-245.
Batzer, MA et al., "Enhanced evolutionary PCR using oligonucleotides with inosine at the 3'-terminus," Nucleic Acids Res. Sep. 25, 1991;19(18):5081.
Beach, D et al., "Functionally homologous cell cycle control genes in budding and fission yeast," Nature Dec. 1982; 300:706-709.

Beauchamp, Co et al., "A new procedure for the synthesis of polyethylene glycol-protein adducts; effects on function, receptor recognition, and clearance of superoxide dismutase, lactoferrin, and alpha 2-macroglobulin," Anal Biochem. May 1983;131(1):25-33.
Bernstein, FC, et al. "The protein data bank: a computer-based archival file for macromolecular structures," J. Mol. Bioi. 1977; 112:535-542.
Boissel, JP et al., "Erylhropoietin structure-function relationships. Mutant proteins that test a model of tertiary structure," J Bioi Chern. Jul. 25, 1993;268(21):15983-93.
Boles, JO et al. "Bio-incorporation of telluromethionine into buried residues of dihydrofolate reductase," Nat Struct Bioi. May 1994;1(5):283-4.
Botstein, D et D Shortie, "Strategies and applications of in vitro mutagenesis," Science. Sep. 20, 1985;229 (4719):1193-201.
Brunner, J. "New photolabeling and crosslinking methods," Annu Rev Biochem. 1993;62:483-514.
Buchner, J. et al., "A method for increasing the yield of properly folded recombinant fusion proteins: Single-chain immunotoxins from renaturation of bacterial inclusion bodies," Anal. Biochem. 1992; 205(2): 263-270.
Bockmann et al. "Functionalization of Poly(ethylene glycol) and Monomethoxy-Poly(ethylene glycol)," Makromol. Chern. 1981;182:1379-84.
Budisa, N et al. "High-level biosynthetic substitution of methionine in proteins by its analogs 2-aminohexanoic acid, selenomethionine, telluromethionine and ethionine in *Escherichia coli*," Eur J Biochem. Jun. 1, 1995;230(2):788-96.
Budisa, Net al., "Bioincorporation oftelluromethionine into proteins: a promising new approach for X-ray structure analysis of proteins," J Mol Bioi. Jul. 25, 1997;270(4):616-23.
Budisa, Net al., "Toward the experimental codon reassignment in vivo: protein building with an expanded amino acid repertoire," FASEB J. Jan. 1999;13(1):41-51.
Cai, X-Y et al., "Expression, Purification, and Characterization of an Activated Cytokine-Suppressive Anti-inftammatory Drug-Binding Protein 2 (CSBP2) Kinase from Baculovirus-lnfected Insect Cells," Protein Expression and Purification 1997; 10(2):263-74.
Carbonell, LF et al., "Baculovirus-mediated expression of bacterial genes in dipteran and mammalian cells," J Viral Oct. 1985;56(1):153-60.
Carrasco, M. and R. Brown, "A Versatile Set of Aminooxy Amino Acids for the Synthesis of Neoglycopeptides," J. Org. Chern. (2003); 68(23): 8853-8858.
Carter, P. "Site-directed mutagenesis," Biochem J. Jul. 1, 1986; 237(1):1-7.
Carter, Petal. "Improved oligonucleotide site-directed mutagenesis using M13 vectors" Nucleic Acids Res. Jun. 25, 1985;13(12):4431-43.
Carter, P. "Improved oligonucleotide-directed mutagenesis using M13 vectors" Methods Enzymol. 1987;154:382-403.
Chaiken, IM. "Semisynthetic peptides and proteins," CRC Grit Rev Biochem. 1981;11(3):255-301.
Chin, JW et al., "Addition of p-azido-L-phenylalanine to the genetic code of *E. coli*," JAm Chern Soc. Aug. 7, 2002;124 (31):9026-7.
Chin, JW et al., "Addition of a photocrosslinking amino acid to the genetic code of *Escherichia coli*," Proc Natl Acad Sci US A. Aug. 20, 2002;99(17):11020-4. Epub Aug. 1, 2002.
Chin, JW et al., "An expanded eukaryotic genetic code," Science. Aug. 15, 2003;301(5635):964-7.
Chin, JW & P. G. Schultz, "In vivo photocrosslinking with unnatural amino acid mutagenesis," Chembiochem. Nov. 4, 2002; 3(11): 1135-7.
Christie, B.D. & Rapoport, H. "Synthesis of Optically Pure Pipecolates from L-Asparagine. Application to the Total Synthesis of (+)-Apovincamine through Amino Acid Decarbonylation and Iminium Ion Cyclization," J. Org. Chern. 1985;50(8):1239-1246.
Clark, Ret al., "Long-acting growl h hormones produced by conjugation with polyethylene glycol," J Bioi Chern. Sep. 6, 1996;271(36):21969-77.
Corey, D.R., Schultz, P.G. "Generation of a hybrid sequence-specific single-stranded deoxyribonuclease," Science 1987; 238(4832):1401-1403.

(56) References Cited

OTHER PUBLICATIONS

Cornish, VW, et al., "Site-Specific Protein Modification Using a Ketone Handle," J. Am. Chem. Soc. 1996; 118 (34):8150-8151.
Cornish, VW et al., "Probing Protein Structure and Function with an Expanded Genetic Code," Angew Chem Int Ed Engl,1995;34(6):621-33.
Craig, J.C. et al. "Absolute Configuration of the Enantiomers of 7-Chloro-4 [[4-(diethylamino)-1-methylbutyl]amino] quinoline (Chloroquine)," J. Org. Chem. 1988; 53(6):1167-1170.
Cregg, JM et al., "Pichia pastoris as a host system for transformations," Mol Cell Biol. Dec. 1985;5(12):3376-85.
Crick, FHC, et al. "General nature of the genetic code for proteins," Nature. Dec. 30, 1961:192:1227-32.
Dale et al., Oligonucleotide-directed random mutagenesis using the phosphorothioate method, Methods Mol. Biol.1996;57:369-374.
Das, S et al., "Transformation of Kluyveromyces fragilis," J Bacteriol. Jun. 1984; 158(3):1165-7.
Dawson, P. E. and S. B. H. Kent, "Synthesis of native proteins by chemical ligation," Annu. Rev. Biochem. 2000; 69:923-60.
De Boer, HA et al., "The lac promoter: a functional hybrid derived from the trp and lac promoters," Proc Natl Acad Sci US A. Jan. 1983;80(1):21-5.
De Louvencourt, L et al., "Transformation of Kluyveromyces lactis by killer plasmid DNA," J Bacteriol. May 1983;154(2):737-42.
Tondelli, L. et al. "Poly(ethylene Glycol) Imidazolyl Formates as Oligomeric Drug-Binding Matrices," J. Controlled Release 1985;1(4):251-7.
Tornoe, CW et al., "Peptidotriazoles on solid phase: [1,2,3]-triazoles by regiospecific copper(i)-catalyzed 1,3-dipolar cycloadditions of terminal alkynes to azides," J Org Chem. May 3, 2002;67(9):3057-64.
Trotter, KM and HA Wood, "Transfection techniques for producing recombinant baculoviruses," in Methods in Molecular Biology-Baculovirus Expression Protocols, val. 39 (1995); Ed. C.D. Richardson, 97-107.
Tschumper, G. et al., "Sequence of a yeast DNA fragment containing a chromosomal replicator and theTRP1 gene," Gene 1980; 10(2):157-66.
Turcatti, G et al. "Probing the structure and function of the tachykinin neurokinin-2 receptor through biosynthetic incorporation offluorescent amino acids at specific sites," J Biol Chem. Aug. 16, 1996;271(33):19991-8.
Van Den Berg, JA et al., "Kluyveromyces as a host for heterologous gene expression: expression and secretion of prochymosin," Biotechnology (NY). Feb. 1990;8(2):135-9.
Van Hest, JC and DA Tirrell, "Efficient introduction of alkene functionality into proteins in vivo," FEBS Lett. May 22, 1998;428(1-2):68-70.
Debinski, W et al. "A wide range of human cancers express interleukin 4 (IL4) receptors that can be targeted with chimeric toxin composed of IL4 and Pseudomonas exotoxin," J Biol Chem. Jul. 5, 1993;268(19):14065-70.
Deiters, A., et al., "Adding Amino Acids with Novel Reactivity to the Genetic Code of Saccharomyces cerevisiae," J. Am. Chem. Soc. 2003; 125(39):11782-11783.
Delgado, C et al., "The uses and properties of PEG-linked proteins," Crit Rev Ther Drug Carrier Syst. 1992;9 (3-4):249-304.
Dennis, MS et al., "Albumin binding as a general strategy for improving the pharmacokinetics of proteins," J Biol Chem. Sep. 20, 2002;277(38):35035-43. Epub Jul. 15, 2002.
Dolphin, CT et al., "Missense mutation in flavin-containing monooxygenase 3 gene, FM03, underlies fish-odour syndrome," Nat Genet. Dec. 1997;17(4):491-4.
Doring, V et al., "Enlarging the amino acid set of Escherichia coli by infiltration of the valine coding pathway," Science. Apr. 20, 2001;292(5516):501-4.
Dougherty, DA. "Unnatural amino acids as probes of protein structure and function," Curr Opin Chem Biol. Dec. 2000;4(6):645-52.

Duewel, H et al., "Incorporation of trifluoromethionine into a phage lysozyme: implications and a new marker for use in protein 19F NMR," Biochemistry. Mar. 18, 1997;36(11):3404-16.
Eghtedarzadeh MK & S Henikoff "Use of oligonucleotides to generate large deletions" Nucleic Acids Res. Jun. 25, 1986;14(12):5115.
ELLING L et MR Kula., "Immunoaffinity partitioning: synthesis and use of polyethylene glycol-oxirane for coupling to bovine serum albumin and monoclonal antibodies," Biotechnol Appl Biochem. Jun. 1991;13(3):354-62.
Ellioti, S et al., "Yeast-derived recombinant human insulin-like growlh factor 1: production, purification, and structural characterization," J Protein Chem. Feb. 1990;9(1):95-104.
Ellman, JA, Mendel, D., Anthony-Cahill, S., Noren, C.J., Schultz, P.G. "Biosynthetic method for introducing unnatural amino acids site-specifically into proteins," Methods in Enz., 1992; 202:301-336.
Ellman, JA, et al. "Site-specific incorporation of novel backbone structures into proteins," Science. Jan. 10, 1992;255 (5041):197-200.
England, P.M., et al., "Backbone mutations in transmembrane domains of a ligand-gated ion channel: implications for the mechanism of gating," Cell. Jan. 8, 1999;96(1):89-98.
Eppstein et al., "Biological Activity of Liposome-Encapsulated Murine Interferon is Mediated by a Cell Membrane Receptor," Proc. Natl. Acad. Sci. U.SA(1985); 82: 3688-3692.
Fieschko, JC et al., "Controlled expression and purification of human immune interferon from high-cell-density fermentations of Saccharomyces cerevisiae," Biotech. Bioeng. (1987) 29(9):1113-21.
Forster, AC et al.,"Programming peptidomimetic syntheses by translating genetic codes designed de novo," Proc Natl Acad Sci US A. May 27, 2003;100(11);6353-7. Epub May 16, 2003.
Frankel, A et al., "Encodamers: unnatural peptide oligomers encoded in RNA," Chem Biol. Nov. 2003;10 (11):1043-50.
Fraser, MJ et al., "Expression of eucaryotic genes in insect cell cultures," In Vitro Cell. Dev. Biol. 1989; 25:225-235.
Friedman, O.M. & R. Chatterrji. "Synthesis of Derivatives of Glutamine as Model Substrates for Anti-Tumor Agents," J. Am. Chem. Soc. 1959; 81(14):3750-3752.
Fritz HJ et al., "Oligonucleotide-directed construction of mutations: a gapped duplex DNA procedure without enzymatic reactions in vitro," Nucleic Acids Res. Jul. 25, 1988;16(14B):6987-99.
Fromm, M. et al., "Expression of Genes Transferred into Monacoland Dicot Plant Cells by Electroporation," Proc. Natl. Acad. Sci. USA (1985) 82:5824-8.
Furter, R. "Expansion of the genetic code: site-directed p-fluorophenylalanine incorporation in Escherichia coli," Protein Sci. Feb. 1998;7(2):419-26.
Gaertner, HF et al., "Construction of protein analogues by site-specific condensation of unprotected fragments," Bioconjug Chem. May-Jun. 1992;3(3):262-8.
Gaertner, HF et al., "Chemo-enzymic backbone engineering of proteins. Site-specific incorporation of synthetic peptides that mimic the 64-74 disulfide loop of granulocyte colony-stimulating factor," J Biol Chem. Mar. 11, 1994;269 (10):7224-30.
Gallivan, JP et al., "Site-specific incorporation of biotinylated amino acids to identify surface-exposed residues in integral membrane proteins," Chem Biol. Oct. 1997;4(10):739-49.
Gellissen, G et al., "Heterologous protein production in yeast," Antonie Van Leeuwenhoek. Aug. 1992;62(1-2):79-93.
Geoghegan, KF and JG Stroh, "Site-directed conjugation of nonpeptide groups to peptides and proteins via periodate oxidation of a 2-amino alcohol. Application to modification at N-terminal serine," Bioconjug Chem. Mar. Apr. 1992;3(2):138-46.
Gillam, S. & M Smith, "Site-specific mutagenesis using synthetic oligodeoxyribonucleotide primers: I. Optimum conditions and minimum oligodeoxyribonucleotide length," Gene 1979; 8(1):81-97.
Gleeson, Ma et al., "Transformation of the methylotrophic yeast hansenula polymorphica," J. Gen. Microbiol. (1986) 132:3459-3465.
Goeddel, DV, "Systems for heterologous gene expression," Methods Enzymol. 1990;185:3-7.

(56) References Cited

OTHER PUBLICATIONS

Goeddel, DV et al., "Synthesis of human fibroblast interferon by *E. coli*," Nucleic Acids Res. Sep. 25, 1980;8 (18):4057-74.
Goodson RJ et NV Katre. "Site-directed pegylation of recombinant interleukin-2 at its glycosylation site," Biotechnology (NY). Apr. 1990;8(4):343-6.
Graves, SWet al., "Expression, purification, and initial kinetic characterization of the large subunit of the human mitochondrial DNA polymerase," Biochemistry. Apr. 28, 1998;37(17):6050-8.
Griffin, BA et al., "Specific Covalent Labeling of Recombinant Protein Molecules Inside Live Cells," Science (1998) 281:269-272.
Grundstrom T et al., "Oligonucleotide-directed mutagenesis by microscale 'shot-gun' gene synthesis," Nucleic Acids Res. May 10, 1985;13(9):3305-16.
Guckian, KM and ET Kool, "Highly Precise Shape Mimicry by a Difluorotoluene Deoxynucleoside, a Replication Competent Substitute for Thymidine," Angew. Chern. Int. Ed. Engl (1998) 36(24):2825-8.
Hamano-Takaku, Fetal., "A mutant *Escherichia coli* tyrosyl-tRNA synthetase utilizes the unnatural amino acid azatyrosine more efficiently than tyrosine," J Bioi Chern. Dec. 22, 2000;275(51):40324-8.
Hang, HC and CR Bertozzi, "Chemoselective approaches to glycoprotein assembly," Ace Chern Res. Sep. 2001;34 (9):727-36.
Harris, JM et al. "Synthesis and Characterization of Poly(ethylene Glycol) Derivatives," J. Polym. Sci. Chern. Ed. 1984; 22:341-352.
Harris, JM. "Laboratory Synthesis of Polyethylene Glycol Derivatives," JMS-Rev. Macromol. Chern. Phys. 1985;C25 (3): 325-373.
Hendrickson, WA et al., "Selenomethionyl proteins produced for analysis by multiwavelength anomalous diffraction (MAD): a vehicle for direct determination of three-dimensional structure," EMBO J. May 1990;9(5):1665-72.
Henikoff, Sand JG Henikoff "Amino Acid Substitution Matrices from Protein Blocks," Proc. Natl. Acad. Sci. USA 1992; 89:10915-9.
Hess, B. et al., "Cooperation of glycolytic enzymes," J. Adv. Enzyme Reg. (1969) 7:149-67.
Hinnen, A et al., "Transformation of yeast," Proc Nail Acad Sci US A. Apr. 1978;75(4):1929-33.
Hirao, I et al., "An unnatural base pair for incorporating amino acid analogues into proteins," Nat Biotechnol. Feb. 2002;20(2):177-82.
Hitzeman, RA et al., "Isolation and characterization of the yeast 3-phosphoglycerokinase gene (PGK) by an immunological screening technique," J. Bioi Chern. Dec. 25, 1980;255(24):12073-80.
Hofmann, K., et H. Bohn. "Studies on polypeptides. XXXVI. The effect of pyrazole-imidazole replacements on the S-protein activating potency of an S-peplide fragment," J. Am Chern, (1966); 88(24):5914-5919.
Hohsaka, T et al., "Efficient Incorporation of Nonnatural Amino Acids with Large Aromatic Groups into Streptavidin in In Vitro Protein Synthesizing Systems," J. Am. Chern. Soc. 1999; 121(1); 34-40.
Hohsaka, T et al., "Incorporation of Two Different Nonnatural Amino Acids Independently into a Single Protein through Extension of the Genetic Code," J. Am. Chern. Soc. 1999; 121(51):12194-12195.
Van Hest, J. C. et al., "Efficient Incorporation of Unsaturated Methionine Analogues into Proteins in Vivo," J. Am. Chern. Soc. 2000 ;122 (7); 1282-1288.
Van Solingen, P. et JB van der Plaal. "Fusion of yeast spheroplasts," J Bacteriol. May 1977;130(2):946-7.
Veronese, FM et al., "Surface modification of proteins. Activation of monomethoxy-polyethylene glycols by phenylchloroformates and modification of ribonuclease and superoxide dismutase," Appl Biochem Biotechnol. Apr. 1985;11(2):141-52.
Vlak, JM et al., "Functional studies on the p10 gene of Autographa californica nuclear polyhedrosis virus using a recombinant expressing a p10-bela-galactosidase fusion gene," J Gen Virol. Apr. 1988;69 (PI4):765-76.
Wang, Q., et al., "Bioconjugation by Copper(I)-Catalyzed Azide-Aikyne [3 + 2] Cycloaddilion," J. Am. Chern. Soc. 2003; 125(11):3192-3193.
Wang, L. et al., "Addition of the keto functional group to the genetic code of *Escherichia coli*," Proc. Nail. Acad. Sci. (2003); 100(1):56-61.
Wang, Let al., "Expanding the genetic code of *Escherichia coli*," Science. Apr. 20, 2001;292(5516):498-500.
Halls et al., (J. Pharmacol. Exp. Therap. 313(2): 677-687, 2005).
Teichman et al. (Curr. Heart Fail. Rep. 7: 75-82, 2010).
Samuel, C.S. (Clin. Med. Res. 3(4): 241-249, 2005).
Feng et al. (Clin. Cancer Res. 13(6): 1695-1702, 2007).
Bullesbach et al. (J. Biol. Chem. 269(18): 13124-13128, 1994).
Roy SS, Mukherjee M, Bhattacharya S, Mandal CN, Kumar LR, Dasgupta S, Bandyopadhyay I, Wakabayashi K. A new cell secreting insulin. Endocrinology. Apr. 1, 2003;144(4):1585-93.
Sudo S, et al. "H3 relaxin is a specific ligand for LGR7 and activates the receptor by interacting with both the ectodomain and the exoloop 2," J Biol Chem. Mar. 7, 2003;278(10):7855-62.
Teerlink JR, Metra M, Felker GM, Ponikowski P, Voors AA, Weatherley BD, Marmor A, Katz A, Grzybowski J, Unemori E, Teichman SL. Relaxin for the treatment of patients with acute heart failure (Pre-RELAX-AHF): a multicentre, randomised, placebo-controlled, parallel-group, dose-finding phase llb study. The Lancet. Apr. 25, 2009;373 (9673):1429-39.
Zhongming Tang, "Biotechnology Drugs—Introduction and Practical Handbook", Chemical Industry Press, Jan. 2008.
Roy et al. "A new cell secreting insulin." Endocrinology. Apr. 1, 2003;144(4):1585-93.
Sudo et al. "H3 relaxin is a specific ligand for LGR7 and activates the receptor by interacting with both the ectodomain and the exoloop 2." Journal of Biological Chemistry. Mar. 7, 2003;278(10):7855-62.
Teerlink et al. "Relaxin for the treatment of patients with acute heart failure (Pre-RELAX-AHF): a multicentre, randomised, placebo-controlled, parallel-group, dose-finding phase llb study." The Lancet. Apr. 25, 2009;373 (9673):1429-39.

| Lane | Sample |
|------|--------|
| 1 | SeeBlue2 MW Marker |
| 2 | RLX-EX-002-129: 0h |
| 3 | RLX-EX-002-129: 2h |
| 4 | RLX-EX-002-129: 4h |
| 5 | RLX-EX-002-129: 6h |

← Pro-Relaxin-BA1-AV13pAF

SDS-PAGE → unPEGylated Relaxin

| Lane # | Lane assignment |
|---|---|
| 1 | MW Marker |
| 2 | --- |
| 3 | wt Relaxin (NR) |
| 4 | --- |
| 5 | MW Marker |
| 6 | --- |
| 7 | wt Relaxin (R) |

SDS-PAGE → 20K PEGylated Relaxin

| Lane # | Lane assignment |
|---|---|
| 1 | MW Marker |
| 2 | --- |
| 3 | 20K PEG Relaxin (NR) |
| 4 | 20K PEG Relaxin (R) |

NUCLEIC ACIDS ENCODING MODIFIED RELAXIN POLYPEPTIDES

CROSS REFERENCE TO RELATED APPLICATIONS

This application is a divisional of U.S. patent application Ser. No. 15/941,033, filed Mar. 30, 2018, now U.S. Pat. No. 10,702,588, which is a divisional of U.S. patent application Ser. No. 15/239,277, filed Aug. 17, 2016, now U.S. Pat. No. 9,962,450, which is a divisional of U.S. patent application Ser. No. 14/152,302, filed Jan. 10, 2014, now U.S. Pat. No. 9,452,222, which is a divisional of U.S. patent application Ser. No. 13/212,101, filed Aug. 17, 2011, now U.S. Pat. No. 8,735,539, which claims benefit to U.S. Provisional Pat. Appl. No. 61/374,582, filed Aug. 17, 2010, each of which is hereby incorporated by reference in its entirety.

SEQUENCE LISTING

This application includes a sequence listing which has been submitted via EFS-Web in a file named "114327o001207.txt" created May 28, 2020, and having a size of 50,344 bytes, which is hereby incorporated by reference in its entirety.

FIELD OF THE INVENTION

This invention relates to relaxin polypeptides optionally modified with at least one non-naturally encoded amino acid.

BACKGROUND OF THE INVENTION

Mature human relaxin is a hormonal peptide of approximately 6000 daltons known to be responsible for remodelling the reproductive tract before parturition, thus facilitating the birth process. This protein appears to modulate the restructuring of connective tissues in target organs to obtain the required changes in organ structure during pregnancy and parturition. See, Hisaw, F. L., Proc. Soc. Exp. Biol. Med., 23: 661-663 (1926); Schwabe, C., et al., Biochem. Biophys. Res. Comm., 75: 503-570 (1977); James, R. et al., Nature, 267: 544-546 (1977). A concise review of relaxin was provided by Sherwood, D. in The Physiology of Reproduction, Chapter 16, "Relaxin", Knobil, E. and Neill, J., et al. (eds.), (Raven Press Ltd., New York), pp. 585-673 (1988). Circulating levels of relaxin are elevated for the entire nine months of pregnancy and drop quickly following delivery.

While predominantly a hormone of pregnancy, relaxin has also been detected in the non-pregnant female as well as in the male. Bryant-Greenwood, G. D., Endocrine Reviews, 3: 62-90 (1982) and Weiss, G., Ann. Rev. Physiol., 46:43-52 (1984) and has most recently been found to be useful in the treatment of heart failure.

Heart failure is defined as the inability of the cardiac pump to move blood as needed to provide for the metabolic needs of body tissue. Decreases in pumping ability arise most often from loss or damage of myocardial tissue. As a result, ventricular emptying is suppressed which leads to an increase in ventricular filling pressure and ventricular wall stress, and to a decrease in cardiac output. As a physiological response to the decrease in cardiac output, numerous neuroendocrine reflexes are activated which cause systemic vasoconstriction, sympathetic stimulation of the heart and fluid retention. Although these reflex responses tend to enhance cardiac output initially, they are detrimental in the long term. The resulting increases in peripheral resistance increase the afterload on the heart and the increases in blood volume further increase ventricular filling pressure. These changes, together with the increased sympathetic stimulation of the heart, lead to further and often decompensating demands on the remaining functional myocardium.

Congestive heart failure, which is a common end point for many cardiovascular disorders, results when the heart is unable to adequately perfuse the peripheral tissues. According to recent estimates, there are about 4 million people in the United States diagnosed with this disease, and more than 50% of these cases are fatal within 5 years of diagnosis [Taylor, M. D. et al., Annual Reports in Med. Chem. 22, 85-94 (1987)].

Current therapy for heart failure, including congestive heart failure, focuses on increasing cardiac output without causing undue demands on the myocardium. To achieve these ends, various combinations of diuretics, vasodilators and inotropic agents are used to decrease blood volume, to decrease peripheral resistance, and to increase force of cardiac contraction. Current therapy therefore depends on balancing the effects of multiple drugs to achieve the clinical needs of individual patients, and is plagued by adverse reactions to the drugs used.

For example, diuretics decrease plasma concentrations of potassium and magnesium and increase the incidence of arrhythmias in patients receiving digitalis. Diuretics can potentiate the circulatory effects of nitrates through volume depletion and lead to decreases in filling pressure of the heart, cardiac output and systemic arterial pressure.

Alpha adrenergic antagonists can lead to marked falls in systemic arterial pressure that compromise coronary perfusion.

Angiotensin converting enzyme inhibitors can have similar effects on arterial pressure and additionally lead to excessive increases in plasma concentrations of potassium.

Drugs that lead to positive inotropy, such as digitalis and beta adrenergic antagonists, have the potential to provoke arrhythmias. In addition, digitalis has a narrow therapeutic index and the catecholamine analogs all tend to loose their effectiveness rapidly, due to receptor downregulation.

Thus there is a need for therapeutic agents that lead to physiologically integrated responses of arterial and venous vasodilation and cardiac inotropy, and are devoid of the disadvantages of the currently used therapeutic agents.

Relaxin has been purified from a variety of species including porcine, murine, equine, shark, tiger, rat, dogfish and human, and shows at least primary and secondary structural homology to insulin and the insulin-like growth factor, however homology between species can be quite low. In the human, relaxin is found in most abundance in the corpora lutea (CL) of pregnancy. However, specific nuclei in the brain have relaxin receptors and other nuclei contain messenger RNA for relaxin. Several nuclei with cells bearing relaxin receptors are found in the area of the hypothalamus.

Two human gene forms have been identified, (H1) and (H2). Hudson, P., et al., Nature, 301: 628-631 (1983); Hudson, P., et al., The EMBO Journal, 3: 2333-2339 (1984); and U.S. Pat. Nos. 4,758,516 and 4,871,670. Only one of the gene forms (H2) has been found to be transcribed in CL. It remains unclear whether the (H1) form is expressed at another tissue site, or whether it represents a pseudo-gene. When synthetic human relaxin (H2) and certain human relaxin analogs were tested for biological activity, the tests revealed a relaxin core necessary for biological activity as well as certain amino acid substitutions for methionine that did not affect biological activity. Johnston, et al., in Peptides: Structure and Function, Proc. Ninth American Peptide Symposium, Deber, C. M., et al. (eds.) (Pierce Chem. Co. 1985).

Methods of making relaxin are also described in U.S. Pat. No. 4,835,251 and in co-pending U.S. Ser. No. 07/908,766 (PCT US90/02085) and Ser. No. 08/080,354 (PCT US94/ 0699). Methods of using relaxin in cardiovascular therapy and in the treatment of neurodegenerative diseases are described in U.S. Pat. No. 5,166,191 and in U.S. Ser. No. 07/902,637 (PCT US92/06927). Certain formulations of human relaxin are described in allowed U.S. Ser. No. 08/050,745.

Recombinant human relaxin (H2) in currently in Phase I human clinical trials in scleroderma patients. Scleroderma is a disease involving an imbalance in tissue reformation giving rise to the overproduction of collagen, and ultimately resulting in swelling and hardening of the skin (and affected organs). Currently treatments delivering relaxin require repeated and prolonged infusions.

SUMMARY OF THE INVENTION

The invention provides relaxin polypeptides optionally modified with at least one non-naturally encoded amino acid. This specification will provide some embodiments, however it should be appreciated that these embodiments are for the purpose of illustrating the invention, and are not to be construed as limiting the scope of the invention as defined by the claims.

In another aspect of the present invention, relaxin polypeptides with at least one non-naturally encoded amino acid are attached to at least one water soluble polymer.

In one aspect, the invention relates to a method of promoting angiogenesis in a mammal in need thereof by administering a therapeutically effective amount of relaxin. In another embodiment, relaxin is administered in an amount sufficient to maintain a serum concentration of at least about 1 ng/ml. In a further embodiment the relaxin polypeptide is human relaxin (hR2).

The present invention provides methods of treating individuals with diminished arterial compliance an effective amount of a formulation comprising a relaxin receptor agonist. In a preferred embodiment the relaxin receptor agonist is a recombinant human relaxin, e.g., human H2 relaxin.

In one embodiment of the invention, the invention provides a method of increasing arterial compliance in a subject, wherein said method comprises measuring global arterial compliance in said subject; determining that said global arterial compliance is diminished in said subject relative to global arterial compliance in a healthy subject; and administering to said subject a pharmaceutical formulation comprising relaxin to increase arterial compliance in said subject. Global arterial compliance may be measured, in one embodiment, from the diastolic decay of the aortic pressure waveform using the area method. In another embodiment, global arterial compliance may be calculated as the stroke volume-to-pulse pressure ratio, where the stroke volume is defined as the ratio of cardiac output to heart rate.

In related embodiments, the local arterial compliance or the regional arterial compliance of a subject may be measured in addition to or as an alternative to the global arterial compliance measurement and, if the local or regional arterial compliance is diminished relative to the local or regional arterial compliance expected for a similarly situated healthy individual, relaxin may be administered to increase arterial compliance in that individual.

In further embodiments, the subject to whom relaxin is administered suffers from one or more of the following disorders: atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, systemic lupus erythematosus, preeclampsia, and hypercholesterolemia. In related embodiments, the invention provides methods of increasing arterial compliance in perimenopausal, menopausal, and post-menopausal women and in individuals who are at risk of one of the aforementioned disorders.

In an additional embodiment of the invention, administration of relaxin increases arterial compliance by at least 10%, 15%, 20% or more, relative to the measured arterial compliance before administration. In still further embodiments, the invention provide for the administration of relaxin to individuals with diminished arterial compliance at a predetermined rate so as to maintain a serum concentration of relaxin from 0.5 to 80 ng/ml. In one embodiment, the relaxin is recombinant human relaxin with one non-naturally encoded amino acid. In yet another embodiment, the relaxin is relaxin with more than one non-naturally encoded amino acid. In yet another embodiment of the present invention, the relaxin has a non-naturally encoded amino acid linked to a water soluble polymer. In related embodiments, the relaxin may be administered daily, in an injectable formulation, as a sustained release formulation, or as a continuos infusion.

In another aspect, the invention relates to the treatment of infections or ischemic wounds by administering a therapeutically effective amount of relaxin. In a particularly preferred embodiment, the infection or ischemic wound is one where injury has resulted from lack of oxygen due to poor circulation.

In yet another aspect of the invention, there is provided a method of using relaxin polypeptides of the present invention for the manufacture of a medicant for the treatment of an infection or ischemic wound, or for the manufacture of a medicant for the promotion of angiogenesis. In another aspect, the present invention relates to the treatment of osteodegenerative joint dysfunction, and in another aspect the treatment of the osteodegenerative joint dysfunction comprises hR2 in addition to one or more adjuvants, including but not limited to glucosamine. In another aspect, the present invention relates to the treatment of alzheimer's disease, and in another aspect the treatment of the alzheimer's disease comprises hR2 in addition to one or more adjuvants, including but not limited to estrogen. In another embodiment, this invention relates to a method of modulating the reproductive physiology of mammals comprising administering to the mammal a therapeutically effective amount of the composition herein.

The invention further provides methods for treating angiotensin-II (AngII)-mediated vasoconstriction. These methods generally comprise administering a formulation comprising an amount of relaxin effective to reverse, inhibit, or reduce the vasoconstricting effects of AngII.

The invention further provides methods for treating endothelin-1 (ET-1)-mediated vasoconstriction. These methods generally comprise administering a formulation comprising an amount of relaxin effective to reverse, inhibit, or reduce the vasoconstricting effects of ET-1. In some embodiments, the methods comprise increasing endothelin type B receptor activation in a cell in a blood vessel by administering relaxin to the individual.

The invention further provides methods for treating an ischemic condition, generally comprising administering a formulation comprising an amount of relaxin effective to stimulate or promote angiogenesis and/or vasodilation, thereby treating the ischemic condition. The methods are useful in treating a variety of ischemic conditions. In some embodiments, methods are provided for treating an ischemic condition which arises as a result of myocardial infarct. In other embodiments, methods are provided for treating an ischemic condition associated with a wound. Thus, the invention further provides methods for promoting wound healing.

The invention further provides methods for stimulating angiogenic and/or vasodilatory cytokine expression generally comprising administering a formulation comprising an amount of relaxin effective to vasodilate blood vessels and/or stimulate or promote angiogenic cytokine production. In some embodiments, the methods provide for stimulating expression of basic fibroblast growth factor (bFGF) and/or vascular endothelial cell growth factor (VEGF). Such methods are useful in treating a wide variety of diseases which can be treated by increasing blood flow at or near the site of disease.

The invention further provides a method of increasing renal vasodilation and hyperfiltration, generally comprising administering a formulation comprising an amount of relaxin. These methods are useful in treating a variety of renal pathologies. Accordingly, the invention further provides methods of treating a renal pathology related to vasoconstriction.

The invention further provides a method of reducing pulmonary hypertension, generally comprising administering a formulation comprising an amount of relaxin.

In a patents assigned to Connetics Corporation and to BAS Medical, In.c, U.S. Pat. Nos. 6,211,147 and 6,780,836 respectively, both incorporated herein by reference, methods of promoting angiogenesis using relaxin were disclosed. In a patent assigned to Genentech, Inc., U.S. Pat. No. 5,759,807, which is herein incorporated by reference, a process for prokaryotic production of relaxin from prorelaxin is disclosed. Yue U.S. Pat. No. 6,251,863 discloses methods of treating osteodegenerative joint dysfunction and methods of treating Alzheimer's by administering relaxin medicaments further comprising glcosamine sulfate and estrogen, respective for each of the conditions, and the specification of this patent is also herein incorporated by reference in its entirety.

In some embodiments, the relaxin polypeptide comprises one or more post-translational modifications. In some embodiments, the relaxin polypeptide is linked to a linker, polymer, or biologically active molecule. In some embodiments, the relaxin polypeptide is linked to a bifunctional polymer, bifunctional linker, or at least one additional relaxin polypeptide.

In some embodiments, the non-naturally encoded amino acid is linked to a water soluble polymer. In some embodiments, the water soluble polymer comprises a poly(ethylene glycol) moiety. In some embodiments, the non-naturally encoded amino acid is linked to the water soluble polymer with a linker or is bonded to the water soluble polymer. In some embodiments, the poly(ethylene glycol) molecule is a bifunctional polymer. In some embodiments, the bifunctional polymer is linked to a second polypeptide. In some embodiments, the second polypeptide is a relaxin polypeptide.

In some embodiments, the relaxin polypeptide comprises at least two amino acids linked to a water soluble polymer comprising a poly(ethylene glycol) moiety. In some embodiments, at least one amino acid is a non-naturally encoded amino acid.

In some embodiments, the relaxin polypeptide comprises at least two amino acids linked to a water soluble polymer comprising a poly(ethylene glycol) moiety. In some embodiments, at least one amino acid is a non-naturally encoded amino acid.

In some embodiments, one or more non-naturally encoded amino acids are incorporated in one or more of the following positions in any of the relaxin or prorelaxin polypeptides, relaxin analogs, prorelaxin, relaxin A chain, relaxin B chain Ala1Asp relaxin, or relaxin polypeptides: in the A chain before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25 (i.e., at the carboxyl terminus of the protein), and any combination thereof (SEQ ID NO: 4) and/or in the B chain before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 (SEQ ID NO: 5 or the corresponding amino acids in SEQ ID NO: 6). In some embodiments, one or more non-naturally encoded amino acids are incorporated in one or more of the following positions in any of the relaxin or prorelaxin polypeptides: in the A chain before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 (i.e., at the carboxyl terminus of the protein), and any combination thereof (SEQ ID NO: 1 or the corresponding amino acids in SEQ ID NO: 2 or 3). In some embodiments, one or more non-naturally encoded amino acids are incorporated in one or more of the following positions in relaxin: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 (i.e., at the carboxyl terminus of the protein of SEQ ID NO: 3).

In some embodiments a non-naturally encoded amino acid is incorporated in the A chain at amino acid position 1 (SEQ ID NO:4). In some embodiments a non-naturally encoded amino acid is incorporated in the A chain at amino acid position 5 (SEQ ID NO:4). In some embodiments a non-naturally encoded amino acid is incorporated in the B chain at amino acid position 7 (SEQ ID NO: 5 or SEQ ID NO: 6). In some embodiments a non-naturally encoded amino acid is incorporated in the A chain at amino acid position 2 (SEQ ID NO:4). In some embodiments a non-naturally encoded amino acid is incorporated in the A chain at amino acid position 13 (SEQ ID NO:4). In some embodiments a non-naturally encoded amino acid is incorporated in the B chain at amino acid position 5 (SEQ ID NO: 5 or SEQ ID NO: 6). In some embodiments a non-naturally encoded amino acid is incorporated in the A chain at amino acid position 18. In some embodiments a non-naturally encoded amino acid is incorporated in the B chain at amino acid position 5. In some embodiments a non-naturally encoded amino acid is incorporated in the B chain at amino acid position 28. In some embodiments, one or more non-naturally encoded amino acids are incorporated in one of the following positions in the relaxin polypeptides: in the A chain at amino acid position 1, 2, 5, 13, 18 (SEQ ID NO: 4 or the corresponding amino acids in SEQ ID NO: 1, SEQ ID NO: 2, SEQ ID NO: 3, or other known relaxin sequences). In some embodiments, one or more non-naturally encoded amino acids are incorporated in one of the following positions in the relaxin polypeptides: in the A chain at amino acid position 1, 2, 5, 13 (SEQ ID NO: 4 or the corresponding amino acids in SEQ ID NO: 1, SEQ ID NO: 2, SEQ ID NO: 3, or other known relaxin sequences). In some embodiments, one or more non-naturally encoded amino acids are incorporated in one of the following positions in the relaxin polypeptides: in the A chain at amino acid position 1, 2, 5 (SEQ ID NO: 4 or the corresponding amino acids in SEQ ID NO: 1, SEQ ID NO: 2, SEQ ID NO: 3, or other known relaxin sequences). In some embodiments, one or more non-naturally encoded amino acids are incorporated in one of the following positions in the relaxin polypeptides: in the A chain at amino acid position 2 or 5 (SEQ ID NO: 4 or the corresponding amino acids in SEQ ID NO: 1, SEQ ID NO: 2, SEQ ID NO: 3, or other known relaxin sequences).

In some embodiments, a non-naturally encoded amino acids is incorporated in one of the following positions in relaxin polypeptides: in the B chain at amino acid position 5 or 7 (SEQ ID NO: 5 or SEQ ID NO: 6, or the corresponding amino acid positions in SEQ ID NOs: 1, 2, or 3). In some embodiments, a non-naturally encoded amino acid is incorporated at position 7 in the B chain (SEQ ID NO: 5 or SEQ ID NO: 6, or the corresponding amino acid positions in SEQ ID NOs: 1, 2, or 3). In some embodiments, a non-naturally encoded amino acid is incorporated at position 5 in the B chain (SEQ ID NO: 5 or SEQ ID NO: 6, or the corresponding amino acid positions in SEQ ID NOs: 1, 2, or 3). In some embodiments, a non-naturally encoded amino acid is incorporated at position 7 in the B chain (SEQ ID NO: 5 or SEQ ID NO: 6, or the corresponding amino acid positions in SEQ ID NOs: 1, 2, or 3).

In one embodiments, a non-naturally encoded amino acids is incorporated in one of the following positions in the relaxin polypeptides: in the A chain at amino acid positions 1, 5, 2, 13, 18 (SEQ ID NO: 4 or corresponding amino acid positions in SEQ ID NO. 1, 2, 3), in the B chain at amino acid positions 7, 5 (SEQ ID NO: 5 or 6, or corresponding amino acid positions in SEQ ID NO: 1, 2, 3). In some embodiments, one or more non-naturally encoded amino acids are incorporated in one of the following positions in the relaxin polypeptides: in the A chain at amino acid positions 1, 5, 2, 13, 18 (SEQ ID NO: 4 or corresponding amino acid positions in SEQ ID NO. 1, 2, 3), in the B chain at amino acid positions 7, 5 (SEQ ID NO: 5 or 6, or corresponding amino acid positions in SEQ ID NO: 1, 2, 3).

In some embodiments, the non-naturally encoded amino acid at one or more of these positions is linked to a water soluble polymer, including but not limited to, positions: in the A chain before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25 (i.e., at the carboxyl terminus of the protein), and any combination thereof (SEQ ID NO: 4 or the corresponding amino acids in known relaxin sequences) and/or in the B chain before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 (SEQ ID NO: 5 or 6 or the corresponding amino acids in known relaxin sequences). In some embodiments, the non-naturally encoded amino acid at one or more of these positions is linked to a water soluble polymer, including but not limited to: in the A chain 1, 2, 5, 13, 18 (SEQ ID NO: 1 or the corresponding amino acids in known relaxin sequences). In some embodiments, the non-naturally encoded amino acid at one or more of these positions is linked to a water soluble polymer, including but not limited to: in the A chain 1, 2, 5 (SEQ ID NO: 1 or the corresponding amino acids in known relaxin sequences). In some embodiments, the non-naturally encoded amino acid at one or more of these positions is linked to a water soluble polymer, including but not limited to: in the A chain 2, 5 (SEQ ID NO: 1 or the corresponding amino acids in known relaxin sequences). In some embodiments, the non-naturally encoded amino acid at one or more of these positions is linked to a water soluble polymer, including but not limited to: in the A chain 2, 5, 13, 18 (SEQ ID NO: 1 or the corresponding amino acids in known relaxin sequences). In some embodiments, the non-naturally encoded amino acid at one or more of these positions is linked to a water soluble polymer, including but not limited to: in the B chain 5, 7 (SEQ ID NO: 5 or 6 or the corresponding amino acid positions in SEQ ID NOs: 1, 2, 3). In some embodiments, the non-naturally encoded amino acid at position 5 in the B chain (SEQ ID NO: 5 or 6 or the corresponding amino acid positions in SEQ ID NOs: 1, 2, 3) is linked to a water soluble polymer. In some embodiments, the non-naturally encoded amino acid at position 7 in the B chain (SEQ ID NO: 5 or 6 or the corresponding amino acid positions in SEQ ID NOs: 1, 2, 3) is linked to a water soluble polymer In some embodiments, one or more non-naturally encoded amino acids are incorporated in one or more of the following positions in any of the relaxin or prorelaxin polypeptides: B chain positions 5, 7 (SEQ ID NO: 5 or 6 or the corresponding amino acid positions in SEQ ID NOs: 1, 2, 3) and A chain positions 1, 5, 2, 13, 18 (SEQ ID NO: 4 or the corresponding amino acid positions in SEQ ID NOs: 1, 2, 3). In some embodiments, one or more non-naturally encoded amino acids are incorporated in one or more of the following positions in any of the relaxin or prorelaxin polypeptides: B chain positions 5, 7 (SEQ ID NO: 5 or 6 or the corresponding amino acid positions in SEQ ID NOs: 1, 2, 3) and A chain positions 1, 5, 2, 13, 18 (SEQ ID NO: 4 or the corresponding amino acid positions in SEQ ID NOs: 1, 2, 3) and the non-naturally encoded amino acid is linked to a water soluble polymer.

Methods of the present invention could be used to promote angiogenesis, promote vasodilation, promote non-hypotensive vasodilation, to treat hypertension, including but not limited to renal hypertension, pulmonary hypertension, and cardiac hypertension (U.S. Pat. Nos. 6,723,702; and 6,780,836 both hereby incorporated by reference in their entirety), discloses formation and use of crystals of a relaxin analog.

Formulations

In the broad practice of the present invention, it also is contemplated that a formulation may contain a mixture of two or more of a relaxin, a relaxin dimer, a relaxin analog, an acylated relaxin, or acylated relaxin analog with at least one of the components of the mixture containing a non-naturally encoded amino acid. In another embodiment of the present invention, the formulations containing a mixture of two or more of relaxin, a relaxin analog, an acylated relaxin, or acylated relaxin analog with at least one of the components of the mixture containing a non-naturally encoded amino acid also includes at least one water soluble polymer attached to at least one of the non-naturally encoded amino acids.

The present invention also includes heterogenous mixtures wherein relaxin polypeptides and relaxin analogs are prepared by the methods disclosed in this invention and are then mixed so that a formulation may be administered to a patient in need thereof which contains, for example, 25% relaxin polypeptide containing a non-naturally encoded amino acid at position 28 of the B chain which has been pegylated, 25% relaxin polypeptide containing a non-naturally encoded amino acid at position 10 of the B chain, said non-naturally encoded amino acid coupled to a water soluble polymer, and 50% relaxin polypeptide wherein a non-naturally encoded amino acid occurs at position 31 of the B chain of relaxin (SEQ ID NO: 2; alternatively SEQ ID NOs: 4, 6, 8, 10, or 12). All different mixtures of different percentage amounts of relaxin polypeptide variants wherein the relaxin polypeptides include a variety (1) with differently sized PEGs, or (2) PEGs are included at different positions in the sequence. This is intended as an example and should in no way be construed as limiting to the formulations made possible by the present invention and will be apparent to those of skill in the art. In an additional embodiment, the relaxin polypeptide variants to include in the formulation mixture will be chosen by their varying dissociation times so that the formulation may provide a sustained release of relaxin for a patient in need thereof.

Formulations of the present invention may include a glucagon.

Other Embodiments of the Present Invention Including Formulation for Inhalation

In an additional embodiment of the present invention, it is possible to use the technology disclosed herein for the production of relaxin analogs with increased pharmacokinetic and pharacodynamic properties for patient use via administration to the lung, resulting in elevated blood levels of relaxin that are sustained for at least 6 hours, and more typically for at least 8, 10, 12, 14, 18, 24 hours or greater post-administration. Another embodiment of the present invention allows for advantageous mixtures of relaxin analogs suitable for therapeutic formulations designed to be administered to patients as an inhalant.

In some embodiments of the present invention, the following sites in the native relaxin molecule may be substituted with non-naturally encoded amino acids and optionally further modified by covalent attachment of a water soluble polymer, such as PEG: the 2 C-termini of the A and B chains, Arg22B, His10B, His5A, Glu4A, Glu17A, Glu13B, and Glu21B.

In addition to native relaxin, the present invention provides for non-native relaxin polypeptides and relaxin analogs having one or more non-naturally encoded amino acids substituted or inserted into the signal sequence that may also provide a site for the incorporation of one or more water soluble polymers, such as PEG. This embodiment of the invention is particularly useful for introducing additional, customized pegylation-sites within the relaxin molecule, for example, for forming a PEG-relaxin having improved resistance to enzymatic degradation. Such an approach provides greater flexibility in the design of an optimized relaxin conjugate having the desired balance of activity, stability, solubility, and pharmacological properties. Mutations can be carried out, i.e., by site specific mutagenesis, at any number of positions within the relaxin molecule. PEGs for use in the present invention may possess a variety of structures: linear, forked, branched, dumbbell, and the like. Typically, PEG is activated with a suitable activating group appropriate for coupling a desired site or sites on the relaxin molecule. An activated PEG will possess a reactive group at a terminus for reaction with relaxin. Representative activated PEG derivatives and methods for conjugating these agents to a drug such as relaxin are known in the art and further described in Zalipsky, S., et al., "Use of Functionalized Poly(Ethylene Glycols) for Modification of Polypeptides" in Polyethylene Glycol Chemistry: Biotechnical and Biomedical Applications, J. M. Harris, Plenus Press, New York (1992), and in Advanced Drug Reviews, 16:157-182 (1995).

In one particular embodiment of the invention, the PEG portion of the conjugate is absent one or more lipophilic groups effective to significantly modify the water-soluble nature of the polymer or of the polymer-relaxin conjugate. That is to say, the polymer or non-relaxin portion of a conjugate of the invention may contain a group of atoms considered to be more lipophilic than hydrophilic (e.g., a carbon chain having from about 2 to 8-12 carbon atoms), however, if the presence of such a group or groups is not effective to significantly alter the hydrophilic nature of the polymer or of the conjugate, then such a moiety may be contained in the conjugates of the invention. That is to say, through site-specific mutations of relaxin, relaxin polypeptides, and relaxin analogs, a relaxin conjugate of the invention itself may exhibit hydrophilic, rather than lipophilic or amphiphilic. In certain embodiments of the invention where a lipophilic moiety may be present, the moiety is preferably not positioned at a terminus of a PEG chain.

Branched PEGs for use in the conjugates of the invention include those described in International Patent Publication WO 96/21469, the contents of which is expressly incorporated herein by reference in its entirety. Generally, branched PEGs can be represented by the formula R(PEG-OH).sub.n, where R represents the central "core" molecule and .sub.n represents the number of arms. Branched PEGs have a central core from which extend 2 or more "PEG" arms. In a branched configuration, the branched polymer core possesses a single reactive site for attachment to relaxin. Branched PEGs for use in the present invention will typically comprise fewer than 4 PEG arms, and more preferably, will comprise fewer than 3 PEG arms. Branched PEGs offer the advantage of having a single reactive site, coupled with a larger, more dense polymer cloud than their linear PEG counterparts. One particular type of branched PEG can be represented as (MeO-PEG-).sub.p R—X, where p equals 2 or 3, R is a central core structure such as lysine or glycerol having 2 or 3 PEG arms attached thereto, and X represents any suitable functional group that is or that can be activated for coupling to relaxin. One particularly preferred branched PEG is mPEG2-NHS (Shearwater Corporation, Alabama) having the structure mPEG2-lysine-succinimide.

In yet another branched architecture, "pendant PEG" has reactive groups for protein coupling positioned along the PEG backbone rather than at the end of PEG chains. The reactive groups extending from the PEG backbone for coupling to relaxin may be the same or different. Pendant PEG structures may be useful but are generally less preferred, particularly for compositions for inhalation.

Alternatively, the PEG-portion of a PEG-relaxin conjugate may possess a forked structure having a branched moiety at one end of the polymer chain and two free reactive groups (or any multiple of 2) linked to the branched moiety for attachment to relaxin. Exemplary forked PEGs are described in International Patent Publication No. WO 99/45964, the content of which is expressly incorporated herein by reference. The forked polyethylene glycol may optionally include an alkyl or "R" group at the opposing end of the polymer chain. More specifically, a forked PEG-relaxin conjugate in accordance with the invention has the formula: R-PEG-L(Y-relaxin)n where R is alkyl, L is a hydrolytically stable branch point and Y is a linking group that provides chemical linkage of the forked polymer to relaxin, and n is a multiple of 2. L may represent a single "core" group, such as "—CH—", or may comprise a longer chain of atoms. Exemplary L groups include lysine, glycerol, pentaerythritol, or sorbitol. Typically, the particular branch atom within the branching moiety is carbon.

In one particular embodiment of the invention, the linkage of the forked PEG to the relaxin molecule, (Y), is hydrolytically stable. In a preferred embodiment, n is 2. Suitable Y moieties, prior to conjugation with a reactive site on relaxin, include but are not limited to active esters, active carbonates, aldehydes, isocyanates, isothiocyanates, epoxides, alcohols, maleimides, vinylsulfones, hydrazides, dithiopyridines, and iodacetamides. Selection of a suitable activating group will depend upon the intended site of attachment on the relaxin molecule and can be readily determined by one of skill in the art. The corresponding Y group in the resulting PEG-relaxin conjugate is that which results from reaction of the activated forked polymer with a suitable reactive site on relaxin. The specific identity of such the final linkage will be apparent to one skilled in the art. For example, if the reactive forked PEG contains an activated ester, such as a succinimide or maleimide ester, conjugation via an amine site on relaxin will result in formation of the corresponding amide linkage. These particular forked polymers are particularly attractive since they provide conjugates having a molar ratio of relaxin to PEG of 2:1 or greater. Such conjugates may be less likely to block the relaxin receptor site, while still providing the flexibility in design to protect the relaxin against enzymatic degradation, e.g., by relaxin degrading enzyme.

In a related embodiment, a forked PEG-relaxin conjugate may be used in the present invention, represented by the formula: R-[PEG-L(Y-relaxin)2]n. In this instance R represents a non-naturally encoded amino acid having attached thereto at least one PEG-di-relaxin conjugate. Specifically, preferred forked polymers in accordance with this aspect of the invention are those were n is selected from the group consisting of 1, 2, 3, 4, 5, and 6. In an alternative embodiment, the chemical linkage between the non-natural amino acid within relaxin, relaxin polypeptide, or relaxin analog and the polymer branch point may be degradable (i.e., hydrolytically unstable). Alternatively, one or more degradable linkages may be contained in the polymer backbone to allow generation in vivo of a PEG-relaxin conjugate having a smaller PEG chain than in the initially administered conjugate. For example, a large and relatively inert conjugate (i.e., having one or more high molecular weight PEG chains attached thereto, e.g., one or more PEG chains having a molecular weight greater than about 10,000, wherein the conjugate possesses essentially no bioactivity) may be administered, which then either in the lung or in the bloodstream, is hydrolyzed to generate a bioactive conjugate possessing a portion of the originally present PEG chain. Upon in-vivo cleavage of the hydrolytically degradable linkage, either free relaxin (depending upon the position of the degradable linkage) or relaxin having a small polyethylene tag attached thereto, is then released and more readily absorbed through the lung and/or circulated in the blood.

In one feature of this embodiment of the invention, the intact polymer-conjugate, prior to hydrolysis, is minimally degraded upon administration, such that hydrolysis of the cleavable bond is effective to govern the slow rate of release of active relaxin into the bloodstream, as opposed to enzymatic degradation of relaxin prior to its release into the systemic circulation.

Appropriate physiologically cleavable linkages include but are not limited to ester, carbonate ester, carbamate, sulfate, phosphate, acyloxyalkyl ether, acetal, and ketal. Such conjugates should possess a physiologically cleavable bond that is stable upon storage and upon administration. For instance, a PEG-cleavable linkage-relaxin conjugate should maintain its integrity upon manufacturing of the final pharmaceutical composition, upon dissolution in an appropriate delivery vehicle, if employed, and upon administration irrespective of route.

Thus, in another embodiment of the present invention, one or more non-naturally encoded amino acids are incorporated into a single chain relaxin or single chain relaxin analog.

In some embodiments, the polypeptide of the invention comprises one or more non-naturally encoded amino acid substitution, addition, or deletion in the signal sequence. In some embodiments, the polypeptide of the invention comprises one or more non-naturally encoded amino acid substitution, addition, or deletion in the signal sequence for relaxin or any of the relaxin analogs or polypeptides disclosed within this specification. In some embodiments, the polypeptide of the invention comprises one or more naturally encoded amino acid substitution, addition, or deletion in the signal sequence as well as one or more non-naturally encoded amino acid substitutions, additions, or deletions in the signal sequence for relaxin or any of the relaxin analogs or polypeptides disclosed within this specification. In some embodiments, one or more non-natural amino acids are incorporated in the leader or signal sequence for relaxin or any of the relaxin analogs or polypeptides disclosed within this specification.

In some embodiments, the relaxin polypeptide comprises a substitution, addition or deletion that modulates affinity of the relaxin polypeptide for a relaxin polypeptide receptor or binding partner, including but not limited to, a protein, polypeptide, small molecule, or nucleic acid. In some embodiments, the relaxin polypeptide comprises a substitution, addition, or deletion that increases the stability of the relaxin polypeptide when compared with the stability of the corresponding relaxin without the substitution, addition, or deletion. Stability and/or solubility may be measured using a number of different assays known to those of ordinary skill in the art. Such assays include but are not limited to SE-HPLC and RP-HPLC. In some embodiments, the relaxin polypeptide comprises a substitution, addition, or deletion that modulates the immunogenicity of the relaxin polypeptide when compared with the immunogenicity of the corresponding relaxin without the substitution, addition, or deletion. In some embodiments, the relaxin polypeptide comprises a substitution, addition, or deletion that modulates serum half-life or circulation time of the relaxin polypeptide when compared with the serum half-life or circulation time of the corresponding relaxin without the substitution, addition, or deletion.

In some embodiments, the relaxin polypeptide comprises a substitution, addition, or deletion that increases the aqueous solubility of the relaxin polypeptide when compared to aqueous solubility of the corresponding relaxin without the substitution, addition, or deletion. In some embodiments, the relaxin polypeptide comprises a substitution, addition, or deletion that increases the solubility of the relaxin polypeptide produced in a host cell when compared to the solubility of the corresponding relaxin without the substitution, addition, or deletion. In some embodiments, the relaxin polypeptide comprises a substitution, addition, or deletion that increases the expression of the relaxin polypeptide in a host cell or increases synthesis in vitro when compared to the expression or synthesis of the corresponding relaxin without the substitution, addition, or deletion. The relaxin polypeptide comprising this substitution retains agonist activity and retains or improves expression levels in a host cell. In some embodiments, the relaxin polypeptide comprises a substitution, addition, or deletion that increases protease resistance of the relaxin polypeptide when compared to the protease resistance of the corresponding relaxin without the substitution, addition, or deletion. In some embodiments, the relaxin polypeptide comprises a substitution, addition, or deletion that modulates signal transduction activity of the relaxin receptor when compared with the activity of the receptor upon interaction with the corresponding relaxin polypeptide without the substitution, addition, or deletion. In some embodiments, the relaxin polypeptide comprises a substitution, addition, or deletion that modulates its binding to another molecule such as a receptor when compared to the binding of the corresponding relaxin polypeptide without the substitution, addition, or deletion. In some embodiments, the relaxin polypeptide comprises a substitution, addition, or deletion that modulates its anti-viral activity compared to the anti-viral activity of the corresponding relaxin polypeptide without the substitution, addition, or deletion. In some embodiments, the relaxin polypeptide comprises a substitution, addition, or deletion that enhances its glucose metabolizing activity compared to the glucose metabolizing activity of the corresponding relaxin polypeptide without the substitution, addition, or deletion.

In some embodiments, the relaxin polypeptide comprises a substitution, addition, or deletion that increases compatibility of the relaxin polypeptide with pharmaceutical preservatives (e.g., m-cresol, phenol, benzyl alcohol) when compared to compatibility of the corresponding relaxin without the substitution, addition, or deletion. This increased compatibility would enable the preparation of a preserved pharmaceutical formulation that maintains the physiochemical properties and biological activity of the protein during storage.

In some embodiments, one or more engineered bonds are created with one or more non-natural amino acids. The intramolecular bond may be created in many ways, including but not limited to, a reaction between two amino acids in the protein under suitable conditions (one or both amino acids may be a non-natural amino acid); a reaction with two amino acids, each of which may be naturally encoded or non-naturally encoded, with a linker, polymer, or other molecule under suitable conditions; etc.

In some embodiments, one or more amino acid substitutions in the relaxin polypeptide may be with one or more naturally occurring or non-naturally encoded amino acids. In some embodiments the amino acid substitutions in the relaxin polypeptide may be with naturally occurring or non-naturally encoded amino acids, provided that at least one substitution is with a non-naturally encoded amino acid. In some embodiments, one or more amino acid substitutions in the relaxin polypeptide may be with one or more naturally occurring amino acids, and additionally at least one substitution is with a non-naturally encoded amino acid.

In some embodiments, the non-naturally encoded amino acid comprises a carbonyl group, an acetyl group, an aminooxy group, a hydrazine group, a hydrazide group, a semicarbazide group, an azide group, or an alkyne group.

In some embodiments, the non-naturally encoded amino acid comprises a carbonyl group. In some embodiments, the non-naturally encoded amino acid has the structure:

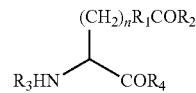

wherein n is 0-10; R1 is an alkyl, aryl, substituted alkyl, or substituted aryl; R2 is H, an alkyl, aryl, substituted alkyl, and substituted aryl; and R3 is H, an amino acid, a polypeptide, or an amino terminus modification group, and R4 is H, an amino acid, a polypeptide, or a carboxy terminus modification group.

In some embodiments, the non-naturally encoded amino acid comprises an aminooxy group. In some embodiments, the non-naturally encoded amino acid comprises a hydrazide group. In some embodiments, the non-naturally encoded amino acid comprises a hydrazine group. In some embodiments, the non-naturally encoded amino acid residue comprises a semicarbazide group.

In some embodiments, the non-naturally encoded amino acid residue comprises an azide group. In some embodiments, the non-naturally encoded amino acid has the structure:

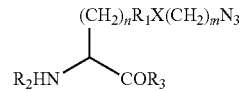

wherein n is 0-10; R1 is an alkyl, aryl, substituted alkyl, substituted aryl or not present; X is O, N, S or not present; m is 0-10; R2 is H, an amino acid, a polypeptide, or an amino terminus modification group, and R3 is H, an amino acid, a polypeptide, or a carboxy terminus modification group.

In some embodiments, the non-naturally encoded amino acid comprises an alkyne group. In some embodiments, the non-naturally encoded amino acid has the structure:

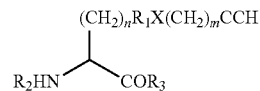

wherein n is 0-10; R1 is an alkyl, aryl, substituted alkyl, or substituted aryl; X is O, N, S or not present; m is 0-10, R2 is H, an amino acid, a polypeptide, or an amino terminus modification group, and R3 is H, an amino acid, a polypeptide, or a carboxy terminus modification group.

In some embodiments, the polypeptide is a relaxin polypeptide agonist, partial agonist, antagonist, partial antagonist, or inverse agonist. In some embodiments, the relaxin polypeptide agonist, partial agonist, antagonist, partial antagonist, or inverse agonist comprises a non-naturally encoded amino acid linked to a water soluble polymer. In some embodiments, the water soluble polymer comprises a poly(ethylene glycol) moiety. In some embodiments, the relaxin polypeptide agonist, partial agonist, antagonist, partial antagonist, or inverse agonist comprises a non-naturally encoded amino acid and one or more post-translational modification, linker, polymer, or biologically active molecule.

The present invention also provides isolated nucleic acids comprising a polynucleotide that hybridizes under stringent conditions nucleic acids that encode relaxin polypeptides of SEQ ID NOs: 1, 2, 3, 4, 5, 6, 7, 8, 9, 10, 11, and 12. The present invention also provides isolated nucleic acids comprising a polynucleotide that hybridizes under stringent conditions nucleic acids that encode relaxin polypeptides of SEQ ID NOs: 1 and 2. The present invention also provides isolated nucleic acids comprising a polynucleotide or polynucleotides that hybridize under stringent conditions to polynucleotides that encode polypeptides shown as SEQ ID NOs: 1, 2, 3, 4, 5, 6, 7, 8, 9, 10, 11, and 12 wherein the polynucleotide comprises at least one selector codon. The present invention also provides isolated nucleic acids comprising a polynucleotide or polynucleotides that hybridize under stringent conditions to polynucleotides that encode polypeptides shown as SEQ ID NOs: 1 and 2 wherein the polynucleotide comprises at least one selector codon. The present invention provides isolated nucleic acids comprising a polynucleotide that encodes the polypeptides shown as SEQ ID NOs.: 1 and 2. The present invention also provides isolated nucleic acids comprising a polynucleotide that encodes the polypeptides shown as SEQ ID NOs.: 1, 2, 3, 4, 5, 6, 7, 8, 9, 10, 11, and 12. The present invention provides isolated nucleic acids comprising a polynucleotide that encodes the polypeptides shown as SEQ ID NOs.: 1 and 2 with one or more non-naturally encoded amino acids. The present invention also provides isolated nucleic acids comprising a polynucleotide that encodes the polypeptides shown as SEQ ID NOs.: 1, 2, 3, 4, 5, 6, 7, 8, 9, 10, 11, and 12 with one or more non-naturally encoded amino acids. It is readily apparent to those of ordinary skill in the art that a number of different polynucleotides can encode any polypeptide of the present invention.

In some embodiments, the selector codon is selected from the group consisting of an amber codon, ochre codon, opal codon, a unique codon, a rare codon, a five-base codon, and a four-base codon.

The present invention also provides methods of making a relaxin polypeptide linked to a water soluble polymer. In some embodiments, the method comprises contacting an isolated relaxin polypeptide comprising a non-naturally encoded amino acid with a water soluble polymer comprising a moiety that reacts with the non-naturally encoded amino acid. In some embodiments, the non-naturally encoded amino acid incorporated into the relaxin polypeptide is reactive toward a water soluble polymer that is otherwise unreactive toward any of the 20 common amino acids. In some embodiments, the non-naturally encoded amino acid incorporated into the relaxin polypeptide is reactive toward a linker, polymer, or biologically active molecule that is otherwise unreactive toward any of the 20 common amino acids.

In some embodiments, the relaxin polypeptide linked to the water soluble polymer is made by reacting a relaxin polypeptide comprising a carbonyl-containing amino acid with a poly(ethylene glycol) molecule comprising an aminooxy, hydrazine, hydrazide or semicarbazide group. In some embodiments, the aminooxy, hydrazine, hydrazide or semicarbazide group is linked to the poly(ethylene glycol) molecule through an amide linkage. In some embodiments, the aminooxy, hydrazine, hydrazide or semicarbazide group is linked to the poly(ethylene glycol) molecule through a carbamate linkage.

In some embodiments, the relaxin polypeptide linked to the water soluble polymer is made by reacting a poly(ethylene glycol) molecule comprising a carbonyl group with a polypeptide comprising a non-naturally encoded amino acid that comprises an aminooxy, hydrazine, hydrazide or semicarbazide group.

In some embodiments, the relaxin polypeptide linked to the water soluble polymer is made by reacting a relaxin polypeptide comprising an alkyne-containing amino acid with a poly(ethylene glycol) molecule comprising an azide moiety. In some embodiments, the azide or alkyne group is linked to the poly(ethylene glycol) molecule through an amide linkage.

In some embodiments, the relaxin polypeptide linked to the water soluble polymer is made by reacting a relaxin polypeptide comprising an azide-containing amino acid with a poly(ethylene glycol) molecule comprising an alkyne moiety. In some embodiments, the azide or alkyne group is linked to the poly(ethylene glycol) molecule through an amide linkage.

In some embodiments, the poly(ethylene glycol) molecule has a molecular weight of between about 0.1 kDa and about 100 kDa. In some embodiments, the poly(ethylene glycol) molecule has a molecular weight of between 0.1 kDa and 50 kDa.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa.

In some embodiments, the water soluble polymer linked to the relaxin polypeptide comprises a polyalkylene glycol moiety. In some embodiments, the non-naturally encoded amino acid residue incorporated into the relaxin polypeptide comprises a carbonyl group, an aminooxy group, a hydrazide group, a hydrazine, a semicarbazide group, an azide group, or an alkyne group. In some embodiments, the non-naturally encoded amino acid residue incorporated into the relaxin polypeptide comprises a carbonyl moiety and the water soluble polymer comprises an aminooxy, hydrazide, hydrazine, or semicarbazide moiety. In some embodiments, the non-naturally encoded amino acid residue incorporated into the relaxin polypeptide comprises an alkyne moiety and the water soluble polymer comprises an azide moiety. In some embodiments, the non-naturally encoded amino acid residue incorporated into the relaxin polypeptide comprises an azide moiety and the water soluble polymer comprises an alkyne moiety.

The present invention also provides compositions comprising a relaxin polypeptide comprising a non-naturally encoded amino acid and a pharmaceutically acceptable carrier. In some embodiments, the non-naturally encoded amino acid is linked to a water soluble polymer.

The present invention also provides cells comprising a polynucleotide encoding the relaxin polypeptide comprising a selector codon. In some embodiments, the cells comprise an orthogonal RNA synthetase and/or an orthogonal tRNA for substituting a non-naturally encoded amino acid into the relaxin polypeptide.

The present invention also provides methods of making a relaxin polypeptide comprising a non-naturally encoded amino acid. In some embodiments, the methods comprise culturing cells comprising a polynucleotide or polynucleotides encoding a relaxin polypeptide, an orthogonal RNA synthetase and/or an orthogonal tRNA under conditions to permit expression of the relaxin polypeptide; and purifying the relaxin polypeptide from the cells and/or culture medium.

The present invention also provides methods of increasing therapeutic half-life, serum half-life or circulation time of relaxin polypeptides. The present invention also provides methods of modulating immunogenicity of relaxin polypeptides. In some embodiments, the methods comprise substituting a non-naturally encoded amino acid for any one or more amino acids in naturally occurring relaxin polypeptides and/or linking the relaxin polypeptide to a linker, a polymer, a water soluble polymer, or a biologically active molecule.

The present invention also provides methods of treating a patient in need of such treatment with an effective amount of a relaxin molecule of the present invention. In some embodiments, the methods comprise administering to the patient a therapeutically-effective amount of a pharmaceutical composition comprising a relaxin polypeptide comprising a non-naturally-encoded amino acid and a pharmaceutically acceptable carrier. In some embodiments, the non-naturally encoded amino acid is linked to a water soluble polymer. In some embodiments, the relaxin polypeptide is glycosylated. In some embodiments, the relaxin polypeptide is not glycosylated.

The present invention also provides relaxin polypeptides comprising a sequence shown in SEQ ID NO: 1 and 2, or any other relaxin polypeptide sequence (a non-limiting example of these would be SEQ ID NOs: 3 through 12) except that at least one amino acid is substituted by a non-naturally encoded amino acid. In some embodiments, the non-naturally encoded amino acid is linked to a water soluble polymer. In some embodiments, the water soluble polymer comprises a poly(ethylene glycol) moiety. In some embodiments, the non-naturally encoded amino acid comprises a carbonyl group, an aminooxy group, a hydrazide group, a hydrazine group, a semicarbazide group, an azide group, or an alkyne group.

The present invention also provides pharmaceutical compositions comprising a pharmaceutically acceptable carrier and a relaxin polypeptide comprising the sequence shown in SEQ ID NOs: 1 through 12, or any other relaxin polypeptide sequence, wherein at least one amino acid is substituted by a non-naturally encoded amino acid. The present invention also provides pharmaceutical compositions comprising a pharmaceutically acceptable carrier and a relaxin polypeptide comprising an A and B chain (e.g. SEQ ID NO: 1, 2, and 3; SEQ ID NOs: 4 and 5 or 4 and 6 would make relaxin, etc.), or any other relaxin polypeptide sequence, wherein at least one amino acid is substituted by a non-naturally encoded amino acid. The present invention also provides pharmaceutical compositions comprising a pharmaceutically acceptable carrier and a relaxin polypeptide comprising the sequence shown in SEQ ID NO: 1, 2, and/or 3. The present invention also provides pharmaceutical compositions comprising a pharmaceutically acceptable carrier and a relaxin polypeptide comprising the sequence shown in SEQ ID NO: 1-3. In some embodiments, the non-naturally encoded amino acid comprises a saccharide moiety. In some embodiments, the water soluble polymer is linked to the polypeptide via a saccharide moiety. In some embodiments, a linker, polymer, or biologically active molecule is linked to the relaxin polypeptide via a saccharide moiety.

The present invention also provides a relaxin polypeptide comprising a water soluble polymer linked by a covalent bond to the relaxin polypeptide at a single amino acid. In some embodiments, the water soluble polymer comprises a poly(ethylene glycol) moiety. In some embodiments, the amino acid covalently linked to the water soluble polymer is a non-naturally encoded amino acid present in the polypeptide.

The present invention provides a relaxin polypeptide comprising at least one linker, polymer, or biologically active molecule, wherein said linker, polymer, or biologically active molecule is attached to the polypeptide through a functional group of a non-naturally encoded amino acid ribosomally incorporated into the polypeptide. In some embodiments, the polypeptide is monoPEGylated. The present invention also provides a relaxin polypeptide comprising a linker, polymer, or biologically active molecule that is attached to one or more non-naturally encoded amino acid wherein said non-naturally encoded amino acid is ribosomally incorporated into the polypeptide at pre-selected sites.

Included within the scope of this invention is the relaxin leader or signal sequence an example of which can be seen as proinulin. The heterologous leader or signal sequence selected should be one that is recognized and processed, e.g. by host cell secretion system to secrete and possibly cleaved by a signal peptidase, by the host cell. A method of treating a condition or disorder with relaxin or a relaxin polypeptide or analog of the present invention is meant to imply treating with relaxin with or without a signal or leader peptide.

The present invention also provides methods of inducing an increase in glucose metabolism, said method comprising administering relaxin to said cells in an amount effective to induce an increase in glucose metabolic activity.

In another embodiment, conjugation of the relaxin polypeptide comprising one or more non-naturally encoded amino acids to another molecule, including but not limited to PEG, provides substantially purified relaxin due to the unique chemical reaction utilized for conjugation to the non-natural amino acid. Conjugation of relaxin comprising one or more non-naturally encoded amino acids to another molecule, such as PEG, may be performed with other purification techniques performed prior to or following the conjugation step to provide substantially pure relaxin.

BRIEF DESCRIPTION OF THE SEVERAL VIEWS OF THE DRAWINGS

FIG. 19A shows the effect of IV infusion with wild-type relaxin on water intake and urine output. FIG. 19B shows a baseline for each group of Long-Evans rats from −16 ours to 0 of Phase I for urine output.

FIG. 19C shows the effect of IV infusion with wild-type relaxin on hematocrit. FIG. 19D shows the effect of IV infusion with wild-type relaxin on plasma BUN in the female Long-Evans rats. FIG. 19E shows water intake for each group of Long-Evans rats from 0 to 6 hours of Phase I. FIG. 19F shows urine output for each group of Long-Evans rats from 0 to 6 hours of Phase I.

FIG. 20A shows the effect of on water intake and urine output. FIG. 20B shows the effect on plasma sodium levels for each group of Long-Evans rats following injection. FIG. 20C shows the effect on plasma sodium change levels for each group of Long-Evans rats following injection. FIG. 20D shows the effect of PEG-Relaxin on plasma osmolarity. FIG. 20E shows the effect of IV infusion with PEG-Relaxin on plasma osmolarity change. FIG. 20F shows the effect of PEG-Relaxin administration on BUN levels. FIG. 20G shows the effect of PEG-relaxin administration on water intake for each group of Long-Evans rats from 0 to 6 hours of Phase II. FIG. 20H shows baseline urine output for each group of Long-Evans rats from −16 to 0 hours of Phase II. FIG. 20I shows the effect of PEG-relaxin administration on urine output for each group of Long-Evans rats from 0 to 6 hours of Phase II.

DEFINITIONS

Figure 1:
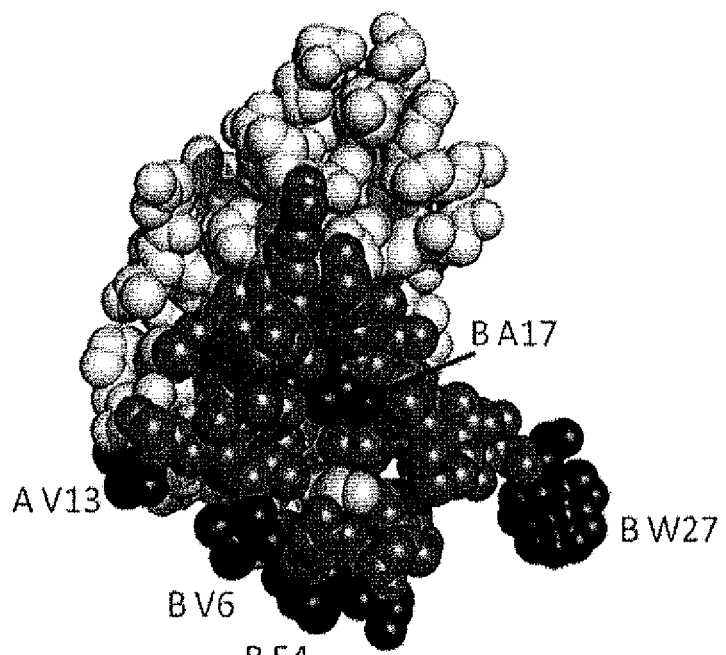
FIG. 1 is a model of the crystal structure of relaxin are shown along with some amino acid residue positions selected for substitution.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "relaxin" or "relaxin polypeptide" and various hyphenated and unhyphenated forms is a reference to one or more such proteins and includes equivalents thereof known to those of ordinary skill in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

The term "substantially purified" refers to a relaxin polypeptide that may be substantially or essentially free of components that normally accompany or interact with the protein as found in its naturally occurring environment, i.e. a native cell, or host cell in the case of recombinantly produced relaxin polypeptides. Relaxin polypeptide that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the relaxin polypeptide or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the relaxin polypeptide or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" relaxin polypeptide as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the relaxin polypeptide has been secreted, including medium either before or after a proliferation step. The term also may encompass buffers or reagents that contain host cell lysates, such as in the case where the relaxin polypeptide is produced intracellularly and the host cells are lysed or disrupted to release the relaxin polypeptide.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. It is readily apparent to those of ordinary skill in the art that a wide variety of reducing agents are suitable for use in the methods and compositions of the present invention.

"Oxidizing agent," as used hereinwith respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic solvents, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N->2,3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially C2-C4 alkanols such as ethanol or isopropanol), or lower alkandiols (especially C2-C4 alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

The term "proinsulin" as used herein is a properly cross-line protein of the formula: B-C-A
wherein:
A is the A chain of relaxin or a functional derivative thereof,
B is the B chain of relaxin or a functional derivative thereof having an .epsilon.-amino group; and
C is the connecting peptide of proinsulin. Preferably, proinsulin is the A chain of human relaxin, the B chain of human relaxin, and C is the natural connecting peptide. When proinsulin is the natural sequence, proinsulin possesses three free amino groups: Phenylalanine(1) (.alpha.-amino group), Lysine(29) (.epsilon.-amino group) and Lysine(64) (.epsilon.-amino group).

The term "relaxin analog" as used herein is a properly cross-lined protein exhibiting relaxin activity of the formula:

A-B wherein:
A is the A chain of relaxin or a functional derivative of the relaxin A chain; and
B is the B chain of relaxin or a functional derivative of the relaxin B chain having an .epsilon.-amino group and at least one of A or B contains an amino acid modification from the natural sequence.

In the present specification, whenever the term relaxin is used in a plural or a generic sense it is intended to encompass both naturally occurring insulins and relaxin analogues and derivatives thereof. By "relaxin polypeptide" as used herein is meant a compound having a molecular structure similar to that of human relaxin including the disulfide bridges between Cys.sup.A7 and Cys.sup.B7 and between Cys.sup.A20 and Cys.sup.B19 and an internal disulfide bridge between Cys.sup.A6 and Cys.sup.A11, and which have relaxin activity.

The term "relaxin" as used herein, refers to human relaxin, whose amino acid sequence and spatial structure are well-known. Human relaxin is comprised of a twenty-one amino acid A-chain and a thirty amino acid B-chain which are cross-linked by disulfide bonds. A properly cross-linked relaxin contains three disulfide bridges: one between position 7 of the A-chain and position 7 of the B-chain, a second between position 20 of the A-chain and position 19 of the B-chain, and a third between positions 6 and 11 of the A-chain [Nicol, D. S. H. W. and Smith, L. F., Nature, 187, 483-485 (1960)].

Relaxin peptides including, but not limited to, relaxin, human; relaxin, porcine; IGF-I, human; relaxin-like growth factor II (69-84); pro-relaxin-like growth factor II (68-102), human; pro-relaxin-like growth factor II (105-128), human; [AspB28]-relaxin, human; [LysB28]-relaxin, human; [LeuB28]-relaxin, human; [ValB28]-relaxin, human; [AlaB28]-relaxin, human; [AspB28, ProB29]-relaxin, human; [LysB28, ProB29]-relaxin, human; [LeuB28, ProB29]-relaxin, human; [ValB28, ProB29]-relaxin, human; [AlaB28, ProB29]-relaxin, human; [GlyA21]-relaxin, human; [GlyA21 GlnB3]-relaxin, human; [AlaA21]-relaxin, human; [AlaA21 Gln.sup.B3] relaxin, human; [GlnB3]-relaxin, human; [GlnB30]-relaxin, human; [GlyA21 GluB30]-relaxin, human; [GlyA21 GlnB3 GluB30]-relaxin, human; [GnB3 GluB30]-relaxin, human; B22-B30 relaxin, human; B23-B30 relaxin, human; B25-B30 relaxin, human; B26-B30 relaxin, human; B27-B30 relaxin, human; B29-B30 relaxin, human; the A chain of human relaxin, and the B chain of human relaxin.

The term "relaxin analog" means a protein that has an A-chain and a B-chain that have substantially the same amino acid sequences as the A-chain and/or B-chain of human relaxin, respectively, but differ from the A-chain and B-chain of human relaxin by having one or more amino acid deletions, one or more amino acid replacements, and/or one or more amino acid additions that do not destroy the relaxin activity of the relaxin analog. A relaxin analog having an isoelectric point that is "higher than" the isoelectric point of relaxin is one type of relaxin analog. Another type of relaxin analog is a "monomeric relaxin analog."

A "monomeric relaxin analog" is a fast-acting analog of human relaxin, including, for example, human relaxin wherein Pro at position B28 is substituted with Asp, Lys, Leu, Val, or Ala, and wherein Lys at position B29 is Lys or is substituted with Pro. Another monomeric relaxin analog, also known as des(B27) human relaxin, is human relaxin wherein Thr at position 27 of the B-chain is deleted. Monomeric relaxin analogs are disclosed in Chance, R. E., et al., U.S. Pat. No. 5,514,646, issued May 7, 1996; Brems, D. N., et al. Protein Engineering, 5, 527-533 (1992); Brange, J. J. V., et al., EPO publication No. 214,826 (published Mar. 18, 1987); and Brange, J. J. V., et al., Current Opinion in Structural Biology, 1, 934-940 (1991). The monomeric relaxin analogs employed in the present formulations are properly cross-linked at the same positions as in human relaxin.

Relaxin peptides including, but not limited to, relaxin, human; relaxin, porcine; IGF-I, human; relaxin-like growth factor II (69-84); pro-relaxin-like growth factor II (68-102), human; pro-relaxin-like growth factor II (105-128), human; [AspB28]-relaxin, human; [LysB28]-relaxin, human; [LeuB28]-relaxin, human; [ValB28]-relaxin, human; [AlaB28]-relaxin, human; [AspB28, ProB29]-relaxin, human; [LysB28, ProB29]-relaxin, human; [LeuB28, ProB29]-relaxin, human; [ValB28, ProB29]-relaxin, human; [AlaB28, ProB29]-relaxin, human; [GlyA21]-relaxin, human; [GlyA21 GlnB3]-relaxin, human; [AlaA21]-relaxin, human; [AlaA21 Gln.sup.B3] relaxin, human; [GlnB3]-relaxin, human; [GlnB30]-relaxin, human; [GlyA21 GluB30]-relaxin, human; [GlyA21 GlnB3 GluB30]-relaxin, human; [GnB3 GluB30]-relaxin, human; B22-B30 relaxin, human; B23-B30 relaxin, human; B25-B30 relaxin, human; B26-B30 relaxin, human; B27-B30 relaxin, human; B29-B30 relaxin, human; the A chain of human relaxin, and the B chain of human relaxin.

In a further aspect, the invention provides recombinant nucleic acids encoding the variant proteins, expression vectors containing the variant nucleic acids, host cells comprising the variant nucleic acids and/or expression vectors, and methods for producing the variant proteins. In an additional aspect, the invention provides treating a relaxin responsive disorder by administering to a patient a variant protein, usually with a pharmaceutical carrier, in a therapeutically effective amount. In a further aspect, the invention provides methods for modulating immunogenicity (particularly reducing immunogenicity) of relaxin polypeptides by altering MHC Class II epitopes.

The term "relaxin polypeptide" also includes the pharmaceutically acceptable salts and prodrugs, and prodrugs of the salts, polymorphs, hydrates, solvates, biologically-active fragments, biologically active variants and stereoisomers of the naturally-occurring relaxin as well as agonist, mimetic, and antagonist variants of the naturally-occurring relaxin and polypeptide fusions thereof. Fusions comprising additional amino acids at the amino terminus, carboxyl terminus, or both, are encompassed by the term "relaxin polypeptide." Exemplary fusions include, but are not limited to, e.g., methionyl relaxin in which a methionine is linked to the N-terminus of relaxin resulting from the recombinant expression of the mature form of relaxin lacking the leader or signal peptide or portion thereof (a methionine is linked to the N-terminus of relaxin resulting from the recombinant expression), fusions for the purpose of purification (including, but not limited to, to poly-histidine or affinity epitopes), fusions with serum albumin binding peptides and fusions with serum proteins such as serum albumin. U.S. Pat. No. 5,750,373, which is incorporated by reference herein, describes a method for selecting novel proteins such as growth hormone and antibody fragment variants having altered binding properties for their respective receptor molecules. The method comprises fusing a gene encoding a protein of interest to the carboxy terminal domain of the gene III coat protein of the filamentous phage M13. Chimeric molecules comprising relaxin and one or more other molecules. The chimeric molecule can contain specific regions or fragments of one or both of the relaxin and the other molecule(s). Any such fragments can be prepared from the proteins by standard biochemical methods, or by expressing a polynucleotide encoding the fragment. Relaxin, or a fragment thereof, can be produced as a fusion protein comprising human serum albumin (HSA), Fc, or a portion thereof. Such fusion constructs are suitable for enhancing expression of the relaxin, or fragment thereof, in an eukaryotic host cell. Exemplary HSA portions include the N-terminal polypeptide (amino acids 1-369, 1-419, and intermediate lengths starting with amino acid 1), as disclosed in U.S. Pat. No. 5,766,883, and publication WO 97/24445, which are incorporated by reference herein. Other chimeric polypeptides can include a HSA protein with relaxin, or fragments thereof, attached to each of the C-terminal and N-terminal ends of the HSA. Such HSA constructs are disclosed in U.S. Pat. No. 5,876,969, which is incorporated by reference herein. Other fusions may be created by fusion of relaxin with a) the Fc portion of an immunoglobulin; b) an analog of the Fc portion of an immunoglobulin; and c) fragments of the Fc portion of an immunoglobulin.

Various references disclose modification of polypeptides by polymer conjugation or glycosylation. The term "relaxin polypeptide" includes polypeptides conjugated to a polymer such as PEG and may be comprised of one or more additional derivitizations of cysteine, lysine, or other residues. In addition, the relaxin polypeptide may comprise a linker or polymer, wherein the amino acid to which the linker or polymer is conjugated may be a non-natural amino acid according to the present invention, or may be conjugated to a naturally encoded amino acid utilizing techniques known in the art such as coupling to lysine or cysteine.

The term "relaxin polypeptide" also includes glycosylated relaxin, such as but not limited to, polypeptides glycosylated at any amino acid position, N-linked or O-linked glycosylated forms of the polypeptide. Variants containing single nucleotide changes are also considered as biologically active variants of relaxin polypeptide. In addition, splice variants are also included. The term "relaxin polypeptide" also includes relaxin polypeptide heterodimers, homodimers, heteromultimers, or homomultimers of any one or more relaxin polypeptides or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

The term "relaxin polypeptide" or "relaxin" encompasses relaxin polypeptides comprising one or more amino acid substitutions, additions or deletions. Relaxin polypeptides of the present invention may be comprised of modifications with one or more natural amino acids in conjunction with one or more non-natural amino acid modification. Exemplary substitutions in a wide variety of amino acid positions in naturally-occurring relaxin polypeptides have been described, including but not limited to substitutions that modulate pharmaceutical stability, that modulate one or more of the biological activities of the relaxin polypeptide, such as but not limited to, increase agonist activity, increase solubility of the polypeptide, decrease protease susceptibility, convert the polypeptide into an antagonist, etc. and are encompassed by the term "relaxin polypeptide." In some embodiments, the relaxin antagonist comprises a non-naturally encoded amino acid linked to a water soluble polymer that is present in a receptor binding region of the relaxin molecule.

In some embodiments, the relaxin polypeptides further comprise an addition, substitution or deletion that modulates biological activity of the relaxin polypeptide. In some embodiments, the relaxin polypeptides further comprise an addition, substitution or deletion that modulates anti-viral activity of the relaxin polypeptide. In some embodiments, the relaxin polypeptides further comprise an addition, substitution or deletion that enhances anti-viral activity of the relaxin polypeptide. For example, the additions, substitutions or deletions may modulate one or more properties or activities of relaxin. For example, the additions, substitutions or deletions may modulate affinity for the relaxin receptor, modulate circulating half-life, modulate therapeutic half-life, modulate stability of the polypeptide, modulate cleavage by proteases, modulate dose, modulate release or bio-availability, facilitate purification, or improve or alter a particular route of administration. Similarly, relaxin polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term "relaxin polypeptide" also encompasses homodimers, heterodimers, homomultimers, and heteromultimers that are linked, including but not limited to those linked directly via non-naturally encoded amino acid side chains, either to the same or different non-naturally encoded amino acid side chains, to naturally-encoded amino acid side chains, or indirectly via a linker. Exemplary linkers including but are not limited to, small organic compounds, water soluble polymers of a variety of lengths such as poly (ethylene glycol) or polydextran, or polypeptides of various lengths.

A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, vaccines, immunogens, hard drugs, soft drugs, carbohydrates, inorganic atoms or molecules, dyes, lipids, nucleosides, radionuclides, oligonucleotides, toxoids, toxins, prokaryotic and eukaryotic cells, viruses, polysaccharides, nucleic acids and portions thereof obtained or derived from viruses, bacteria, insects, animals or any other cell or cell type, liposomes, microparticles and micelles. The relaxin polypeptides may be added in a micellular formulation; see U.S. Pat. No. 5,833,948, which is incorporated by reference herein in its entirety. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; and 4,569,789 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired length or molecular weight, and may be selected to provide a particular desired spacing or conformation between one or more molecules linked to the relaxin and its receptor or relaxin.

Where substituent groups are specified by their conventional chemical formulas, written from left to right, they equally encompass the chemically identical substituents that would result from writing the structure from right to left, for example, the structure CH2O is equivalent to the structure —OCH2.

The term "substituents" includes but is not limited to "non-interfering substituents". "Non-interfering substituents" are those groups that yield stable compounds. Suitable non-interfering substituents or radicals include, but are not limited to, halo, C1-C10 alkyl, C2-C10 alkenyl, C2-C10 alkynyl, C1-C10 alkoxy, C1-C12 aralkyl, C1-C12 alkaryl, C3-C12 cycloalkyl, C3-C12 cycloalkenyl, phenyl, substituted phenyl, toluoyl, xylenyl, biphenyl, C2-C12 alkoxyalkyl, C2-C12 alkoxyaryl, C7-C12-aryloxyalkyl, C7-C12 oxyaryl, C1-C6 alkylsulfinyl, C1-C10 alkylsulfonyl, —(CH2)m-O—(C1-C10 alkyl) wherein m is from 1 to 8, aryl, substituted aryl, substituted alkoxy, fluoroalkyl, heterocyclic radical, substituted heterocyclic radical, nitroalkyl, —NO2, —CN, —NRC(O)—(C1-C10 alkyl), —C(O)—(C1-C10 alkyl), C2-C10 alkyl thioalkyl, —C(O)O—(C1-C10 alkyl), —OH, —SO2, =S, —COOH, —NR2, carbonyl, —C(O)—(C1-C10 alkyl)-CF3, —C(O)—CF3, —C(O)NR2, —(C1-C10 aryl)-S—(C6-C10 aryl), —C(O)—(C1-C10 aryl), —(CH2)m-O—(—(CH2)m-O—(C1-C10 alkyl) wherein each m is from 1 to 8, —C(O)NR2, —C(S)NR2, —SO2NR2, —NRC(O) NR2, —NRC(S) NR2, salts thereof, and the like. Each R as used herein is H, alkyl or substituted alkyl, aryl or substituted aryl, aralkyl, or alkaryl.

The term "halogen" includes fluorine, chlorine, iodine, and bromine.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C1-C10 means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —CH2CH2- and —CH2CH2CH2CH2-, and further includes those groups described below as "heteroalkylene." Typically, an alkyl (or alkylene) group will have from 1 to 24 carbon atoms, with those groups having 10 or fewer carbon atoms being a particular embodiment of the methods and compositions described herein. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH2-CH2-O—CH3, —CH2-CH2-NH—CH3, —CH2-CH2-N(CH3)-CH3, —CH2-S—CH2-CH3, —CH2-CH2, —S(O)—CH3, —CH2-CH2-S(O)2-CH3, —CH═CH—O—CH3, —Si (CH3)3, —CH2-CH═N—OCH3, and —CH═CH—N (CH3)-CH3. Up to two heteroatoms may be consecutive, such as, for example, —CH2-NH—OCH3 and —CH2-O—Si(CH3)3. Similarly, the term "heteroalkylene" by itself or as part of another substituent means a divalent radical derived from heteroalkyl, as exemplified, but not limited by, —CH2-CH2-S—CH2 CH2- and —CH2-S—CH2-CH2-NH—CH2-. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C(O)2R' represents both —C(O)2R' and —R'C(O)2.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

As used herein, the term "water soluble polymer" refers to any polymer that is soluble in aqueous solvents. Linkage of water soluble polymers to relaxin polypeptides can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding, altered binding to one or more binding partners, and altered receptor dimerization or multimerization. The water soluble polymer may or may not have its own biological activity, and may be utilized as a linker for attaching relaxin to other substances, including but not limited to one or more relaxin polypeptides, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin.

As used herein, the term "polyalkylene glycol" or "poly (alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The term "aryl" means, unless otherwise stated, a polyunsaturated, aromatic, hydrocarbon substituent which can be a single ring or multiple rings (including but not limited to, from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, arylalkyl) includes both aryl and heteroaryl rings as defined above. Thus, the term "arylalkyl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy)propyl, and the like).

Each of the above terms (including but not limited to, "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", OC(O)R', —C(O)R', —CO2R', —CONR'R", —OC(O)NR'R", —NR"C(O)R', NR'C(O)NR"R'", —NR"C(O)2R', —NR—C(NR'R"R''')=NR"", NR C(NR'R")=NR', —S(O)R', —S(O)2R', —S(O)2NR'R", NRSO2R', —CN and —NO2 in a number ranging from zero to (2m'+1), where m' is the total number of carbon atoms in such a radical. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF3 and —CH2CF3) and acyl (including but not limited to, —C(O)CH3, —C(O)CF3, —C(O)CH2OCH3, and the like).

Similar to the substituents described for the alkyl radical, substituents for the aryl and heteroaryl groups are varied and are selected from, but are not limited to: halogen, OR', =O, =NR', =N—OR', —NR'R", —SR', -halogen, —SiR'R"R'", OC(O)R', —C(O)R', CO2R', —CONR'R", —OC(O)NR'R", —NR"C(O)R', NR' C(O)NR"R'", —NR"C(O)2R', NR—C(NR'R"R')=NR"", NR C(NR'R")=NR', —S(O)R', —S(O)2R', —S(O)2NR'R", NRSO2R', —CN and —NO2, —R', —N3, —CH(Ph)2, fluoro(C1-C4)alkoxy, and fluoro(C1-C4)alkyl, in a number ranging from zero to the total number of open valences on the aromatic ring system; and where R', R", R'" and R"" are independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

As used herein, the term "modulated serum half-life" means the positive or negative change in circulating half-life of a modified relaxin relative to its non-modified form. Serum half-life is measured by taking blood samples at various time points after administration of relaxin, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of relaxin, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule or an increase or decrease in receptor-mediated clearance of the molecule.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g., α-methyl alanine), D-amino acids, histidine-like amino acids (e.g., 2-amino-histidine, β-hydroxy-histidine, homohistidine, α-fluoromethyl-histidine and α-methyl-histidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class I-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:

| | |
|---|---|
| 1) | Alanine (A), Glycine (G); |
| 2) | Aspartic acid (D), Glutamic acid (E); |
| 3) | Asparagine (N), Glutamine (Q); |
| 4) | Arginine (R), Lysine (K); |
| 5) | Isoleucine (I), Leucine (L), Methionine (M), Valine (V); |
| 6) | Phenylalanine (F), Tyrosine (Y), Tryptophan (W); |
| 7) | Serine (S), Threonine (T); and |
| 8) | Cysteine (C), Methionine (M) |

(see, e.g., Creighton, Proteins: Structures and Molecular Properties (W H Freeman & Co.; 2nd edition (December 1993).

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

One example of an algorithm that is suitable for determining percent sequence identity and sequence similarity are the BLAST and BLAST 2.0 algorithms, which are described in Altschul et al. (1997) Nuc. Acids Res. 25:3389-3402, and Altschul et al. (1990) J. Mol. Biol. 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, PNA, or other nucleic acid mimics, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

The term "subject" as used herein, refers to an animal, in some embodiments a mammal, and in other embodiments a human, who is the object of treatment, observation or experiment. An animal may be a companion animal (e.g., dogs, cats, and the like), farm animal (e.g., cows, sheep, pigs, horses, and the like) or a laboratory animal (e.g., rats, mice, guinea pigs, and the like).

The term "effective amount" as used herein refers to that amount of the modified non-natural amino acid polypeptide being administered which will relieve to some extent one or more of the symptoms of the disease, condition or disorder being treated. Compositions containing the modified non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

In prophylactic applications, compositions containing the relaxin polypeptide are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

The term "protected" refers to the presence of a "protecting group" or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in or with the methods and compositions described herein, including photolabile groups such as Nvoc and MeNvoc. Other protecting groups known in the art may also be used in or with the methods and compositions described herein.

By way of example only, blocking/protecting groups may be selected from:

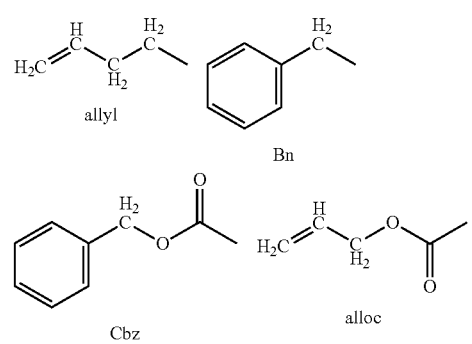

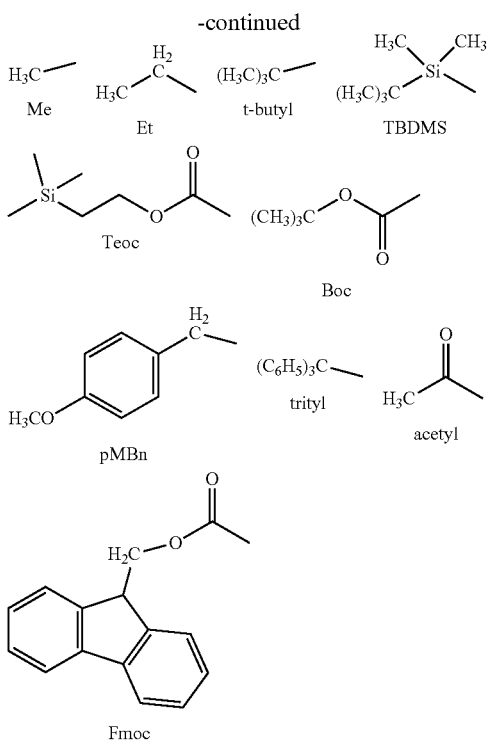

Other protecting groups are described in Greene and Wuts, Protective Groups in Organic Synthesis, 3rd Ed., John Wiley & Sons, New York, N.Y., 1999, which is incorporated herein by reference in its entirety.

In therapeutic applications, compositions containing the modified non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

Relaxin polypeptides of the present invention can be used to modulate vasoconstriction, NO production, ET-1, Ang II, and platelet aggregation. In one embodiment of the present invention, a patient in need thereof receives a therapeutic amount of relaxin polypeptides of the present invention that would decrease the patient's vasoconstriction over the baseline of their seeking treatment by 10%, 15%, 20%, 25%, 30%, 35%, 40%, 45%, 50%, 55%, 60%, 65%, 70%, 75%, 80%, 85%, 90%, 95%, 100%, more than 100%, 150%, more than 150%, 200%, more than 200%. In another embodiment of the present invention is a method of treatment of a patient in need thereof to increase the patient's NO production by administering a therapeutically effective amount of relaxin polypeptide to increase NO production by 10%, 15%, 20%, 25%, 30%, 35%, 40%, 45%, 50%, 55%, 60%, 65%, 70%, 75%, 80%, 85%, 90%, 95%, 100%, more than 100%, 150%, more than 150%, 200%, more than 200%.

In one embodiment of the present invention is a method of treatment of a patient in need thereof with a therapeutic amount of relaxin polypeptides of the present invention that decreases the patient's platelet aggregation by 10%, 15%, 20%, 25%, 30%, 35%, 40%, 45%, 50%, 55%, 60%, 65%, 70%, 75%, 80%, 85%, 90%, 95%, 100%, more than 100%, 150%, more than 150%, 200%, more than 200%. In another embodiment of the present invention is a method of treatment of a patient in need thereof with a therapeutic amount of relaxin polypeptides to decrease hypertrophy. In another embodiment of the present invention is a method of treatment of a patient in need thereof with a therapeutic amount of relaxin polypeptides of the present invention that decreases the patient's CF-stimulated protein synthesis by 10%, 15%, 20%, 25%, 30%, 35%, 40%, 45%, 50%, 55%, 60%, 65%, 70%, 75%, 80%, 85%, 90%, 95%, 100%, more than 100%, 150%, more than 150%, 200%, more than 200%. In another embodiment of the present invention is a method of treatment of a patient in need thereof to increase the patient's ANP expression by administering a therapeutically effective amount of relaxin polypeptide to increase NO production by 10%, 15%, 20%, 25%, 30%, 35%, 40%, 45%, 50%, 55%, 60%, 65%, 70%, 75%, 80%, 85%, 90%, 95%, 100%, more than 100%, 150%, more than 150%, 200%, more than 200%.

Present methods whereby a peg-relaxin of the present invention has a 10-fold increase in AUC as compared to a wild type relaxin 15-fold increase; more than 15-fold increase; 20-fold increase; more than 20-fold increase; 25 fold increase; more than 25-fold increase; 30-fold increase; more than 30-fold increase; 35-fold increase; more than 35-fold increase; 40-fold increase; more than 40-fold increase; 45-fold increase; more than 45-fold increase; 50-fold increase; more than 50-fold increase; 55-fold increase; more than 55-fold increase; 60-fold increase; more than 60-fold increase; 65-fold increase; more than 65-fold increase; 70-fold increase; more than 70-fold increase; 75-fold increase; more than 75-fold increase; 80-fold increase; more than 80-fold increase; 85-fold increase; more than 85-fold increase; 90-fold increase; more than 90-fold increase; 95-fold increase; more than 95-fold increase; 100-fold increase; more than 100-fold increase.

The term "treating" is used to refer to either prophylactic and/or therapeutic treatments.

Non-naturally encoded amino acid polypeptides presented herein may include isotopically-labelled compounds with one or more atoms replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as 2H, 3H, 13C, 14C, 15N, 18O, 17O, 35S, 18F, 36Cl, respectively. Certain isotopically-labelled compounds described herein, for example those into which radioactive isotopes such as 3H and 14C are incorporated, may be useful in drug and/or substrate tissue distribution assays. Further, substitution with isotopes such as deuterium, i.e., 2H, can afford certain therapeutic advantages resulting from greater metabolic stability, for example increased in vivo half-life or reduced dosage requirements.

All isomers including but not limited to diastereomers, enantiomers, and mixtures thereof are considered as part of the compositions described herein. In additional or further embodiments, the non-naturally encoded amino acid polypeptides are metabolized upon administration to an organism in need to produce a metabolite that is then used to produce a desired effect, including a desired therapeutic effect. In further or additional embodiments are active metabolites of non-naturally encoded amino acid polypeptides.

In some situations, non-naturally encoded amino acid polypeptides may exist as tautomers. In addition, the non-naturally encoded amino acid polypeptides described herein can exist in unsolvated as well as solvated forms with pharmaceutically acceptable solvents such as water, ethanol, and the like. The solvated forms are also considered to be disclosed herein. Those of ordinary skill in the art will recognize that some of the compounds herein can exist in several tautomeric forms. All such tautomeric forms are considered as part of the compositions described herein.

Unless otherwise indicated, conventional methods of mass spectroscopy, NMR, HPLC, protein chemistry, biochemistry, recombinant DNA techniques and pharmacology, within the skill of the art are employed.

DETAILED DESCRIPTION

I. Introduction

Relaxin polypeptides comprising at least one unnatural amino acid are provided in the invention. In certain embodiments of the invention, the relaxin polypeptide with at least one unnatural amino acid includes at least one post-translational modification. In one embodiment, the at least one post-translational modification comprises attachment of a molecule including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups. For example, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2]cycloaddition chemistry methodologies are utilized. In another example, the first reactive group is the azido moiety (including but not limited to, in the unnatural amino acid p-azido-L-phenylalanine) and the second reactive group is the alkynyl moiety. In certain embodiments of the modified relaxin polypeptide of the present invention, at least one unnatural amino acid (including but not limited to, unnatural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell. A linker, polymer, water soluble polymer, or other molecule may attach the molecule to the polypeptide. The molecule may be linked directly to the polypeptide.

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, glycosylation, acetylation, acylation, lipid-modification, palmitoylation, palmitate addition, phosphorylation, glycolipid-linkage modification, and the like.

In some embodiments, the relaxin polypeptide comprises one or more non-naturally encoded amino acids for glycosylation, acetylation, acylation, lipid-modification, palmitoylation, palmitate addition, phosphorylation, or glycolipid-linkage modification of the polypeptide. In some embodiments, the relaxin polypeptide comprises one or more non-naturally encoded amino acids for glycosylation of the polypeptide. In some embodiments, the relaxin polypeptide comprises one or more naturally encoded amino acids for glycosylation, acetylation, acylation, lipid-modification, palmitoylation, palmitate addition, phosphorylation, or glycolipid-linkage modification of the polypeptide. In some embodiments, the relaxin polypeptide comprises one or more naturally encoded amino acids for glycosylation of the polypeptide.

In some embodiments, the relaxin polypeptide comprises one or more non-naturally encoded amino acid additions and/or substitutions that enhance glycosylation of the polypeptide. In some embodiments, the relaxin polypeptide comprises one or more deletions that enhance glycosylation of the polypeptide. In some embodiments, the relaxin polypeptide comprises one or more non-naturally encoded amino acid additions and/or substitutions that enhance glycosylation at a different amino acid in the polypeptide. In some embodiments, the relaxin polypeptide comprises one or more deletions that enhance glycosylation at a different amino acid in the polypeptide. In some embodiments, the relaxin polypeptide comprises one or more non-naturally encoded amino acid additions and/or substitutions that enhance glycosylation at a non-naturally encoded amino acid in the polypeptide. In some embodiments, the relaxin polypeptide comprises one or more non-naturally encoded amino acid additions and/or substitutions that enhance glycosylation at a naturally encoded amino acid in the polypeptide. In some embodiments, the relaxin polypeptide comprises one or more naturally encoded amino acid additions and/or substitutions that enhance glycosylation at a different amino acid in the polypeptide. In some embodiments, the relaxin polypeptide comprises one or more non-naturally encoded amino acid additions and/or substitutions that enhance glycosylation at a naturally encoded amino acid in the polypeptide. In some embodiments, the relaxin polypeptide comprises one or more non-naturally encoded amino acid additions and/or substitutions that enhance glycosylation at a non-naturally encoded amino acid in the polypeptide.

In one embodiment, the post-translational modification comprises attachment of an oligosaccharide to an asparagine by a GlcNAc-asparagine linkage (including but not limited to, where the oligosaccharide comprises (GlcNAc-Man)2-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence, an epitope tag, a FLAG tag, a polyhistidine tag, a GST fusion, and/or the like. Examples of secretion signal sequences include, but are not limited to, a prokaryotic secretion signal sequence, a eukaryotic secretion signal sequence, a eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences, include, but are not limited to, STII (prokaryotic), Fd GIII and M13 (phage), Bgl2 (yeast), and the signal sequence bla derived from a transposon. Any such sequence may be modified to provide a desired result with the polypeptide, including but not limited to, substituting one signal sequence with a different signal sequence, substituting a leader sequence with a different leader sequence, etc.

The protein or polypeptide of interest can contain at least one, at least two, at least three, at least four, at least five, at least six, at least seven, at least eight, at least nine, or ten or more unnatural amino acids. The unnatural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein is substituted with an unnatural amino acid.

The present invention provides methods and compositions based on relaxin comprising at least one non-naturally encoded amino acid. Introduction of at least one non-naturally encoded amino acid into relaxin can allow for the application of conjugation chemistries that involve specific chemical reactions, including, but not limited to, with one or more non-naturally encoded amino acids while not reacting with the commonly occurring 20 amino acids. In some embodiments, relaxin comprising the non-naturally encoded amino acid is linked to a water soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the non-naturally encoded amino acid. Known chemistry methodologies of a wide variety are suitable for use in the present invention to incorporate a water soluble polymer into the protein. Such methodologies include but are not limited to a Huisgen [3+2] cycloaddition reaction (see, e.g., Padwa, A. in Comprehensive Organic Synthesis, Vol. 4, (1991) Ed. Trost, B. M., Pergamon, Oxford, p. 1069-1109; and, Huisgen, R. in 1,3-Dipolar Cycloaddition Chemistry, (1984) Ed. Padwa, A., Wiley, New York, p. 1-176) with, including but not limited to, acetylene or azide derivatives, respectively.

Because the Huisgen [3+2] cycloaddition method involves a cycloaddition rather than a nucleophilic substitution reaction, proteins can be modified with extremely high selectivity. The reaction can be carried out at room temperature in aqueous conditions with excellent regioselectivity (1,4>1,5) by the addition of catalytic amounts of Cu(I) salts to the reaction mixture. See, e.g., Tornoe, et al., (2002) J. Org. Chem. 67:3057-3064; and, Rostovtsev, et al., (2002) Angew. Chem. Int. Ed. 41:2596-2599; and WO 03/101972. A molecule that can be added to a protein of the invention through a [3+2] cycloaddition includes virtually any molecule with a suitable functional group or substituent including but not limited to an azido or acetylene derivative. These molecules can be added to an unnatural amino acid with an acetylene group, including but not limited to, p-propargyloxyphenylalanine, or azido group, including but not limited to p-azido-phenylalanine, respectively.

The five-membered ring that results from the Huisgen [3+2] cycloaddition is not generally reversible in reducing environments and is stable against hydrolysis for extended periods in aqueous environments. Consequently, the physical and chemical characteristics of a wide variety of substances can be modified under demanding aqueous conditions with the active PEG derivatives of the present invention. Even more importantly, because the azide and acetylene moieties are specific for one another (and do not, for example, react with any of the 20 common, genetically-encoded amino acids), proteins can be modified in one or more specific sites with extremely high selectivity.

The invention also provides water soluble and hydrolytically stable derivatives of PEG derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon.

More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

The present invention provides conjugates of substances having a wide variety of functional groups, substituents or moieties, with other substances including but not limited to a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor;

a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. The present invention also includes conjugates of substances having azide or acetylene moieties with PEG polymer derivatives having the corresponding acetylene or azide moieties. For example, a PEG polymer containing an azide moiety can be coupled to a biologically active molecule at a position in the protein that contains a non-genetically encoded amino acid bearing an acetylene functionality. The linkage by which the PEG and the biologically active molecule are coupled includes but is not limited to the Huisgen [3+2] cycloaddition product.

It is well established in the art that PEG can be used to modify the surfaces of biomaterials (see, e.g., U.S. Pat. No. 6,610,281; Mehvar, R., J. Pharm Pharm Sci., 3(1):125-136 (2000) which are incorporated by reference herein). The invention also includes biomaterials comprising a surface having one or more reactive azide or acetylene sites and one or more of the azide- or acetylene-containing polymers of the invention coupled to the surface via the Huisgen [3+2] cycloaddition linkage. Biomaterials and other substances can also be coupled to the azide- or acetylene-activated polymer derivatives through a linkage other than the azide or acetylene linkage, such as through a linkage comprising a carboxylic acid, amine, alcohol or thiol moiety, to leave the azide or acetylene moiety available for subsequent reactions.

The invention includes a method of synthesizing the azide- and acetylene-containing polymers of the invention. In the case of the azide-containing PEG derivative, the azide can be bonded directly to a carbon atom of the polymer. Alternatively, the azide-containing PEG derivative can be prepared by attaching a linking agent that has the azide moiety at one terminus to a conventional activated polymer so that the resulting polymer has the azide moiety at its terminus. In the case of the acetylene-containing PEG derivative, the acetylene can be bonded directly to a carbon atom of the polymer. Alternatively, the acetylene-containing PEG derivative can be prepared by attaching a linking agent that has the acetylene moiety at one terminus to a conventional activated polymer so that the resulting polymer has the acetylene moiety at its terminus.

More specifically, in the case of the azide-containing PEG derivative, a water soluble polymer having at least one active hydroxyl moiety undergoes a reaction to produce a substituted polymer having a more reactive moiety, such as a mesylate, tresylate, tosylate or halogen leaving group, thereon. The preparation and use of PEG derivatives containing sulfonyl acid halides, halogen atoms and other leaving groups are known to those of ordinary skill in the art. The resulting substituted polymer then undergoes a reaction to substitute for the more reactive moiety an azide moiety at the terminus of the polymer. Alternatively, a water soluble polymer having at least one active nucleophilic or electrophilic moiety undergoes a reaction with a linking agent that has an azide at one terminus so that a covalent bond is formed between the PEG polymer and the linking agent and the azide moiety is positioned at the terminus of the polymer. Nucleophilic and electrophilic moieties, including amines, thiols, hydrazides, hydrazines, alcohols, carboxylates, aldehydes, ketones, thioesters and the like, are known to those of ordinary skill in the art.

More specifically, in the case of the acetylene-containing PEG derivative, a water soluble polymer having at least one active hydroxyl moiety undergoes a reaction to displace a halogen or other activated leaving group from a precursor that contains an acetylene moiety. Alternatively, a water soluble polymer having at least one active nucleophilic or electrophilic moiety undergoes a reaction with a linking agent that has an acetylene at one terminus so that a covalent bond is formed between the PEG polymer and the linking agent and the acetylene moiety is positioned at the terminus of the polymer. The use of halogen moieties, activated leaving group, nucleophilic and electrophilic moieties in the context of organic synthesis and the preparation and use of PEG derivatives is well established to practitioners in the art.

The invention also provides a method for the selective modification of proteins to add other substances to the modified protein, including but not limited to water soluble polymers such as PEG and PEG derivatives containing an azide or acetylene moiety. The azide- and acetylene-containing PEG derivatives can be used to modify the properties of surfaces and molecules where biocompatibility, stability, solubility and lack of immunogenicity are important, while at the same time providing a more selective means of attaching the PEG derivatives to proteins than was previously known in the art.

General Recombinant Nucleic Acid Methods for Use with the Invention

In numerous embodiments of the present invention, nucleic acids encoding a relaxin polypeptide of interest will be isolated, cloned and often altered using recombinant methods. Such embodiments are used, including but not limited to, for protein expression or during the generation of variants, derivatives, expression cassettes, or other sequences derived from a relaxin polypeptide. In some embodiments, the sequences encoding the polypeptides of the invention are operably linked to a heterologous promoter.

A nucleotide sequence encoding a relaxin polypeptide comprising a non-naturally encoded amino acid may be synthesized on the basis of the amino acid sequence of the parent polypeptide, including but not limited to, having the amino acid sequence shown in SEQ ID NO: 1 and SEQ ID NO: 2 and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced.

This invention utilizes routine techniques in the field of recombinant genetics. Basic texts disclosing the general methods of use in this invention include Sambrook et al., Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)).

General texts which describe molecular biological techniques include Berger and Kimmel, Guide to Molecular Cloning Techniques, Methods in Enzymology volume 152 Academic Press, Inc., San Diego, Calif. (Berger); Sambrook et al., Molecular Cloning A Laboratory Manual (2nd Ed.), Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, including but not limited to, the generation of genes or polynucleotides that include selector codons for production of proteins that include unnatural amino acids, orthogonal tRNAs, orthogonal synthetases, and pairs thereof.

Various types of mutagenesis are used in the invention for a variety of purposes, including but not limited to, to produce novel synthetases or tRNAs, to mutate tRNA molecules, to mutate polynucleotides encoding synthetases, to produce libraries of tRNAs, to produce libraries of synthetases, to produce selector codons, to insert selector codons that encode unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, PCT-mediated mutagenesis, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the present invention. In one embodiment, mutagenesis can be guided by known information of the naturally occurring molecule or altered or mutated naturally occurring molecule, including but not limited to, sequence, sequence comparisons, physical properties, secondary, tertiary, or quaternary structure, crystal structure or the like.

The texts and examples found herein describe these procedures. Additional information is found in the following publications and references cited within: Ling et al., Approaches to DNA mutagenesis: an overview, Anal Biochem. 254(2): 157-178 (1997); Dale et al., Oligonucleotide-directed random mutagenesis using the phosphorothioate method, Methods Mol. Biol. 57:369-374 (1996); Smith, In vitro mutagenesis, Ann. Rev. Genet. 19:423-462 (1985); Botstein & Shortle, Strategies and applications of in vitro mutagenesis, Science 229:1193-1201 (1985); Carter, Site-directed mutagenesis, Biochem. J. 237:1-7 (1986); Kunkel, The efficiency of oligonucleotide directed mutagenesis, in Nucleic Acids & Molecular Biology (Eckstein, F. and Lilley, D. M. J. eds., Springer Verlag, Berlin) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382 (1987); Bass et al., Mutant Trp repressors with new DNA-binding specificities, Science 242:240-245 (1988); Zoller & Smith, Oligonucleotide-directed mutagenesis using M13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8785 (1985); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Sayers et al., 5'-3' Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Improved enzymatic in vitro reactions in the gapped duplex DNA approach to oligonucleotide-directed construction of mutations, Nucl. Acids Res. 16: 7207 (1988); Fritz et al., Oligonucleotide-directed construction of mutations: a gapped duplex DNA procedure without enzymatic reactions in vitro, Nucl. Acids Res. 16: 6987-6999 (1988); Kramer et al., Different base/base mismatches are corrected with different efficiencies by the methyl-directed DNA mismatch-repair system of *E. coli*, Cell 38:879-887 (1984); Carter et al., Improved oligonucleotide site-directed mutagenesis using M13 vectors, Nucl. Acids Res. 13: 4431-4443 (1985); Carter, Improved oligonucleotide-directed mutagenesis using M13 vectors, Methods in Enzymol. 154: 382-403 (1987); Eghtedarzadeh & Henikoff, Use of oligonucleotides to generate large deletions, Nucl. Acids Res. 14: 5115 (1986); Wells et al., Importance of hydrogen-bond formation in stabilizing the transition state of subtilisin, Phil. Trans. R. Soc. Lond. A 317: 415-423 (1986); Nambiar et al., Total synthesis and cloning of a gene coding for the ribonuclease S protein, Science 223: 1299-1301 (1984); Sakmar and Khorana, Total synthesis and expression of a gene for the alpha-subunit of bovine rod outer segment guanine nucleotide-binding protein (transducin), Nucl. Acids Res. 14: 6361-6372 (1988); Wells et al., Cassette mutagenesis: an efficient method for generation of multiple mutations at defined sites, Gene 34:315-323 (1985); Grundstrom et al., Oligonucleotide-directed mutagenesis by microscale 'shot-gun' gene synthesis, Nucl. Acids Res. 13: 3305-3316 (1985); Mandecki, Oligonucleotide-directed double-strand break repair in plasmids of *Escherichia coli*: a method for site-specific mutagenesis, Proc. Natl. Acad. Sci. USA, 83:7177-7181 (1986); Arnold, Protein engineering for unusual environments, Current Opinion in Biotechnology 4:450-455 (1993); Sieber, et al., Nature Biotechnology, 19:456-460 (2001); W. P. C. Stemmer, Nature 370, 389-91 (1994); and, I. A. Lorimer, I. Pastan, Nucleic Acids Res. 23, 3067-8 (1995). Additional details on many of the above methods can be found in Methods in Enzymology Volume 154, which also describes useful controls for trouble-shooting problems with various mutagenesis methods.

Oligonucleotides, e.g., for use in mutagenesis of the present invention, e.g., mutating libraries of synthetases, or altering tRNAs, are typically synthesized chemically according to the solid phase phosphoramidite triester method described by Beaucage and Caruthers, Tetrahedron Letts. 22(20):1859-1862, (1981) e.g., using an automated synthesizer, as described in Needham-VanDevanter et al., Nucleic Acids Res., 12:6159-6168 (1984).

The invention also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. The vector can be, for example, in the form of a plasmid, a cosmid, a phage, a bacterium, a virus, a naked polynucleotide, or a conjugated polynucleotide. The vectors are introduced into cells and/or microorganisms by standard methods including electroporation (Fromm et al., Proc. Natl. Acad. Sci. USA 82, 5824 (1985)), infection by viral vectors, high velocity ballistic penetration by small particles with the nucleic acid either within the matrix of small beads or particles, or on the surface (Klein et al., Nature 327, 70-73 (1987)), and/or the like. Techniques suitable for the transfer of nucleic acid into cells in vitro include the use of liposomes, microinjection, cell fusion, DEAE-dextran, the calcium phosphate precipitation method, etc. In vivo gene transfer techniques include, but are not limited to, transfection with viral (typically retroviral) vectors and viral coat protein-liposome mediated transfection [Dzau et al., Trends in Biotechnology 11:205-210 (1993)]. In some situations it may be desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life.

The engineered host cells can be cultured in conventional nutrient media modified as appropriate for such activities as, for example, screening steps, activating promoters or selecting transformants. These cells can optionally be cultured into transgenic organisms. Other useful references, including but not limited to for cell isolation and culture (e.g., for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg New York) and Atlas and Parks (eds.) The Handbook of Microbiological Media (1993) CRC Press, Boca Raton, Fla.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, kits are commercially available for the purification of plasmids from bacteria, (see, e.g., EasyPrep™, FlexiPrep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or both. See, Gillam & Smith, Gene 8:81 (1979); Roberts, et al., Nature, 328:731 (1987); Schneider, E., et al., Protein Expr. Purif. 6(1):10-14 (1995); Ausubel, Sambrook, Berger (all supra). A catalogue of bacteria and bacteriophages useful for cloning is provided, e.g., by the ATCC, e.g., The ATCC Catalogue of Bacteria and Bacteriophage (1992) Gherna et al. (eds) published by the ATCC. Additional basic procedures for sequencing, cloning and other aspects of molecular biology and underlying theoretical considerations are also found in Watson et al. (1992) Recombinant DNA Second Edition Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. available on the World Wide Web at mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

Selector Codons

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), an ochre codon, or an opal codon (UGA), an unnatural codon, a four or more base codon, a rare codon, or the like. It is readily apparent to those of ordinary skill in the art that there is a wide range in the number of selector codons that can be introduced into a desired gene or polynucleotide, including but not limited to, one or more, two or more, three or more, 4, 5, 6, 7, 8, 9, 10 or more in a single polynucleotide encoding at least a portion of the relaxin polypeptide. It is also readily apparent to those of ordinary skill in the art that there is a wide range in the number of selector codons that can be introduced into a desired gene or polynucleotide, including but not limited to, one or more, two or more, three or more, 4, 5, 6, 7, 8, 9, 10 or more total found in the A chain and B chain polynucleotide sequences encoding at least a portion of the relaxin polypeptide.

In one embodiment, the methods involve the use of a selector codon that is a stop codon for the incorporation of one or more unnatural amino acids in vivo. For example, an O-tRNA is produced that recognizes the stop codon, including but not limited to, UAG, and is aminoacylated by an O-RS with a desired unnatural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), 5'-3' Exonucleases in phosphorothioate-based oligonucleotide-directed mutagenesis. Nucleic Acids Res, 16:791-802. When the O-RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., Biochemistry, 32:7939 (1993). In this case, the synthetic tRNA competes with the naturally occurring tRNAArg, which exists as a minor species in Escherichia coli. Some organisms do not use all triplet codons. An unassigned codon AGA in Micrococcus luteus has been utilized for insertion of amino acids in an in vitro transcription/translation extract. See, e.g., Kowal and Oliver, Nucl. Acid. Res., 25:4685 (1997). Components of the present invention can be generated to use these rare codons in vivo.

Selector codons also comprise extended codons, including but not limited to, four or more base codons, such as, four, five, six or more base codons. Examples of four base codons include, but are not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple unnatural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple unnatural amino acids can be encoded in the same cell using a four or more base codon. See, Anderson et al., (2002) Exploring the Limits of Codon and Anticodon Size, Chemistry and Biology, 9:237-244; Magliery, (2001) Expanding the Genetic Code: Selection of Efficient Suppressors of Four-base Codons and Identification of "Shifty" Four-base Codons with a Library Approach in Escherichia coli, J. Mol. Biol. 307: 755-769.

For example, four-base codons have been used to incorporate unnatural amino acids into proteins using in vitro biosynthetic methods. See, e.g., Ma et al., (1993) Biochemistry, 32:7939; and Hohsaka et al., (1999) J. Am. Chem. Soc., 121:34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) J. Am. Chem. Soc., 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) J. Mol. Biol., 298:195. In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) An unnatural base pair for incorporating amino acid analogues into protein, Nature Biotechnology, 20:177-182. See, also, Wu, Y., et al., (2002) J. Am. Chem. Soc. 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) J. Am. Chem. Soc., 111:8322; and Piccirilli et al., (1990) Nature, 343:33; Kool, (2000) Curr. Opin. Chem. Biol., 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) Curr. Opin. Chem. Biol., 4:602; and Guckian and Kool, (1998) Angew. Chem. Int. Ed. Engl., 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) J. Am. Chem. Soc., 121:11585-6; and Ogawa et al., (2000) J. Am. Chem. Soc., 122:3274. A 3MN:3MN self-pair can be synthesized by KF with efficiency and selectivity sufficient for biological function. See, e.g., Ogawa et al., (2000) J. Am. Chem. Soc., 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) J. Am. Chem. Soc., 123:7439. A novel metallobase pair, Dipic:Py, has also been developed, which forms a stable pair upon binding Cu(II). See, Meggers et al., (2000) J. Am. Chem. Soc., 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods known to one of ordinary skill in the art and described herein to include, for example, one or more selector codon for the incorporation of an unnatural amino acid. For example, a nucleic acid for a protein of interest is mutagenized to include one or more selector codon, providing for the incorporation of one or more unnatural amino acids. The invention includes any such variant, including but not limited to, mutant, versions of any protein, for example, including at least one unnatural amino acid. Similarly, the invention also includes corresponding nucleic acids, i.e., any nucleic acid with one or more selector codon that encodes one or more unnatural amino acid.

Nucleic acid molecules encoding a protein of interest such as a relaxin polypeptide may be readily mutated to introduce a cysteine at any desired position of the polypeptide. Cysteine is widely used to introduce reactive molecules, water soluble polymers, proteins, or a wide variety of other molecules, onto a protein of interest. Methods suitable for the incorporation of cysteine into a desired position of a polypeptide are known to those of ordinary skill in the art, such as those described in U.S. Pat. No. 6,608,183, which is incorporated by reference herein, and standard mutagenesis techniques.

Non-Naturally Encoded Amino Acids

A very wide variety of non-naturally encoded amino acids are suitable for use in the present invention. Any number of non-naturally encoded amino acids can be introduced into a relaxin polypeptide. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, a relaxin polypeptide that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2] cycloaddition product.

The generic structure of an alpha-amino acid is illustrated as follows (Formula I):

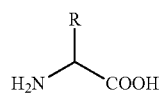

A non-naturally encoded amino acid is typically any structure having the above-listed formula wherein the R group is any substituent other than one used in the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides.

However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). See, also, U.S. Pat. Nos. 7,045,337 and 7,083,970, which are incorporated by reference herein. In addition to unnatural amino acids that contain novel side chains, unnatural amino acids that may be suitable for use in the present invention also optionally comprise modified backbone structures, including but not limited to, as illustrated by the structures of Formula II and III:

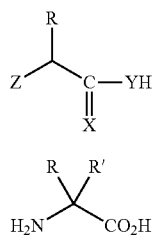

wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a C 6-C20 straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, g-substituted derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAc b-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) Incorporation of azides into recombinant proteins for chemoselective modification by the Staudinger ligation, PNAS 99:19-24, which is incorporated by reference herein, for additional methionine analogs. International Application No. PCT/US06/47822 entitled "Compositions Containing, Methods Involving, and Uses of Non-natural Amino Acids and Polypeptides," which is incorporated by reference herein, describes reductive alkylation of an aromatic amine moieties, including but not limited to, p-amino-phenylalanine and reductive amination.

In one embodiment, compositions of relaxin polypeptide that include an unnatural amino acid (such as p-(propargyloxy)-phenalanine) are provided. Various compositions comprising p-(propargyloxy)-phenylalanine and, including but not limited to, proteins and/or cells, are also provided. In one aspect, a composition that includes the p-(propargyloxy)-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

The chemical moieties via unnatural amino acids that can be incorporated into proteins offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. Photoreactive unnatural amino acids (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a [3+2]cycloaddition reaction.

A non-natural amino acid incorporated into a polypeptide at the amino terminus can be composed of an R group that is any substituent other than one used in the twenty natural amino acids and a 2nd reactive group different from the NH2 group normally present in α-amino acids (see Formula I). A similar non-natural amino acid can be incorporated at the carboxyl terminus with a 2nd reactive group different from the COOH group normally present in α-amino acids (see Formula I).

The unnatural amino acids of the invention may be selected or designed to provide additional characteristics unavailable in the twenty natural amino acids. For example, unnatural amino acid may be optionally designed or selected to modify the biological properties of a protein, e.g., into which they are incorporated. For example, the following properties may be optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

Structure and Synthesis of Non-Natural Amino Acids: Carbonyl, Carbonyl-Like, Masked Carbonyl, Protected Carbonyl Groups, and Hydroxylamine Groups In some embodiments the present invention provides relaxin linked to a water soluble polymer, e.g., a PEG, by an oxime bond.

Many types of non-naturally encoded amino acids are suitable for formation of oxime bonds. These include, but are not limited to, non-naturally encoded amino acids containing a carbonyl, dicarbonyl, or hydroxylamine group. Such amino acids are described in U.S. Patent Publication Nos. 2006/0194256, 2006/0217532, and 2006/0217289 and WO 2006/069246 entitled "Compositions containing, methods involving, and uses of non-natural amino acids and polypeptides," which are incorporated herein by reference in their entirety. Non-naturally encoded amino acids are also described in U.S. Pat. Nos. 7,083,970 and 7,045,337, which are incorporated by reference herein in their entirety.

Some embodiments of the invention utilize relaxin polypeptides that are substituted at one or more positions with a para-acetylphenylalanine amino acid. The synthesis of p-acetyl-(+/−)-phenylalanine and m-acetyl-(+/−)-phenylalanine are described in Zhang, Z., et al., Biochemistry 42: 6735-6746 (2003), incorporated by reference. Other carbonyl- or dicarbonyl-containing amino acids can be similarly prepared by one of ordinary skill in the art. Further, non-limiting examplary syntheses of non-natural amino acid that are included herein are presented in FIGS. 4, 24-34 and 36-39 of U.S. Pat. No. 7,083,970, which is incorporated by reference herein in its entirety.

Amino acids with an electrophilic reactive group allow for a variety of reactions to link molecules via nucleophilic addition reactions among others. Such electrophilic reactive groups include a carbonyl group (including a keto group and a dicarbonyl group), a carbonyl-like group (which has reactivity similar to a carbonyl group (including a keto group and a dicarbonyl group) and is structurally similar to a carbonyl group), a masked carbonyl group (which can be readily converted into a carbonyl group (including a keto group and a dicarbonyl group)), or a protected carbonyl group (which has reactivity similar to a carbonyl group (including a keto group and a dicarbonyl group) upon deprotection). Such amino acids include amino acids having the structure of Formula (IV):

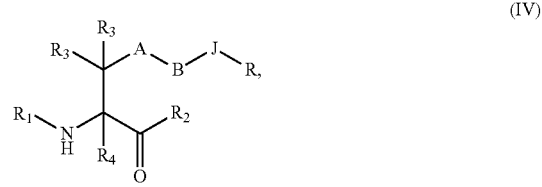

(IV)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

J is

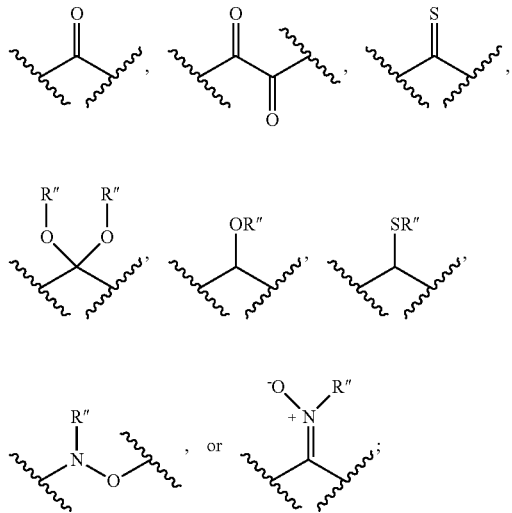

R is H, alkyl, substituted alkyl, cycloalkyl, or substituted cycloalkyl;

each R" is independently H, alkyl, substituted alkyl, or a protecting group, or when more than one R" group is present, two R" optionally form a heterocycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

with a proviso that when A is phenylene and each $R_3$ is H, B is present; and that when A is —(CH$_2$)$_4$— and each $R_3$ is H, B is not —NHC(O)(CH$_2$CH$_2$)—; and that when A and B are absent and each $R_3$ is H, R is not methyl.

In addition, having the structure of Formula (V) are included:

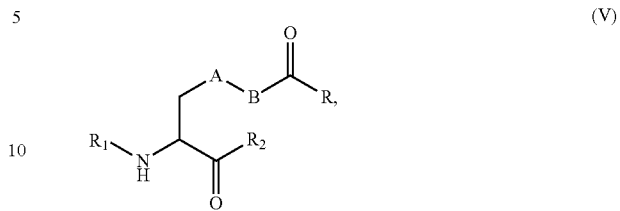

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

with a proviso that when A is phenylene, B is present; and that when A is —(CH$_2$)$_4$—, B is not —NHC(O)(CH$_2$CH$_2$)—; and that when A and B are absent, R is not methyl.

In addition, amino acids having the structure of Formula (VI) are included:

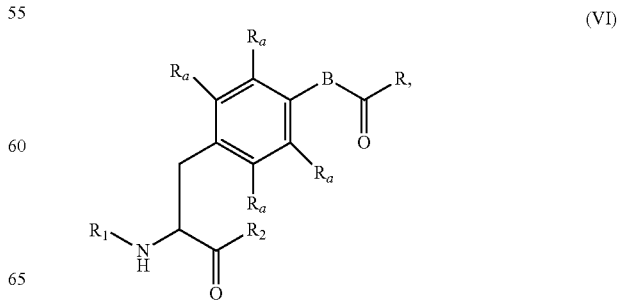

wherein:

B is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, the following amino acids are included:

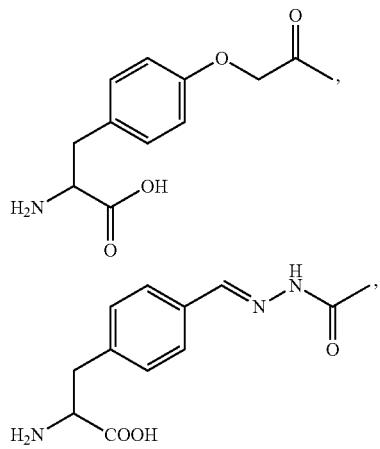

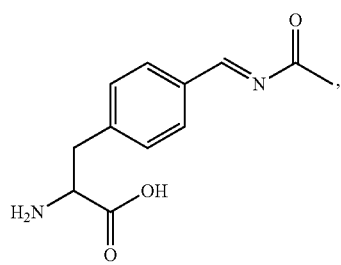

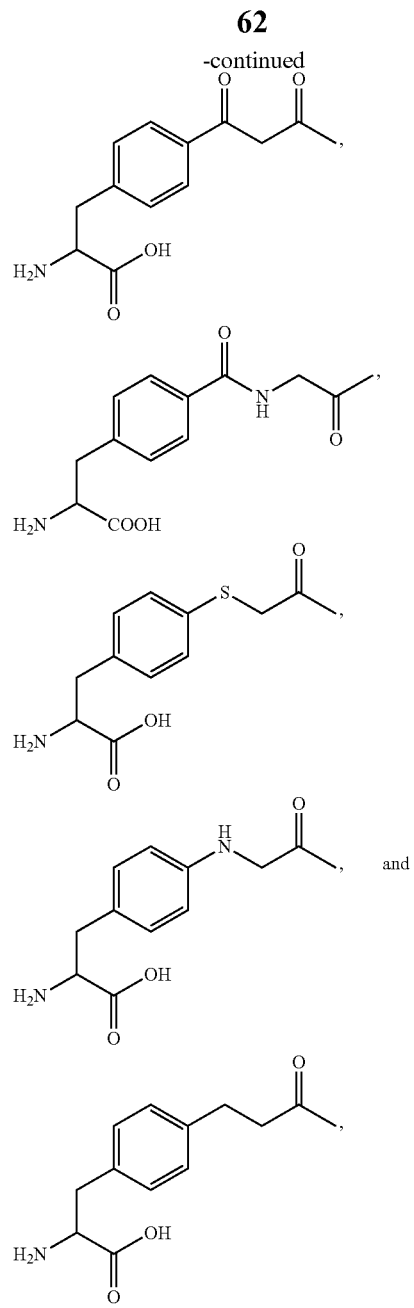

wherein such compounds are optionally amino protected group, carboxyl protected or a salt thereof. In addition, any of the following non-natural amino acids may be incorporated into a non-natural amino acid polypeptide.

In addition, the following amino acids having the structure of Formula (VII) are included:

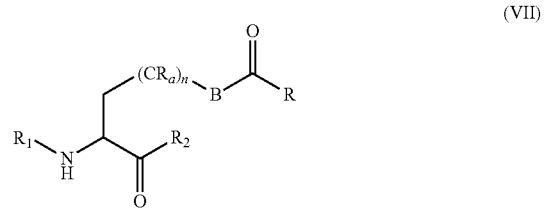

(VII)

wherein
B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide; each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8; with a proviso that when A is —(CH$_2$)$_4$—, B is not —NHC(O)(CH$_2$CH$_2$)—.

In addition, the following amino acids are included:

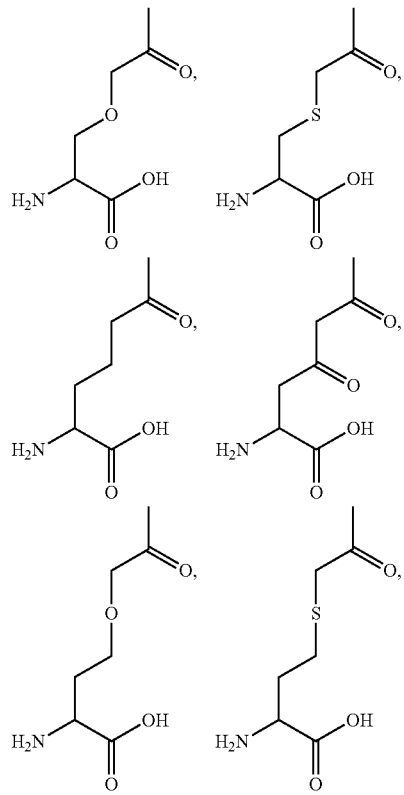

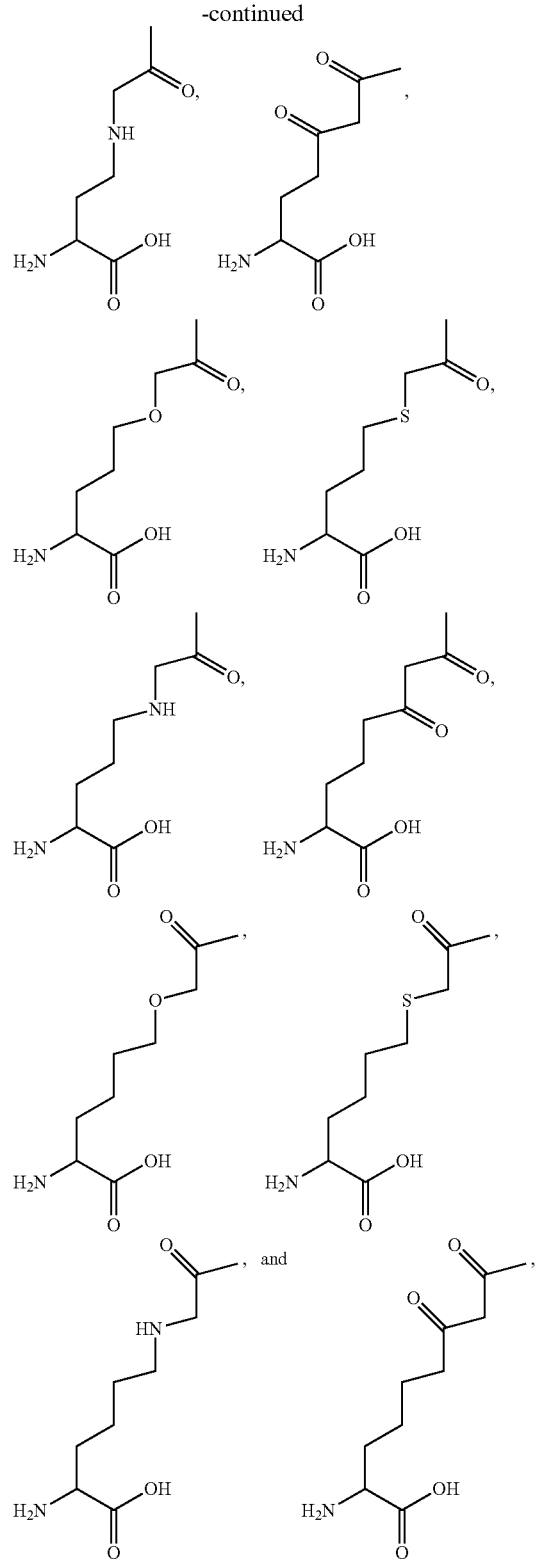

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (VIII) are included:

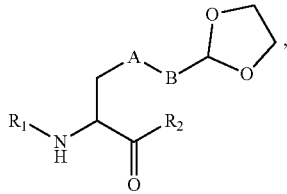
(VIII)

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide.

In addition, the following amino acids having the structure of Formula (IX) are included:

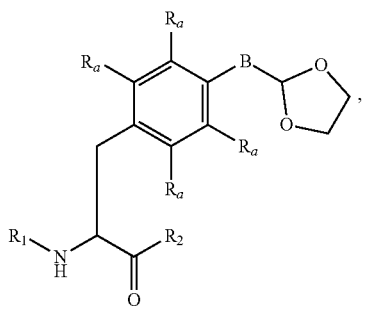
(IX)

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide;

wherein each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, the following amino acids are included:

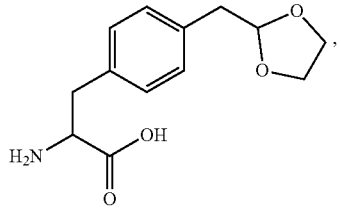

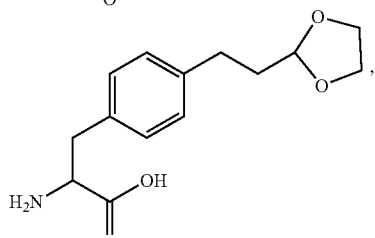

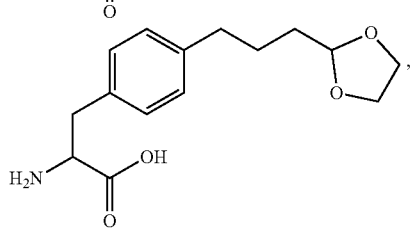

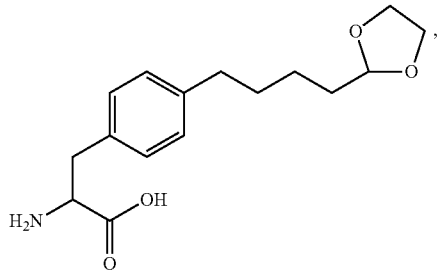

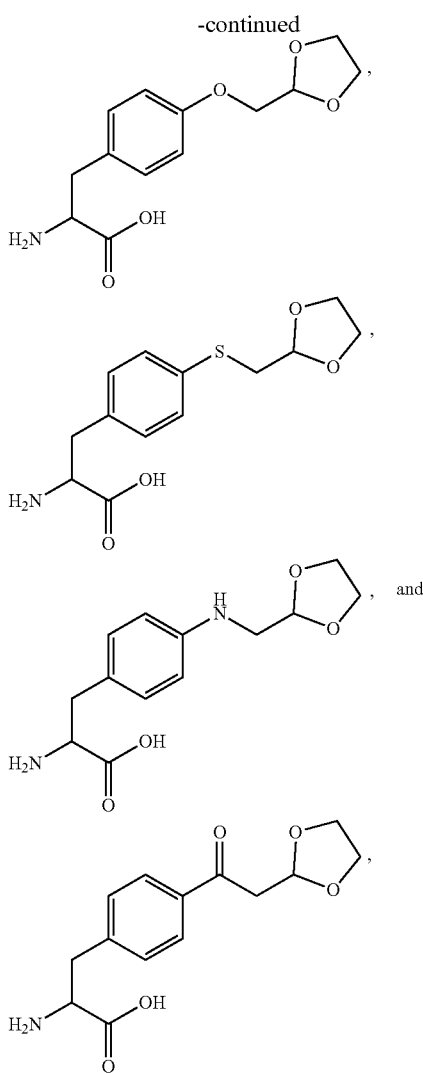

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (X) are included:

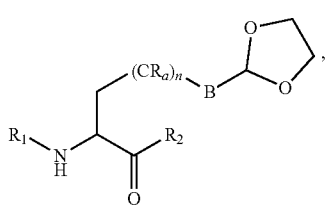

(X)

wherein B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

R1 is optional, and when present, is H, an amino protecting group, resin, amino acid, polypeptide, or polynucleotide; and R2 is optional, and when present, is OH, an ester protecting group, resin, amino acid, polypeptide, or polynucleotide;

each Ra is independently selected from the group consisting of H, halogen, alkyl, substituted alkyl, —N(R')2, —C(O)kR' where k is 1, 2, or 3, —C(O)N(R')2, —OR', and —S(O)kR', where each R' is independently H, alkyl, or substituted alkyl; and n is 0 to 8.

In addition, the following amino acids are included:

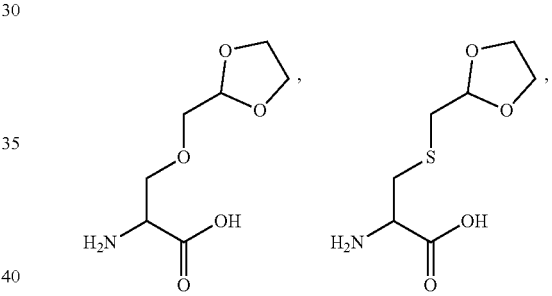

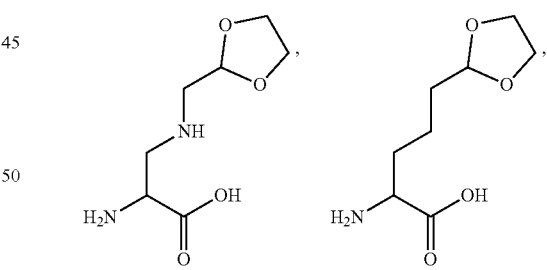

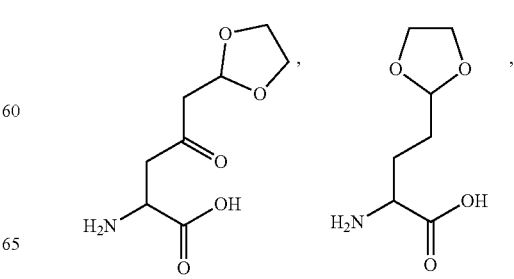

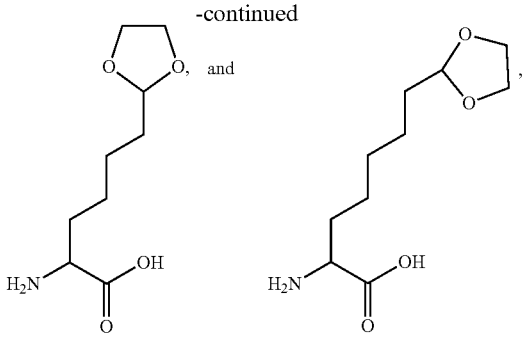

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition to monocarbonyl structures, the non-natural amino acids described herein may include groups such as dicarbonyl, dicarbonyl like, masked dicarbonyl and protected dicarbonyl groups.

For example, the following amino acids having the structure of Formula (XI) are included:

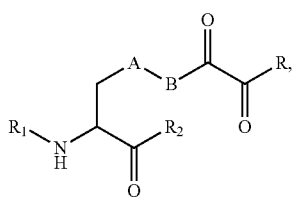

(XI)

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
B is optional, and when present is a linker selected from the group consisting of lower alkylene, substituted lower alkylene, lower alkenylene, substituted lower alkenylene, lower heteroalkylene, substituted lower heteroalkylene, —O—, 0-(alkylene or substituted alkylene)-, —S—, S-(alkylene or substituted alkylene)-, —S(O)k- where k is 1, 2, or 3, —S(O)k(alkylene or substituted alkylene)-, C(O)—, C(O)-(alkylene or substituted alkylene)-, —C(S)—, C(S)-(alkylene or substituted alkylene)-, —N(R')—, NR'-(alkylene or substituted alkylene)-, C(O)N(R')—, CON(R')-(alkylene or substituted alkylene)-, —CSN(R')—, CSN(R')-(alkylene or substituted alkylene)-, N(R')CO-(alkylene or substituted alkylene)-, N(R')C(O)O—, S(O)kN(R')—, N(R')C(O)N(R')—, N(R')C(S)N(R')—, N(R')S(O)kN(R')—, N(R')—N═, —C(R')═N—, —C(R')═N—N(R')—, —C(R')═N—N═, C(R')2-N═N—, and C(R')2 N(R') N(R')—, where each R' is independently H, alkyl, or substituted alkyl;
R is H, alkyl, substituted alkyl, cycloalkyl, or substituted cycloalkyl;

R1 is optional, and when present, is H, an amino protecting group, resin, amino acid, polypeptide, or polynucleotide; and
R2 is optional, and when present, is OH, an ester protecting group, resin, amino acid, polypeptide, or polynucleotide.

In addition, the following amino acids having the structure of Formula (XII) are included:

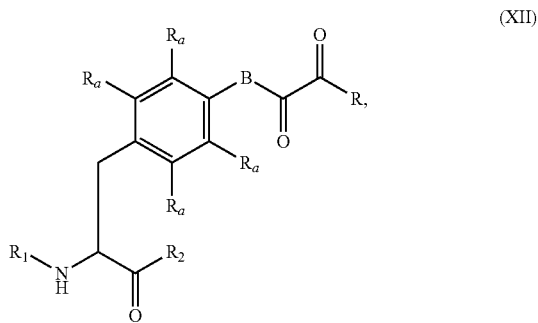

(XII)

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;
R is H, alkyl, substituted alkyl, cycloalkyl, or substituted cycloalkyl;
R1 is optional, and when present, is H, an amino protecting group, resin, amino acid, polypeptide, or polynucleotide; and
R2 is optional, and when present, is OH, an ester protecting group, resin, amino acid, polypeptide, or polynucleotide;
wherein each Ra is independently selected from the group consisting of H, halogen, alkyl, substituted alkyl, —N(R')2, —C(O)kR' where k is 1, 2, or 3, —C(O)N(R')2, —OR', and —S(O)kR', where each R' is independently H, alkyl, or substituted alkyl.

In addition, the following amino acids are included:

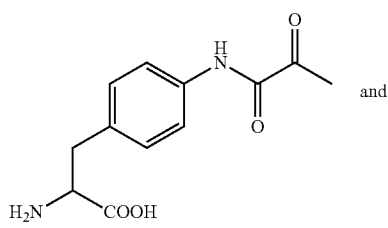

and

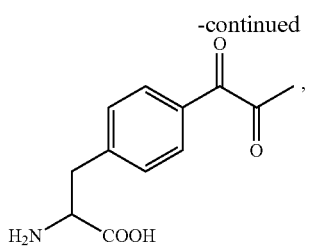

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (XIII) are included:

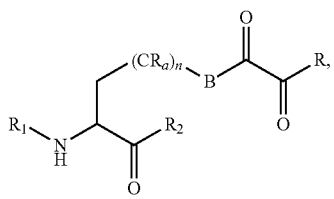

(XIII)

wherein B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide;

each Ra is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8.

In addition, the following amino acids are included:

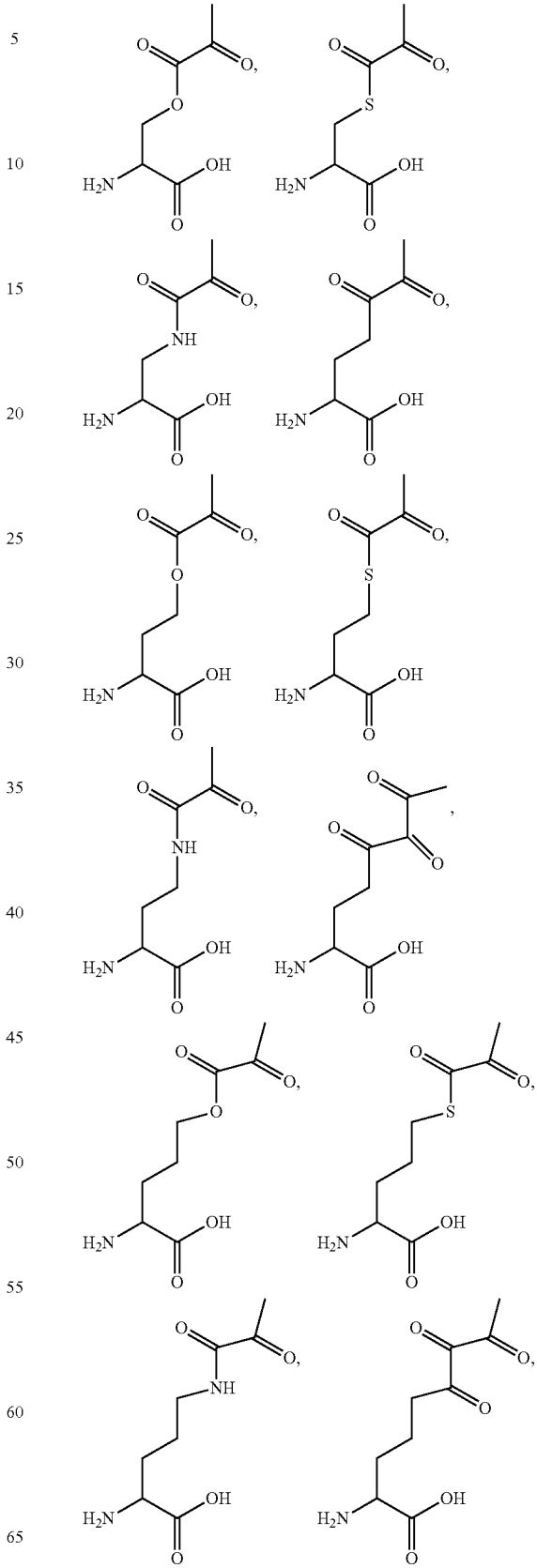

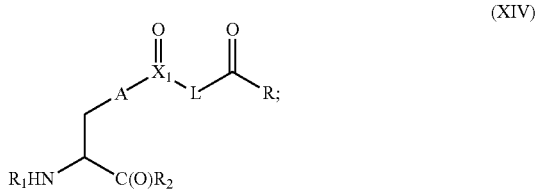

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (XIV) are included:

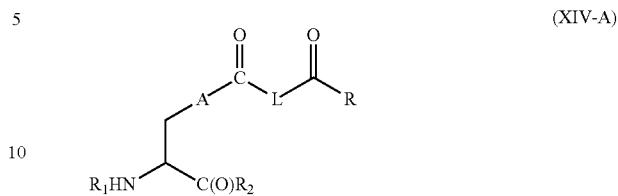

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
R1 is optional, and when present, is H, an amino protecting group, resin, amino acid, polypeptide, or polynucleotide; and
R2 is optional, and when present, is OH, an ester protecting group, resin, amino acid, polypeptide, or polynucleotide;
X1 is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XIV-A) are included:

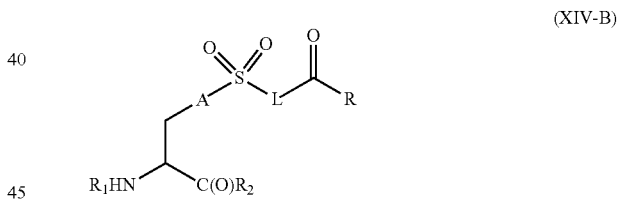

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
R1 is optional, and when present, is H, an amino protecting group, resin, amino acid, polypeptide, or polynucleotide; and
R2 is optional, and when present, is OH, an ester protecting group, resin, amino acid, polypeptide, or polynucleotide;
L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XIV-B) are included:

$$\text{(XIV-B)}$$

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
R1 is optional, and when present, is H, an amino protecting group, resin, amino acid, polypeptide, or polynucleotide; and
R2 is optional, and when present, is OH, an ester protecting group, resin, amino acid, polypeptide, or polynucleotide;
L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XV) are included:

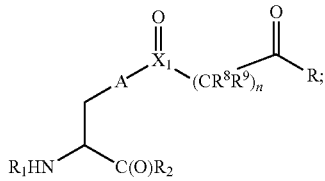

(XV)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
$X_1$ is C, S, or S(O); and n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XV-A) are included:

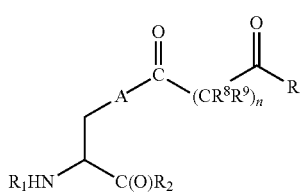

(XV-A)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
n is 0, 1, 2, 3, 4, or 5; and each $R^8$ and R9 on each $CR^8R9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XV-B) are included:

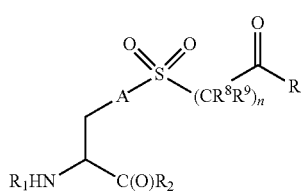

(XV-B)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
n is 0, 1, 2, 3, 4, or 5; and each $R^8$ and R9 on each $CR^8R9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XVI) are included:

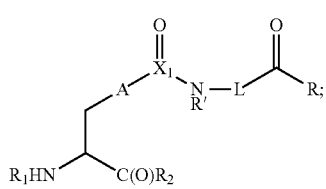

(XVI)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;

$X_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XVI-A) are included:

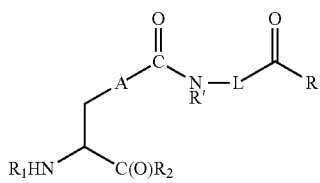

(XVI-A)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XVI-B) are included:

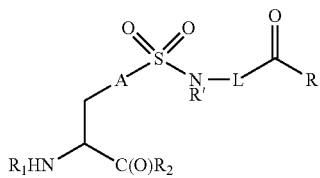

(XVI-B)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
L is alkylene, substituted alkylene, N(R')(alkylene) or N(R')(substituted alkylene), where R' is H, alkyl, substituted alkyl, cycloalkyl, or substituted cycloalkyl.

In addition, amino acids having the structure of Formula (XVII) are included:

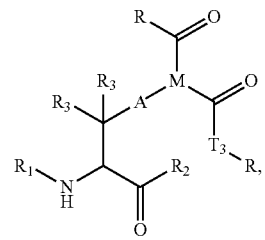

(XVII)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; M is —C($R_3$)—,

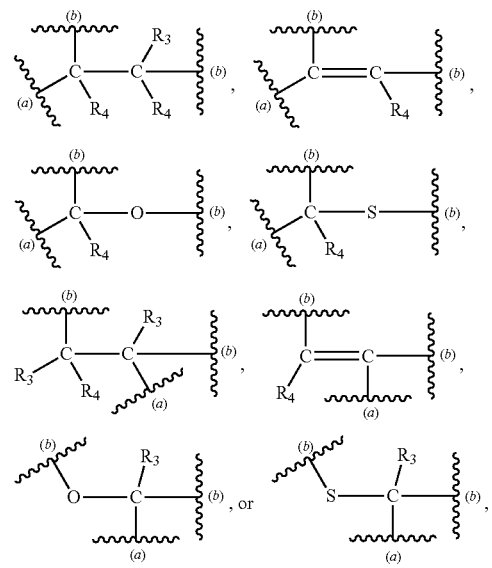

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl;
R is H, halogen, alkyl, substituted alkyl, cycloalkyl, or substituted cycloalkyl;
$T_3$ is a bond, C(R)(R), O, or S, and R is H, halogen, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide.

In addition, amino acids having the structure of Formula (XVIII) are included:

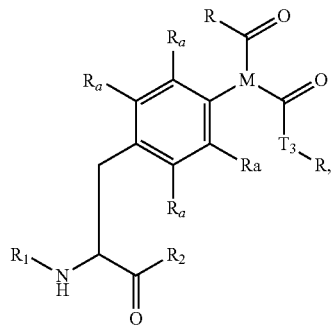
(XVIII)

wherein:
M is —C(R₃)—,

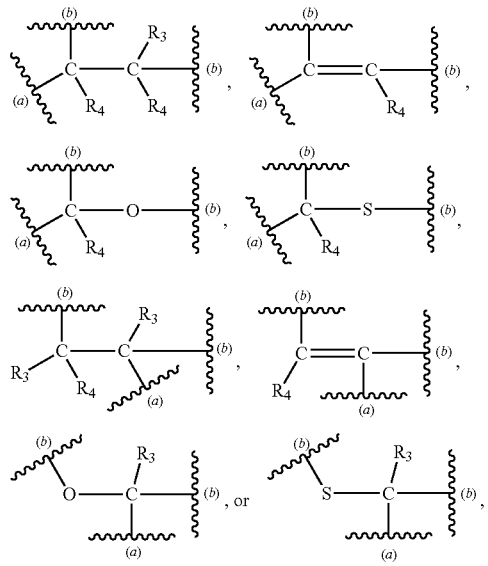

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl;
R is H, halogen, alkyl, substituted alkyl, cycloalkyl, or substituted cycloalkyl;
$T_3$ is a bond, C(R)(R), O, or S, and R is H, halogen, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
each $R_a$ is independently selected from the group consisting of H, halogen, alkyl, substituted alkyl, —N(R')₂, —C(O)ₖR' where k is 1, 2, or 3, —C(O)N(R')₂, —OR', and —S(O)ₖR', where each R' is independently H, alkyl, or substituted alkyl.

In addition, amino acids having the structure of Formula (XIX) are included:

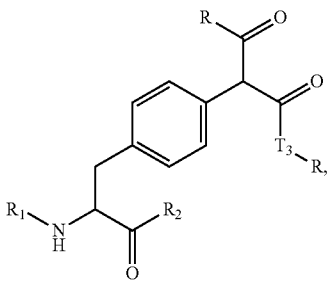
(XIX)

wherein:
R is H, halogen, alkyl, substituted alkyl, cycloalkyl, or substituted cycloalkyl; and $T_3$ is O, or S.

In addition, amino acids having the structure of Formula (XX) are included:

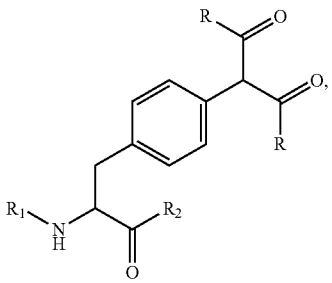
(XX)

wherein:
R is H, halogen, alkyl, substituted alkyl, cycloalkyl, or substituted cycloalkyl.

In addition, the following amino acids having structures of Formula (XXI) are included:

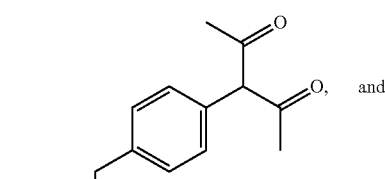
and
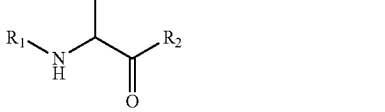

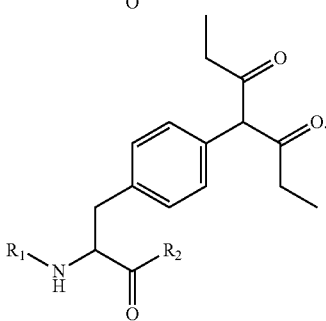

In some embodiments, a polypeptide comprising a non-natural amino acid is chemically modified to generate a reactive carbonyl or dicarbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et. al., Bioconjug. Chem. 3: 262-268 (1992); Geoghegan, K. & Stroh, J., Bioconjug. Chem. 3:138-146 (1992); Gaertner et al., J. Biol. Chem. 269:7224-7230 (1994). However, methods known in the art are restricted to the amino acid at the N-terminus of the peptide or protein.

In the present invention, a non-natural amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685.

The carbonyl or dicarbonyl functionality can be reacted selectively with a hydroxylamine-containing reagent under mild conditions in aqueous solution to form the corresponding oxime linkage that is stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl or dicarbonyl group allows for selective modification in the presence of the other amino acid side chains. See, e.g., Cornish, V. W., et al., J. Am. Chem. Soc. 118: 8150-8151 (1996); Geoghegan, K. F. & Stroh, J. G., Bioconjug. Chem. 3:138-146 (1992); Mahal, L. K., et al., Science 276:1125-1128 (1997).

Structure and Synthesis of Non-Natural Amino Acids: Hydroxylamine-Containing Amino Acids U.S. patent application Ser. No. 11/316,534 (U.S. Publication No. 20060189529) is incorporated by reference in its entirety. Thus, the disclosures provided in Section V (entitled "Non-natural Amino Acids"), Part B (entitled "Structure and Synthesis of Non-Natural Amino Acids: Hydroxylamine-Containing Amino Acids"), in U.S. patent application Ser. No. 11/316,534 (U.S. Publication No. 20060189529) apply fully to the methods, compositions (including Formulas I-XXXV), techniques and strategies for making, purifying, characterizing, and using non-natural amino acids, non-natural amino acid polypeptides and modified non-natural amino acid polypeptides described herein to the same extent as if such disclosures were fully presented herein. U.S. Patent Publication Nos. 2006/0194256, 2006/0217532, and 2006/0217289 and WO 2006/069246 entitled "Compositions containing, methods involving, and uses of non-natural amino acids and polypeptides," are also incorporated herein by reference in their entirety.

Chemical Synthesis of Unnatural Amino Acids

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of ordinary skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) J. Med. Chem., 38, 4660-4669; King, F. E. & Kidd, D. A. A. (1949) A New Synthesis of Glutamine and of γ-Dipeptides of Glutamic Acid from Phthylated Intermediates. J. Chem. Soc., 3315-3319; Friedman, O. M. & Chatterrji, R. (1959) Synthesis of Derivatives of Glutamine as Model Substrates for Anti-Tumor Agents. J. Am. Chem. Soc. 81, 3750-3752; Craig, J. C. et al. (1988) Absolute Configuration of the Enantiomers of 7-Chloro-4 [[4-(diethylamino)-1-methylbutyl]amino]quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Prolines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and Iminium Ion Cyclization. J. Org. Chem. 50:1239-1246; Barton et al., (1987) Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives. Tetrahedron 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, U.S. Patent Publication No. US 2004/0198637 entitled "Protein Arrays," which is incorporated by reference herein.

A. Carbonyl Reactive Groups

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

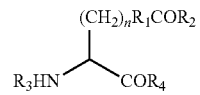

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

The synthesis of p-acetyl-(+/−)-phenylalanine and m-acetyl-(+/−)-phenylalanine is described in Zhang, Z., et al., Biochemistry 42: 6735-6746 (2003), which is incorporated by reference herein. Other carbonyl-containing amino acids can be similarly prepared by one of ordinary skill in the art.

In some embodiments, a polypeptide comprising a non-naturally encoded amino acid is chemically modified to generate a reactive carbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et al., Bioconjug. Chem. 3: 262-268 (1992); Geoghegan, K. & Stroh, J., Bioconjug. Chem. 3:138-146 (1992); Gaertner et al., J. Biol. Chem. 269:7224-7230 (1994). However, methods known in the art are restricted to the amino acid at the N-terminus of the peptide or protein.

In the present invention, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., J Am. Chem. Soc. 81, 475-481 (1959); Shao, J. and Tam, J. P., J. Am. Chem. Soc. 117:3893-3899 (1995). Moreover, the unique reactivity of the carbonyl group allows for selective modification in the presence of the other amino acid side chains. See, e.g., Cornish, V. W., et al., J Am. Chem. Soc. 118:8150-8151 (1996); Geoghegan, K. F. & Stroh, J. G., Bioconjug. Chem. 3:138-146 (1992); Mahal, L. K., et al., Science 276:1125-1128 (1997).

B. Hydrazine, Hydrazide or Semicarbazide Reactive Groups

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

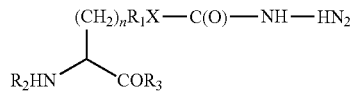

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the alphatic group on the aryl ring.

Hydrazide-, hydrazine-, and semicarbazide-containing amino acids are available from commercial sources. For instance, L-glutamate-□-hydrazide is available from Sigma Chemical (St. Louis, Mo.). Other amino acids not available commercially can be prepared by one of ordinary skill in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., J Am. Chem. Soc. 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

C. Aminooxy-Containing Amino Acids

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semi-carbazides, the enhanced nucleophilicity of the aminooxy group permits it to react efficiently and selectively with a variety of molecules that contain aldehydes or other functional groups with similar chemical reactivity. See, e.g., Shao, J. and Tam, J., J. Am. Chem. Soc. 117:3893-3899 (1995); H. Hang and C. Bertozzi, Acc. Chem. Res. 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

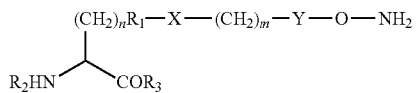

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, J. Org. Chem. 68: 8853-8858 (2003). Certain aminooxy-containing amino acids, such as L-2-amino-4-(aminooxy)butyric acid), have been isolated from natural sources (Rosenthal, G., Life Sci. 60: 1635-1641 (1997). Other aminooxy-containing amino acids can be prepared by one of ordinary skill in the art.

D. Azide and Alkyne Reactive Groups

The unique reactivity of azide and alkyne functional groups makes them extremely useful for the selective modification of polypeptides and other biological molecules. Organic azides, particularly alphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., *Science* 301:964-7 (2003); Wang, Q., et al., *J. Am. Chem. Soc.* 125, 3192-3193 (2003); Chin, J. W., et al., *J. Am. Chem. Soc.* 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing relaxin polypeptide can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., *J. Am. Chem. Soc.* 125, 3192-3193 (2003); Tornoe, C. W., et al., *J. Org. Chem.* 67:3057-3064 (2002); Rostovtsev, et al., *Angew. Chem. Int. Ed.* 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the relaxin polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, *Science* 287, 2007-2010 (2000). The azide-containing amino acid can be either an alkyl azide (including but not limited to, 2-amino-6-azido-1-hexanoic acid) or an aryl azide (p-azido-phenylalanine).

Exemplary water soluble polymers containing an aryl ester and a phosphine moiety can be represented as follows:

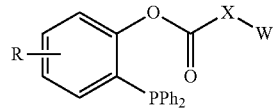

wherein X can be O, N, S or not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —$S(O)_2R'$, —$S(O)_2NR'R"$, —CN and —$NO_2$. R', R", R''' and R'''' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —$C(O)CH_3$, —$C(O)CF_3$, —$C(O)CH_2OCH_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

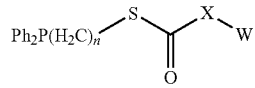

wherein n is 1-10; X can be O, N, S or not present, Ph is phenyl, and W is a water soluble polymer.

Exempla alkyne-containing amino acids can be represented as follows:

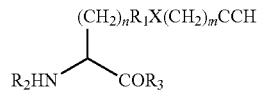

wherein n is 0-10; $R_1$ is an alkyl, aryl, substituted alkyl, or substituted aryl or not present; X is O, N, S or not present; m is 0-10, $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the acetylene moiety is positioned in the para position relative to the alkyl side chain. In some embodiments, n is 1, $R_1$ is phenyl, X is O, m is 1 and the propargyloxy group is positioned in the para position relative to the alkyl side chain (i.e., O-propargyl-tyrosine). In some embodiments, n is 1, $R_1$ and X are not present and m is 0 (i.e., proparylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., *J. Am. Chem. Soc.* 125: 11782-11783 (2003), and 4-alkynyl-L-phenylalanine can be synthesized as described in Kayser, B., et al., *Tetrahedron* 53(7): 2475-2484 (1997). Other alkyne-containing amino acids can be prepared by one of ordinary skill in the art.

Exemplary azide-containing amino acids can be represented as follows:

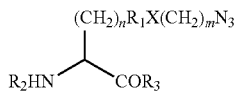

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the azide moiety is positioned para to the alkyl side chain. In some embodiments, n is 0-4 and $R_1$ and X are not present, and m=0. In some embodiments, n is 1, $R_1$ is phenyl, X is O, m is 2 and the β-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, TL). For those azide-containing amino acids that are not commercially available, the azide group can be prepared relatively readily using standard methods known to those of ordinary skill in the art, including but not limited to, via displacement of a suitable leaving group (including but not limited to, halide, mesylate, tosylate) or via opening of a suitably protected lactone. See, e.g., *Advanced Organic Chemistry* by March (Third Edition, 1985, Wiley and Sons, New York).

E. Aminothiol Reactive Groups

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, *J Am. Chem. Soc.* 1995, 117 (14) 3893-3899. In some embodiments, beta-substituted aminothiol amino acids can be incorporated into relaxin polypeptides and then reacted with water soluble polymers comprising an aldehyde functionality. In some embodiments, a water soluble polymer, drug conjugate or other payload can be coupled to a relaxin polypeptide comprising a beta-substituted aminothiol amino acid via formation of the thiazolidine.

F. Additional Reactive Groups

Additional reactive groups and non-naturally encoded amino acids, including but not limited to para-amino-phenylalanine, that can be incorporated into relaxin polypeptides of the invention are described in the following patent applications which are all incorporated by reference in their entirety herein: U.S. Patent Publication No. 2006/0194256, U.S. Patent Publication No. 2006/0217532, U.S. Patent Publication No. 2006/0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594. These applications also discuss reactive groups that may be present on PEG or other polymers, including but not limited to, hydroxylamine (aminooxy) groups for conjugation.

Cellular Uptake of Unnatural Amino Acids

Unnatural amino acid uptake by a cell is one issue that is typically considered when designing and selecting unnatural amino acids, including but not limited to, for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which unnatural amino acids, if any, are taken up by cells. See, e.g., the toxicity assays in, e.g., U.S. Patent Publication No. US 2004/0198637 entitled "Protein Arrays" which is incorporated by reference herein; and Liu, D. R. & Schultz, P. G. (1999) Progress toward the evolution of an organism with an expanded genetic code. PNAS United States 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, including but not limited to, in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, including but not limited to, as developed by Maxygen, Inc. (available on the World Wide Web at maxygen.com), is optionally used to develop novel enzymes and pathways. See, e.g., Stemmer (1994), Rapid evolution of a protein in vitro by DNA shuffling, Nature 370(4):389-391; and, Stemmer, (1994), DNA shuffling by random fragmentation and reassembly: In vitro recombination for molecular evolution, Proc. Natl. Acad. Sci. USA., 91:10747-10751. Similarly DesignPath™, developed by Genencor (available on the World Wide Web at genencor.com) is optionally used for metabolic pathway engineering, including but not limited to, to engineer a pathway to create O-methyl-L-tyrosine in a cell. This technology reconstructs existing pathways in host organisms using a combination of new genes, including but not limited to, those identified through functional genomics, and molecular evolution and design. Diversa Corporation (available on the World Wide Web at diversa.com) also provides technology for rapidly screening libraries of genes and gene pathways, including but not limited to, to create new pathways.

Typically, the unnatural amino acid produced with an engineered biosynthetic pathway of the invention is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Polypeptides with Unnatural Amino Acids

The incorporation of an unnatural amino acid can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), adding a biologically active molecule, attaching a polymer, attaching a radionuclide, modulating serum half-life, modulating tissue penetration (e.g. tumors), modulating active transport, modulating tissue, cell or organ specificity or distribution, modulating immunogenicity, modulating protease resistance, etc. Proteins that include an unnatural amino acid can have enhanced or even entirely new catalytic or biophysical properties. For example, the following properties are optionally modified by inclusion of an unnatural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or non-covalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function.

See, e.g., Dougherty, (2000) Unnatural Amino Acids as Probes of Protein Structure and Function, Current Opinion in Chemical Biology, 4:645-652.

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Proteins or polypeptides of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein.

By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like. In one aspect, the post-translational modification includes attachment of an oligosaccharide (including but not limited to, (GlcNAc-Man)2-Man-GlcNAc-GlcNAc)) to an asparagine by a GlcNAc-asparagine linkage. See Table 1 which lists some examples of N-linked oligosaccharides of eukaryotic proteins (additional residues can also be present, which are not shown). In another aspect, the post-translational modification includes attachment of an oligosaccharide (including but not limited to, Gal-GalNAc, Gal-GlcNAc, etc.) to a serine or threonine by a GalNAc-serine or GalNAc-threonine linkage, or a GlcNAc-serine or a GlcNAc-threonine linkage.

TABLE 1

Examples of oligosaccharides through GLCNAC-linkage

| Type | Base Structure |
|---|---|
| HIGH-MANNOSE | Manα1-6 \ Manα1-3 / Manα1-6 \ Manα1-3 / Manβ1-4GlcNAcβ1-4GlcNAcβ1-Asn |

TABLE 1-continued

Examples of oligosaccharides through GLCNAC-linkage

| Type | Base Structure |
|---|---|
| HYBRID | GlcNAcβ1-2 — Manα1-6 \ Manα1-3 / > Manβ1-4GlcNAcβ1-4GlcNAcβ1-Asn |
| COMPLEX | GlcNAcβ1-2 — Manα1-6 \ GlcNAcβ1-2 — Manα1-3 / > Manβ1-4GlcNAcβ1-4GlcNAcβ1-Asn |
| XYLOSE | Manα1-6 \ Xylβ1-2 / > Manβ1-4GlcNAcβ1-4GlcNAcβ1-Asn |

In yet another aspect, the post-translation modification includes proteolytic processing of precursors (including but not limited to, calcitonin precursor, calcitonin gene-related peptide precursor, preproparathyroid hormone, preproinsulin, proinsulin, prepro-opiomelanocortin, pro-opiomelanocortin andthe like), assembly into a multisubunit protein or macromolecular assembly, translation to another site in the cell (including but not limited to, to organelles, such as the endoplasmic reticulum, the Golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) J. Am. Chem. Soc., 118:8150-8151; Mahal, et al., (1997) Science, 276:1125-1128; Wang, et al., (2001) Science 292:498-500; Chin, et al., (2002) J. Am. Chem. Soc. 124:9026-9027; Chin, et al., (2002) Proc. Natl. Acad. Sci., 99:11020-11024; Wang, et al., (2003) Proc. Natl. Acad. Sci., 100:56-61; Zhang, et al., (2003) Biochemistry, 42:6735-6746; and, Chin, et al., (2003) Science, 301:964-7, all of which are incorporated by reference herein. This allows the selective labeling of virtually any protein with a host of reagents including fluorophores, crosslinking agents, saccharide derivatives and cytotoxic molecules. See also, U.S. Pat. No. 6,927,042 entitled "Glycoprotein synthesis," which is incorporated by reference herein. Post-translational modifications, including but not limited to, through an azido amino acid, can also made through the Staudinger ligation (including but not limited to, with triarylphosphine reagents). See, e.g., Kiick et al., (2002) Incorporation of azides into recombinant proteins for chemoselective modification by the Staudinger ligation, PNAS 99:19-24.

This invention provides another highly efficient method for the selective modification of proteins, which involves the genetic incorporation of unnatural amino acids, including but not limited to, containing an azide or alkynyl moiety into proteins in response to a selector codon. These amino acid side chains can then be modified by, including but not limited to, a Huisgen [3+2] cycloaddition reaction (see, e.g., Padwa, A. in Comprehensive Organic Synthesis, Vol. 4, (1991) Ed. Trost, B. M., Pergamon, Oxford, p. 1069-1109; and, Huisgen, R. in 1,3-Dipolar Cycloaddition Chemistry, (1984) Ed. Padwa, A., Wiley, New York, p. 1-176) with, including but not limited to, alkynyl or azide derivatives, respectively. Because this method involves a cycloaddition rather than a nucleophilic substitution, proteins can be modified with extremely high selectivity. This reaction can be carried out at room temperature in aqueous conditions with excellent regioselectivity (1,4>1,5) by the addition of catalytic amounts of Cu(I) salts to the reaction mixture. See, e.g., Tornoe, et al., (2002) J. Org. Chem. 67:3057-3064; and, Rostovtsev, et al., (2002) Angew. Chem. Int. Ed. 41:2596-2599. Another method that can be used is the ligand exchange on a bisarsenic compound with a tetracysteine motif, see, e.g., Griffin, et al., (1998) Science 281:269-272.

A molecule that can be added to a protein of the invention through a [3+2]cycloaddition includes virtually any molecule with an azide or alkynyl derivative. Molecules include, but are not limited to, dyes, fluorophores, crosslinking agents, saccharide derivatives, polymers (including but not limited to, derivatives of polyethylene glycol), photocrosslinkers, cytotoxic compounds, affinity labels, derivatives of biotin, resins, beads, a second protein or polypeptide (or more), polynucleotide(s) (including but not limited to, DNA, RNA, etc.), metal chelators, cofactors, fatty acids, carbohydrates, and the like. These molecules can be added to an unnatural amino acid with an alkynyl group, including but not limited to, p-propargyloxyphenylalanine, or azido group, including but not limited to, p-azido-phenylalanine, respectively.

In Vivo Generation of Relaxin Polypeptides Comprising Non-Naturally-Encoded Amino Acids The relaxin polypeptides of the invention can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Pat. Nos. 7,045,337 and 7,083,970 which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O-RS). Typically, the O-RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides, and are generally suitable for use in the present invention. For example, keto-specific O-tRNA/aminoacyl-tRNA synthetases are described in Wang, L., et al., Proc. Natl. Acad. Sci. USA 100:56-61 (2003) and Zhang, Z. et al., Biochem. 42(22):6735-6746 (2003). Exemplary O-RS, or portions thereof, are encoded by polynucleotide sequences and include amino acid sequences disclosed in U.S. Pat. Nos. 7,045,337 and 7,083,970, each incorporated herein by reference. Corresponding O-tRNA molecules for use with the O-RSs are also described in U.S. Pat. Nos. 7,045,337 and 7,083,970 which are incorporated by reference herein. Additional examples of O-tRNA/aminoacyl-tRNA synthetase pairs are described in WO 2005/007870, WO 2005/007624; and WO 2005/019415.

An example of an azide-specific O-tRNA/aminoacyl-tRNA synthetase system is described in Chin, J. W., et al., J. Am. Chem. Soc. 124:9026-9027 (2002). Exemplary O-RS sequences for p-azido-L-Phe include, but are not limited to, nucleotide sequences SEQ ID NOs: 14-16 and 29-32 and amino acid sequences SEQ ID NOs: 46-48 and 61-64 as disclosed in U.S. Pat. No. 7,083,970 which is incorporated by reference herein. Exemplary O-tRNA sequences suitable for use in the present invention include, but are not limited to, nucleotide sequences SEQ ID NOs: 1-3 as disclosed in U.S. Pat. No. 7,083,970, which is incorporated by reference herein. Other examples of O-tRNA/aminoacyl-tRNA synthetase pairs specific to particular non-naturally encoded amino acids are described in U.S. Pat. No. 7,045,337 which is incorporated by reference herein. O-RS and O-tRNA that incorporate both keto- and azide-containing amino acids in *S. cerevisiae* are described in Chin, J. W., et al., Science 301:964-967 (2003).

Several other orthogonal pairs have been reported. Glutaminyl (see, e.g., Liu, D. R., and Schultz, P. G. (1999) Proc. Natl. Acad. Sci. U.S.A 96:4780-4785), aspartyl (see, e.g., Pastrnak, M., et al., (2000) Helv. Chim. Acta 83:2277-2286), and tyrosyl (see, e.g., Ohno, S., et al., (1998) J. Biochem. (Tokyo, Jpn.) 124:1065-1068; and, Kowal, A. K., et al., (2001) Proc. Natl. Acad. Sci. U.S.A 98:2268-2273) systems derived from *S. cerevisiae* tRNA's and synthetases have been described for the potential incorporation of unnatural amino acids in *E. coli*. Systems derived from the *E. coli* glutaminyl (see, e.g., Kowal, A. K., et al., (2001) Proc. Natl. Acad. Sci. U.S.A 98:2268-2273) and tyrosyl (see, e.g., Edwards, H., and Schimmel, P. (1990) Mol. Cell. Biol. 10:1633-1641) synthetases have been described for use in *S. cerevisiae*. The *E. coli* tyrosyl system has been used for the incorporation of 3-iodo-L-tyrosine in vivo, in mammalian cells. See, Sakamoto, K., et al., (2002) Nucleic Acids Res. 30:4692-4699.

Use of O-tRNA/aminoacyl-tRNA synthetases involves selection of a specific codon which encodes the non-naturally encoded amino acid. While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the relaxin polynucleotide coding sequence using mutagenesis methods known in the art (including but not limited to, site-specific mutagenesis, cassette mutagenesis, restriction selection mutagenesis, etc.).

Methods for generating components of the protein biosynthetic machinery, such as O-RSs, O-tRNAs, and orthogonal O-tRNA/O-RS pairs that can be used to incorporate a non-naturally encoded amino acid are described in Wang, L., et al., Science 292: 498-500 (2001); Chin, J. W., et al., J. Am. Chem. Soc. 124:9026-9027 (2002); Zhang, Z. et al., Biochemistry 42: 6735-6746 (2003). Methods and compositions for the in vivo incorporation of non-naturally encoded amino acids are described in U.S. Pat. No. 7,045,337, which is incorporated by reference herein. Methods for selecting an orthogonal tRNA-tRNA synthetase pair for use in vivo translation system of an organism are also described in U.S. Pat. Nos. 7,045,337 and 7,083,970 which are incorporated by reference herein. PCT Publication No. WO 04/035743 entitled "Site Specific Incorporation of Keto Amino Acids into Proteins," which is incorporated by reference herein in its entirety, describes orthogonal RS and tRNA pairs for the incorporation of keto amino acids. PCT Publication No. WO 04/094593 entitled "Expanding the Eukaryotic Genetic Code," which is incorporated by reference herein in its entirety, describes orthogonal RS and tRNA pairs for the incorporation of non-naturally encoded amino acids in eukaryotic host cells.

Methods for producing at least one recombinant orthogonal aminoacyl-tRNA synthetase (O-RS) comprise: (a) generating a library of (optionally mutant) RSs derived from at least one aminoacyl-tRNA synthetase (RS) from a first organism, including but not limited to, a prokaryotic organism, such as *Methanococcus jannaschii, Methanobacterium thermoautotrophicum, Halobacterium, Escherichia coli, A. fulgidus, P. furiosus, P. horikoshii, A. pernix, T. thermophilus*, or the like, or a eukaryotic organism; (b) selecting (and/or screening) the library of RSs (optionally mutant RSs) for members that aminoacylate an orthogonal tRNA (O-tRNA) in the presence of a non-naturally encoded amino acid and a natural amino acid, thereby providing a pool of active (optionally mutant) RSs; and/or, (c) selecting (optionally through negative selection) the pool for active RSs (including but not limited to, mutant RSs) that preferentially aminoacylate the O-tRNA in the absence of the non-naturally encoded amino acid, thereby providing the at least one recombinant O-RS; wherein the at least one recombinant O-RS preferentially aminoacylates the O-tRNA with the non-naturally encoded amino acid.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, including but not limited to, alanine.

Libraries of mutant RSs can be generated using various techniques known in the art, including but not limited to rational design based on protein three dimensional RS structure, or mutagenesis of RS nucleotides in a random or rational design technique. For example, the mutant RSs can be generated by site-specific mutations, random mutations, diversity generating recombination mutations, chimeric constructs, rational design and by other methods described herein or known in the art.

In one embodiment, selecting (and/or screening) the library of RSs (optionally mutant RSs) for members that are active, including but not limited to, that aminoacylate an orthogonal tRNA (O-tRNA) in the presence of a non-naturally encoded amino acid and a natural amino acid, includes: introducing a positive selection or screening marker, including but not limited to, an antibiotic resistance gene, or the like, and the library of (optionally mutant) RSs into a plurality of cells, wherein the positive selection and/or screening marker comprises at least one selector codon, including but not limited to, an amber, ochre, or opal codon; growing the plurality of cells in the presence of a selection agent; identifying cells that survive (or show a specific response) in the presence of the selection and/or screening agent by suppressing the at least one selector codon in the positive selection or screening marker, thereby providing a subset of positively selected cells that contains the pool of active (optionally mutant) RSs. Optionally, the selection and/or screening agent concentration can be varied.

In one aspect, the positive selection marker is a chloramphenicol acetyltransferase (CAT) gene and the selector codon is an amber stop codon in the CAT gene. Optionally, the positive selection marker is β-lactamase gene and the selector codon is an amber stop codon in the β-lactamase gene. In another aspect the positive screening marker comprises a fluorescent or luminescent screening marker or an affinity based screening marker (including but not limited to, a cell surface marker).

In one embodiment, negatively selecting or screening the pool for active RSs (optionally mutants) that preferentially aminoacylate the O-tRNA in the absence of the non-naturally encoded amino acid includes: introducing a negative selection or screening marker with the pool of active (optionally mutant) RSs from the positive selection or screening into a plurality of cells of a second organism, wherein the negative selection or screening marker comprises at least one selector codon (including but not limited to, an antibiotic resistance gene, including but not limited to, a chloramphenicol acetyltransferase (CAT) gene); and, identifying cells that survive or show a specific screening response in a first medium supplemented with the non-naturally encoded amino acid and a screening or selection agent, but fail to survive or to show the specific response in a second medium not supplemented with the non-naturally encoded amino acid and the selection or screening agent, thereby providing surviving cells or screened cells with the at least one recombinant O-RS. For example, a CAT identification protocol optionally acts as a positive selection and/or a negative screening in determination of appropriate O-RS recombinants. For instance, a pool of clones is optionally replicated on growth plates containing CAT (which comprises at least one selector codon) either with or without one or more non-naturally encoded amino acid. Colonies growing exclusively on the plates containing non-naturally encoded amino acids are thus regarded as containing recombinant O-RS. In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungi, a yeast, an archaebacterium, a eubacterium, a plant, an insect, a protist, etc. In other embodiments, the screening marker comprises a fluorescent or luminescent screening marker or an affinity based screening marker.

In another embodiment, screening or selecting (including but not limited to, negatively selecting) the pool for active (optionally mutant) RSs includes: isolating the pool of active mutant RSs from the positive selection step (b); introducing a negative selection or screening marker, wherein the negative selection or screening marker comprises at least one selector codon (including but not limited to, a toxic marker gene, including but not limited to, a ribonuclease barnase gene, comprising at least one selector codon), and the pool of active (optionally mutant) RSs into a plurality of cells of a second organism; and identifying cells that survive or show a specific screening response in a first medium not supplemented with the non-naturally encoded amino acid, but fail to survive or show a specific screening response in a second medium supplemented with the non-naturally encoded amino acid, thereby providing surviving or screened cells with the at least one recombinant O-RS, wherein the at least one recombinant O-RS is specific for the non-naturally encoded amino acid. In one aspect, the at least one selector codon comprises about two or more selector codons. Such embodiments optionally can include wherein the at least one selector codon comprises two or more selector codons, and wherein the first and second organism are different (including but not limited to, each organism is optionally, including but not limited to, a prokaryote, a eukaryote, a mammal, an *Escherichia coli*, a fungi, a yeast, an archaebacteria, a eubacteria, a plant, an insect, a protist, etc.). Also, some aspects include wherein the negative selection marker comprises a ribonuclease barnase gene (which comprises at least one selector codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O-RS) can further comprise: (d) isolating the at least one recombinant O-RS; (e) generating a second set of O-RS (optionally mutated) derived from the at least one recombinant O-RS; and, (f) repeating steps (b) and (c) until a mutated O-RS is obtained that comprises an ability to preferentially aminoacylate the O-tRNA. Optionally, steps (d)-(f) are repeated, including but not limited to, at least about two times. In one aspect, the second set of mutated O-RS derived from at least one recombinant O-RS can be generated by mutagenesis, including but not limited to, random mutagenesis, site-specific mutagenesis, recombination or a combination thereof.

The stringency of the selection/screening steps, including but not limited to, the positive selection/screening step (b), the negative selection/screening step (c) or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the reporter is detected by luminescence. Optionally, the reporter is displayed on a cell surface, on a phage display or the like and selected based upon affinity or catalytic activity involving the non-naturally encoded amino acid or an analogue. In one embodiment, the mutated synthetase is displayed on a cell surface, on a phage display or the like.

Methods for producing a recombinant orthogonal tRNA (O-tRNA) include: (a) generating a library of mutant tRNAs derived from at least one tRNA, including but not limited to, a suppressor tRNA, from a first organism; (b) selecting (including but not limited to, negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS (O-RS), thereby providing at least one recombinant O-tRNA; wherein the at least one recombinant O-tRNA recognizes a selector codon and is not efficiency recognized by the RS from the second organism and is preferentially aminoacylated by the O-RS. In some embodiments the at least one tRNA is a suppressor tRNA and/or comprises a unique three base codon of natural and/or unnatural bases, or is a nonsense codon, a rare codon, an unnatural codon, a codon comprising at least 4 bases, an amber codon, an ochre codon, or an opal stop codon. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, including but not limited to, prokaryotes (including but not limited to, *Methanococcus jannaschii, Methanobacterium thermoautotrophicum, Escherichia coli, Halobacterium*, etc.), eukaryotes, mammals, fungi, yeasts, archaebacteria, eubacteria, plants, insects, protists, etc. Additionally, the recombinant tRNA is optionally aminoacylated by a non-naturally encoded amino acid, wherein the non-naturally encoded amino acid is biosynthesized in vivo either naturally or through genetic manipulation. The non-naturally encoded amino acid is optionally added to a growth medium for at least the first or second organism.

In one aspect, selecting (including but not limited to, negatively selecting) or screening the library for (optionally mutant) tRNAs that are aminoacylated by an aminoacyl-tRNA synthetase (step (b)) includes: introducing a toxic marker gene, wherein the toxic marker gene comprises at least one of the selector codons (or a gene that leads to the production of a toxic or static agent or a gene essential to the organism wherein such marker gene comprises at least one selector codon) and the library of (optionally mutant) tRNAs into a plurality of cells from the second organism; and, selecting surviving cells, wherein the surviving cells contain the pool of (optionally mutant) tRNAs comprising at least one orthogonal tRNA or nonfunctional tRNA. For example, surviving cells can be selected by using a comparison ratio cell density assay.

In another aspect, the toxic marker gene can include two or more selector codons. In another embodiment of the methods, the toxic marker gene is a ribonuclease barnase gene, where the ribonuclease barnase gene comprises at least one amber codon. Optionally, the ribonuclease barnase gene can include two or more amber codons.

In one embodiment, selecting or screening the pool of (optionally mutant) tRNAs for members that are aminoacylated by an introduced orthogonal RS (O-RS) can include: introducing a positive selection or screening marker gene, wherein the positive marker gene comprises a drug resistance gene (including but not limited to, Q-lactamase gene, comprising at least one of the selector codons, such as at least one amber stop codon) or a gene essential to the organism, or a gene that leads to detoxification of a toxic agent, along with the O-RS, and the pool of (optionally mutant) tRNAs into a plurality of cells from the second organism; and, identifying surviving or screened cells grown in the presence of a selection or screening agent, including but not limited to, an antibiotic, thereby providing a pool of cells possessing the at least one recombinant tRNA, where the at least one recombinant tRNA is aminoacylated by the O-RS and inserts an amino acid into a translation product encoded by the positive marker gene, in response to the at least one selector codons. In another embodiment, the concentration of the selection and/or screening agent is varied.

Methods for generating specific O-tRNA/O-RS pairs are provided. Methods include: (a) generating a library of mutant tRNAs derived from at least one tRNA from a first organism; (b) negatively selecting or screening the library for (optionally mutant) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS (O-RS), thereby providing at least one recombinant O-tRNA. The at least one recombinant O-tRNA recognizes a selector codon and is not efficiency recognized by the RS from the second organism and is preferentially aminoacylated by the O-RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of a non-naturally encoded amino acid and a natural amino acid, thereby providing a pool of active (optionally mutant) RSs; and, (f) negatively selecting or screening the pool for active (optionally mutant) RSs that preferentially aminoacylate the at least one recombinant O-tRNA in the absence of the non-naturally encoded amino acid, thereby providing the at least one specific O-tRNA/O-RS pair, wherein the at least one specific O-tRNA/O-RS pair comprises at least one recombinant O-RS that is specific for the non-naturally encoded amino acid and the at least one recombinant O-tRNA. Specific O-tRNA/O-RS pairs produced by the methods are included. For example, the specific O-tRNA/O-RS pair can include, including but not limited to, a mutRNATyr-mutTyrRS pair, such as a mutRNATyr-SS12TyrRS pair, a mutRNALeu-mutLeuRS pair, a mutRNAThr-mutThrRS pair, a mutRNAGlu-mutGluRS pair, or the like. Additionally, such methods include wherein the first and third organism are the same (including but not limited to, *Methanococcus jannaschii*).

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from a second organism; and, selecting for surviving cells in the first set that fail to survive in the duplicate cell set or screening for cells showing a specific screening response that fail to give such response in the duplicate cell set, wherein the first set and the duplicate cell set are grown in the presence of a selection or screening agent, wherein the surviving or screened cells comprise the orthogonal tRNA-tRNA synthetase pair for use in the in the in vivo translation system of the second organism. In one embodiment, comparing and selecting or screening includes an in vivo complementation assay. The concentration of the selection or screening agent can be varied.

The organisms of the present invention comprise a variety of organism and a variety of combinations. For example, the first and the second organisms of the methods of the present invention can be the same or different. In one embodiment, the organisms are optionally a prokaryotic organism, including but not limited to, *Methanococcus jannaschii, Methanobacterium thermoautotrophicum, Halobacterium, Escherichia coli, A. fulgidus, P. furiosus, P. horikoshii, A. pernix, T. thermophilus*, or the like. Alternatively, the organisms optionally comprise a eukaryotic organism, including but not limited to, plants (including but not limited to, complex plants such as monocots, or dicots), algae, protists, fungi (including but not limited to, yeast, etc), animals (including but not limited to, mammals, insects, arthropods, etc.), or the like. In another embodiment, the second organism is a prokaryotic organism, including but not limited to, *Methanococcus jannaschii, Methanobacterium thermoautotrophicum, Halobacterium, Escherichia coli, A. fulgidus, Halobacterium, P. furiosus, P. horikoshii, A. pernix, T. thermophilus*, or the like. Alternatively, the second organism can be a eukaryotic organism, including but not limited to, a yeast, a animal cell, a plant cell, a fungus, a mammalian cell, or the like. In various embodiments the first and second organisms are different.

Location of Non-Naturally-Occurring Amino Acids in Relaxin Polypeptides

The present invention contemplates incorporation of one or more non-naturally-occurring amino acids into relaxin polypeptides. One or more non-naturally-occurring amino acids may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids and/or inserting the non-naturally-occurring amino acid in a location that is not required for activity.

A variety of biochemical and structural approaches can be employed to select the desired sites for substitution with a non-naturally encoded amino acid within the Insulinpolypeptide. It is readily apparent to those of ordinary skill in the art that any position of the polypeptide chain is suitable for selection to incorporate a non-naturally encoded amino acid, and selection may be based on rational design or by random selection for any or no particular desired purpose. Selection of desired sites may be for producing a relaxin molecule having any desired property or activity, including but not limited to, agonists, super-agonists, inverse agonists, antagonists, receptor binding modulators, receptor activity modulators, dimer or multimer formation, no change to activity or property compared to the native molecule, or manipulating any physical or chemical property of the polypeptide such as solubility, aggregation, or stability. For example, locations in the polypeptide required for biological activity of relaxin polypeptides can be identified using point mutation analysis, alanine scanning, saturation mutagenesis and screening for biological activity, or homolog scanning methods known in the art. Other methods can be used to identify residues for modification of relaxin polypeptides include, but are not limited to, sequence profiling (Bowie and Eisenberg, Science 253(5016): 164-70, (1991)), rotamer library selections (Dahiyat and Mayo, Protein Sci 5(5): 895-903 (1996); Dahiyat and Mayo, Science 278(5335): 82-7 (1997); Desjarlais and Handel, Protein Science 4: 2006-2018 (1995); Harbury et al, PNAS USA 92(18): 8408-8412 (1995); Kono et al., Proteins: Structure, Function and Genetics 19: 244-255 (1994); Hellinga and Richards, PNAS USA 91: 5803-5807 (1994)); and residue pair potentials (Jones, Protein Science 3: 567-574, (1994)), and rational design using Protein Design Automation® technology. (See U.S. Pat. Nos. 6,188,965; 6,269,312; 6,403,312; WO98/47089, which are incorporated by reference). Residues that are critical for relaxin bioactivity, residues that are involved with pharmaceutical stability, antibody epitopes, or receptor binding residues may be mutated. U.S. Pat. Nos. 5,580,723; 5,834,250; 6,013,478; 6,428,954; and 6,451,561, which are incorporated by reference herein, describe methods for the systematic analysis of the structure and function of polypeptides such as relaxin by identifying active domains which influence the activity of the polypeptide with a target substance. Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-naturally encoded amino acid, again depending on the desired activity sought for the polypeptide. Another alternative would be to simply make serial substitutions in each position on the polypeptide chain with a non-naturally encoded amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

The structure and activity of mutants of relaxin polypeptides that contain deletions can also be examined to determine regions of the protein that are likely to be tolerant of substitution with a non-naturally encoded amino acid. In a similar manner, protease digestion and monoclonal antibodies can be used to identify regions of relaxin that are responsible for binding the relaxin receptor. Once residues that are likely to be intolerant to substitution with non-naturally encoded amino acids have been eliminated, the impact of proposed substitutions at each of the remaining positions can be examined. Models may be generated from the three-dimensional crystal structures of other relaxin family members and relaxin receptors. Protein Data Bank (PDB, available on the World Wide Web at resb.org) is a centralized database containing three-dimensional structural data of large molecules of proteins and nucleic acids. Models may be made investigating the secondary and tertiary structure of polypeptides, if three-dimensional structural data is not available. Thus, those of ordinary skill in the art can readily identify amino acid positions that can be substituted with non-naturally encoded amino acids.

Relaxin A Chain

| Residue Name | Residue#/ SEQ ID NO: 1 | complex solvent accessibility | | | chain A/B interface | | |
|---|---|---|---|---|---|---|---|
| | | Residue Average | Mainchain Average | Sidechain Average | Residue Average | Mainchain Average | Sidechain Average |
| LEU | 2 | 2.393927 | 2.336841 | 2.451013 | 0.00913 | 0.018259 | 0 |
| TYR | 3 | 1.05745 | 1.412109 | 0.880121 | 0.448218 | 0.164923 | 0.589865 |
| SER | 4 | 2.039557 | 1.726208 | 2.666253 | 0.094701 | 0.127334 | 0.029435 |
| ALA | 5 | 1.47603 | 1.32887 | 2.064669 | 0.040922 | 0.051152 | 0 |
| LEU | 6 | 0.520247 | 0.621696 | 0.418798 | 0.174242 | 0.189235 | 0.159248 |
| ALA | 7 | 0.476043 | 0.450361 | 0.578769 | 0.512186 | 0.474717 | 0.662064 |
| ASN | 8 | 1.252271 | 0.865912 | 1.638629 | 0.32958 | 0.460124 | 0.199036 |
| LYS | 9 | 0.886439 | 0.727133 | 1.013884 | 0.424786 | 0.531522 | 0.339397 |
| CYS | 10 | 0.307912 | 0.414588 | 0.094561 | 0.731348 | 0.802621 | 0.588801 |
| CYS | 11 | 0.791671 | 0.774527 | 0.825959 | 1.267628 | 1.170385 | 1.462113 |
| HIS | 12 | 1.644891 | 1.389182 | 1.815363 | 0.902367 | 0.910146 | 0.897182 |
| VAL | 13 | 1.432029 | 1.329367 | 1.568911 | 0.865782 | 1.041144 | 0.631966 |
| GLY | 14 | 0.721258 | 0.721258 | 0 | 0.814179 | 0.814179 | 0 |
| CYS | 15 | 0.405285 | 0.470822 | 0.274212 | 0.79239 | 0.856379 | 0.664412 |
| THR | 16 | 0.511268 | 0.367613 | 0.702808 | 1.096358 | 1.011865 | 1.209014 |
| LYS | 17 | 0.376592 | 0.233542 | 0.491032 | 2.691742 | 1.414171 | 3.713799 |
| ARG | 18 | 0.97893 | 0.478638 | 1.264811 | 1.626733 | 1.12903 | 1.911135 |
| SER | 19 | 0.416177 | 0.424198 | 0.405482 | 0.476934 | 0.49423 | 0.453873 |
| LEU | 20 | 0.155542 | 0.267306 | 0.043778 | 0.735924 | 0.711222 | 0.760627 |
| ALA | 21 | 0.478645 | 0.507787 | 0.362075 | 1.105314 | 1.045545 | 1.344386 |
| ARG | 22 | 1.273184 | 1.102102 | 1.370945 | 0.551495 | 0.572567 | 0.539454 |
| PHE | 23 | 1.054989 | 1.153619 | 0.998629 | 0.428106 | 0.829454 | 0.198764 |
| CYS | 24 | 1.352353 | 1.506838 | 1.146374 | 2.07439 | 2.22276 | 1.876563 |

Relaxin B Chain

| Residue Name | Residue#/ SEQ ID NO: 2 | complex solvent accessibility | | | chain A/B interface | | |
|---|---|---|---|---|---|---|---|
| | | Residue Average | Mainchain Average | Sidechain Average | Residue Average | Mainchain Average | Sidechain Average |
| SER | 2 | 2.241497 | 2.362674 | 1.999142 | 1.249697 | 1.108926 | 1.531239 |
| TRP | 3 | 1.036157 | 1.320435 | 0.922445 | 0.774516 | 1.009561 | 0.680498 |
| MET | 4 | 0.765903 | 0.783709 | 0.748097 | 1.378683 | 1.318601 | 1.438766 |
| GLU | 5 | 1.401968 | 1.102195 | 1.641786 | 1.60857 | 1.38927 | 1.784009 |
| GLU | 6 | 1.209446 | 0.935167 | 1.428869 | 0.994341 | 1.251666 | 0.788481 |
| VAL | 7 | 1.123345 | 1.08403 | 1.175766 | 1.917498 | 1.613757 | 2.322484 |
| ILE | 8 | 0.478044 | 0.594216 | 0.361873 | 1.329975 | 1.726264 | 0.933686 |
| LYS | 9 | 1.135226 | 0.723724 | 1.464427 | 2.332893 | 1.427852 | 3.056925 |
| LEU | 10 | 0.579 | 0.504927 | 0.653072 | 0.906043 | 1.195675 | 0.616411 |
| CYS | 11 | 0.862862 | 0.806072 | 0.976442 | 1.030881 | 0.795964 | 1.500714 |
| GLY | 12 | 1.089858 | 1.089858 | 0 | 0.604306 | 0.604306 | 0 |
| ARG | 13 | 3.079311 | 1.482092 | 3.992007 | 0.024047 | 0.066128 | 0 |
| GLU | 14 | 1.46883 | 0.992251 | 1.680643 | 0.137036 | 0.204496 | 0.107054 |
| LEU | 15 | 0.378917 | 0.508368 | 0.249467 | 0.743117 | 0.470105 | 1.016129 |
| VAL | 16 | 1.018006 | 0.820163 | 1.281796 | 0.279417 | 0.29034 | 0.264852 |
| ARG | 17 | 1.660023 | 0.937977 | 2.072621 | 0.048147 | 0.132403 | 0 |
| ALA | 18 | 0.51055 | 0.547669 | 0.362075 | 0.379088 | 0.387335 | 0.346101 |
| GLN | 19 | 0.436502 | 0.481692 | 0.400351 | 1.12185 | 0.733873 | 1.432231 |
| ILE | 20 | 1.321723 | 0.993689 | 1.649758 | 0.294635 | 0.473331 | 0.115939 |
| ALA | 21 | 1.001017 | 0.958569 | 1.170807 | 0.362917 | 0.40431 | 0.197346 |
| ILE | 22 | 0.381207 | 0.565133 | 0.197281 | 0.689578 | 0.665212 | 0.713943 |
| CYS | 23 | 0.888302 | 0.931778 | 0.80135 | 0.782559 | 0.685197 | 0.977284 |
| GLY | 24 | 1.608804 | 1.608804 | 0 | 0.25224 | 0.25224 | 0 |
| MET | 25 | 1.419412 | 1.489301 | 1.349524 | 0.239722 | 0.18572 | 0.293724 |
| SER | 26 | 1.07028 | 1.249672 | 0.711497 | 0.582382 | 0.433677 | 0.879791 |
| THR | 27 | 2.199516 | 2.265998 | 2.110873 | 0.228179 | 0.155968 | 0.32446 |
| TRP | 28 | 4.74167 | 3.651826 | 4.971111 | 0 | 0 | 0 |

In some embodiments, the relaxin polypeptides of the invention comprise one or more non-naturally encoded amino acids positioned in a region of the protein that does not disrupt the structure of the polypeptide.

Exemplary residues of incorporation of anon-naturally encoded amino acid may be those that are excluded from potential receptor binding regions, may be fully or partially solvent exposed, have minimal or no hydrogen-bonding interactions with nearby residues, may be minimally exposed to nearby reactive residues, may be on one or more of the exposed faces, may be a site or sites that are juxtaposed to a second relaxin, or other molecule or fragment thereof, may be in regions that are highly flexible, or structurally rigid, as predicted by the three-dimensional, secondary, tertiary, or quaternary structure of relaxin, bound or unbound to its receptor, or coupled or not coupled to another biologically active molecule, or may modulate the conformation of the relaxin itself or a dimer or multimer comprising one or more relaxin, by altering the flexibility or rigidity of the complete structure as desired.

One of ordinary skill in the art recognizes that such analysis of relaxin enables the determination of which amino acid residues are surface exposed compared to amino acid residues that are buried within the tertiary structure of the protein. Therefore, it is an embodiment of the present invention to substitute a non-naturally encoded amino acid for an amino acid that is a surface exposed residue.

In some embodiments, one or more non-naturally encoded amino acids are incorporated in one or more of the following positions in relaxin: in the A chain before position 1 (i.e. at the N-terminus), 1, 2, 3, 4, 5, 6, 7, 8, 9, 10, 11, 12, 13, 14, 15, 16, 17, 18, 19, 20, 21, 22 (i.e., at the carboxyl terminus of the protein), and any combination thereof (SEQ ID NO: 1) or in the B chain before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 (SEQ ID NO: 2).

An examination of the crystal structure of relaxin and its interaction with the relaxin receptor can indicate which certain amino acid residues have side chains that are fully or partially accessible to solvent. The side chain of a non-naturally encoded amino acid at these positions may point away from the protein surface and out into the solvent.

In some embodiments, the non-naturally encoded amino acid at one or more of these positions is linked to a water soluble polymer, including but not limited to, positions: in the A chain before position 1 (i.e. at the N-terminus), 1, 2, 3, 4, 5, 6, 7, 8, 9, 10, 11, 12, 13, 14, 15, 16, 17, 18, 19, 20, 21, 22 (i.e., at the carboxyl terminus of the protein), and any combination thereof (SEQ ID NO: 1) or in the B chain before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 (SEQ ID NO: 2).

A wide variety of non-naturally encoded amino acids can be substituted for, or incorporated into, a given position in a relaxin polypeptide. In general, a particular non-naturally encoded amino acid is selected for incorporation based on an examination of the three dimensional crystal structure of a relaxin polypeptide or other relaxin family member or relaxin analog with its receptor, a preference for conservative substitutions (i.e., aryl-based non-naturally encoded amino acids, such as p-acetylphenylalanine or O-propargyl-tyrosine substituting for Phe, Tyr or Trp), and the specific conjugation chemistry that one desires to introduce into the relaxin polypeptide (e.g., the introduction of 4-azidophenyl-alanine if one wants to effect a Huisgen [3+2]cycloaddition with a water soluble polymer bearing an alkyne moiety or a amide bond formation with a water soluble polymer that bears an aryl ester that, in turn, incorporates a phosphine moiety)

In one embodiment, the method further includes incorporating into the protein the unnatural amino acid, where the unnatural amino acid comprises a first reactive group; and contacting the protein with a molecule (including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thio-acid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above, or any other desirable compound or substance) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (including but not limited to, in unnatural amino acid p-propargyloxyphenylalanine) and the second reactive group is the azido moiety. In another example, the first reactive group is the azido moiety (including but not limited to, in the unnatural amino acid p-azido-L-phenylalanine) and the second reactive group is the alkynyl moiety.

In some cases, the non-naturally encoded amino acid substitution(s) will be combined with other additions, substitutions or deletions within the relaxin polypeptide to affect other biological traits of the relaxin polypeptide. In some cases, the other additions, substitutions or deletions may increase the stability (including but not limited to, resistance to proteolytic degradation) of the relaxin polypeptide or increase affinity of the relaxin polypeptide for its receptor. In some cases, the other additions, substitutions or deletions may increase the pharmaceutical stability of the relaxin polypeptide. In some cases, the other additions, substitutions or deletions may enhance the anti-viral activity of the relaxin polypeptide. In some cases, the other additions, substitutions or deletions may increase the solubility (including but not limited to, when expressed in *E. coli* or other host cells) of the relaxin polypeptide. In some embodiments additions, substitutions or deletions may increase the relaxin polypeptide solubility following expression in *E. coli* or other recombinant host cells. In some embodiments sites are selected for substitution with a naturally encoded or non-natural amino acid in addition to another site for incorporation of a non-natural amino acid that results in increasing the polypeptide solubility following expression in *E. coli* or other recombinant host cells. In some embodiments, the relaxin polypeptides comprise another addition, substitution or deletion that modulates affinity for the relaxin polypeptide receptor, binding proteins, or associated ligand, modulates signal transduction after binding to the relaxin receptor, modulates circulating half-life, modulates release or bioavailability, facilitates purification, or improves or alters a particular route of administration. In some embodiments, the relaxin polypeptides comprise an addition, substitution or deletion that increases the affinity of the relaxin variant for its receptor. Similarly, relaxin polypeptides can comprise chemical or enzyme cleavage sequences, protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification, transport through tissues or cell membranes, prodrug release or activation, relaxin size reduction, or other traits of the polypeptide.

In some embodiments, the substitution of a non-naturally encoded amino acid generates a relaxin antagonist. In some embodiments, a non-naturally encoded amino acid is substituted or added in a region involved with receptor binding. In some embodiments, relaxin antagonists comprise at least one substitution that cause relaxin to act as an antagonist. In some embodiments, the relaxin antagonist comprises a non-naturally encoded amino acid linked to a water soluble polymer that is present in a receptor binding region of the relaxin molecule.

In some cases, 1, 2, 3, 4, 5, 6, 7, 8, 9, 10, or more amino acids are substituted with one or more non-naturally-encoded amino acids. In some cases, the relaxin polypeptide further includes 1, 2, 3, 4, 5, 6, 7, 8, 9, 10, or more substitutions of one or more non-naturally encoded amino acids for naturally-occurring amino acids. For example, in some embodiments, one or more residues in relaxin are substituted with one or more non-naturally encoded amino acids. In some cases, the one or more non-naturally encoded residues are linked to one or more lower molecular weight linear or branched PEGs, thereby enhancing binding affinity and comparable serum half-life relative to the species attached to a single, higher molecular weight PEG.

In some embodiments, up to two of the following residues of relaxin are substituted with one or more non-naturally-encoded amino acids.

Expression in Non-Eukaryotes and Eukaryotes

To obtain high level expression of a cloned relaxin polynucleotide, one typically subclones polynucleotides encoding a relaxin polypeptide of the invention into an expression vector that contains a strong promoter to direct transcription, a transcription/translation terminator, and if for a nucleic acid encoding a protein, a ribosome binding site for translational initiation. Suitable bacterial promoters are known to those of ordinary skill in the art and described, e.g., in Sambrook et al. and Ausubel et al.

Bacterial expression systems for expressing relaxin polypeptides of the invention are available in, including but not limited to, *E. coli*, *Bacillus* sp., *Pseudomonas fluorescens, Pseudomonas aeruginosa, Pseudomonas putida*, and *Salmonella* (Palva et al., Gene 22:229-235 (1983); Mosbach et al., Nature 302:543-545 (1983)). Kits for such expression systems are commercially available. Eukaryotic expression systems for mammalian cells, yeast, and insect cells are known to those of ordinary skill in the art and are also commercially available. In cases where orthogonal tRNAs and aminoacyl tRNA synthetases (described above) are used to express the relaxin polypeptides of the invention, host cells for expression are selected based on their ability to use the orthogonal components. Exemplary host cells include Gram-positive bacteria (including but not limited to *B. brevis, B. subtilis*, or *Streptomyces*) and Gram-negative bacteria (*E. coli, Pseudomonas fluorescens, Pseudomonas aeruginosa, Pseudomonas putida*), as well as yeast and other eukaryotic cells. Cells comprising O-tRNA/O-RS pairs can be used as described herein.

A eukaryotic host cell or non-eukaryotic host cell of the present invention provides the ability to synthesize proteins that comprise unnatural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L or more). The production of large quantities (including but not limited to, greater that that typically possible with other methods, including but not limited to, in vitro translation) of a protein in a eukaryotic cell including at least one unnatural amino acid is a feature of the invention.

A eukaryotic host cell or non-eukaryotic host cell of the present invention provides the ability to biosynthesize proteins that comprise unnatural amino acids in large useful quantities. For example, proteins comprising an unnatural amino acid can be produced at a concentration of, including but not limited to, at least 10 µg/liter, at least 50 µg/liter, at least 75 g/liter, at least 100 µg/liter, at least 200 µg/liter, at least 250 µg/liter, or at least 500 µg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

A number of vectors suitable for expression of relaxin are commercially available. Useful expression vectors for eukaryotic hosts, include but are not limited to, vectors comprising expression control sequences from SV40, bovine papilloma virus, adenovirus and cytomegalovirus. Such vectors include pCDNA3.1(+)\Hyg (Invitrogen, Carlsbad, Calif., USA) and pCI-neo (Stratagene, La Jolla, Calif., USA). Bacterial plasmids, such as plasmids from *E. coli*, including pBR322, pET3a and pET12a, wider host range plasmids, such as RP4, phage DNAs, e.g., the numerous derivatives of phage lambda, e.g., NM989, and other DNA phages, such as M13 and filamentous single stranded DNA phages may be used. The 2 plasmid and derivatives thereof, the POT1 vector (U.S. Pat. No. 4,931,373 which is incorporated by reference), the pJSO37 vector described in (Okkels, Ann. New York Aced. Sci. 782, 202 207, 1996) and pPICZ A, B or C (Invitrogen) may be used with yeast host cells. For insect cells, the vectors include but are not limited to, pVL941, pBG311 (Cate et al., "Isolation of the Bovine and Human Genes for Mullerian Inhibiting Substance and Expression of the Human Gene In Animal Cells", Cell, 45, pp. 685 98 (1986), pBluebac 4.5 and pMelbac (Invitrogen, Carlsbad, Calif.).

The nucleotide sequence encoding a relaxin polypeptide may or may not also include sequence that encodes a signal peptide. The signal peptide is present when the polypeptide is to be secreted from the cells in which it is expressed. Such signal peptide may be any sequence. The signal peptide may be prokaryotic or eukaryotic. Coloma, M (1992) J. Imm. Methods 152:89 104) describe a signal peptide for use in mammalian cells (murine Ig kappa light chain signal peptide). Other signal peptides include but are not limited to, the α-factor signal peptide from S. cerevisiae (U.S. Pat. No. 4,870,008 which is incorporated by reference herein), the signal peptide of mouse salivary amylase (O. Hagenbuchle et al., Nature 289, 1981, pp. 643-646), a modified carboxypeptidase signal peptide (L. A. Valls et al., Cell 48, 1987, pp. 887-897), the yeast BAR1 signal peptide (WO 87/02670, which is incorporated by reference herein), and the yeast aspartic protease 3 (YAP3) signal peptide (cf. M. Egel-Mitani et al., Yeast 6, 1990, pp. 127-137).

Examples of suitable mammalian host cells are known to those of ordinary skill in the art. Such host cells may be Chinese hamster ovary (CHO) cells, (e.g. CHO-K1; ATCC CCL-61), Green Monkey cells (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture. These cell lines and others are available from public depositories such as the American Type Culture Collection, Rockville, Md. In order to provide improved glycosylation of the relaxin polypeptide, a mammalian host cell may be modified to express sialyltransferase, e.g. 1,6-sialyltransferase, e.g. as described in U.S. Pat. No. 5,047,335, which is incorporated by reference herein.

Methods for the introduction of exogenous DNA into mammalian host cells include but are not limited to, calcium phosphate-mediated transfection, electroporation, DEAE-dextran mediated transfection, liposome-mediated transfection, viral vectors and the transfection methods described by Life Technologies Ltd, Paisley, UK using Lipofectamin 2000 and Roche Diagnostics Corporation, Indianapolis, USA using FuGENE 6. These methods are well known in the art and are described by Ausbel et al. (eds.), 1996, Current Protocols in Molecular Biology, John Wiley & Sons, New York, USA. The cultivation of mammalian cells may be performed according to established methods, e.g. as disclosed in (Animal Cell Biotechnology, Methods and Protocols, Edited by Nigel Jenkins, 1999, Human Press Inc. Totowa, N.J., USA and Harrison Mass. and Rae IF, General Techniques of Cell Culture, Cambridge University Press 1997).

Expression Systems, Culture, and Isolation

Relaxin polypeptides may be expressed in any number of suitable expression systems including, for example, yeast, insect cells, mammalian cells, and bacteria. A description of exemplary expression systems is provided below.

Yeast As used herein, the term "yeast" includes any of the various yeasts capable of expressing a gene encoding a relaxin polypeptide. Such yeasts include, but are not limited to, ascosporogenous yeasts (Endomycetales), basidiosporogenous yeasts and yeasts belonging to the Fungi imperfecti (Blastomycetes) group. The ascosporogenous yeasts are divided into two families, Spermophthoraceae and Saccharomycetaceae. The latter is comprised of four subfamilies, Schizosaccharomycoideae (e.g., genus Schizosaccharomyces), Nadsonioideae, Lipomycoideae and Saccharomycoideae (e.g., genera Pichia, Kluyveromyces and Saccharomyces). The basidiosporogenous yeasts include the genera Leucosporidium, Rhodosporidium, Sporidiobolus, Filobasidium, and Filobasidiella. Yeasts belonging to the Fungi Imperfecti (Blastomycetes) group are divided into two families, Sporobolomycetaceae (e.g., genera Sporobolomyces and Bullera) and Cryptococcaceae (e.g., genus Candida).

Of particular interest for use with the present invention are species within the genera Pichia, Kluyveromyces, Saccharomyces, Schizosaccharomyces, Hansenula, Torulopsis, and Candida, including, but not limited to, P. pastoris, P. guillerimondii, S. cerevisiae, S. carlsbergensis, S. diastaticus, S. douglasii, S. kluyveri, S, norbensis, S. oviformis, K. lactis, K. fragilis, C. albicans, C. maltosa, and H. polymorpha.

The selection of suitable yeast for expression of relaxin polypeptides is within the skill of one of ordinary skill in the art. In selecting yeast hosts for expression, suitable hosts may include those shown to have, for example, good secretion capacity, low proteolytic activity, good secretion capacity, good soluble protein production, and overall robustness. Yeast are generally available from a variety of sources including, but not limited to, the Yeast Genetic Stock Center, Department of Biophysics and Medical Physics, University of California (Berkeley, Calif.), and the American Type Culture Collection ("ATCC") (Manassas, Va.).

The term "yeast host" or "yeast host cell" includes yeast that can be, or has been, used as a recipient for recombinant vectors or other transfer DNA. The term includes the progeny of the original yeast host cell that has received the recombinant vectors or other transfer DNA. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a relaxin polypeptide, are included in the progeny intended by this definition.

Expression and transformation vectors, including extra-chromosomal replicons or integrating vectors, have been developed for transformation into many yeast hosts. For example, expression vectors have been developed for S. cerevisiae (Sikorski et al., GENETICS (1989) 122:19; Ito et al., J. BACTERIOL. (1983) 153:163; Hinnen et al., PROC. NATL. ACAD. SCI. USA (1978) 75:1929); C. albicans (Kurtz et al., MOL. CELL. BIOL. (1986) 6:142); C. maltosa (Kunze et al., J. BASIC MICROBIOL. (1985) 25:141); H. polymorpha (Gleeson et al., J. GEN. MICROBIOL. (1986) 132:3459; Roggenkamp et al., MOL. GENETICS AND GENOMICS (1986) 202:302); K. fragilis (Das et al., J. BACTERIOL. (1984) 158:1165); K. lactis (De Louvencourt et al., J. BACTERIOL. (1983) 154:737; Van den Berg et al., BIOTECHNOLOGY (NY) (1990) 8:135); P. guillerimondii (Kunze et al., J. BASIC MICROBIOL. (1985) 25:141); P. pastoris (U.S. Pat. Nos. 5,324,639; 4,929,555; and 4,837, 148; Cregg et al., MOL. CELL. BIOL. (1985) 5:3376); Schizosaccharomyces pombe (Beach et al., NATURE (1982) 300:706); and Y. lipolytica; A. nidulans (Ballance et al., BIOCHEM. BIOPHYS. RES. COMMUN. (1983) 112:284-89; Tilburn et al., GENE (1983) 26:205-221; and Yelton et al., PROC. NATL. ACAD. SCI. USA (1984) 81:1470-74); A. niger (Kelly and Hynes, EMBO J. (1985) 4:475-479); T. reesia (EP 0 244 234); and filamentous fungi such as, e.g., Neurospora, Penicillium, Tolypocladium (WO 91/00357), each incorporated by reference herein.

Control sequences for yeast vectors are known to those of ordinary skill in the art and include, but are not limited to, promoter regions from genes such as alcohol dehydrogenase (ADH) (EP 0 284 044); enolase; glucokinase; glucose-6-phosphate isomerase; glyceraldehyde-3-phosphate-dehydrogenase (GAP or GAPDH); hexokinase; phosphofructokinase; 3-phosphoglycerate mutase; and pyruvate kinase (PyK) (EP 0 329 203). The yeast PHO5 gene, encoding acid phosphatase, also may provide useful promoter sequences (Miyanohara et al., PROC. NATL. ACAD. SCI. USA (1983) 80:1). Other suitable promoter sequences for use with yeast hosts may include the promoters for 3-phosphoglycerate kinase (Hitzeman et al., J. BIOL. CHEM. (1980) 255: 12073); and other glycolytic enzymes, such as pyruvate decarboxylase, triosephosphate isomerase, and phosphoglucose isomerase (Holland et al., BIOCHEMISTRY (1978) 17:4900; Hess et al., J. ADV. ENZYME REG. (1969) 7:149). Inducible yeast promoters having the additional advantage of transcription controlled by growth conditions may include the promoter regions for alcohol dehydrogenase 2; isocytochrome C; acid phosphatase; metallothionein; glyceraldehyde-3-phosphate dehydrogenase; degradative enzymes associated with nitrogen metabolism; and enzymes responsible for maltose and galactose utilization. Suitable vectors and promoters for use in yeast expression are further described in EP 0 073 657.

Yeast enhancers also may be used with yeast promoters. In addition, synthetic promoters may also function as yeast promoters. For example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197, which are incorporated by reference herein. Other examples of hybrid promoters include promoters that consist of the regulatory sequences of the ADH2, GAL4, GAL10, or PHO5 genes, combined with the transcriptional activation region of a glycolytic enzyme gene such as GAP or PyK. See EP 0 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. BIOL. CHEM. (1981) 256:1385). In addition, the origin of replication from the 2µ plasmid origin is suitable for yeast. A suitable selection gene for use in yeast is the trp1 gene present in the yeast plasmid. See Tschumper et al., GENE (1980) 10:157; Kingsman et al., GENE (1979) 7:141. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

Methods of introducing exogenous DNA into yeast hosts are known to those of ordinary skill in the art, and typically include, but are not limited to, either the transformation of spheroplasts or of intact yeast host cells treated with alkali cations. For example, transformation of yeast can be carried out according to the method described in Hsiao et al., PROC. NATL. ACAD. SCI. USA (1979) 76:3829 and Van Solingen et al., J. BACT. (1977) 130:946. However, other methods for introducing DNA into cells such as by nuclear injection, electroporation, or protoplast fusion may also be used as described generally in SAMBROOK ET AL., MOLECULAR CLONING: A LAB. MANUAL (2001). Yeast host cells may then be cultured using standard techniques known to those of ordinary skill in the art.

Other methods for expressing heterologous proteins in yeast host cells are known to those of ordinary skill in the art. See generally U.S. Patent Publication No. 20020055169, U.S. Pat. Nos. 6,361,969; 6,312,923; 6,183,985; 6,083,723; 6,017,731; 5,674,706; 5,629,203; 5,602,034; and 5,089,398; U.S. Reexamined Pat. Nos. RE37,343 and RE35,747; PCT Published Patent Applications WO 99/07862; WO 98/37208; and WO 98/26080; European Patent Applications EP 0 946 736; EP 0 732 403; EP 0 480 480; WO 90/10277; EP 0 340 986; EP 0 329 203; EP 0 324 274; and EP 0 164 556. See also Gellissen et al., ANTONIE VAN LEEUWENHOEK (1992) 62(1-2):79-93; Romanos et al., YEAST (1992) 8(6):423-488; Goeddel, METHODS IN ENZYMOLOGY (1990) 185:3-7, each incorporated by reference herein.

The yeast host strains may be grown in fermentors during the amplification stage using standard feed batch fermentation methods known to those of ordinary skill in the art. The fermentation methods may be adapted to account for differences in a particular yeast host's carbon utilization pathway or mode of expression control. For example, fermentation of a *Saccharomyces* yeast host may require a single glucose feed, complex nitrogen source (e.g., casein hydrolysates), and multiple vitamin supplementation. In contrast, the methylotrophic yeast *P. pastoris* may require glycerol, methanol, and trace mineral feeds, but only simple ammonium (nitrogen) salts for optimal growth and expression. See, e.g., U.S. Pat. No. 5,324,639; Elliott et al., J. PROTEIN CHEM. (1990) 9:95; and Fieschko et al., BIOTECH. BIOENG. (1987) 29:1113, incorporated by reference herein.

Such fermentation methods, however, may have certain common features independent of the yeast host strain employed. For example, a growth limiting nutrient, typically carbon, may be added to the fermentor during the amplification phase to allow maximal growth. In addition, fermentation methods generally employ a fermentation medium designed to contain adequate amounts of carbon, nitrogen, basal salts, phosphorus, and other minor nutrients (vitamins, trace minerals and salts, etc.). Examples of fermentation media suitable for use with *Pichia* are described in U.S. Pat. Nos. 5,324,639 and 5,231,178, which are incorporated by reference herein.

Baculovirus-Infected Insect Cells

The term "insect host" or "insect host cell" refers to a insect that can be, or has been, used as a recipient for recombinant vectors or other transfer DNA. The term includes the progeny of the original insect host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a relaxin polypeptide, are included in the progeny intended by this definition. Baculovirus expression of relaxin polypeptides is useful in the present invention and the use of rDNA technology, polypeptides or precursors thereof because relaxin may be biosynthesized in any number of host cells including bacteria, mammalian cells, insect cells, yeast or fungi. An embodiment of the present invention includes biosynthesis of relaxin, modified relaxin, relaxin polypeptides, or relaxin analogs in bacteria, yeast or mammalian cells. Another embodiment of the present invention involves biosynthesis done in *E. coli* or a yeast. Examples of biosynthesis in mammalian cells and transgenic animals are described in Hakola, K. [Molecular and Cellular Endocrinology, 127:59-69, (1997)].

The selection of suitable insect cells for expression of relaxin polypeptides is known to those of ordinary skill in the art. Several insect species are well described in the art and are commercially available including *Aedes aegypti, Bombyx mori, Drosophila melanogaster, Spodoptera frugiperda*, and *Trichoplusia ni*. In selecting insect hosts for expression, suitable hosts may include those shown to have, inter alia, good secretion capacity, low proteolytic activity, and overall robustness. Insect are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.).

Generally, the components of a baculovirus-infected insect expression system include a transfer vector, usually a bacterial plasmid, which contains both a fragment of the baculovirus genome, and a convenient restriction site for insertion of the heterologous gene to be expressed; a wild type baculovirus with sequences homologous to the baculovirus-specific fragment in the transfer vector (this allows for the homologous recombination of the heterologous gene in to the baculovirus genome); and appropriate insect host cells and growth media. The materials, methods and techniques used in constructing vectors, transfecting cells, picking plaques, growing cells in culture, and the like are known in the art and manuals are available describing these techniques.

After inserting the heterologous gene into the transfer vector, the vector and the wild type viral genome are transfected into an insect host cell where the vector and viral genome recombine. The packaged recombinant virus is expressed and recombinant plaques are identified and purified. Materials and methods for baculovirus/insect cell expression systems are commercially available in kit form from, for example, Invitrogen Corp. (Carlsbad, Calif.). These techniques are generally known to those of ordinary skill in the art and fully described in SUMMERS AND SMITH, TEXAS AGRICULTURAL EXPERIMENT STATION BULLETIN NO. 1555 (1987), herein incorporated by reference. See also, RICHARDSON, 39 METHODS IN MOLECULAR BIOLOGY: BACULOVIRUS EXPRESSION PROTOCOLS (1995); AUSUBEL ET AL., CURRENT PROTOCOLS IN MOLECULAR BIOLOGY 16.9-16.11 (1994); KING AND POSSEE, THE BACULOVIRUS SYSTEM: A LABORATORY GUIDE (1992); and O'REILLY ET AL., BACULOVIRUS EXPRESSION VECTORS: A LABORATORY MANUAL (1992).

Indeed, the production of various heterologous proteins using baculovirus/insect cell expression systems is known to those of ordinary skill in the art. See, e.g., U.S. Pat. Nos. 6,368,825; 6,342,216; 6,338,846; 6,261,805; 6,245,528; 6,225,060; 6,183,987; 6,168,932; 6,126,944; 6,096,304; 6,013,433; 5,965,393; 5,939,285; 5,891,676; 5,871,986; 5,861,279; 5,858,368; 5,843,733; 5,762,939; 5,753,220; 5,605,827; 5,583,023; 5,571,709; 5,516,657; 5,290,686; WO 02/06305; WO 01/90390; WO 01/27301; WO 01/05956; WO 00/55345; WO 00/20032; WO 99/51721; WO 99/45130; WO 99/31257; WO 99/10515; WO 99/09193; WO 97/26332; WO 96/29400; WO 96/25496; WO 96/06161; WO 95/20672; WO 93/03173; WO 92/16619; WO 92/02628; WO 92/01801; WO 90/14428; WO 90/10078; WO 90/02566; WO 90/02186; WO 90/01556; WO 89/01038; WO 89/01037; WO 88/07082, which are incorporated by reference herein.

Vectors that are useful in baculovirus/insect cell expression systems are known in the art and include, for example, insect expression and transfer vectors derived from the baculovirus Autographacalifornica nuclear polyhedrosis virus (AcNPV), which is a helper-independent, viral expression vector. Viral expression vectors derived from this system usually use the strong viral polyhedrin gene promoter to drive expression of heterologous genes. See generally, O'Reilly ET AL., BACULOVIRUS EXPRESSION VECTORS: A LABORATORY MANUAL (1992).

Prior to inserting the foreign gene into the baculovirus genome, the above-described components, comprising a promoter, leader (if desired), coding sequence of interest, and transcription termination sequence, are typically assembled into an intermediate transplacement construct (transfer vector). Intermediate transplacement constructs are often maintained in a replicon, such as an extra chromosomal element (e.g., plasmids) capable of stable maintenance in a host, such as bacteria. The replicon will have a replication system, thus allowing it to be maintained in a suitable host for cloning and amplification. More specifically, the plasmid may contain the polyhedrin polyadenylation signal (Miller, ANN. REV. MICROBIOL. (1988) 42:177) and a prokaryotic ampicillin-resistance (amp) gene and origin of replication for selection and propagation in *E. coli*.

One commonly used transfer vector for introducing foreign genes into AcNPV is pAc373. Many other vectors, known to those of skill in the art, have also been designed including, for example, pVL985, which alters the polyhedrin start codon from ATG to ATT, and which introduces a BamHI cloning site 32 base pairs downstream from the ATT. See Luckow and Summers, VIROLOGY 170:31 (1989). Other commercially available vectors include, for example, PBlueBac4.5/V5-His; pBlueBacHis2; pMelBac; pBlueBac4.5 (Invitrogen Corp., Carlsbad, Calif.).

After insertion of the heterologous gene, the transfer vector and wild type baculoviral genome are co-transfected into an insect cell host. Methods for introducing heterologous DNA into the desired site in the baculovirus virus are known in the art. See SUMMERS AND SMITH, TEXAS AGRICULTURAL EXPERIMENT STATION BULLETIN NO. 1555 (1987); Smith et al., MOL. CELL. BIOL. (1983) 3:2156; Luckow and Summers, VIROLOGY (1989) 170:31. For example, the insertion can be into a gene such as the polyhedrin gene, by homologous double crossover recombination; insertion can also be into a restriction enzyme site engineered into the desired baculovirus gene. See Miller et al., BIOESSAYS (1989) 11(4):91.

Transfection may be accomplished by electroporation. See TROTTER AND WOOD, 39 METHODS IN MOLECULAR BIOLOGY (1995); Mann and King, J. GEN. VIROL. (1989) 70:3501. Alternatively, liposomes may be used to transfect the insect cells with the recombinant expression vector and the baculovirus. See, e.g., Liebman et al., BIOTECHNIQUES (1999) 26(1):36; Graves et al., BIOCHEMISTRY (1998) 37:6050; Nomura et al., J. BIOL. CHEM. (1998) 273(22):13570; Schmidt et al., PROTEIN EXPRESSION AND PURIFICATION (1998) 12:323; Siffert et al., NATURE GENETICS (1998) 18:45; TILKINS ET AL., CELL BIOLOGY: A LABORATORY HANDBOOK 145-154 (1998); Cai et al., PROTEIN EXPRESSION AND PURIFICATION (1997) 10:263; Dolphin et al., NATURE GENETICS (1997) 17:491; Kost et al., GENE (1997) 190:139; Jakobsson et al., J. BIOL. CHEM. (1996) 271:22203; Rowles et al., J. BIOL. CHEM. (1996) 271(37): 22376; Reverey et al., J. BIOL. CHEM. (1996) 271(39): 23607-10; Stanley et al., J. BIOL. CHEM. (1995) 270:4121; Sisk et al., J. VIROL. (1994) 68(2):766; and Peng et al., BIOTECHNIQUES (1993) 14(2):274. Commercially available liposomes include, for example, Cellfectin® and Lipofectin® (Invitrogen, Corp., Carlsbad, Calif.). In addition, calcium phosphate transfection may be used. See TROTTER AND WOOD, 39 METHODS IN MOLECULAR BIOLOGY (1995); Kitts, NAR (1990) 18(19):5667; and Mann and King, J. GEN. VIROL. (1989) 70:3501.

Baculovirus expression vectors usually contain a baculovirus promoter. A baculovirus promoter is any DNA sequence capable of binding a baculovirus RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Moreover, expression may be either regulated or constitutive.

Structural genes, abundantly transcribed at late times in the infection cycle, provide particularly useful promoter sequences. Examples include sequences derived from the gene encoding the viral polyhedron protein (FRIESEN ET AL., The Regulation of Baculovirus Gene Expression in THE MOLECULAR BIOLOGY OF BACULOVIRUSES (1986); EP 0 127 839 and 0 155 476) and the gene encoding the p10 protein (Vlak et al., J. GEN. VIROL. (1988) 69:765).

The newly formed baculovirus expression vector is packaged into an infectious recombinant baculovirus and subsequently grown plaques may be purified by techniques known to those of ordinary skill in the art. See Miller et al., BIOESSAYS (1989) 11(4):91; SUMMERS AND SMITH, TEXAS AGRICULTURAL EXPERIMENT STATION BULLETIN NO. 1555 (1987).

Recombinant baculovirus expression vectors have been developed for infection into several insect cells. For example, recombinant baculoviruses have been developed for, inter alia, *Aedes aegypti* (ATCC No. CCL-125), *Bombyx mori* (ATCC No. CRL-8910), *Drosophila melanogaster* (ATCC No. 1963), *Spodoptera frugiperda*, and *Trichoplusia ni*. See Wright, NATURE (1986) 321:718; Carbonell et al., J. VIROL. (1985) 56:153; Smith et al., MOL. CELL. BIOL. (1983) 3:2156. See generally, Fraser et al., IN VITRO CELL. DEV. BIOL. (1989) 25:225. More specifically, the cell lines used for baculovirus expression vector systems commonly include, but are not limited to, Sf9 (*Spodoptera frugiperda*) (ATCC No. CRL-1711), Sf21 (*Spodoptera frugiperda*) (Invitrogen Corp., Cat. No. 11497-013 (Carlsbad, Calif.)), Tri-368 (*Trichopulsia ni*), and High-Five™ BTI-TN-5B1-4 (*Trichopulsia ni*).

Cells and culture media are commercially available for both direct and fusion expression of heterologous polypeptides in a baculovirus/expression, and cell culture technology is generally known to those of ordinary skill in the art.

E. Coli, Pseudomonas Species, and Other Prokaryotes

Bacterial expression techniques are known to those of ordinary skill in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers is present, which provide for different characteristics.

A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al., ANNU. REV. GENET. (1984) 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., NATURE (1977) 198:1056], and maltose. Additional examples include promoter sequences derived from biosynthetic enzymes such as tryptophan (trp) [Goeddel et al., NUC. ACIDS RES. (1980) 8:4057; Yelverton et al., NUCL. ACIDS RES. (1981) 9:731; U.S. Pat. No. 4,738,921; EP Pub. Nos. 036 776 and 121 775, which are incorporated by reference herein]. The β-galactosidase (bla) promoter system [Weissmann (1981) "The cloning of interferon and other mistakes." In Interferon 3 (Ed. I. Gresser)], bacteriophage lambda PL [Shimatake et al., NATURE (1981) 292:128] and T5 [U.S. Pat. No. 4,689,406, which are incorporated by reference herein] promoter systems also provide useful promoter sequences. Preferred methods of the present invention utilize strong promoters, such as the T7 promoter to induce relaxin polypeptides at high levels. Examples of such vectors are known to those of ordinary skill in the art and include the pET29 series from Novagen, and the pPOP vectors described in WO99/05297, which is incorporated by reference herein. Such expression systems produce high levels of relaxin polypeptides in the host without compromising host cell viability or growth parameters. pET19 (Novagen) is another vector known in the art.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551, 433, which is incorporated by reference herein]. For example, the tac promoter is a hybrid trp-lac promoter comprised of both trp promoter and lac operon sequences that is regulated by the lac repressor [Amann et al., GENE (1983) 25:167; de Boer et al., PROC. NATL. ACAD. SCI. (1983) 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., J. MOL. BIOL. (1986) 189:113; Tabor et al., Proc Natl. Acad. Sci. (1985) 82:1074]. In addition, a hybrid promoter can also be comprised of a bacteriophage promoter and an *E. coli* operator region (EP Pub. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al., NATURE (1975) 254:34]. The SD sequence is thought to promote binding of mRNA to the ribosome by the pairing of bases between the SD sequence and the 3' and of *E. coli* 16S rRNA [Steitz et al. "Genetic signals and nucleotide sequences in messenger RNA", In Biological Regulation and Development: Gene Expression (Ed. R. F. Goldberger, 1979)]. To express eukaryotic genes and prokaryotic genes with weak ribosome-binding site [Sambrook et al. "Expression of cloned genes in *Escherichia coli*", Molecular Cloning: A Laboratory Manual, 1989].

The term "bacterial host" or "bacterial host cell" refers to a bacterial that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a relaxin polypeptide, are included in the progeny intended by this definition.

The selection of suitable host bacteria for expression of relaxin polypeptides is known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. Other examples of suitable *E. coli* hosts include, but are not limited to, strains of BL21, DH10B, or derivatives thereof. In another embodiment of the methods of the present invention, the *E. coli* host is a protease minus strain including, but not limited to, OMP- and LON-. The host cell strain may be a species of *Pseudomonas*, including but not limited to, *Pseudomonas fluorescens, Pseudomonas aeruginosa*, and *Pseudomonas putida. Pseudomonas fluorescens* biovar 1, designated strain MB101, is known to be useful for recombinant production and is available for therapeutic protein production processes. Examples of a *Pseudomonas* expression system include the system available from The Dow Chemical Company as a host strain (Midland, Mich. available on the World Wide Web at dow.com).

Once a recombinant host cell strain has been established (i.e., the expression construct has been introduced into the host cell and host cells with the proper expression construct are isolated), the recombinant host cell strain is cultured under conditions appropriate for production of relaxin polypeptides. As will be apparent to one of skill in the art, the method of culture of the recombinant host cell strain will be dependent on the nature of the expression construct utilized and the identity of the host cell. Recombinant host strains are normally cultured using methods that are known to those of ordinary skill in the art. Recombinant host cells are typically cultured in liquid medium containing assimilatable sources of carbon, nitrogen, and inorganic salts and, optionally, containing vitamins, amino acids, growth factors, and other proteinaceous culture supplements known to those of ordinary skill in the art. Liquid media for culture of host cells may optionally contain antibiotics or anti-fungals to prevent the growth of undesirable microorganisms and/or compounds including, but not limited to, antibiotics to select for host cells containing the expression vector.

Recombinant host cells may be cultured in batch or continuous formats, with either cell harvesting (in the case where the relaxin polypeptide accumulates intracellularly) or harvesting of culture supernatant in either batch or continuous formats. For production in prokaryotic host cells, batch culture and cell harvest are preferred.

The relaxin polypeptides of the present invention are normally purified after expression in recombinant systems. The relaxin polypeptide may be purified from host cells or culture medium by a variety of methods known to the art. Relaxin polypeptides produced in bacterial host cells may be poorly soluble or insoluble (in the form of inclusion bodies). In one embodiment of the present invention, amino acid substitutions may readily be made in the relaxin polypeptide that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods known to those of ordinary skill in the art. Host cell disruption or homogenization may be performed using well known techniques including, but not limited to, enzymatic cell disruption, sonication, dounce homogenization, or high pressure release disruption. In one embodiment of the method of the present invention, the high pressure release technique is used to disrupt the *E. coli* host cells to release the inclusion bodies of the relaxin polypeptides. When handling inclusion bodies of relaxin polypeptide, it may be advantageous to minimize the homogenization time on repetitions in order to maximize the yield of inclusion bodies without loss due to factors such as solubilization, mechanical shearing or proteolysis.

Insoluble or precipitated relaxin polypeptide may then be solubilized using any of a number of suitable solubilization agents known to the art. The relaxin polyeptide may be solubilized with urea or guanidine hydrochloride. The volume of the solubilized relaxin polypeptide should be minimized so that large batches may be produced using conveniently manageable batch sizes. This factor may be significant in a large-scale commercial setting where the recombinant host may be grown in batches that are thousands of liters in volume. In addition, when manufacturing relaxin polypeptide in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the relaxin polypeptide inclusion bodies in place of the harsher denaturing agent guanidine hydrochloride. The use of urea significantly reduces the risk of damage to stainless steel equipment utilized in the manufacturing and purification process of relaxin polypeptide while efficiently solubilizing the relaxin polypeptide inclusion bodies.

In the case of soluble relaxin protein, the relaxin may be secreted into the periplasmic space or into the culture medium. In addition, soluble relaxin may be present in the cytoplasm of the host cells. It may be desired to concentrate soluble relaxin prior to performing purification steps. Standard techniques known to those of ordinary skill in the art may be used to concentrate soluble relaxin from, for example, cell lysates or culture medium. In addition, standard techniques known to those of ordinary skill in the art may be used to disrupt host cells and release soluble relaxin from the cytoplasm or periplasmic space of the host cells.

When relaxin polypeptide is produced as a fusion protein, the fusion sequence may be removed. Removal of a fusion sequence may be accomplished by enzymatic or chemical cleavage. Enzymatic removal of fusion sequences may be accomplished using methods known to those of ordinary skill in the art. The choice of enzyme for removal of the fusion sequence will be determined by the identity of the fusion, and the reaction conditions will be specified by the choice of enzyme as will be apparent to one of ordinary skill in the art. Chemical cleavage may be accomplished using reagents known to those of ordinary skill in the art, including but not limited to, cyanogen bromide, TEV protease, and other reagents. The cleaved relaxin polypeptide may be purified from the cleaved fusion sequence by methods known to those of ordinary skill in the art. Such methods will be determined by the identity and properties of the fusion sequence and the relaxin polypeptide, as will be apparent to one of ordinary skill in the art. Methods for purification may include, but are not limited to, size-exclusion chromatography, hydrophobic interaction chromatography, ion-exchange chromatography or dialysis or any combination thereof.

The relaxin polypeptide may also be purified to remove DNA from the protein solution. DNA may be removed by any suitable method known to the art, such as precipitation or ion exchange chromatography, but may be removed by precipitation with a nucleic acid precipitating agent, such as, but not limited to, protamine sulfate. The relaxin polypeptide may be separated from the precipitated DNA using standard well known methods including, but not limited to, centrifugation or filtration. Removal of host nucleic acid molecules is an important factor in a setting where the relaxin polypeptide is to be used to treat humans and the methods of the present invention reduce host cell DNA to pharmaceutically acceptable levels.

Methods for small-scale or large-scale fermentation can also be used in protein expression, including but not limited to, fermentors, shake flasks, fluidized bed bioreactors, hollow fiber bioreactors, roller bottle culture systems, and stirred tank bioreactor systems. Each of these methods can be performed in a batch, fed-batch, or continuous mode process.

Human relaxin polypeptides of the invention can generally be recovered using methods standard in the art. For example, culture medium or cell lysate can be centrifuged or filtered to remove cellular debris. The supernatant may be concentrated or diluted to a desired volume or diafiltered into a suitable buffer to condition the preparation for further purification. Further purification of the relaxin polypeptide of the present invention includes separating deamidated and clipped forms of the relaxin polypeptide variant from the intact form.

Any of the following exemplary procedures can be employed for purification of relaxin polypeptides of the invention: affinity chromatography; anion- or cation-exchange chromatography (using, including but not limited to, DEAE SEPHAROSE); chromatography on silica; high performance liquid chromatography (HPLC); reverse phase HPLC; gel filtration (using, including but not limited to, SEPHADEX G-75); hydrophobic interaction chromatography; size-exclusion chromatography; metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), SDS-PAGE, or extraction.

Proteins of the present invention, including but not limited to, proteins comprising unnatural amino acids, peptides comprising unnatural amino acids, antibodies to proteins comprising unnatural amino acids, binding partners for proteins comprising unnatural amino acids, etc., can be purified, either partially or substantially to homogeneity, according to standard procedures known to and used by those of skill in the art. Accordingly, polypeptides of the invention can be recovered and purified by any of a number of methods known to those of ordinary skill in the art, including but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins or peptides comprising unnatural amino acids) are used as purification reagents, including but not limited to, for affinity-based purification of proteins or peptides comprising one or more unnatural amino acid(s). Once purified, partially or to homogeneity, as desired, the polypeptides are optionally used for a wide variety of utilities, including but not limited to, as assay components, therapeutics, prophylaxis, diagnostics, research reagents, and/or as immunogens for antibody production. Antibodies generated against polypeptides of the present invention may be obtained by administering the polypeptides or epitope-bearing fragments, or cells to an animal, preferably a non-human animal, using routine protocols. One of ordinary skill in the art could generate antibodies using a variety of known techniques. Also, transgenic mice, or other organisms, including other mammals, may be used to express humanized antibodies. The above-described antibodies may be employed to isolate or to identify clones expressing the polypeptide or to purify the polypeptides. Antibodies against polypeptides of the present invention may also be employed to treat diseases.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use as a vaccine, a polypeptide or a nucleic acid vector will be normally provided as a vaccine formulation (composition). The formulation may further comprise a suitable carrier. Since a polypeptide may be broken down in the stomach, it may be administered parenterally (for instance, subcutaneous, intramuscular, intravenous, or intradermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The vaccine formulation may also include adjuvant systems for enhancing the immunogenicity of the formulation which are known to those of ordinary skill in the art. The dosage will depend on the specific activity of the vaccine and can be readily determined by routine experimentation.

Expression in Alternate Systems

Several strategies have been employed to introduce unnatural amino acids into proteins in non-recombinant host cells, mutagenized host cells, or in cell-free systems. These systems are also suitable for use in making the Relaxin polypeptides of the present invention. Derivatization of amino acids with reactive side-chains such as Lys, Cys and Tyr resulted in the conversion of lysine to $N^2$-acetyl-lysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem*, 69:923 (2000). Chemical peptide ligation and native chemical ligation are described in U.S. Pat. No. 6,184,344, U.S. Patent Publication No. 2004/0138412, U.S. Patent Publication No. 2003/0208046, WO 02/098902, and WO 03/042235, which are incorporated by reference herein. A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl.*, 1995, 34:621 (1995); C. J. Noren, S. J. Anthony-Cahill, M. C. Griffith, P. G. Schultz, *A general method for site-specific incorporation of unnatural amino acids into proteins, Science* 244:182-188 (1989); and, J. D. Bain, C. G. Glabe, T. A. Dix, A. R. Chamberlin, E. S. Diala, *Biosynthetic site-specific incorporation of a non-natural amino acid into a polypeptide, J. Am. Chem. Soc.* 111:8013-8014(1989). A broad range of functional groups has been introduced into proteins for studies of protein stability, protein folding, enzyme mechanism, and signal transduction.

In addition to other references noted herein, a variety of purification/protein folding methods are known to those of ordinary skill in the art, including, but not limited to, those set forth in R. Scopes, Protein Purification, Springer-Verlag, N.Y. (1982); Deutscher, Methods in Enzymology Vol. 182: Guide to Protein Purification, Academic Press, Inc. N.Y. (1990); Sandana, (1997) Bioseparation of Proteins, Academic Press, Inc.; Bollag et al. (1996) Protein Methods, 2nd Edition Wiley-Liss, NY; Walker, (1996) The Protein Protocols Handbook Humana Press, NJ, Harris and Angal, (1990) Protein Purification Applications: A Practical Approach IRL Press at Oxford, Oxford, England; Harris and Angal, Protein Purification Methods: A Practical Approach IRL Press at Oxford, Oxford, England; Scopes, (1993) Protein Purification: Principles and Practice 3rd Edition Springer Verlag, NY; Janson and Ryden, (1998) Protein Purification: Principles, High Resolution Methods and Applications, Second Edition Wiley-VCH, NY; and Walker (1998), Protein Protocols on CD-ROM Humana Press, NJ; and the references cited therein.

One advantage of producing a protein or polypeptide of interest with an unnatural amino acid in a eukaryotic host cell or non-eukaryotic host cell is that typically the proteins or polypeptides will be folded in their native conformations. However, in certain embodiments of the invention, those of skill in the art will recognize that, after synthesis, expression and/or purification, proteins or peptides can possess a conformation different from the desired conformations of the relevant polypeptides. In one aspect of the invention, the expressed protein or polypeptide is optionally denatured and then renatured. This is accomplished utilizing methods known in the art, including but not limited to, by adding a chaperonin to the protein or polypeptide of interest, by solubilizing the proteins in a chaotropic agent such as guanidine HCl, utilizing protein disulfide isomerase, etc.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are known to those of ordinary skill in the art (see, the references above, and Debinski, et al. (1993) J. Biol. Chem., 268: 14065-14070; Kreitman and Pastan (1993) Bioconjug. Chem., 4: 581-585; and Buchner, et al., (1992) Anal. Biochem., 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of relaxin polypeptide, the relaxin polypeptide thus produced may be misfolded and thus lacks or has reduced biological activity. The bioactivity of the protein may be restored by "refolding". In general, misfolded relaxin polypeptide is refolded by solubilizing (where the relaxin polypeptide is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. Relaxin polypeptide may be refolded using standard methods known in the art, such as those described in U.S. Pat. Nos. 4,511,502, 4,511,503, and 4,512,922, which are incorporated by reference herein. The relaxin polypeptide may also be cofolded with other proteins to form heterodimers or heteromultimers.

After refolding, the relaxin may be further purified. Purification of relaxin may be accomplished using a variety of techniques known to those of ordinary skill in the art, including hydrophobic interaction chromatography, size exclusion chromatography, ion exchange chromatography, reverse-phase high performance liquid chromatography, affinity chromatography, and the like or any combination thereof. Additional purification may also include a step of drying or precipitation of the purified protein.

After purification, relaxin may be exchanged into different buffers and/or concentrated by any of a variety of methods known to the art, including, but not limited to, diafiltration and dialysis. Relaxin that is provided as a single purified protein may be subject to aggregation and precipitation.

The purified relaxin may be at least 90% pure (as measured by reverse phase high performance liquid chromatography, RP-HPLC, or sodium dodecyl sulfate-polyacrylamide gel electrophoresis, SDS-PAGE) or at least 95% pure, or at least 98% pure, or at least 99% or greater pure. Regardless of the exact numerical value of the purity of the relaxin, the relaxin is sufficiently pure for use as a pharmaceutical product or for further processing, such as conjugation with a water soluble polymer such as PEG.

Certain relaxin molecules may be used as therapeutic agents in the absence of other active ingredients or proteins (other than excipients, carriers, and stabilizers, serum albumin and the like), or they may be complexed with another protein or a polymer.

General Purification Methods

Any one of a variety of isolation steps may be performed on the cell lysate, extract, culture medium, inclusion bodies, periplasmic space of the host cells, cytoplasm of the host cells, or other material, comprising relaxin polypeptide or on any relaxin polypeptide mixtures resulting from any isolation steps including, but not limited to, affinity chromatography, ion exchange chromatography, hydrophobic interaction chromatography, gel filtration chromatography, high performance liquid chromatography ("HPLC"), reversed phase-HPLC ("RP-HPLC"), expanded bed adsorption, or any combination and/or repetition thereof and in any appropriate order.

Equipment and other necessary materials used in performing the techniques described herein are commercially available. Pumps, fraction collectors, monitors, recorders, and entire systems are available from, for example, Applied Biosystems (Foster City, Calif.), BioRad Laboratories, Inc. (Hercules, Calif.), and Amersham Biosciences, Inc. (Piscataway, N.J.). Chromatographic materials including, but not limited to, exchange matrix materials, media, and buffers are also available from such companies.

Equilibration, and other steps in the column chromatography processes described herein such as washing and elution, may be more rapidly accomplished using specialized equipment such as a pump. Commercially available pumps include, but are not limited to, HILOAD® Pump P-50, Peristaltic Pump P-1, Pump P-901, and Pump P-903 (Amersham Biosciences, Piscataway, N.J.).

Examples of fraction collectors include RediFrac Fraction Collector, FRAC-100 and FRAC-200 Fraction Collectors, and SUPERFRAC® Fraction Collector (Amersham Biosciences, Piscataway, N.J.). Mixers are also available to form pH and linear concentration gradients. Commercially available mixers include Gradient Mixer GM-1 and In-Line Mixers (Amersham Biosciences, Piscataway, N.J.).

The chromatographic process may be monitored using any commercially available monitor. Such monitors may be used to gather information like UV, pH, and conductivity. Examples of detectors include Monitor UV-1, UVICORD® S II, Monitor UV-M II, Monitor UV-900, Monitor UPC-900, Monitor pH/C-900, and Conductivity Monitor (Amersham Biosciences, Piscataway, N.J.). Indeed, entire systems are commercially available including the various AKTA® systems from Amersham Biosciences (Piscataway, N.J.).

In one embodiment of the present invention, for example, the relaxin polypeptide may be reduced and denatured by first denaturing the resultant purified relaxin polypeptide in urea, followed by dilution into TRIS buffer containing a reducing agent (such as DTT) at a suitable pH. In another embodiment, the relaxin polypeptide is denatured in urea in a concentration range of between about 2 M to about 9 M, followed by dilution in TRIS buffer at a pH in the range of about 5.0 to about 8.0. The refolding mixture of this embodiment may then be incubated. In one embodiment, the refolding mixture is incubated at room temperature for four to twenty-four hours. The reduced and denatured relaxin polypeptide mixture may then be further isolated or purified.

As stated herein, the pH of the first relaxin polypeptide mixture may be adjusted prior to performing any subsequent isolation steps. In addition, the first relaxin polypeptide mixture or any subsequent mixture thereof may be concentrated using techniques known in the art. Moreover, the elution buffer comprising the first relaxin polypeptide mixture or any subsequent mixture thereof may be exchanged for a buffer suitable for the next isolation step using techniques known to those of ordinary skill in the art.

Ion Exchange Chromatoraphy

In one embodiment, and as an optional, additional step, ion exchange chromatography may be performed on the first relaxin polypeptide mixture. See generally ION EXCHANGE CHROMATOGRAPHY: PRINCIPLES AND METHODS (Cat. No. 18-1114-21, Amersham Biosciences (Piscataway, N.J.)). Commercially available ion exchange columns include HITRAP®, HIPREP®, and HILOAD® Columns (Amersham Biosciences, Piscataway, N.J.). Such columns utilize strong anion exchangers such as Q SEPHAROSE® Fast Flow, Q SEPHAROSE® High Performance, and Q SEPHAROSE® XL; strong cation exchangers such as SP SEPHAROSE® High Performance, SP SEPHAROSE® Fast Flow, and SP SEPHAROSE® XL; weak anion exchangers such as DEAE SEPHAROSE® Fast Flow; and weak cation exchangers such as CM SEPHAROSE® Fast Flow (Amersham Biosciences, Piscataway, N.J.). Anion or cation exchange column chromatography may be performed on the relaxin polypeptide at any stage of the purification process to isolate substantially purified relaxin polypeptide. The cation exchange chromatography step may be performed using any suitable cation exchange matrix. Useful cation exchange matrices include, but are not limited to, fibrous, porous, non-porous, microgranular, beaded, or cross-linked cation exchange matrix materials. Such cation exchange matrix materials include, but are not limited to, cellulose, agarose, dextran, polyacrylate, polyvinyl, polystyrene, silica, polyether, or composites of any of the foregoing.

The cation exchange matrix may be any suitable cation exchanger including strong and weak cation exchangers. Strong cation exchangers may remain ionized over a wide pH range and thus, may be capable of binding relaxin over a wide pH range. Weak cation exchangers, however, may lose ionization as a function of pH. For example, a weak cation exchanger may lose charge when the pH drops below about pH 4 or pH 5. Suitable strong cation exchangers include, but are not limited to, charged functional groups such as sulfopropyl (SP), methyl sulfonate (S), or sulfoethyl (SE). The cation exchange matrix may be a strong cation exchanger, preferably having a relaxin binding pH range of about 2.5 to about 6.0. Alternatively, the strong cation exchanger may have a relaxin binding pH range of about pH 2.5 to about pH 5.5. The cation exchange matrix may be a strong cation exchanger having a relaxin binding pH of about 3.0. Alternatively, the cation exchange matrix may be a strong cation exchanger, preferably having a relaxin binding pH range of about 6.0 to about 8.0. The cation exchange matrix may be a strong cation exchanger preferably having a relaxin binding pH range of about 8.0 to about 12.5. Alternatively, the strong cation exchanger may have a relaxin binding pH range of about pH 8.0 to about pH 12.0.

Prior to loading the relaxin, the cation exchange matrix may be equilibrated, for example, using several column volumes of a dilute, weak acid, e.g., four column volumes of 20 mM acetic acid, pH 3. Following equilibration, the relaxin may be added and the column may be washed one to several times, prior to elution of substantially purified relaxin, also using a weak acid solution such as a weak acetic acid or phosphoric acid solution. For example, approximately 2-4 column volumes of 20 mM acetic acid, pH 3, may be used to wash the column. Additional washes using, e.g., 2-4 column volumes of 0.05 M sodium acetate, pH 5.5, or 0.05 M sodium acetate mixed with 0.1 M sodium chloride, pH 5.5, may also be used. Alternatively, using methods known in the art, the cation exchange matrix may be equilibrated using several column volumes of a dilute, weak base.

Alternatively, substantially purified relaxin may be eluted by contacting the cation exchanger matrix with a buffer having a sufficiently low pH or ionic strength to displace the relaxin from the matrix. The pH of the elution buffer may range from about pH 2.5 to about pH 6.0. More specifically, the pH of the elution buffer may range from about pH 2.5 to about pH 5.5, about pH 2.5 to about pH 5.0. The elution buffer may have a pH of about 3.0. In addition, the quantity of elution buffer may vary widely and will generally be in the range of about 2 to about 10 column volumes.

Following adsorption of the relaxin polypeptide to the cation exchanger matrix, substantially purified relaxin polypeptide may be eluted by contacting the matrix with a buffer having a sufficiently high pH or ionic strength to displace the relaxin polypeptide from the matrix. Suitable buffers for use in high pH elution of substantially purified relaxin polypeptide may include, but not limited to, citrate, phosphate, formate, acetate, HEPES, and MES buffers ranging in concentration from at least about 5 mM to at least about 100 mM.

Reverse-Phase Chromatography

RP-HPLC may be performed to purify proteins following suitable protocols that are known to those of ordinary skill in the art. See, e.g., Pearson et al., ANAL BIOCHEM. (1982) 124:217-230 (1982); Rivier et al., J. CHROM. (1983) 268:112-119; Kunitani et al., J. CHROM. (1986) 359:391-402. RP-HPLC may be performed on the relaxin polypeptide to isolate substantially purified relaxin polypeptide. In this regard, silica derivatized resins with alkyl functionalities with a wide variety of lengths, including, but not limited to, at least about C3 to at least about C30, at least about C3 to at least about C20, or at least about C3 to at least about C18, resins may be used. Alternatively, a polymeric resin may be used. For example, TosoHaas Amberchrome CG1000sd resin may be used, which is a styrene polymer resin. Cyano or polymeric resins with a wide variety of alkyl chain lengths may also be used. Furthermore, the RP-HPLC column may be washed with a solvent such as ethanol. The Source RP column is another example of a RP-HPLC column.

A suitable elution buffer containing an ion pairing agent and an organic modifier such as methanol, isopropanol, tetrahydrofuran, acetonitrile or ethanol, may be used to elute the relaxin polypeptide from the RP-HPLC column. The most commonly used ion pairing agents include, but are not limited to, acetic acid, formic acid, perchloric acid, phosphoric acid, trifluoroacetic acid, heptafluorobutyric acid, triethylamine, tetramethylammonium, tetrabutylammonium, and triethylammonium acetate. Elution may be performed using one or more gradients or isocratic conditions, with gradient conditions preferred to reduce the separation time and to decrease peak width. Another method involves the use of two gradients with different solvent concentration ranges. Examples of suitable elution buffers for use herein may include, but are not limited to, ammonium acetate and acetonitrile solutions.

Hydrophobic Interaction Chromatography Purification Techniques

Hydrophobic interaction chromatography (HIC) may be performed on the relaxin polypeptide. See generally HYDROPHOBIC INTERACTION CHROMATOGRAPHY HANDBOOK: PRINCIPLES AND METHODS (Cat. No. 18-1020-90, Amersham Biosciences (Piscataway, N.J.) which is incorporated by reference herein. Suitable HIC matrices may include, but are not limited to, alkyl- or aryl-substituted matrices, such as butyl-, hexyl-, octyl- or phenyl-substituted matrices including agarose, cross-linked agarose, sepharose, cellulose, silica, dextran, polystyrene, poly(methacrylate) matrices, and mixed mode resins, including but not limited to, a polyethyleneamine resin or a butyl- or phenyl-substituted poly(methacrylate) matrix. Commercially available sources for hydrophobic interaction column chromatography include, but are not limited to, HITRAP®, HIPREP®, and HILOAD® columns (Amersham Biosciences, Piscataway, N.J.).

Briefly, prior to loading, the HIC column may be equilibrated using standard buffers known to those of ordinary skill in the art, such as an acetic acid/sodium chloride solution or HEPES containing ammonium sulfate. Ammonium sulfate may be used as the buffer for loading the HIC column. After loading the relaxin polypeptide, the column may then washed using standard buffers and conditions to remove unwanted materials but retaining the relaxin polypeptide on the HIC column. The relaxin polypeptide may be eluted with about 3 to about 10 column volumes of a standard buffer, such as a HEPES buffer containing EDTA and lower ammonium sulfate concentration than the equilibrating buffer, or an acetic acid/sodium chloride buffer, among others. A decreasing linear salt gradient using, for example, a gradient of potassium phosphate, may also be used to elute the relaxin molecules. The eluant may then be concentrated, for example, by filtration such as diafiltration or ultrafiltration. Diafiltration may be utilized to remove the salt used to elute the relaxin polypeptide.

Other Purification Techniques

Yet another isolation step using, for example, gel filtration (GEL FILTRATION: PRINCIPLES AND METHODS (Cat. No. 18-1022-18, Amersham Biosciences, Piscataway, N.J.) which is incorporated by reference herein, hydroxyapatite chromatography (suitable matrices include, but are not limited to, HA-Ultrogel, High Resolution (Calbiochem), CHT Ceramic Hydroxyapatite (BioRad), Bio—Gel HTP Hydroxyapatite (BioRad)), HPLC, expanded bed adsorption, ultrafiltration, diafiltration, lyophilization, and the like, may be performed on the first relaxin polypeptide mixture or any subsequent mixture thereof, to remove any excess salts and to replace the buffer with a suitable buffer for the next isolation step or even formulation of the final drug product.

The yield of relaxin polypeptide, including substantially purified relaxin polypeptide, may be monitored at each step described herein using techniques known to those of ordinary skill in the art. Such techniques may also be used to assess the yield of substantially purified relaxin polypeptide following the last isolation step. For example, the yield of relaxin polypeptide may be monitored using any of several reverse phase high pressure liquid chromatography columns, having a variety of alkyl chain lengths such as cyano RP-HPLC, C18RP-HPLC; as well as cation exchange HPLC and gel filtration HPLC.

In specific embodiments of the present invention, the yield of relaxin after each purification step may be at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.9%, or at least about 99.99%, of the relaxin in the starting material for each purification step.

Purity may be determined using standard techniques, such as SDS-PAGE, or by measuring relaxin polypeptide using Western blot and ELISA assays. For example, polyclonal antibodies may be generated against proteins isolated from negative control yeast fermentation and the cation exchange recovery. The antibodies may also be used to probe for the presence of contaminating host cell proteins.

RP-HPLC material Vydac C4 (Vydac) consists of silica gel particles, the surfaces of which carry C4-alkyl chains. The separation of relaxin polypeptide from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silicagel). The Hydroxyapatite Ultrogel eluate is acidified by adding trifluoroacetic acid and loaded onto the Vydac C4 column. For washing and elution an acetonitrile gradient in diluted trifluoroacetic acid is used. Fractions are collected and immediately neutralized with phosphate buffer. The relaxin polypeptide fractions which are within the IPC limits are pooled.

DEAE Sepharose (Pharmacia) material consists of diethylaminoethyl (DEAE)-groups which are covalently bound to the surface of Sepharose beads. The binding of relaxin polypeptide to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and relaxin polypeptide is eluted with a buffer with increased ionic strength. The column is packed with DEAE Sepharose fast flow. The column volume is adjusted to assure a relaxin polypeptide load in the range of 3-10 mg relaxin polypeptide/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, relaxin polypeptide is eluted from the column with elution buffer (sodium chloride, sodium/potassium phosphate) and collected in a single fraction in accordance with the master elution profile. The eluate of the DEAE Sepharose column is adjusted to the specified conductivity. The resulting drug substance is sterile filtered into Teflon bottles and stored at −70° C.

Additional methods that may be employed include, but are not limited to, steps to remove endotoxins. Endotoxins are lipopoly-saccharides (LPSs) which are located on the outer membrane of Gram-negative host cells, such as, for example, *Escherichia coli*. Methods for reducing endotoxin levels are known to one of ordinary skill in the art and include, but are not limited to, purification techniques using silica supports, glass powder or hydroxyapatite, reverse-phase, affinity, size-exclusion, anion-exchange chromatography, hydrophobic interaction chromatography, a combination of these methods, and the like. Modifications or additional methods may be required to remove contaminants such as co-migrating proteins from the polypeptide of interest. Methods for measuring endotoxin levels are known to one of ordinary skill in the art and include, but are not limited to, Limulus Amebocyte Lysate (LAL) assays. The Endosafe™-PTS assay is a colorimetric, single tube system that utilizes cartridges preloaded with LAL reagent, chromogenic substrate, and control standard endotoxin along with a handheld spectrophotometer. Alternate methods include, but are not limited to, a Kinetic LAL method that is turbidmetric and uses a 96 well format.

A wide variety of methods and procedures can be used to assess the yield and purity of a relaxin protein comprising one or more non-naturally encoded amino acids, including but not limited to, the Bradford assay, SDS-PAGE, silver stained SDS-PAGE, coomassie stained SDS-PAGE, mass spectrometry (including but not limited to, MALDI-TOF) and other methods for characterizing proteins known to one of ordinary skill in the art.

Additional methods include, but are not limited to: SDS-PAGE coupled with protein staining methods, immunoblotting, matrix assisted laser desorption/ionization-mass spectrometry (MALDI-MS), liquid chromatography/mass spectrometry, isoelectric focusing, analytical anion exchange, chromatofocusing, and circular dichroism.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.*, 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.,* 284:29 (2000); trifluoromethionine has been used to replace methionine in bacteriophage T4 lysozyme to study its interaction with chitooligosaccharide ligands by $^{19}$F NMR, see, e.g., H. Duewel, E. Daub, V. Robinson and J. F. Honek, *Biochemistry,* 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.,* 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.,* 9:1665 (1990); J. O. Boles, K. Lewinski, M. Kunkle, J. D. Odom, B. Dunlap, L. Lebioda and M. Hatada, *Nat. Struct. Biol.,* 1:283 (1994); N. Budisa, B. Steipe, P. Demange, C. Eckerskorn, J. Kellermann and R. Huber, *Eur. J. Biochem.,* 230:788 (1995); and, N. Budisa, W. Karnbrock, S. Steinbacher, A. Humm, L. Prade, T. Neuefeind, L. Moroder and R. Huber, *J. Mol. Biol.,* 270:616 (1997). Methionine analogs with alkene or alkyne functionalities have also been incorporated efficiently, allowing for additional modification of proteins by chemical means. See, e.g., J. C. van Hest and D. A. Tirrell, *FEBS Lett.,* 428:68 (1998); J. C. van Hest, K. L. Kiick and D. A. Tirrell, *J. Am. Chem. Soc.,* 122:1282 (2000); and, K. L. Kiick and D. A. Tirrell, Tetrahedron, 56:9487 (2000); U.S. Pat. No. 6,586,207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of Ala$^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry,* 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.,* 364:272 (1995); and, N. Sharma, R. Furter, P. Kast and D. A. Tirrell, *FEBS Lett.,* 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S. Nishimura, *J. Biol. Chem.,* 275:40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science,* 292:501 (2001). ValRS can misaminoacylate tRNAVal with Cys, Thr, or aminobutyrate (Abu); these noncognate amino acids are subsequently hydrolyzed by the editing domain. After random mutagenesis of the *Escherichia coli* chromosome, a mutant *Escherichia coli* strain was selected that has a mutation in the editing site of VaRS. This edit-defective ValRS incorrectly charges tRNAVal with Cys. Because Abu sterically resembles Cys (—SH group of Cys is replaced with —CH3 in Abu), the mutant VaRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. H. C., Barrett, L. Brenner, S. Watts-Tobin, R. *General nature of the genetic code for proteins. Nature,* 192:1227-1232 (1961); Hofmann, K., Bohn, H. *Studies on polypeptides. XXXVI. The effect of pyrazole-imidazole replacements on the S-protein activating potency of an S-peptide fragment, J. Am Chem,* 88(24):5914-5919 (1966); Kaiser, E. T. *Synthetic approaches to biologically active peptides and proteins including enyzmes, Acc Chem Res,* 22:47-54 (1989); Nakatsuka, T., Sasaki, T., Kaiser, E. T. *Peptide segment coupling catalyzed by the semisynthetic enzyme thiosubtilisin, J Am Chem Soc,* 109:3808-3810 (1987); Schnolzer, M., Kent, S B H. *Constructing proteins by dovetailing unprotected synthetic peptides: backbone-engineered HIV protease, Science,* 256(5054):221-225 (1992); Chaiken, I. M. *Semisynthetic peptides and proteins, CRC Crit Rev Biochem,* 11(3):255-301 (1981); Offord, R. E. *Protein engineering by chemical means? Protein Eng.,* 1(3):151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science,* 266(5183):243 (1994).

Chemical modification has been used to introduce a variety of unnatural side chains, including cofactors, spin labels and oligonucleotides into proteins in vitro. See, e.g., Corey, D. R., Schultz, P. G. *Generation of a hybrid sequence-specific single-stranded deoxyribonuclease, Science,* 238(4832):1401-1403 (1987); Kaiser, E. T., Lawrence D. S., Rokita, S. E. *The chemical modification of enzymatic specificity, Annu Rev Biochem,* 54:565-595 (1985); Kaiser, E. T., Lawrence, D. S. *Chemical mutation of enyzme active sites, Science,* 226(4674):505-511 (1984); Neet, K. E., Nanci A, Koshland, D. E. *Properties of thiol-subtilisin, J Biol. Chem,* 243(24):6392-6401 (1968); Polgar, L. et M. L. Bender. *A new enzyme containing a synthetically formed active site. Thiol-subtilisin. J. Am Chem Soc,* 88:3153-3154 (1966); and, Pollack, S. J., Nakayama, G. Schultz, P. G. *Introduction of nucleophiles and spectroscopic probes into antibody combining sites, Science,* 242(4881):1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. *New Photolabeling and crosslinking* methods, *Annu. Rev Biochem,* 62:483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci,* 83(22):8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins, Science,* 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am Chem Soc,* 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz.,* vol. 202, 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. *5'-3' Exonucleases in phosphorothioate-based olignoucleotide-directed mutagensis, Nucleic Acids Res,* 16(3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) *Nature Structural Biology* 10(6):425-432; and, Ellman, J. A., Mendel, D., Schultz, P. G. *Site-specific incorporation of novel backbone structures into proteins, Science,* 255(5041):197-200 (1992).

A tRNA may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term "ribozyme" is interchangeable with "catalytic RNA." Cech and coworkers (Cech, 1987, Science, 236:1532-1539; McCorkle et al., 1987, Concepts Biochem. 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. Studies have identified RNA molecules that can catalyze aminoacyl-RNA bonds on their own (2')3'-termini (Illangakekare et al., 1995 Science 267:643-647), and an RNA molecule which can transfer an amino acid from one RNA molecule to another (Lohse et al., 1996, Nature 381:442-444).

U.S. Patent Application Publication 2003/0228593, which is incorporated by reference herein, describes methods to construct ribozymes and their use in aminoacylation of tRNAs with naturally encoded and non-naturally encoded amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in Chemistry and Biology 2003, 10:1077-1084 and U.S. Patent Application Publication 2003/0228593, which are incorporated by reference herein.

Chemical aminoacylation methods include, but are not limited to, those introduced by Hecht and coworkers (Hecht, S. M. Acc. Chem. Res. 1992, 25, 545; Heckler, T. G.; Roesser, J. R.; Xu, C.; Chang, P.; Hecht, S. M. Biochemistry 1988, 27, 7254; Hecht, S. M.; Alford, B. L.; Kuroda, Y.; Kitano, S. J. Biol. Chem. 1978, 253, 4517) and by Schultz, Chamberlin, Dougherty and others (Cornish, V. W.; Mendel, D.; Schultz, P. G. Angew. Chem. Int. Ed. Engl. 1995, 34, 621; Robertson, S. A.; Ellman, J. A.; Schultz, P. G. J. Am. Chem. Soc. 1991, 113, 2722; Noren, C. J.; Anthony-Cahill, S. J.; Griffith, M. C.; Schultz, P. G. Science 1989, 244, 182; Bain, J. D.; Glabe, C. G.; Dix, T. A.; Chamberlin, A. R. J. Am. Chem. Soc. 1989, 111, 8013; Bain, J. D. et al. Nature 1992, 356, 537; Gallivan, J. P.; Lester, H. A.; Dougherty, D. A. Chem. Biol. 1997, 4, 740; Turcatti, et al. J. Biol. Chem. 1996, 271, 19991; Nowak, M. W. et al. Science, 1995, 268, 439; Saks, M. E. et al. J. Biol. Chem. 1996, 271, 23169; Hohsaka, T. et al. J. Am. Chem. Soc. 1999, 121, 34), which are incorporated by reference herein, to avoid the use of synthetases in aminoacylation. Such methods or other chemical aminoacylation methods may be used to aminoacylate tRNA molecules.

Methods for generating catalytic RNA may involve generating separate pools of randomized ribozyme sequences, performing directed evolution on the pools, screening the pools for desirable aminoacylation activity, and selecting sequences of those ribozymes exhibiting desired aminoacylation activity.

Ribozymes can comprise motifs and/or regions that facilitate acylation activity, such as a GGU motif and a U-rich region. For example, it has been reported that U-rich regions can facilitate recognition of an amino acid substrate, and a GGU-motif can form base pairs with the 3' termini of a tRNA. In combination, the GGU and motif and U-rich region facilitate simultaneous recognition of both the amino acid and tRNA simultaneously, and thereby facilitate aminoacylation of the 3' terminus of the tRNA.

Ribozymes can be generated by in vitro selection using a partially randomized r24mini conjugated with tRNA$^{Asn}_{CCCG}$, followed by systematic engineering of a consensus sequence found in the active clones. An exemplary ribozyme obtained by this method is termed "Fx3 ribozyme" and is described in U.S. Pub. App. No. 2003/0228593, the contents of which is incorporated by reference herein, acts as a versatile catalyst for the synthesis of various aminoacyl-tRNAs charged with cognate non-natural amino acids.

Immobilization on a substrate may be used to enable efficient affinity purification of the aminoacylated tRNAs. Examples of suitable substrates include, but are not limited to, agarose, sepharose, and magnetic beads. Ribozymes can be immobilized on resins by taking advantage of the chemical structure of RNA, such as the 3'-cis-diol on the ribose of RNA can be oxidized with periodate to yield the corresponding dialdehyde to facilitate immobilization of the RNA on the resin. Various types of resins can be used including inexpensive hydrazide resins wherein reductive amination makes the interaction between the resin and the ribozyme an irreversible linkage. Synthesis of aminoacyl-tRNAs can be significantly facilitated by this on-column aminoacylation technique. Kourouklis et al. Methods 2005; 36:239-4 describe a column-based aminoacylation system.

Isolation of the aminoacylated tRNAs can be accomplished in a variety of ways. One suitable method is to elute the aminoacylated tRNAs from a column with a buffer such as a sodium acetate solution with 10 mM EDTA, a buffer containing 50 mM N-(2-hydroxyethyl)piperazine-N'-(3-propanesulfonic acid), 12.5 mM KCl, pH 7.0, 10 mM EDTA, or simply an EDTA buffered water (pH 7.0).

The aminoacylated tRNAs can be added to translation reactions in order to incorporate the amino acid with which the tRNA was aminoacylated in a position of choice in a polypeptide made by the translation reaction. Examples of translation systems in which the aminoacylated tRNAs of the present invention may be used include, but are not limited to cell lysates. Cell lysates provide reaction components necessary for in vitro translation of a polypeptide from an input mRNA. Examples of such reaction components include but are not limited to ribosomal proteins, rRNA, amino acids, tRNAs, GTP, ATP, translation initiation and elongation factors and additional factors associated with translation. Additionally, translation systems may be batch translations or compartmentalized translation. Batch translation systems combine reaction components in a single compartment while compartmentalized translation systems separate the translation reaction components from reaction products that can inhibit the translation efficiency. Such translation systems are available commercially.

Further, a coupled transcription/translation system may be used. Coupled transcription/translation systems allow for both transcription of an input DNA into a corresponding mRNA, which is in turn translated by the reaction components. An example of a commercially available coupled transcription/translation is the Rapid Translation System (RTS, Roche Inc.). The system includes a mixture containing *E. coli* lysate for providing translational components such as ribosomes and translation factors. Additionally, an RNA polymerase is included for the transcription of the input DNA into an mRNA template for use in translation. RTS can use compartmentalization of the reaction components by way of a membrane interposed between reaction compartments, including a supply/waste compartment and a transcription/translation compartment.

Aminoacylation of tRNA may be performed by other agents, including but not limited to, transferases, polymerases, catalytic antibodies, multi-functional proteins, and the like.

Stephan in Scientist 2005 Oct. 10; pages 30-33 describes additional methods to incorporate non-naturally encoded amino acids into proteins. Lu et al. in Mol Cell. 2001 October; 8(4):759-69 describe a method in which a protein is chemically ligated to a synthetic peptide containing unnatural amino acids (expressed protein ligation).

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, *Science*, 268:439 (1995); and, D. A. Dougherty, *Curr. Opin. Chem. Biol.*, 4:645 (2000). A Xenopus oocyte was coinjected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, *J. Biol. Chem.*, 271: 19991 (1996); the incorporation of biotinylated amino acids to identify surface-exposed residues in ion channels, see, e.g., J. P. Gallivan, H. A. Lester and D. A. Dougherty, *Chem. Biol.*, 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, *Cell*, 96:89 (1999); and, T. Lu, A. Y. Ting, J. Mainland, L. Y. Jan, P. G. Schultz and J. Yang, *Nat. Neurosci.*, 4:239 (2001).

The ability to incorporate unnatural amino acids directly into proteins in vivo offers a wide variety of advantages including but not limited to, high yields of mutant proteins, technical ease, the potential to study the mutant proteins in cells or possibly in living organisms and the use of these mutant proteins in therapeutic treatments and diagnostic uses. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.*, 7:419 (1998).

It may also be possible to obtain expression of a relaxin polynucleotide of the present invention using a cell-free (in-vitro) translational system. Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D. M. and J. R. Swartz, Biotechnology and Bioengineering, 74:309-316 (2001); Kim, D. M. and J. R. Swartz, Biotechnology Letters, 22, 1537-1542, (2000); Kim, D. M., and J. R. Swartz, Biotechnology Progress, 16, 385-390, (2000); Kim, D. M., and J. R. Swartz, Biotechnology and Bioengineering, 66, 180-188, (1999); and Patnaik, R. and J. R. Swartz, Biotechniques 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of relaxin polypeptides comprising a non-naturally encoded amino acid includes the mRNA-peptide fusion technique. See, e.g., R. Roberts and J. Szostak, Proc. Natl Acad. Sci. (USA) 94:12297-12302 (1997); A. Frankel, et al., Chemistry & Biology 10:1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of relaxin polypeptides comprising one or more non-naturally encoded amino acids to identify polypeptides having desired properties. More recently, in vitro ribosome translations with purified components have been reported that permit the synthesis of peptides substituted with non-naturally encoded amino acids. See, e.g., A. Forster et al., Proc. Natl Acad. Sci. (USA) 100:6353 (2003).

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 (α or β), elongation factor T (EF-Tu), or termination factors. Cell-free systems may also be coupled transcription/translation systems wherein DNA is introduced to the system, transcribed into mRNA and the mRNA translated as described in Current Protocols in Molecular Biology (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

Macromolecular Polymers Coupled to Relaxin Polypeptides

Various modifications to the non-natural amino acid polypeptides described herein can be effected using the compositions, methods, techniques and strategies described herein. These modifications include the incorporation of further functionality onto the non-natural amino acid component of the polypeptide, including but not limited to, a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to relaxin polypeptides of the present invention to modulate biological properties of the relaxin polypeptide, and/or provide new biological properties to the relaxin molecule. These macromolecular polymers can be linked to the Relaxin polypeptide via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated relaxin polypeptide preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tri-, tetra-, etc.) and combine said conjugates with the mono-polymer:protein conjugate prepared using the methods of the present invention, and have a mixture with a predetermined proportion of mono-polymer:protein conjugates.

The polymer selected may be water soluble so that the protein to which it is attached does not precipitate in an aqueous environment, such as a physiological environment. The polymer may be branched or unbranched. For therapeutic use of the end-product preparation, the polymer will be pharmaceutically acceptable.

Examples of polymers include but are not limited to polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethyleneglycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof, mixtures thereof; and derivatives of the foregoing.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

As used herein, and when contemplating PEG: relaxin polypeptide conjugates, the term "therapeutically effective amount" refers to an amount which gives the desired benefit to a patient. The amount will vary from one individual to another and will depend upon a number of factors, including the overall physical condition of the patient and the underlying cause of the condition to be treated. The amount of relaxin polypeptide used for therapy gives an acceptable rate of change and maintains desired response at a beneficial level. A therapeutically effective amount of the present compositions may be readily ascertained by one of ordinary skill in the art using publicly available materials and procedures.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods known to those of ordinary skill in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the relaxin polypeptide by the formula:

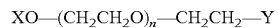

$XO-(CH_2CH_2O)_n-CH_2CH_2-Y$ where n is 2 to 10,000 and X is H or a terminal modification, including but not limited to, a $C_{1-4}$ alkyl, a protecting group, or a terminal functional group.

In some cases, a PEG used in the invention terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a relaxin polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the Relaxin polypeptide to form a Huisgen [3+2]cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the Relaxin polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). The molecular weight of PEG may be of a wide range, including but not limited to, between about 100 Da and about 100,000 Da or more. PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, PEG is between about 100 Da and about 50,000 Da. In some embodiments, PEG is between about 100 Da and about 40,000 Da. In some embodiments, PEG is between about 1,000 Da and about 40,000 Da. In some embodiments, PEG is between about 5,000 Da and about 40,000 Da. In some embodiments, PEG is between about 10,000 Da and about 40,000 Da. Branched chain PEGs, including but not limited to, PEG molecules with each chain having a MW ranging from 1-100 kDa (including but not limited to, 1-50 kDa or 5-20 kDa) can also be used. The molecular weight of each chain of the branched chain PEG may be, including but not limited to, between about 1,000 Da and about 100,000 Da or more. The molecular weight of each chain of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of each chain of the branched chain PEG is between about 1,000 Da and about 50,000 Da. In some embodiments, the molecular weight of each chain of the branched chain PEG is between about 1,000 Da and about 40,000 Da. In some embodiments, the molecular weight of each chain of the branched chain PEG is between about 5,000 Da and about 40,000 Da. In some embodiments, the molecular weight of each chain of the branched chain PEG is between about 5,000 Da and about 20,000 Da. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the Relaxin polypeptide variant with a PEG derivative contains a chemical functionality that is reactive with the chemical functionality present on the side chain of the non-naturally encoded amino acid.

The invention provides in some embodiments azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly(ethylene)glycol and other related polymers, including poly(dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly (ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula $-CH_2CH_2O-(CH_2CH_2O)_n-CH_2CH_2-$, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone. The molecular weight of PEG may be of a wide range, including but not limited to, between about 100 Da and about 100,000 Da or more. The molecular weight of PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of PEG is between about 100 Da and about 50,000 Da. In some embodiments, the molecular weight of PEG is between about 100 Da and about 40,000 Da. In some embodiments, the molecular weight of PEG is between about 1,000 Da and about 40,000 Da. In some embodiments, the molecular weight of PEG is between about 5,000 Da and about 40,000 Da. In some embodiments, the molecular weight of PEG is between about 10,000 Da and about 40,000 Da.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(-PEG-OH)$_m$ in which R is derived from a core moiety, such as glycerol, glycerol oligomers, or pentaerythritol, and m represents the number of arms. Multiarmed PEG molecules, such as those described in U.S. Pat. Nos. 5,932,462; 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(-YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

It is understood by those of ordinary skill in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da. The molecular weight of each chain of the polymer backbone may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of each chain of the polymer backbone is between about 100 Da and about 50,000 Da. In some embodiments, the molecular weight of each chain of the polymer backbone is between about 100 Da and about 40,000 Da. In some embodiments, the molecular weight of each chain of the polymer backbone is between about 1,000 Da and about 40,000 Da. In some embodiments, the molecular weight of each chain of the polymer backbone is between about 5,000 Da and about 40,000 Da. In some embodiments, the molecular weight of each chain of the polymer backbone is between about 10,000 Da and about 40,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure:

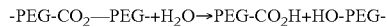

wherein:
N=N=N is an azide moiety;
B is a linking moiety, which may be present or absent;
POLY is a water-soluble non-antigenic polymer;
A is a linking moiety, which may be present or absent and which may be the same as B or different; and
X is a second functional group.

Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described above are contemplated to be suitable for use in the present invention.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those of ordinary skill in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the present invention.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182: 1379 (1981), Zalipsky et al. Eur. Polym. J. 19:1177 (1983)), hydrazide (See, e.g., Andresz et al. Makromol. Chem. 179: 301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. Nos. 5,824,784, 5,252,714), maleimide (see, e.g., Goodson et al. Biotechnology (NY) 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314(1993)), acrylol (see, e.g., Sawhney et al., Macromolecules, 26:581 (1993)), vinylsulfone (see, e.g., U.S. Pat. No. 5,900,461). All of the above references and patents are incorporated herein by reference.

In certain embodiments of the present invention, the polymer derivatives of the invention comprise a polymer backbone having the structure:

wherein:
X is a functional group as described above; and
n is about 20 to about 4000.

In another embodiment, the polymer derivatives of the invention comprise a polymer backbone having the structure:

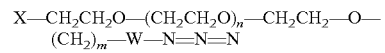

wherein:
W is an aliphatic or aromatic linker moiety comprising between 1-10 carbon atoms;
n is about 20 to about 4000; and
X is a functional group as described above. m is between 1 and 10.

The azide-containing PEG derivatives of the invention can be prepared by a variety of methods known in the art and/or disclosed herein. In one method, shown below, a water soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing PEG polymer.

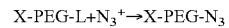

As shown, a suitable polymer backbone for use in the present invention has the formula X-PEG-L, wherein PEG is poly(ethylene glycol) and X is a functional group which does not react with azide groups and L is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone. Examples of suitable leaving groups include, but are not limited to, chloride, bromide, iodide, mesylate, tresylate, and tosylate.

In another method for preparation of the azide-containing polymer derivatives of the present invention, a linking agent bearing an azide functionality is contacted with a water soluble polymer backbone having an average molecular weight from about 800 Da to about 100,000 Da, wherein the linking agent bears a chemical functionality that will react selectively with a chemical functionality on the PEG polymer, to form an azide-containing polymer derivative product wherein the azide is separated from the polymer backbone by a linking group.

An exemplary reaction scheme is shown below:

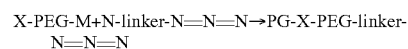

wherein:
PEG is poly(ethylene glycol) and X is a capping group such as alkoxy or a functional group as described above; and
M is a functional group that is not reactive with the azide functionality but that will react efficiently and selectively with the N functional group.

Examples of suitable functional groups include, but are not limited to, M being a carboxylic acid, carbonate or active ester if N is an amine; M being a ketone if N is a hydrazide or aminooxy moiety; M being a leaving group if N is a nucleophile.

Purification of the crude product may be accomplished by known methods including, but are not limited to, precipitation of the product followed by chromatography, if necessary.

A more specific example is shown below in the case of PEG diamine, in which one of the amines is protected by a protecting group moiety such as tert-butyl-Boc and the resulting mono-protected PEG diamine is reacted with a linking moiety that bears the azide functionality:

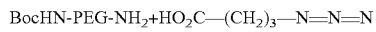

BocHN-PEG-NH$_2$+HO$_2$C—(CH$_2$)$_3$—N=N=N

In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-PEG-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido PEG would allow the attachment of a molecule having an activated electrophilic group, such as an aldehyde, ketone, activated ester, activated carbonate and so forth, to one terminus of the PEG and a molecule having an acetylene group to the other terminus of the PEG.

In another embodiment of the invention, the polymer derivative has the structure:

X-A-POLY-B—C≡C—R wherein:
R can be either H or an alkyl, alkene, alkyoxy, or aryl or substituted aryl group;
B is a linking moiety, which may be present or absent;
POLY is a water-soluble non-antigenic polymer;
A is a linking moiety, which may be present or absent and which may be the same as B or different; and
X is a second functional group.

Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described above are contemplated to be useful in the present invention.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

In another embodiment of the present invention, the polymer derivatives comprise a polymer backbone having the structure:

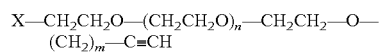

X—CH$_2$CH$_2$O—(CH$_2$CH$_2$O)$_n$—CH$_2$CH$_2$—O—(CH$_2$)$_m$—C≡CH wherein:
X is a functional group as described above;
n is about 20 to about 4000; and
m is between 1 and 10.

Specific examples of each of the heterobifunctional PEG polymers are shown below.

The acetylene-containing PEG derivatives of the invention can be prepared using methods known to those of ordinary skill in the art and/or disclosed herein. In one method, a water soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired acetylene-containing polymer.

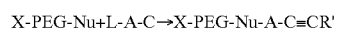

X-PEG-Nu+L-A-C→X-PEG-Nu-A-C≡CR'

As shown, a preferred polymer backbone for use in the reaction has the formula X-PEG-Nu, wherein PEG is poly(ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment of the present invention, A is an aliphatic linker of between 1-10 carbon atoms or a substituted aryl ring of between 6-14 carbon atoms. X is a functional group which does not react with azide groups and L is a suitable leaving group In another method for preparation of the acetylene-containing polymer derivatives of the invention, a PEG polymer having an average molecular weight from about 800 Da to about 100,000 Da, bearing either a protected functional group or a capping agent at one terminus and a suitable leaving group at the other terminus is contacted by an acetylene anion.

An exemplary reaction scheme is shown below:

X-PEG-L+-C≡CR'—X-PEG-C≡CR' wherein:
PEG is poly(ethylene glycol) and X is a capping group such as alkoxy or a functional group as described above; and
R' is either H, an alkyl, alkoxy, aryl or aryloxy group or a substituted alkyl, alkoxyl, aryl or aryloxy group.

In the example above, the leaving group L should be sufficiently reactive to undergo SN2-type displacement when contacted with a sufficient concentration of the acetylene anion. The reaction conditions required to accomplish SN2 displacement of leaving groups by acetylene anions are known to those of ordinary skill in the art.

Purification of the crude product can usually be accomplished by methods known in the art including, but are not limited to, precipitation of the product followed by chromatography, if necessary.

Water soluble polymers can be linked to the relaxin polypeptides of the invention. The water soluble polymers may be linked via a non-naturally encoded amino acid incorporated in the relaxin polypeptide or any functional group or substituent of a non-naturally encoded or naturally encoded amino acid, or any functional group or substituent added to a non-naturally encoded or naturally encoded amino acid. Alternatively, the water soluble polymers are linked to a relaxin polypeptide incorporating a non-naturally encoded amino acid via a naturally-occurring amino acid (including but not limited to, cysteine, lysine or the amine group of the N-terminal residue). In some cases, the relaxin polypeptides of the invention comprise 1, 2, 3, 4, 5, 6, 7, 8, 9, 10 non-natural amino acids, wherein one or more non-naturally-encoded amino acid(s) are linked to water soluble polymer(s) (including but not limited to, PEG and/or oligosaccharides). In some cases, the relaxin polypeptides of the invention further comprise 1, 2, 3, 4, 5, 6, 7, 8, 9, 10, or more naturally-encoded amino acid(s) linked to water soluble polymers. In some cases, the relaxin polypeptides of the invention comprise one or more non-naturally encoded amino acid(s) linked to water soluble polymers and one or more naturally-occurring amino acids linked to water soluble polymers. In some embodiments, the water soluble polymers used in the present invention enhance the serum half-life of the relaxin polypeptide relative to the unconjugated form.

The number of water soluble polymers linked to a relaxin polypeptide (i.e., the extent of PEGylation or glycosylation) of the present invention can be adjusted to provide an altered (including but not limited to, increased or decreased) pharmacologic, pharmacokinetic or pharmacodynamic characteristic such as in vivo half-life. In some embodiments, the half-life of relaxin is increased at least about 10, 20, 30, 40, 50, 60, 70, 80, 90 percent, 2-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 50-fold, or at least about 100-fold over an unmodified polypeptide.

PEG Derivatives Containing a Strong Nucleophilic Group (i.e., Hydrazide, Hydrazine, Hydroxylamine or Semicarbazide)

In one embodiment of the present invention, a relaxin polypeptide comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure:

RO—(CH2CH2O)n-O—(CH2)m-O-NH2 where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivative will have the structure:

RO—(CH2CH2O)n-O—(CH2)m-X—NH—NH2 where R is a simple alkyl (methyl, ethyl, propyl, etc.), m is 2-10 and n is 100-1,000 and X is optionally a carbonyl group (C═O) that can be present or absent.

In some embodiments, the semicarbazide-containing PEG derivative will have the structure:

RO—(CH2CH2O)n-O—(CH2)m-NH—C(O)—NH—NH2 where R is a simple alkyl (methyl, ethyl, propyl, etc.), m is 2-10 and n is 100-1,000.

In another embodiment of the invention, a relaxin polypeptide comprising a carbonyl-containing amino acid is modified with a PEG derivative that contains a terminal hydroxylamine, hydrazide, hydrazine, or semicarbazide moiety that is linked to the PEG backbone by means of an amide linkage.

In some embodiments, the hydroxylamine-terminal PEG derivatives have the structure:

RO—(CH2CH2O)n-O—(CH2)2-NH—C(O)(CH2)m-O-NH2 where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure:

RO—(CH2CH2O)n-O—(CH2)2-NH—C(O)(CH2)m-X—NH—NH2 where R is a simple alkyl (methyl, ethyl, propyl, etc.), m is 2-10, n is 100-1,000 and X is optionally a carbonyl group (C═O) that can be present or absent.

In some embodiments, the semicarbazide-containing PEG derivatives have the structure:

RO—(CH2CH2O)n-O—(CH2)2-NH—C(O)(CH2)m-NH—C(O)—NH—NH2 where R is a simple alkyl (methyl, ethyl, propyl, etc.), m is 2-10 and n is 100-1,000.

In another embodiment of the invention, a relaxin polypeptide comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa and, may be from 5-20 kDa.

In another embodiment of the invention, a relaxin polypeptide comprising a non-naturally encoded amino acid is modified with a PEG derivative having a branched structure. For instance, in some embodiments, the hydrazine- or hydrazide-terminal PEG derivative will have the following structure:

[RO—(CH2CH2O)n-O—(CH2)2-NH—C(O)]2CH(CH2)m-X—NH—NH2 where R is a simple alkyl (methyl, ethyl, propyl, etc.), m is 2-10 and n is 100-1,000, and X is optionally a carbonyl group (C=O) that can be present or absent.

In some embodiments, the PEG derivatives containing a semicarbazide group will have the structure:

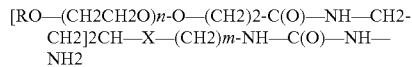
[RO—(CH2CH2O)n-O—(CH2)2-C(O)—NH—CH2—CH2]2CH—X—(CH2)m-NH—C(O)—NH—NH2 where R is a simple alkyl (methyl, ethyl, propyl, etc.), X is optionally NH, O, S, C(O) or not present, m is 2-10 and n is 100-1,000.

In some embodiments, the PEG derivatives containing a hydroxylamine group will have the structure:

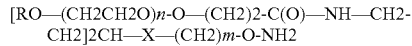
[RO—(CH2CH2O)n-O—(CH2)2-C(O)—NH—CH2—CH2]2CH—X—(CH2)m-O-NH2 where R is a simple alkyl (methyl, ethyl, propyl, etc.), X is optionally NH, O, S, C(O) or not present, m is 2-10 and n is 100-1,000.

The degree and sites at which the water soluble polymer(s) are linked to the relaxin polypeptide can modulate the binding of the relaxin polypeptide to the relaxin polypeptide receptor. In some embodiments, the linkages are arranged such that the relaxin polypeptide binds the relaxin polypeptide receptor with a Kd of about 400 nM or lower, with a Kd of 150 nM or lower, and in some cases with a Kd of 100 nM or lower, as measured by an equilibrium binding assay, such as that described in Spencer et al., J. Biol. Chem., 263:7862-7867 (1988).

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTAL AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, Macromol. Chem. Phys. C25: 325-373 (1985); Scouten, Methods in Enzymology 135: 30-65 (1987); Wong et al., Enzyme Microb. Technol. 14: 866-874 (1992); Delgado et al., Critical Reviews in Therapeutic Drug Carrier Systems 9: 249-304 (1992); Zalipsky, Bioconjugate Chem. 6: 150-165 (1995).

Methods for activation of polymers can also be found in WO 94/17039, U.S. Pat. No. 5,324,844, WO 94/18247, WO 94/04193, U.S. Pat. Nos. 5,219,564, 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese at al., App. Biochem. Biotech. 11: 141-52 (1985)). All references and patents cited are incorporated by reference herein.

PEGylation (i.e., addition of any water soluble polymer) of relaxin polypeptides containing a non-naturally encoded amino acid, such as p-azido-L-phenylalanine, is carried out by any convenient method. For example, relaxin polypeptide is PEGylated with an alkyne-terminated mPEG derivative. Briefly, an excess of solid mPEG(5000)-O—CH2-C⍰CH is added, with stirring, to an aqueous solution of p-azido-L-Phe-containing relaxin polypeptide at room temperature. Typically, the aqueous solution is buffered with a buffer having a pKa near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated relaxin polypeptide variants from free mPEG (5000)-O—CH2-C≡CH and any high-molecular weight complexes of the pegylated relaxin polypeptide which may form when unblocked PEG is activated at both ends of the molecule, thereby crosslinking relaxin polypeptide variant molecules. The conditions during hydrophobic interaction chromatography are such that free mPEG(5000)-O—CH2-C≡CH flows through the column, while any crosslinked PEGylated relaxin polypeptide variant complexes elute after the desired forms, which contain one relaxin polypeptide variant molecule conjugated to one or more PEG groups. Suitable conditions vary depending on the relative sizes of the cross-linked complexes versus the desired conjugates and are readily determined by those of ordinary skill in the art. The eluent containing the desired conjugates is concentrated by ultrafiltration and desalted by diafiltration.

If necessary, the PEGylated relaxin polypeptide obtained from the hydrophobic chromatography can be purified further by one or more procedures known to those of ordinary skill in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (Preneta, A Z in PROTEIN PURIFICATION METHODS, A PRACTICAL APPROACH (Harris & Angal, Eds.) IRL Press 1989, 293-306). The purity of the relaxin-PEG conjugate can be assessed by proteolytic degradation (including but not limited to, trypsin cleavage) followed by mass spectrometry analysis. Pepinsky R B., et al., J. Pharmcol. & Exp. Ther. 297(3):1059-66 (2001).

A water soluble polymer linked to an amino acid of a relaxin polypeptide of the invention can be further derivatized or substituted without limitation.

Azide-Containing PEG Derivatives

In another embodiment of the invention, a relaxin polypeptide is modified with a PEG derivative that contains an azide moiety that will react with an alkyne moiety present on the side chain of the non-naturally encoded amino acid. In general, the PEG derivatives will have an average molecular weight ranging from 1-100 kDa and, in some embodiments, from 10-40 kDa.

In some embodiments, the azide-terminal PEG derivative will have the structure:

RO—(CH2CH2O)n-O—(CH2)m-N3 where R is a simple alkyl (methyl, ethyl, propyl, etc.), m is 2-10 and n is 100-1,000 (i.e., average molecular weight is between 5-40 kDa).

In another embodiment, the azide-terminal PEG derivative will have the structure:

RO—(CH2CH2O)n-O—(CH2)m-NH—C(O)—(CH2)p-N3 where R is a simple alkyl (methyl, ethyl, propyl, etc.), m is 2-10, p is 2-10 and n is 100-1,000 (i.e., average molecular weight is between 5-40 kDa).

In another embodiment of the invention, a relaxin polypeptide comprising a alkyne-containing amino acid is modified with a branched PEG derivative that contains a terminal azide moiety, with each chain of the branched PEG having a MW ranging from 10-40 kDa and may be from 5-20 kDa. For instance, in some embodiments, the azide-terminal PEG derivative will have the following structure:

[RO—(CH2CH2O)n-O—(CH2)2-NH—C(O)]2CH(CH2)m-X—(CH2)pN3 where R is a simple alkyl (methyl, ethyl, propyl, etc.), m is 2-10, p is 2-10, and n is 100-1,000, and X is optionally an O, N, S or carbonyl group (C=O), in each case that can be present or absent.

Alkyne-Containing PEG Derivatives

In another embodiment of the invention, a relaxin polypeptide is modified with a PEG derivative that contains an alkyne moiety that will react with an azide moiety present on the side chain of the non-naturally encoded amino acid.

In some embodiments, the alkyne-terminal PEG derivative will have the following structure:

RO—(CH2CH2O)n-O—(CH2)m-C≡CH where R is a simple alkyl (methyl, ethyl, propyl, etc.), m is 2-10 and n is 100-1,000 (i.e., average molecular weight is between 5-40 kDa).

In another embodiment of the invention, a relaxin polypeptide comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure:

RO—(CH2CH2O)n-O—(CH2)m-NH—C(O)—(CH2)p-C≡CH where R is a simple alkyl (methyl, ethyl, propyl, etc.), m is 2-10, p is 2-10 and n is 100-1,000.

In another embodiment of the invention, a relaxin polypeptide comprising an azide-containing amino acid is modified with a branched PEG derivative that contains a terminal alkyne moiety, with each chain of the branched PEG having a MW ranging from 10-40 kDa and may be from 5-20 kDa. For instance, in some embodiments, the alkyne-terminal PEG derivative will have the following structure:

[RO—(CH2CH2O)n-O—(CH2)2-NH—C(O)]2CH(CH2)m-X—(CH2)pC≡CH where R is a simple alkyl (methyl, ethyl, propyl, etc.), m is 2-10, p is 2-10, and n is 100-1,000, and X is optionally an O, N, S or carbonyl group (C=O), or not present.

Phosphine-Containing PEG Derivatives

In another embodiment of the invention, a relaxin polypeptide is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives will have an average molecular weight ranging from 1-100 kDa and, in some embodiments, from 10-40 kDa.

In some embodiments, the PEG derivative will have the structure:

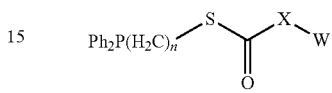

wherein n is 1-10; X can be O, N, S or not present, Ph is phenyl, and W is a water soluble polymer.

In some embodiments, the PEG derivative will have the structure:

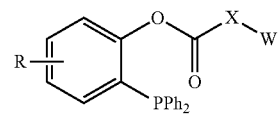

wherein X can be O, N, S or not present, Ph is phenyl, W is a water soluble polymer and R can be H, alkyl, aryl, substituted alkyl and substituted aryl groups. Exemplary R groups include but are not limited to —CH2, —C(CH3)3, —OR', —NR'R", —SR', -halogen, —C(O)R', —CONR'R", —S(O)2R', —S(O)2NR'R", —CN and —NO2. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF3 and —CH2CF3) and acyl (including but not limited to, —C(O)CH3, —C(O)CF3, —C(O)CH2OCH3, and the like).

Other PEG Derivatives and General PEGylation Techniques

Other exemplary PEG molecules that may be linked to relaxin polypeptides, as well as PEGylation methods include, but are not limited to, those described in, e.g., U.S. Patent Publication No. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/0056171; 2001/0044526; 2001/0021763; U.S. Pat. Nos. 6,646,110; 5,824,778; 5,476,653;

5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

Additional polymer and PEG derivatives including but not limited to, hydroxylamine (aminooxy) PEG derivatives, are described in the following patent applications which are all incorporated by reference in their entirety herein: U.S. Patent Publication No. 2006/0194256, U.S. Patent Publication No. 2006/0217532, U.S. Patent Publication No. 2006/0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594.

Heterologous Fc Fusion Proteins

The relaxin compounds described above may be fused directly or via a peptide linker to the Fc portion of an immunoglobulin. Immunoglobulins are molecules containing polypeptide chains held together by disulfide bonds, typically having two light chains and two heavy chains. In each chain, one domain (V) has a variable amino acid sequence depending on the antibody specificity of the molecule. The other domains (C) have a rather constant sequence common to molecules of the same class.

As used herein, the Fc portion of an immunoglobulin has the meaning commonly given to the term in the field of immunology. Specifically, this term refers to an antibody fragment which is obtained by removing the two antigen binding regions (the Fab fragments) from the antibody. One way to remove the Fab fragments is to digest the immunoglobulin with papain protease. Thus, the Fc portion is formed from approximately equal sized fragments of the constant region from both heavy chains, which associate through non-covalent interactions and disulfide bonds. The Fc portion can include the hinge regions and extend through the CH2 and CH3 domains to the C-terminus of the antibody. Representative hinge regions for human and mouse immunoglobulins can be found in Antibody Engineering, A Practical Guide, Borrebaeck, C. A. K., ed., W. H. Freeman and Co., 1992, the teachings of which are herein incorporated by reference. The Fc portion can further include one or more glycosylation sites. The amino acid sequences of numerous representative Fc proteins containing a hinge region, CH2 and CH3 domains, and one N-glycosylation site are well known in the art.

There are five types of human immunoglobulin Fc regions with different effector functions and pharmacokinetic properties: IgG, IgA, IgM, IgD, and IgE. IgG is the most abundant immunoglobulin in serum. IgG also has the longest half-life in serum of any immunoglobulin (23 days). Unlike other immunoglobulins, IgG is efficiently recirculated following binding to an Fc receptor. There are four IgG subclasses G1, G2, G3, and G4, each of which has different effector functions. G1, G2, and G3 can bind C1q and fix complement while G4 cannot. Even though G3 is able to bind C1q more efficiently than G1, G1 is more effective at mediating complement-directed cell lysis. G2 fixes complement very inefficiently. The C1q binding site in IgG is located at the carboxy terminal region of the CH2 domain.

All IgG subclasses are capable of binding to Fc receptors (CD16, CD32, CD64) with G1 and G3 being more effective than G2 and G4. The Fc receptor binding region of IgG is formed by residues located in both the hinge and the carboxy terminal regions of the CH2 domain.

IgA can exist both in a monomeric and dimeric form held together by a J-chain. IgA is the second most abundant Ig in serum, but it has a half-life of only 6 days. IgA has three effector functions. It binds to an IgA specific receptor on macrophages and eosinophils, which drives phagocytosis and degranulation, respectively. It can also fix complement via an unknown alternative pathway.

IgM is expressed as either a pentamer or a hexamer, both of which are held together by a J-chain. IgM has a serum half-life of 5 days. It binds weakly to C1q via a binding site located in its CH3 domain. IgD has a half-life of 3 days in serum. It is unclear what effector functions are attributable to this Ig. IgE is a monomeric Ig and has a serum half-life of 2.5 days. IgE binds to two Fc receptors which drives degranulation and results in the release of proinflammatory agents.

Depending on the desired in vivo effect, the heterologous fusion proteins of the present invention may contain any of the isotypes described above or may contain mutated Fc regions wherein the complement and/or Fc receptor binding functions have been altered. Thus, the heterologous fusion proteins of the present invention may contain the entire Fc portion of an immunoglobulin, fragments of the Fc portion of an immunoglobulin, or analogs thereof fused to an interferon beta compound.

The fusion proteins of the present invention can consist of single chain proteins or as multi-chain polypeptides. Two or more Fc fusion proteins can be produced such that they interact through disulfide bonds that naturally form between Fc regions. These multimers can be homogeneous with respect to the interferon beta compound or they may contain different interferon beta compounds fused at the N-terminus of the Fc portion of the fusion protein.

Regardless of the final structure of the fusion protein, the Fc or Fc-like region may serve to prolong the in vivo plasma half-life of the interferon beta compound fused at the N-terminus. Also, the interferon beta component of a fusion protein compound should retain at least one biological activity of interferon beta. An increase in therapeutic or circulating half-life can be demonstrated using the method described herein or known in the art, wherein the half-life of the fusion protein is compared to the half-life of the interferon beta compound alone. Biological activity can be determined by in vitro and in vivo methods known in the art.

Since the Fc region of IgG produced by proteolysis has the same in vivo half-life as the intact IgG molecule and Fab fragments are rapidly degraded, it is believed that the relevant sequence for prolonging half-life reside in the CH2 and/or CH3 domains. Further, it has been shown in the literature that the catabolic rates of IgG variants that do not bind the high-affinity Fc receptor or C1q are indistinguishable from the rate of clearance of the parent wild-type antibody, indicating that the catabolic site is distinct from the sites involved in Fc receptor or C1q binding. [Wawrzynczak et al., (1992) Molecular Immunology 29:221]. Site-directed mutagenesis studies using a murine IgG1 Fc region suggested that the site of the IgG1 Fc region that controls the catabolic rate is located at the CH2-CH3 domain interface. Fc regions can be modified at the catabolic site to optimize the half-life of the fusion proteins. The Fc region used for the fusion proteins of the present invention may be derived from an IgG1 or an IgG4 Fc region, and may contain both the CH2 and CH3 regions including the hinge region.

Heterologous Albumin Fusion Proteins

Relaxin described herein may be fused directly or via a peptide linker, water soluble polymer, or prodrug linker to albumin or an analog, fragment, or derivative thereof. Generally, the albumin proteins that are part of the fusion proteins of the present invention may be derived from albumin cloned from any species, including human. Human serum albumin (HSA) consists of a single non-glycosylated polypeptide chain of 585 amino acids with a formula molecular weight of 66,500. The amino acid sequence of human HSA is known [See Meloun, et al. (1975) FEBS Letters 58:136; Behrens, et al. (1975) Fed. Proc. 34:591; Lawn, et al. (1981) Nucleic Acids Research 9:6102-6114; Minghetti, et al. (1986) J. Biol. Chem. 261:6747, each of which are incorporated by reference herein]. A variety of polymorphic variants as well as analogs and fragments of albumin have been described. [See Weitkamp, et al., (1973) Ann. Hum. Genet. 37:219]. For example, in EP 322,094, various shorter forms of HSA. Some of these fragments of HSA are disclosed, including HSA(1-373), HSA(1-388), HSA(1-389), HSA(1-369), and HSA(1-419) and fragments between 1-369 and 1-419. EP 399,666 discloses albumin fragments that include HSA(1-177) and HSA(1-200) and fragments between HSA(1-177) and HSA(1-200).

It is understood that the heterologous fusion proteins of the present invention include relaxin compounds that are coupled to any albumin protein including fragments, analogs, and derivatives wherein such fusion protein is biologically active and has a longer plasma half-life than the relaxin compound alone. Thus, the albumin portion of the fusion protein need not necessarily have a plasma half-life equal to that of native human albumin. Fragments, analogs, and derivatives are known or can be generated that have longer half-lives or have half-lives intermediate to that of native human albumin and the relaxin compound of interest.

The heterologous fusion proteins of the present invention encompass proteins having conservative amino acid substitutions in the relaxin compound and/or the Fc or albumin portion of the fusion protein. A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Except as otherwise specifically provided herein, conservative substitutions are preferably made with naturally occurring amino acids.

Wild-type albumin and immunoglobulin proteins can be obtained from a variety of sources. For example, these proteins can be obtained from a cDNA library prepared from tissue or cells which express the mRNA of interest at a detectable level. Libraries can be screened with probes designed using the published DNA or protein sequence for the particular protein of interest. For example, immunoglobulin light or heavy chain constant regions are described in Adams, et al. (1980) Biochemistry 19:2711-2719; Goughet, et al. (1980) Biochemistry 19:2702-2710; Dolby, et al. (1980) Proc. Natl. Acad. Sci. USA 77:6027-6031; Rice et al. (1982) Proc. Natl. Acad. Sci. USA 79:7862-7862; Falkner, et al. (1982) Nature 298:286-288; and Morrison, et al. (1984) Ann. Rev. Immunol. 2:239-256. Some references disclosing albumin protein and DNA sequences include Meloun, et al. (1975) FEBS Letters 58:136; Behrens, et al. (1975) Fed. Proc. 34:591; Lawn, et al. (1981) Nucleic Acids Research 9:6102-6114; and Minghetti, et al. (1986) J. Biol. Chem. 261:6747.

Characterization of the Heterologous Fusion Proteins of the Present Invention

Numerous methods exist to characterize the fusion proteins of the present invention. Some of these methods include, but are not limited to: SDS-PAGE coupled with protein staining methods or immunoblotting using anti-IgG or anti-HSA antibodies. Other methods include matrix assisted laser desorption/ionization-mass spectrometry (MALDI-MS), liquid chromatography/mass spectrometry, isoelectric focusing, analytical anion exchange, chromatofocusing, and circular dichroism, for example.

Enhancing Affinity for Serum Albumin

Various molecules can also be fused to the relaxin polypeptides of the invention to modulate the half-life of relaxin polypeptides in serum. In some embodiments, molecules are linked or fused to relaxin polypeptides of the invention to enhance affinity for endogenous serum albumin in an animal.

For example, in some cases, a recombinant fusion of a relaxin polypeptide and an albumin binding sequence is made. Exemplary albumin binding sequences include, but are not limited to, the albumin binding domain from streptococcal protein G (see. e.g., Makrides et al., J. Pharmacol. Exp. Ther. 277:534-542 (1996) and Sjolander et al., J, Immunol. Methods 201:115-123 (1997)), or albumin-binding peptides such as those described in, e.g., Dennis, et al., J. Biol. Chem. 277:35035-35043 (2002).

In other embodiments, the relaxin polypeptides of the present invention are acylated with fatty acids. In some cases, the fatty acids promote binding to serum albumin. See, e.g., Kurtzhals, et al., Biochem. J. 312:725-731 (1995).

In other embodiments, the relaxin polypeptides of the invention are fused directly with serum albumin (including but not limited to, human serum albumin). Those of skill in the art will recognize that a wide variety of other molecules can also be linked to relaxin in the present invention to modulate binding to serum albumin or other serum components.

Glycosylation of Relaxin Polypeptides

The invention includes relaxin polypeptides incorporating one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to relaxin polypeptides either in vivo or in vitro. In some embodiments of the invention, a relaxin polypeptide comprising a carbonyl-containing non-naturally encoded amino acid is modified with a saccharide derivatized with an aminooxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the relaxin polypeptide. See, e.g., H. Liu, et al. J. Am. Chem. Soc. 125: 1702-1703 (2003).

In some embodiments of the invention, a relaxin polypeptide comprising a carbonyl-containing non-naturally encoded amino acid is modified directly with a glycan with defined structure prepared as an aminooxy derivative. One of ordinary skill in the art will recognize that other functionalities, including azide, alkyne, hydrazide, hydrazine, and semicarbazide, can be used to link the saccharide to the non-naturally encoded amino acid.

In some embodiments of the invention, a relaxin polypeptide comprising an azide or alkynyl-containing non-naturally encoded amino acid can then be modified by, including but not limited to, a Huisgen [3+2] cycloaddition reaction with, including but not limited to, alkynyl or azide derivatives, respectively. This method allows for proteins to be modified with extremely high selectivity.

Relaxin Dimers and Multimers

The present invention also provides for relaxin and relaxin analog combinations such as homodimers, heterodimers, homomultimers, or heteromultimers (i.e., trimers, tetramers, etc.) where relaxin containing one or more non-naturally encoded amino acids is bound to another relaxin or relaxin variant thereof or any other polypeptide that is not relaxin or relaxin variant thereof, either directly to the polypeptide backbone or via a linker. Due to its increased molecular weight compared to monomers, the relaxin dimer or multimer conjugates may exhibit new or desirable properties, including but not limited to different pharmacological, pharmacokinetic, pharmacodynamic, modulated therapeutic half-life, or modulated plasma half-life relative to the monomeric relaxin. For examples of monomeric relaxin analogs see, for example, Balschmidt, P., et al., U.S. Pat. No. 5,164,366, issued Nov. 17, 1992; Brange, J., et al., U.S. Pat. No. 5,618,913, issued Apr. 8, 1997; Chance, R. E., et al., U.S. Pat. No. 5,514,646, issued May 7, 1996; and Ertl, J., et al., EPO publication number 885,961, Dec. 23, 1998. Some embodiments of the present invention provide monomeric relaxin analogs containing one or more non-naturally encoded amino acid residues and in some embodiments these include monomeric relaxin analogs wherein position B28 is Asp, Lys, Ile, Leu, Val or Ala and the amino acid residue at position B29 is Lys or Pro; monomeric relaxin analog with Lys(B28)Pro(B29)-human relaxin; monomeric relaxin analog Asp(B28)-human relaxin; and monomeric relaxin analog Lys(B3)Ile(B28)-human relaxin. In some embodiments, relaxin dimers of the invention will modulate signal transduction of the relaxin receptor. In other embodiments, the relaxin dimers or multimers of the present invention will act as a relaxin receptor antagonist, agonist, or modulator.

In some embodiments, one or more of the relaxin molecules present in a relaxin containing dimer or multimer comprises a non-naturally encoded amino acid linked to a water soluble polymer.

In some embodiments, the relaxin polypeptides are linked directly, including but not limited to, via an Asn-Lys amide linkage or Cys-Cys disulfide linkage. In some embodiments, the relaxin polypeptides, and/or the linked non-relaxin molecule, will comprise different non-naturally encoded amino acids to facilitate dimerization, including but not limited to, an alkyne in one non-naturally encoded amino acid of a first relaxin polypeptide and an azide in a second non-naturally encoded amino acid of a second molecule will be conjugated via a Huisgen [3+2] cycloaddition. Alternatively, relaxin, and/or the linked non-relaxin molecule comprising a ketone-containing non-naturally encoded amino acid can be conjugated to a second polypeptide comprising a hydroxylamine-containing non-naturally encoded amino acid and the polypeptides are reacted via formation of the corresponding oxime.

Alternatively, the two relaxin polypeptides, and/or the linked non-relaxin molecule, are linked via a linker. Any hetero- or homo-bifunctional linker can be used to link the two molecules, and/or the linked non-relaxin molecules, which can have the same or different primary sequence. In some cases, the linker used to tether the relaxin, and/or the linked non-relaxin molecules together can be a bifunctional PEG reagent. The linker may have a wide range of molecular weight or molecular length. Larger or smaller molecular weight linkers may be used to provide a desired spatial relationship or conformation between relaxin and the linked entity or between relaxin and its receptor, or between the linked entity and its binding partner, if any. Linkers having longer or shorter molecular length may also be used to provide a desired space or flexibility between relaxin and the linked entity, or between the linked entity and its binding partner, if any.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

In some embodiments, the invention provides multimers comprising one or more relaxin polypeptide, formed by reactions with water soluble activated polymers that have the structure:

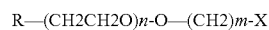

R—(CH2CH2O)n-O—(CH2)m-X wherein n is from about 5 to 3,000, m is 2-10, X can be an azide, an alkyne, a hydrazine, a hydrazide, an aminooxy group, a hydroxylamine, an acetyl, or carbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

Measurement of Relaxin Polypeptide Activity and Affinity of Relaxin Polypeptide for the Relaxin Receptor Relaxin polypeptide activity can be determined using standard or known in vitro or in vivo assays. Relaxin polypeptides may be analyzed for biological activity by suitable methods known in the art. Such assays include, but are not limited to, activation of interferon-responsive genes, receptor binding assays, anti-viral activity assays, cytopathic effect inhibition assays, (Familletti et. al., Meth. Enzymol. 78:387-394), anti-proliferative assays, (Aebersold and Sample, Meth. Enzymol. 119:579-582), immunomodulatory assays (U.S. Pat. Nos. 4,914,033; 4,753,795), and assays that monitor the induction of MHC molecules (e.g., Hokland et al, Meth. Enzymol. 119:688-693), as described in Meager, J. Immunol. Meth., 261:21-36 (2002).

Glucose uptake in 3T3-1 adipocytes may be assessed using the following method. 3T3-L1 cells are obtained from the American Type Culture Collection (ATCC, Rockville, Md.). Cells are cultured in growth medium (GM) containing 10% iron-enriched fetal bovine serum in Dulbecco's modified Eagle's medium. For standard adipocyte differentiation, 2 days after cells reached confluency (referred as day 0), cells are exposed to differentiation medium (DM) containing 10% fetal bovine serum, 10 µg/ml of relaxin, 1 M dexamethasone, and 0.5 µM isobutylmethylxanthine, for 48 hours. Cells then are maintained in post differentiation medium containing 10% fetal bovine serum, and 10 µg/ml of relaxin. In vitro potency may be measured with the glucose uptake assays which are known to those of ordinary skill in the art. In vitro potency can be defined as the measure of glucose uptake of a relaxin compound in a cell-based assay and is a measure of the biological potency of the relaxin compound. It can be expressed as the EC50 which is the effective concentration of compound that results in 50% activity in a single dose-response experiment.

Glucose Transport Assay—Relaxin Dependent—Hexose uptake, as assayed by the accumulation of 0.1 mM 2-deoxy-D-[14C]glucose, is measured as follows: 3T3-L1 adipocytes in 12-well plates are washed twice with KRP buffer (136 mM NaCl, 4.7 mM KCl, 10 mM NaPO4, 0.9 mM CaCl2), 0.9 mM MgSO4, pH 7.4) warmed to 37° C. and containing 0.2% BSA, incubated in Leibovitz's L-15 medium containing 0.2% BSA for 2 hours at 37° C. in room air, washed twice again with KRP containing, 0.2% BSA buffer, and incubated in KRP, 0.2% BSA buffer in the absence (Me2SO only) or presence of wortmannin for 30 minutes at 37° C. in room air. Relaxin is then added to a final concentration of 100 nM for 15 minutes, and the uptake of 2-deoxy-D-[14C] glucose is measured for the last 4 minutes. Nonspecific uptake, measured in the presence of 10 M cytochalasin B, is subtracted from all values. Protein concentrations are determined with the Pierce bicinchoninic acid assay. Uptake is measured routinely in triplicate or quadruplicate for each experiment. The effect of acute and chronic pretreatment of 3T3-L1 adipocytes with FGF-21 in the presence of relaxin may be investigated.

Glucose Transport Assay—Relaxin Independent—3T3-L1 fibroblast are plated in 96-well plates and differentiated into fat cells (adipocytes) for 2 weeks. After differentiation they are starved in serum-free medium and treated with various relaxin polypeptides of the present invention for 24 hours. Upon treatment, cells are washed twice with KRBH buffer, containing 0.1% BSA. Glucose uptake is performed in the presence of labeled glucose in KPBH buffer. This allows qualitative evaluation of a variety of relaxin polypeptides and analogs produced by means of the present invention, and those which have been pegylated as pegylation has been known to cause a decrease in efficiency of the native molecule, and compare the efficacy of different insulins. Additionally, relaxin polypeptides of the present invention may be shown to induce glucose uptake in an ex vivo tissue model.

In the ex vivo glucose transport model, the glucose transport assay is described as follows: Krebs-Henseleit Buffer Stock Solutions—Stock 1: NaCl (1.16 M); KCl (0.046 M); KH2PO4 (0.0116 M); NaHCO$_3$ (0.0253 M). Stock 2: CaCl2) (0.025 M); MgSO4 (2H2O) (0.0116 M). BSA: Use ICN Cohn Fraction V, fatty acid free BSA directly without dialysing. Media Preparation: Add 50 ml of Krebs stock 1 to 395 ml of dH2O and gas with 95% O2/5% CO2 for 1 hour. Add 50 ml of stock 2 and bring to 500 ml with dH2O. Add 500 mg of ICN fatty acid free BSA. Preincubation and Incubation Media: 32 mM Mannitol, 8 mM Glucos. Wash Media: 40 mM Mannitol, 2 mM Pyruvate. Transport Media: 39 mM Mannitol, 1 mM 2-DG; 32 mM Mannitol, 8 mM 3-O-MG. Relaxin Solution: (Porcine Relaxin [Lilly] 100,000,000 µU/ml) at a final concentration of 2000 µU/ml or 13.3 nM. Radioactive Label Media Preparation: Specific activities used: 2DG=1.5 mCi/ml; 3-O-MG=437 µCi/ml; or, Mannitol=8 µCi/m. Rats are anesthetized with 0.1 cc Nembutal per 100 g body weight. Muscle tissue is excised and rinsed in 0.9% saline then placed in pre-incubation media (2 ml) at 29° C. for 1 hour. The muscle tissue is transferred to incubation media (2 ml; same as pre-incubation except including relaxin or test compound) and incubated for 30 minutes (depends upon experimental conditions). The muscle tissue is then transferred to wash media (2 ml) for 10 minutes at 29° C., then transferred to label media (1.5 ml) for 10 min (3-O-MG) or 20 min (2DG). The muscle tissue is trimmed, weighed and placed in polypropylene tubes on dry ice. 1 ml of 1 N KOH is added to the tubes which are then placed in a 70° C. water bath for 10-15 minutes, vortexing the tubes every few minutes. The tubes are cooled on ice and 1 ml of 1 N HCl is added, then mixed well. 200 of supernatant is then put in duplicate scintillation vials and counted on a scintillation counter compared to known radioactive standards.

For contraction, the muscles are first incubated for 1 hour in preincubation/incubation media. After 1 hour, one muscle of each pair (one pair per rat) is pinned to the stimulation apparatus and the other muscle is transferred to a new flask of incubation media. The contracted muscle is stimulated by 200 msec trains of 70 Hz with each impulse in a train being 0.1 msec. The trains are delivered at 1/sec at 10-15V for 2×10 minutes with a 1 minute rest in between. At the end of the stimulation period, the muscle is removed from the stimulation apparatus and placed in wash media for 10 minutes, followed by label media as outlined above.

Average quantities of relaxin, relaxin polypeptides, and/or relaxin analogues of the present invention may vary and in particular should be based upon the recommendations and prescription of a qualified physician. The exact amount of relaxin, relaxin polypeptides, and/or relaxin analogues of the present invention is a matter of preference subject to such factors as the exact type and/or severity of the condition being treated, the condition of the patient being treated, as well as the other ingredients in the composition. The invention also provides for administration of a therapeutically effective amount of another active agent. The amount to be given may be readily determined by one of ordinary skill in the art based upon therapy with relaxin, available relaxin therapies, and/or other relaxin analogues.

Pharmaceutical compositions of the invention may be manufactured in a conventional manner.

EXAMPLES

The following examples are offered to illustrate, but do not limit the claimed invention.

Example 1

This example describes one of the many potential sets of criteria for the selection of sites of incorporation of non-naturally encoded amino acids into relaxin.

Figure 2:
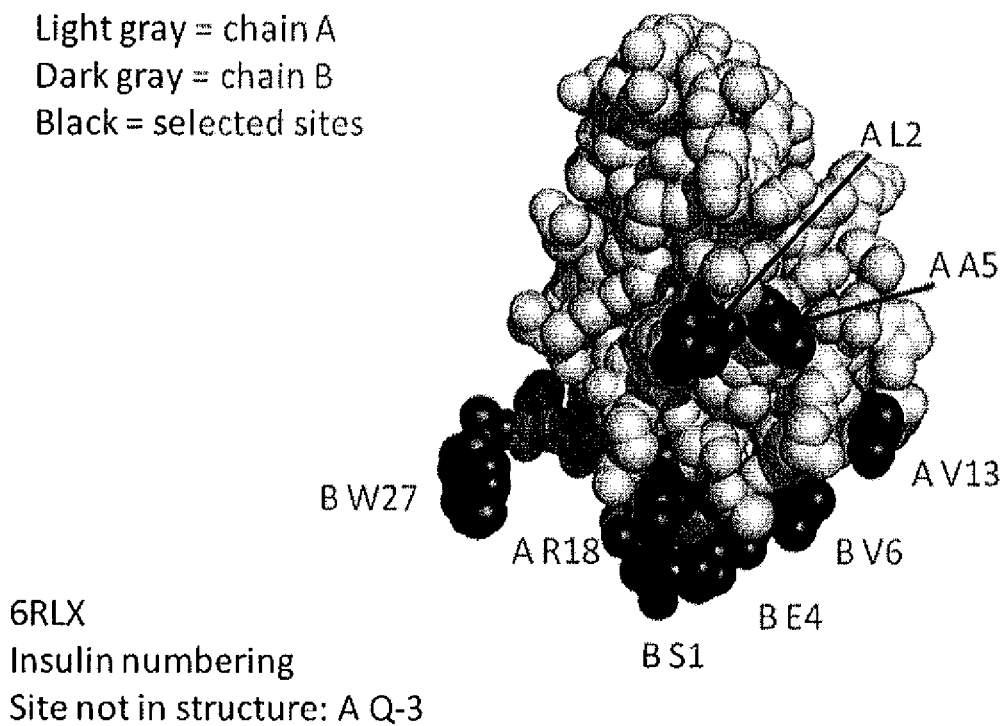
FIG. 2 is a model of the crystal structure of relaxin are shown along with some amino acid residue positions selected for substitution.
Figure 3:
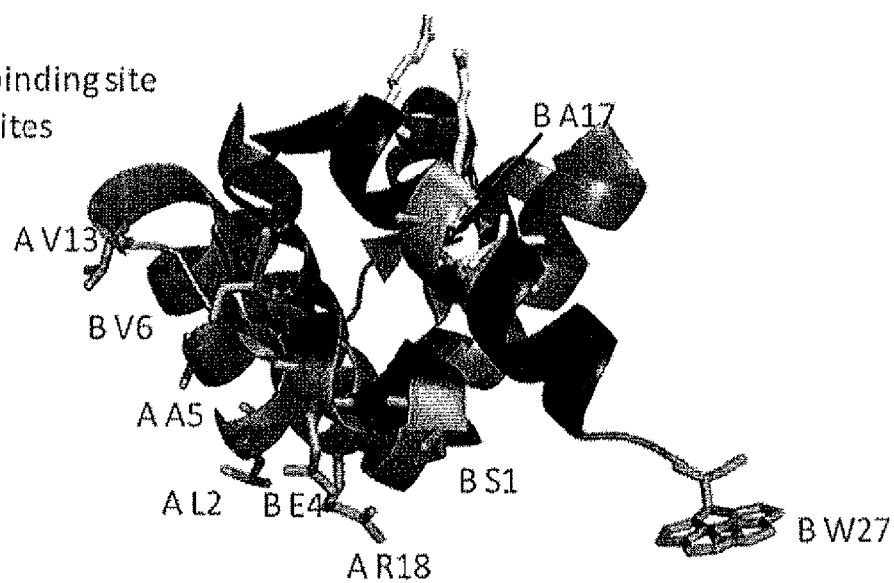
FIG. 3 is a model of the crystal structure of relaxin are shown along with some amino acid residue positions selected for substitution.
Figure 4:
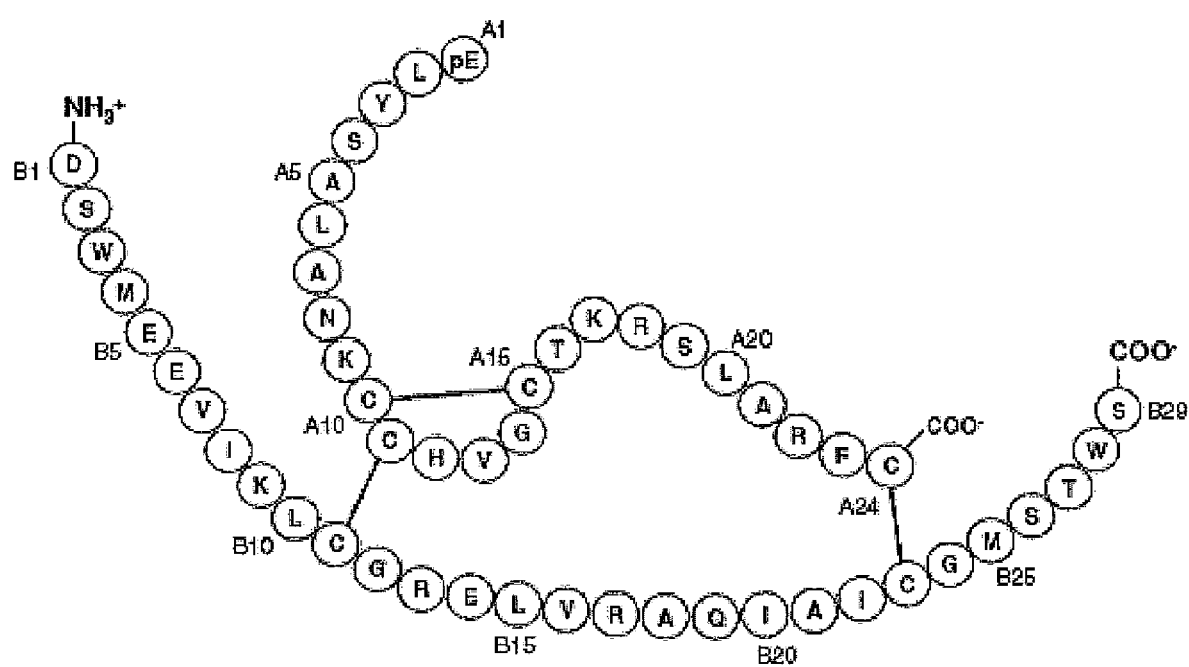
FIG. 4 is a drawing of the structure of the A and B chain of human relaxin.

FIGS. 1-4 show the structure and the sequence of relaxin and the table below includes sequences with the A chain, B chain, relaxin and prorelaxin. Relaxin polypeptides were generated by substituting a naturally encoded amino acid with a non-naturally encoded amino acid. Each polypeptide had one of the amino acids substituted with para-acetylphenylalanine (pAcF or pAF). The polypeptides generated lacked the leader sequence and were A/B chain relaxin polypeptides (SEQ ID NO. 1-3). Each of the polypeptides generated had a non-naturally encoded amino acid substitution at one of the following positions 1, 5, 18, 13, 2 of SEQ ID NO: 4 or in those positions of the A chain of any of the known relaxin sequences or 5, 7, 18, 28 of SEQ ID NO: 5 or 6 in those same positions of the B chain of any of the known relaxin sequences. FIG. 2 shows the structure of human relaxin that was labeled using the PyMOL software (DeLano Scientific; Palo Alto, Calif.) and some amino acids corresponding to those substituted with para-acetylphenylalanine in relaxin polypeptides of the invention.

Another set of criteria for the selection of preferred sites of incorporation of non-naturally encoded amino acids includes using and comparing crystal structures from the Protein Data Bank, or other data banks, are used to model the structure of relaxin and residues are identified that 1) would not interfere with binding to their receptor, and 2) would not be present in the interior of the protein. In some embodiments, one or more non-naturally encoded amino acids are incorporated at, but not limited to, one or more of the following positions of relaxin: 1, 5, 18, 13, 2 of SEQ ID NO: 4 or in those positions of the A chain of any of the known relaxin sequences or 5, 7, 18, 28 of SEQ ID NO: 5 or 6 in those same positions of the B chain of any of the known relaxin sequences.

The following criteria were used to evaluate each position of relaxin and relaxin analogs for the introduction of a non-naturally encoded amino acid: the residue (a) should not interfere with binding of the receptor based on structural analysis, b) should not be affected by alanine or homolog scanning mutagenesis (c) should be surface exposed and exhibit minimal van der Waals or hydrogen bonding interactions with surrounding residues, (d) should be either deleted or variable in relaxin variants, (e) would result in conservative changes upon substitution with a non-naturally encoded amino acid and (f) could be found in either highly flexible regions or structurally rigid regions. In addition, further calculations can be performed on the relaxin molecule, utilizing the Cx program (Pintar et al. (2002) Bioinformatics, 18, pp 980) to evaluate the extent of protrusion for each protein atom.

In some embodiments, one or more non-naturally encoded amino acids are incorporated in one or more of the following positions in the A chain of relaxin: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25 (i.e., at the carboxyl terminus of the protein) (SEQ ID NO: 4 or the corresponding amino acids in SEQ ID NOs: 1-3). In some embodiments, one or more non-naturally encoded amino acids are incorporated in one or more of the following positions in the B chain of relaxin: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 (i.e., at the carboxyl terminus of the protein) (SEQ ID NO: 5 or 6 or the corresponding amino acids in SEQ ID NOs: 1-3). In some embodiments, one or more non-naturally encoded amino acids are incorporated in one or more of the following positions in relaxin: 1, 5, 31, 2, 13, 29, 18, 52 (SEQ ID NO: 1 or the corresponding amino acids in SEQ ID NOs: 2 and 3). In some embodiments, one or more non-naturally encoded amino acids are incorporated in one or more of the following positions in relaxin: 5, 31, 2, 13, 29, 18, 52 (SEQ ID NO: 1 or the corresponding amino acids in SEQ ID NOs: 2 and 3). In some embodiments, one or more non-naturally encoded amino acids are incorporated in one or more of the following positions in relaxin: 1, 5, 31, 2, 13, 29 (SEQ ID NO: 1 or the corresponding amino acids in SEQ ID NOs: 2 and 3). In some embodiments, one or more non-naturally encoded amino acids are incorporated in one or more of the following positions in relaxin: 5, 31, 2, 13, 29 (SEQ ID NO: 1 or the corresponding amino acids in SEQ ID NOs: 2 and 3). In some embodiments, one or more non-naturally encoded amino acids are incorporated in one or more of the following positions in relaxin: 1, 5, 31, 2, 13 (SEQ ID NO: 1 or the corresponding amino acids in SEQ ID NOs: 2 and 3). In some embodiments, one or more non-naturally encoded amino acids are incorporated in one or more of the following positions in relaxin: 5, 31, 2, 13 (SEQ ID NO: 1 or the corresponding amino acids in SEQ ID NOs: 2 and 3).

Example 2

This example details cloning and expression of a relaxin polypeptide including a non-naturally encoded amino acid in E. coli.

Methods for cloning relaxin are known to those of ordinary skill in the art. Polypeptideandpolynucleotidesequencesforrelaxinandcloningofrelaxinintohostcellsare detailed in U.S. Pat. Nos. 4,758,516; 5,166,191; 5,179,195, 5,945,402; and 5,759,807; all of which patents are herein incorporated by reference.

cDNA encoding relaxin is shown as SEQ ID NOs: 12 and the mature polypeptide amino acid sequence is shown as SEQ ID NO: 1.

TABLE 1

Relaxin Sequences Cited

| SEQ ID NO: | Sequence Name | Sequence |
|---|---|---|
| 1 | Relaxin amino acid sequence | QLYSALANKCCHVGCTKRSLARFCDSWMEEV IKLCGRELVRAQIAICGMSTWS |
| 2 | Relaxin amino acid sequence B1 Ala | QLYSALANKCCHVGCTKRSLARFCASWMEEV IKLCGRELVRAQIAICGMSTWS |

TABLE 1-continued

Relaxin Sequences Cited

| SEQ ID NO: | Sequence Name | Sequence |
|---|---|---|
| 3 | Pro-relaxin amino acid sequence | DSWMEEVIKLCGRELVRAQIAICGMSTWSRREAEDLQVGQVELGGGPGAGSLQPLALEGSLQKRQLYSALANKCCHVGCTKRSLARFC |
| 4 | Relaxin A chain, amino acid sequence | QLYSALANKCCHVGCTKRSLARFC |
| 5 | Relaxin B chain, amino acid sequence | DSWMEEVIKLCGRELVRAQIAICGMSTWS |
| 6 | Relaxin B chain, amino acid sequence with B1 Ala | ASWMEEVIKLCGRELVRAQIAICGMSTWS |
| 7 | C peptide amino acid sequence | RREAEDLQVGQVELGGGPGAGSLQPLALEGSLQKR |
| 8 | Relaxin leader amino acid sequence | MKKNIAFLLKR |
| 9 | Insulin leader amino acid sequence | MIEGGR |
| 10 | Relaxin A chain, nucleic acid sequence | caactctacagtgcattggctaataaatgttgccatgttggttgtaccaaaagatctcttgctagattttgc |
| 11 | Relaxin B chain, nucleic acid sequence | gactcatggatggaggaagttattaaattatgcggccgcgaattagttcgcgcgcagattgccatttgcggcatgagcacctggagc |
| 12 | Relaxin, A and B chains, nucleic acid sequence | caactctacagtgcattggctaataaatgttgccatgttggttgtaccaaaagatctcttgctagattttgcgactcatggatggaggaagttattaaattatgcggccgcgaattagttcgcgcgcagattgccatttgcggcatgagcacctggagc |
| 13 | Relaxin leader nucleic acid sequence | atgaaaaagaatatcgcatttcttcttaaacgg |
| 14 | Insulin leader nucleic acid sequence | atgattgaaggtggtcgt |
| 15 | Example of a relaxin expression construct amino acid sequence | MIEGGRDSWMEEVIKLCGRELVRAQIAICGMSTWSRREAEDLQVGQVELGGGPGAGSLQPLALEGSLQKRQLYSALANKCCHVGCTKRSLARFC |

An introduced translation system that comprises an orthogonal tRNA (O-tRNA) and an orthogonal aminoacyl tRNA synthetase (O-RS) is used to express relaxin or relaxin analogs containing a non-naturally encoded amino acid. The O-RS preferentially aminoacylates the O-tRNA with a non-naturally encoded amino acid. In turn the translation system inserts the non-naturally encoded amino acid into the relaxin or relaxin analog, in response to an encoded selector codon. Suitable O-RS and O-tRNA sequences are described in WO 2006/068802 entitled "Compositions of Aminoacyl-tRNA Synthetase and Uses Thereof" (E9; SEQ ID NO: 16) and WO 2007/021297 entitled "Compositions of tRNA and Uses Thereof" (F13; SEQ ID NO: 17), which are incorporated by reference in their entirety herein.

TABLE 2

Sequences Cited

| | | |
|---|---|---|
| SEQ ID NO: 18 | *M. jannaschii* mtRNA$^{Tyr}_{CUA}$ | tRNA |
| SEQ ID NO: 19 | HLAD03; an optimized amber supressor tRNA | tRNA |
| SEQ ID NO: 20 | HL325A; an optimized AGGA frameshift supressor tRNA | tRNA |
| SEQ ID NO: 21 | Aminoacyl tRNA synthetase for the incorporation of p-azido-L-phenylalanine p-Az-PheRS (6) | RS |
| SEQ ID NO: 22 | Aminoacyl tRNA synthetase for the incorporation of p-benzoyl-L-phenylalaninep-BpaRS(1) | RS |
| SEQ ID NO: 23 | Aminoacyl tRNA synthetase for the incorporation of propargyl-phenylalanine Propargyl-PheRS | RS |

TABLE 2-continued

Sequences Cited

| | | |
|---|---|---|
| SEQ ID NO: 24 | Aminoacyl tRNA synthetase for the incorporation of propargyl-phenylalanine Propargyl-PheRS | RS |
| SEQ ID NO: 25 | Aminoacyl tRNA synthetase for the incorporation of propargyl-phenylalanine Propargyl-PheRS | RS |
| SEQ ID NO: 26 | Aminoacyl tRNA synthetase for the incorporation of p-azido-phenylalanine p-Az-PheRS(1) | RS |
| SEQ ID NO: 27 | Aminoacyl tRNA synthetase for the incorporation of p-azido-phenylalanine p-Az-PheRS(3) | RS |
| SEQ ID NO: 28 | Aminoacyl tRNA synthetase for the incorporation of p-azido-phenylalanine p-Az-PheRS(4) | RS |
| SEQ ID NO: 29 | Aminoacyl tRNA synthetase for the incorporation of p-azido-phenylalanine p-Az-PheRS(2) | RS |
| SEQ ID NO: 30 | Aminoacyl tRNA synthetase for the incorporation of p-acetyl-phenylalanine (LW1) | RS |
| SEQ ID NO: 31 | Aminoacyl tRNA synthetase for the incorporation of p-acetyl-phenylalanine (LW5) | RS |
| SEQ ID NO: 32 | Aminoacyl tRNA synthetase for the incorporation of p-acetyl-phenylalanine (LW6) | RS |
| SEQ ID NO: 33 | Aminoacyl tRNA synthetase for the incorporation of p-azido-phenylalanine (AzPheRS-5) | RS |
| SEQ ID NO: 34 | Aminoacyl tRNA synthetase for the incorporation of p-azido-phenylalanine (AzPheRS-6) | RS |

The transformation of *E. coli* with plasmids containing the modified relaxin or relaxin analog gene and the orthogonal aminoacyl tRNA synthetase/tRNA pair (specific for the desired non-naturally encoded amino acid) allows the site-specific incorporation of non-naturally encoded amino acid into the relaxin polypeptide.

Wild type mature relaxin is amplified by PCR from a cDNA synthesis reaction using standard protocols and cloned into pET30 (NcoI-BamHI). Prior to or alternatively following sequence confirmation, relaxin including an N-terminal HIHIHHSGG sequence is subcloned into a suppression vector containing an amber suppressor tyrosyl tRNATyr/CUA from *Methanococcus jannaschii* (Mj tRNA-Tyr/CUA) under constitutive control of a synthetic promoter derived from the *E. coli* lipoprotein promoter sequence (Miller, J. H., Gene, 1986), as well as the orthogonal tyrosyl-tRNA-synthetase (MjTyrRS) under control of the *E. coli* GlnRS promoter. Expression of relaxin is under control of the T7 promoter. Amber mutations are introduced using standard quick change mutation protocols (Stratagene; La Jolla, Calif.). Constructs are sequence verified.

Testing of long-acting relaxin compounds may be done using the STZ diabetic rat model (PCO 08-400-209).

Suppression with Para-Acetyl-Phenylalanine (pAcF)

Plasmids (e.g. pt_RLX_BA1_AV13am_p1395 (AXID2381)) were used to transform into the *Escherichia coli* strain W3110B57 to produce RLX-BA1-AV13pAF W3110 B2 strain of *E. coli* in which expression of the T7 polymerase was under control of an arabinose-inducible promoter. Overnight bacterial cultures were diluted 1:100 into shake flasks containing 2× YT culture media and grown at 37° C. to an $OD_{600}$ of ~0.8. Protein expression was induced by the addition of arabinose (0.2% final), and para-acetyl-phenylalanine (pAcF) to a final concentration of 4 mM. Cultures were incubated at 37° C. for 5 hours. Cells were pelleted and resuspended in B-PER lysis buffer (Pierce) 100 ul/OD/ml+10 ug/ml DNase and incubated at 37° C. for 30 min. Cellular material was removed by centrifugation and the supernatant removed. The pellet was re-suspended in an equal amount of SDS-PAGE protein loading buffer. All samples were loaded on a 4-12% PAGE gel with MES and DTT. Methods for purification of relaxin are known to those of ordinary skill in the art and are confirmed by SDS-PAGE, Western Blot analyses, or electrospray-ionization ion trap mass spectrometry and the like.

His-tagged mutant relaxin proteins can be purified using methods known to those of ordinary skill in the art. The ProBond Nickel-Chelating Resin (Invitrogen, Carlsbad, Calif.) may be used via the standard His-tagged protein purification procedures provided by the manufacturer. Functional measurements of the proteins may be done through methods known in the art, methods provided within this application and incorporated references, and alternatively an ELISA on live cells can be developed to assess relaxin polypeptides of the invention.

TABLE 3

Analyses of Relaxin Variants

| Batch/Description | SDS-PAGE | LAL (EU/mg) | conc. at A280 | RP-HPLC purity | SE-HPLC purity |
|---|---|---|---|---|---|
| WT Relaxin[3] | NR Major band migrates near the 6 kDa MW standard | NT | 2.4 | 91.2% | NT |
| 20K PEGylated Q1pAF[1, 3, 4] | NR Major band migrates between the 49 and 38 kDa MW standards | 7.7 | 3.4 | 100% | NT |
| 20K PEGylated A5pAF[1, 3, 4] | | 3.6 | 2.4 | 100% | NT |
| 20K PEGylated R18pAF[1, 3, 4] | | 16.1 | 2.4 | 100% | NT |
| 20K PEGylated E5pAF[2, 3] | | NT | 0.6 | 99.8% | NT |
| 20K PEGylated V7pAF[2, 3, 4] | | 10.5 | 2.3 | 99.4% | NT |
| 20K PEGylated A18pAF[2, 3] | | NT | 2.0 | 99.0% | NT |
| 20K PEGylated W28pAF[2, 3, 4] | | 9.1 | 2.2 | 99.4% | NT |
| 20K PEGylated V13pAF[1, 3, 4] | | 5.1 | 3.7 | 99.5% | NT |

TABLE 3-continued

Analyses of Relaxin Variants

| Batch/Description | SDS-PAGE | LAL (EU/mg) | onc. at A280 | RP-HPLC purity | SE-HPLC purity |
|---|---|---|---|---|---|
| 20K PEGylated E5pAF[2] | | NT | 0.6 | 99.6% | NT |
| 20K PEGylated L2pAF[1] | | 0.0 | 1.6 | 99.5% | NT |
| WT Relaxin[3] | NR Major band migrates near the 6 kDa MW standard | 0.1 | 2.5 | 85.6% | NT |
| 20K PEGylated Q1pAF[1, 3] | NR Major band migrates between the 49 and 38 kDa MW standards | <0.4 | 2.3 | 99.3% | 99.3% |
| 5K PEGylated V13pAF[1, 3] | NR Major band migrates near the 14 kDa MW standard | 5.4 | 1.5 | 99.4% | 99.8% |
| 10K PEGylated V13pAF[1, 3] | NR Major band migrates between the 28 and 17 kDa MW standards | 9.8 | 1.8 | 99.4% | 99.5% |
| 20K PEGylated V13pAF[1, 3] | NR Major band migrates between the 49 and 38 kDa MW standards | 4.7 | 1.9 | 99.0% | 99.5% |
| 30K PEGylated V13pAF[1, 3] | NR Major band migrates between the 62 and 49 kDa MW standards | 8.0 | 2.1 | 99.5% | 99.8% |

Samples not reduced (NR);
NT = Not Tested
[1] pAcF substitution located on A-chain
[2] pAcF substitution located on B-chain
[3] Asp to Ala substitution on B-chain (BA1)
[4] used for initial PK

Example 3

This example details expression of Pro-relaxin polypeptides by E. co.

E. coli expressed Pro-relaxin as a single chain protein composed of 88 amino acids. Upon digestion with trypsin and carboxypeptidase, a connecting peptide and leader sequence are removed. The resulting peptide is a small 6 kDa two-chain peptide member of the insulin superfamily which consists of a 24 residue A-chain and a 29 residue B-chain. The structural fold is characterized by two peptide chains which are held together by two interchain (Cys11-Cys36, and Cys24-Cys48) and one intrachain (Cys10-Cys15) disulfide bonds. The tertiary structure based on a crystal structure of human relaxin-2 revealed a compact fold comprising three helical segments and a short extended region that enclose a hydrophobic core.

Relaxin with one or more non-naturally encoded amino acid(s) provides a unique chemistry and enables a specific PEGylated recombinant variant containing a biosynthetically incorporated, chemically reactive, carbonyl group, by replacement of a natural amino acid with para-acetylphenylalanine (pAcF), providing a unique covalent site of attachment for a poly(ethylene) glycol (PEG).

Example 4

This example details expression of Pro-relaxin polypeptides by E. coli.

This example describes the scale up of relaxin polypeptide production using a five (5) liter fermentor. These methods and scale up may also be used for 10 L, 30 L, 150 L and 1000 L batches. In some embodiments of the present invention, at least 2 g of relaxin protein is produced for each liter of cell culture. In another embodiment of the present invention, at least 4 g of relaxin protein is produced for each liter of cell culture. In another embodiment of the present invention, at least 6 g of relaxin protein is produced for each

TABLE 4

Relaxin Variant Loss of Activity

| Variant | In vitro Activity Fold Loss | PEG size | In vivo PK Term HL (hr) | In vivo pharm | Shake flask | Fermentor Titer (cell paste) | Analytical characterization |
|---|---|---|---|---|---|---|---|
| RLX-A-AV13 | 17 | 5K, 10K, 20K, 30K | 2.6 (5K), 8.7 (10K), 13.8 (20K), 26.8 (30K) | | yes | 1 gm/L | SDS-PAGE, conc., LAL, RP-HPLC, SE-HPLC |
| RLX-A-AQ1 | 12 | 20K | 10.7 | 20K shows efficacy | yes | 720 mg/L | SDS-PAGE, conc., RP-HPLC, LAL, SE-HPLC |
| RLX-A-AA5 | 12 | 20K | 12.2 | | yes | | SDS-PAGE, conc., RP-HPLC, LAL |
| RLX-A-BV7 | 15 | 20K | 13.1 | | yes | | SDS-PAGE, conc., RP-HPLC, LAL |
| RLX-A-AL2 | 17 | 20K | | | yes | | SDS-PAGE, conc., RP-HPLC |
| RLX-A-BE5 | 17 | 20K | | | yes | | SDS-PAGE, conc., RP-HPLC |
| RLX-A-AR18 | 21 | 20K | 12.5 | | yes | | SDS-PAGE, conc., RP-HPLC, LAL |
| RLX-BE5 | 22 | 20K | | | yes | | SDS-PAGE, conc., RP-HPLC |
| RLX-A-BA18 | 48 | 20K | | | yes | | SDS-PAGE, conc., RP-HPLC |
| RLX-A-BW28 | 48 | 20K | 13.9 | | yes | | SDS-PAGE, conc., RP-HPLC, LAL | liter of cell culture. In another embodiment of the present invention, at least 8 g of relaxin protein is produced for each liter of cell culture. In another embodiment of the present invention, at least 10 g of relaxin protein is produced for each liter of cell culture. In another embodiment of the present invention, at least 15 g of relaxin protein is produced for each liter of cell culture. In another embodiment of the present invention, at least 20 g of relaxin protein is produced for each liter of cell culture.

2.1 Seed Shake Flasks

*Escherichia coli* strain W3110B57 [F-IN(rrnD-rrnE) lambda-araB::g1 tetA fhuA::dhfr ompT::cat] harboring plasmid pt_RLX_BA1_AV13am_p1395 (AXID2381) was used to produce RLX-BA1-AV13pAF. A single research cell bank (RCB) vial was removed from −80° C. and thawed at room temperature, then 50 μL was used to inoculate 50 mL of Seed Media (a chemically defined medium) supplemented with 50 μg/mL kanamycin sulfate in a 250 mL baffled Erlenmeyer flask. The primary seed culture was grown for approximately 18 hours at 37° C. and 250 rpm (1-inch throw). The primary seed culture was sub-cultured into a secondary seed culture to an optical density measured at 600 nm wavelength (OD600) of 0.05 in a 500 mL baffled Erlenmeyer flask containing 100 mL of Seed Medium supplemented with 50 μg/mL kanamycin sulfate. The secondary seed culture was grown at 37° C. and 250 rpm (1-inch throw) for approximately 8 hours or when the OD600 reached between 2 and 4.

2.2 Fermentors

Sartorius Biostat B 5-L vessels were filled with 2.1-L of Production Media (a chemically defined medium) supplemented with 50 μg/L of kanamycin sulfate. Secondary seed cultures were used to inoculate the fermentors to an initial OD600 of 0.035. The cultures were grown 37° C. and the dissolved oxygen was set to maintain 30% (air saturation) with a primary agitation (480-1200 rpm) cascade and a secondary O2 cascade. An air flow rate of 5 LPM with 6 psi back pressure was maintained throughout the fermentation. The pH of the culture was set at 7.2±0.05 with the addition of 15% ammonium hydroxide and Dow Chemical P2000 antifoam was added as needed for foam control. When the culture reached an OD600 of between 35±5 (when the initial glycerol in the batch medium was nearly depleted), a bolus feed of 200 mL was given initiated and at the same time the pH set point was adjusted from 7.2 to 6.6. After the initial bolus feed, a continuous feed was initiated at a rate of 0.25 mL/L/min and continued until harvest. Immediately after starting the feed, 2.5 mL/L (0.2 g/L final culture volume) of a 100 g/L L-Ala-pAcF dipeptide solution made in water was added to the fermentor. Fifteen minutes after dipeptide addition, the culture was induced by adding L-arabinose (recipe given in PTR-FGF-002) to a concentration of 2 g/L (final culture volume). The culture was grown 6 hours after arabinose addition and harvested.

Figure 5:
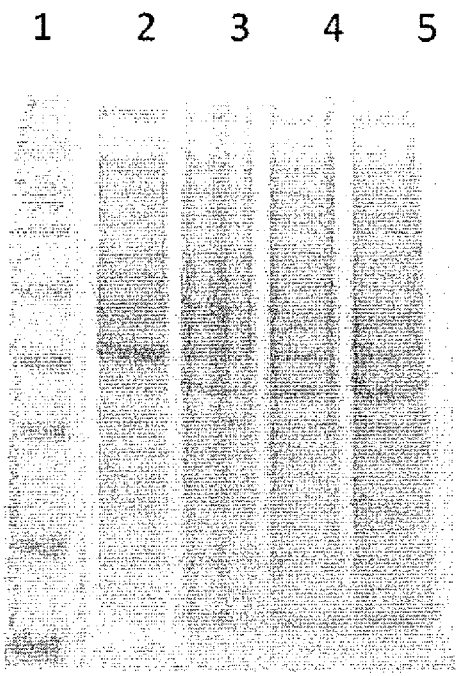
FIG. 5 shows an SDS-PAGE gel of the prorelaxin produced by these methods with a chain B1 amimo acid as Ala and a para-acetyl phenylalanine in the $13^{th}$ amino acid position of the A chain, substituted for valine.
Figure 6A:
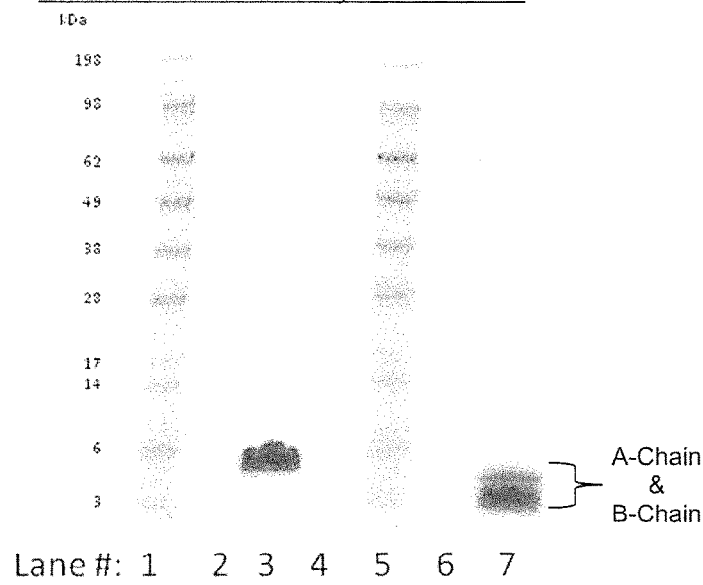
FIG. 6A shows an SDS-PAGE gel of unPEGylated relaxin V13pAF alongside a molecular weight marker in lane 1 and recombinant and non-recombinant WT relaxin in lanes 3 and 7 (non-reduced (NR) and reduced (R)).
Figure 6B:
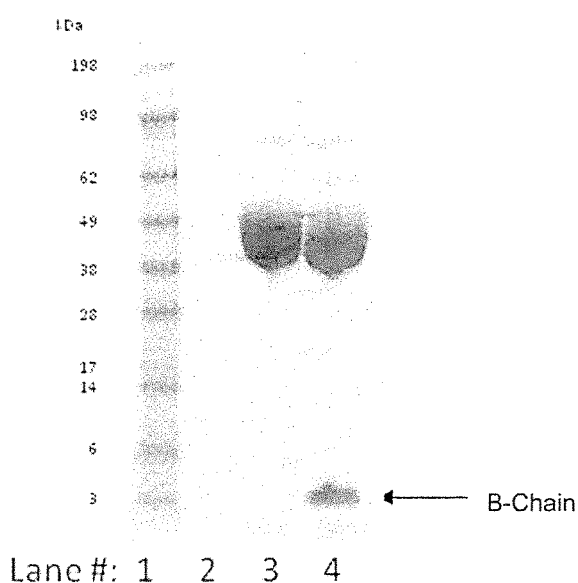
FIG. 6B shows an SDS-PAGE gel of PEGylated relaxin V13pAF in lanes 3 and 4 (non-reduced (NR) and reduced (R)) alongside a molecular weight marker in lane 1.
Figure 7:
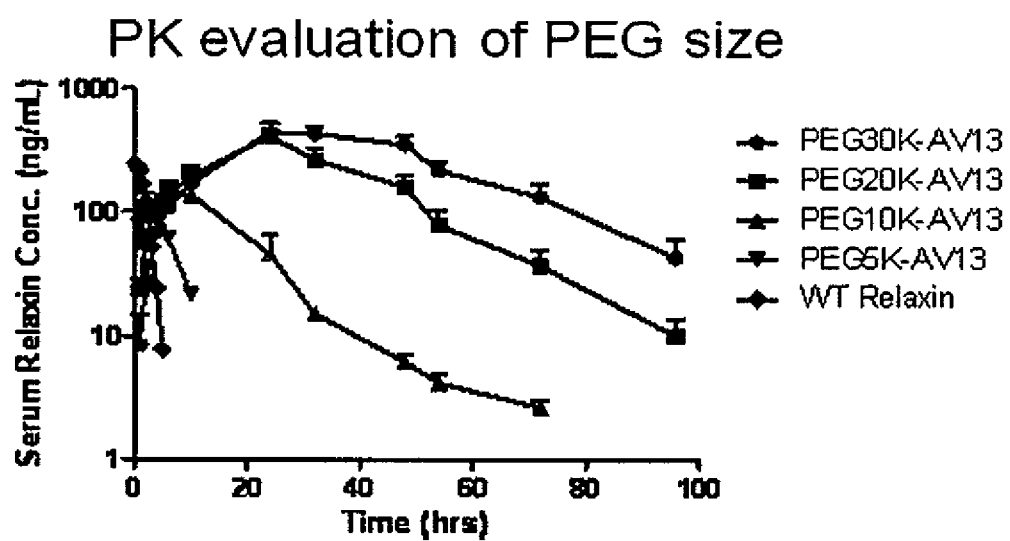
FIG. 7 shows a graph of SD rat serum relaxin concentration in ng/mL over time for differently PEGylated AV13 and wild type relaxin polypeptides.

FIG. 5 shows an SDS-PAGE gel of the prorelaxin produced by these methods with a chain B1 amimo acid as Ala and a para-acetyl phenylalanine in the 13$^{th}$ amino acid position of the A chain, substituted for valine.

Example 5

This example details introduction of a carbonyl-containing amino acid and subsequent reaction with an aminooxy-containing PEG.

This Example demonstrates a method for the generation of a relaxin polypeptide that incorporates a ketone-containing non-naturally encoded amino acid that is subsequently reacted with an aminooxy-containing PEG of approximately 5,000 MW. Each of the residues before position 1 (i.e. at the N-terminus), 1, 2, 3, 4, 5, 6, 7, 8, 9, 10, 11, 12, 13, 14, 15, 16, 17, 18, 19, 20, 21, 22 (i.e., at the carboxyl terminus of the protein of SEQ ID NO: 1 or the corresponding amino acids in SEQ ID NOs: 3, 5, 7, 9, 11) and each of the residues before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 (i.e., at the carboxyl terminus of the protein of SEQ ID NO: 2 or the corresponding amino acids in SEQ ID NOs: 4, 6, 8, 10, 12) is separately substituted with a non-naturally encoded amino acid having the following structure:

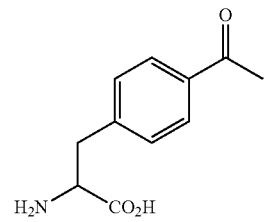

The sequences utilized for site-specific incorporation of p-acetyl-phenylalanine into relaxin are SEQ ID NO: 1 and 2 (A and B chains of relaxin), and SEQ ID NO: 16 or 17 (muttRNA, *M. jannaschii*), and 15, 29, 30 or 31 (TyrRS LW1, 5, or 6) described in Example 2 above.

Once modified, the relaxin polypeptide variant comprising the carbonyl-containing amino acid is reacted with an aminooxy-containing PEG derivative of the form:

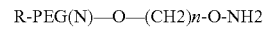

R-PEG(N)—O—(CH2)$n$-O-NH2 where R is methyl, n is 3 and N is approximately 5,000 MW. The purified relaxin containing p-acetylphenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. J. Am. Chem. Soc. 1959, 81, pp 475). The PEG-relaxin is then diluted into appropriate buffer for immediate purification and analysis.

Example 6

This example details introduction of a carbonyl-containing amino acid and subsequent reaction with an aminooxy-containing PEG.

This Example demonstrates a method for the generation of a relaxin polypeptide that incorporates a ketone-containing non-naturally encoded amino acid that is subsequently reacted with an aminooxy-containing PEG of approximately 20,000 MW. Each of the residues before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 (i.e., at the carboxyl terminus of the protein of SEQ ID NO: 1 or the corresponding amino acids in SEQ ID NOs: 2 and 3) is separately substituted with a non-naturally encoded amino acid having the following structure:

*[Chemical structure: p-acetylphenylalanine - phenyl ring with acetyl group (C(=O)CH3) at para position and CH2-CH(NH2)-CO2H side chain]*

The sequences utilized for site-specific incorporation of p-aminophenylalanine into relaxin are SEQ ID NO: 4 and 5 or 6 (A and B chains of relaxin), and SEQ ID NO: 16 or 17 (muttRNA, *M. jannaschii*), and sequences described above and incorporated for site-specific incorporation of p-aminophenylalanine.

Once modified, the relaxin polypeptide variant comprising the carbonyl-containing amino acid is reacted with an aminooxy-containing PEG derivative of the form:

R-PEG(N)—O—(CH2)$n$-O-NH2 where R is methyl, n is 3 and N is approximately 20,000 MW. The purified relaxin containing p-aminophenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. J. Am. Chem. Soc. 1959, 81, pp 475). The PEG-relaxin is then diluted into appropriate buffer for immediate purification and analysis.

Example 7

This example details introduction of a carbonyl-containing amino acid and subsequent reaction with an aminooxy-containing PEG.

This Example demonstrates a method for the generation of a relaxin polypeptide that incorporates a ketone-containing non-naturally encoded amino acid that is subsequently reacted with an aminooxy-containing PEG of approximately 20,000 MW. Each of the residues before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 (i.e., at the carboxyl terminus of the protein of SEQ ID NO: 1 or the corresponding amino acid positions in SEQ ID NOs: 2 and 3) is separately substituted with a non-naturally encoded amino acid having the following structure:

*[Chemical structure: p-acetylphenylalanine]*

The sequences utilized for site-specific incorporation of p-aminophenylalanine into relaxin are SEQ ID NO: 13, and SEQ ID NO: 16 or 17 (muttRNA, *M. jannaschii*), and sequences described above and incorporated for site-specific incorporation of p-aminophenylalanine.

Once modified, the relaxin polypeptide variant comprising the carbonyl-containing amino acid is reacted with an aminooxy-containing PEG derivative of the form:

R-PEG(N)—O—(CH2)$n$-O-NH2 where R is methyl, n is 3 and N is approximately 20,000 MW. The purified relaxin containing p-aminophenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. J. Am. Chem. Soc. 1959, 81, pp 475). The PEG-relaxin is then diluted into appropriate buffer for immediate purification and analysis.

Example 8

This example details introduction of a carbonyl-containing amino acid and subsequent reaction with an aminooxy-containing PEG.

This Example demonstrates a method for the generation of a relaxin polypeptide that incorporates a ketone-containing non-naturally encoded amino acid that is subsequently reacted with an aminooxy-containing PEG of approximately 20,000 MW. Each of the residues before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 (i.e., at the carboxyl terminus of the protein of SEQ ID NO: 1 or the corresponding amino acid positions in SEQ ID NOs: 2 and 3) is separately substituted with a non-naturally encoded amino acid having the following structure:

*[Chemical structure: p-acetylphenylalanine]*

The sequences utilized for site-specific incorporation of p-aminophenylalanine into relaxin are SEQ ID NO: 1, and SEQ ID NO: 16 or 17 (muttRNA, *M. jannaschii*), and sequences described above and incorporated for site-specific incorporation of p-aminophenylalanine.

Once modified, the relaxin polypeptide variant comprising the carbonyl-containing amino acid is reacted with an aminooxy-containing PEG derivative of the form:

R-PEG(N)—O—(CH2)$n$-O-NH2 where R is methyl, n is 3 and N is approximately 20,000 MW. The purified relaxin containing p-aminophenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. J.

Example 9

This example details introduction of a carbonyl-containing amino acid and subsequent reaction with an aminooxy-containing PEG.

This Example demonstrates a method for the generation of a relaxin polypeptide that incorporates a ketone-containing non-naturally encoded amino acid that is subsequently reacted with an aminooxy-containing PEG of approximately 30,000 MW. Each of the residues before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 (i.e., at the carboxyl terminus of the protein of SEQ ID NO: 1 or the corresponding positions in SEQ ID NOs: 2 and 3) is separately substituted with a non-naturally encoded amino acid having the following structure:

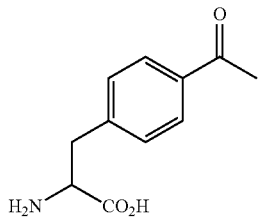

The sequences utilized for site-specific incorporation of p-aminophenylalanine into relaxin are SEQ ID NO: 1 (or SEQ ID NO: 2, or 3), and SEQ ID NO: 16 or 17 (muttRNA, *M. jannaschii*), and sequences described above and incorporated for site-specific incorporation of p-aminophenylalanine.

Once modified, the relaxin polypeptide variant comprising the carbonyl-containing amino acid is reacted with an aminooxy-containing PEG derivative of the form:

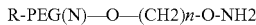

R-PEG(N)—O—(CH2)$n$-O-NH2 where R is methyl, n is 3 and N is approximately 30,000 MW. The purified relaxin containing p-aminophenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. J. Am. Chem. Soc. 1959, 81, pp 475). The PEG-relaxin is then diluted into appropriate buffer for immediate purification and analysis.

Example 10

This example details introduction of a carbonyl-containing amino acid and subsequent reaction with an aminooxy-containing PEG.

This Example demonstrates a method for the generation of a relaxin polypeptide that incorporates a ketone-containing non-naturally encoded amino acid that is subsequently reacted with an aminooxy-containing PEG of approximately 40,000 MW. Each of the residues before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 (i.e., at the carboxyl terminus of the protein of SEQ ID NO: 1 or the corresponding positions in SEQ ID NOs: 2 and 3) is separately substituted with a non-naturally encoded amino acid having the following structure:

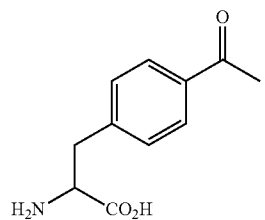

The sequences utilized for site-specific incorporation of p-aminophenylalanine into relaxin are SEQ ID NO: 13 (or SEQ ID NO: 1, 2, or 14), and SEQ ID NO: 16 or 17 (muttRNA, *M. jannaschii*), and sequences described above and incorporated for site-specific incorporation of p-aminophenylalanine.

Once modified, the relaxin polypeptide variant comprising the carbonyl-containing amino acid is reacted with an aminooxy-containing PEG derivative of the form:

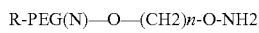

R-PEG(N)—O—(CH2)$n$-O-NH2 where R is methyl, n is 3 and N is approximately 40,000 MW. The purified relaxin containing p-aminophenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. J. Am. Chem. Soc. 1959, 81, pp 475). The PEG-relaxin is then diluted into appropriate buffer for immediate purification and analysis.

Example 11

This example details introduction of a carbonyl-containing amino acid and subsequent reaction with an aminooxy-containing PEG.

This Example demonstrates a method for the generation of a relaxin polypeptide that incorporates a ketone-containing non-naturally encoded amino acid that is subsequently reacted with an aminooxy-containing PEG of approximately 10,000 MW. Each of the residues before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 (i.e., at the carboxyl terminus of the protein of SEQ ID NO: 1 or the corresponding positions in SEQ ID NOs: 2 and 3) is separately substituted with a non-naturally encoded amino acid having the following structure:

The sequences utilized for site-specific incorporation of p-aminophenylalanine into relaxin are SEQ ID NO: 13 (or corresponding positions in SEQ ID NO: 1, 2, or 14), and SEQ ID NO: 16 or 17 (muttRNA, *M. jannaschii*), and sequences described above and incorporated for site-specific incorporation of p-aminophenylalanine.

Once modified, the relaxin polypeptide variant comprising the carbonyl-containing amino acid is reacted with an aminooxy-containing PEG derivative of the form:

R-PEG(N)—O—(CH2)n-O—NH2 where R is methyl, n is 3 and N is approximately 10,000 MW. The purified relaxin containing p-aminophenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. J. Am. Chem. Soc. 1959, 81, pp 475). The PEG-relaxin is then diluted into appropriate buffer for immediate purification and analysis.

Example 12

Conjugation with a PEG consisting of a hydroxylamine group linked to the PEG via an amide linkage.

A PEG reagent having the following structure is coupled to a ketone-containing non-naturally encoded amino acid using the procedure described in Examples 3-9:

R-PEG(N)—O—(CH$_2$)$_2$—NH—C(O)(CH$_2$)$_n$—O—NH$_2$ where R=methyl, n=4 and N is approximately 5,000 MW-40,000 MW. The reaction, purification, and analysis conditions are as described and known in the art.

Example 13

This example details the introduction of two distinct non-naturally encoded amino acids into relaxin polypeptides and relaxin analog polypeptides.

This example demonstrates a method for the generation of a relaxin polypeptide that incorporates non-naturally encoded amino acid comprising a ketone functionality at two positions among the following residues: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 (i.e., at the carboxyl terminus of the protein of SEQ ID NO: 1 or the corresponding positions in SEQ ID NOs: 2 and 3). The relaxin polypeptide is prepared as described above, except that the selector codon is introduced at two distinct sites within the nucleic acid.

Example 14

This example details conjugation of relaxin polypeptide or relaxin analog polypeptide to a hydrazide-containing PEG and subsequent in situ reduction.

A relaxin polypeptide incorporating a carbonyl-containing amino acid is prepared according to the procedure described above. Once modified, a hydrazide-containing PEG having the following structure is conjugated to the relaxin polypeptide:

R-PEG(N)—O—(CH2)2-NH—C(O)(CH2)n-X—NH—NH2 where R=methyl, n=2 and N=5,000; 10,000, 20,000; 30,000; or 40,000 MW and X is a carbonyl (C=O) group. The purified relaxin containing p-acetylphenylalanine is dissolved at between 0.1-10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 1 to 100-fold excess of hydrazide-containing PEG, and the corresponding hydrazone is reduced in situ by addition of stock 1M NaCNBH3 (Sigma Chemical, St. Louis, Mo.), dissolved in H$_2$O, to a final concentration of 10-50 mM. Reactions are carried out in the dark at 4° C. to RT for 18-24 hours. Reactions are stopped by addition of 1 M Tris (Sigma Chemical, St. Louis, Mo.) at about pH 7.6 to a final Tris concentration of 50 mM or diluted into appropriate buffer for immediate purification.

Example 15

This example details conjugation of relaxin polypeptide or relaxin analog polypeptide to a hydrazide-containing PEG and subsequent in situ reduction.

A relaxin polypeptide incorporating a carbonyl-containing amino acid is prepared according to the procedure described above. Once modified, a hydrazide-containing PEG having the following structure is conjugated to the relaxin polypeptide:

R-PEG(N)—O—(CH2)2-NH—C(O)(CH2)n-X—NH—NH2 where R=methyl, n=2 and N=20,000 MW and X is a carbonyl (C=O) group. The purified relaxin containing p-acetylphenylalanine is dissolved at between 0.1-10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 1 to 100-fold excess of hydrazide-containing PEG, and the corresponding hydrazone is reduced in situ by addition of stock 1M NaCNBH3 (Sigma Chemical, St. Louis, Mo.), dissolved in H2O, to a final concentration of 10-50 mM. Reactions are carried out in the dark at 4° C. to RT for 18-24 hours. Reactions are stopped by addition of 1 M Tris (Sigma Chemical, St. Louis, Mo.) at about pH 7.6 to a final Tris concentration of 50 mM or diluted into appropriate buffer for immediate purification.

Example 16

This example details introduction of an alkyne-containing amino acid into a relaxin polypeptide or relaxin analog polypeptide and derivatization with mPEG-azide.

The following residues, before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 (i.e., at the carboxyl terminus of the protein of SEQ ID NO: 1 or the corresponding positions in SEQ ID NOs: 2 and 3), are each substituted with the following non-naturally encoded amino acid:

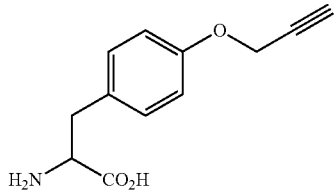 [SMILES: C#CCOc1ccc(CC(N)C(=O)O)cc1]

The sequences utilized for site-specific incorporation of p-propargyl-tyrosine into relaxin are SEQ ID NO: 1 (or corresponding positions in SEQ ID NO:2 or 3), SEQ ID NO: 16 or 17 (muttRNA, *M. jannaschii*), and 22, 23 or 24 described above. The relaxin polypeptide containing the propargyl tyrosine is expressed in *E. coli* and purified using the conditions described above.

The purified relaxin containing propargyl-tyrosine dissolved at between 0.1-10 mg/mL in PB buffer (100 mM sodium phosphate, 0.15 M NaCl, pH=8) and a 10 to 1000-fold excess of an azide-containing PEG is added to the reaction mixture. A catalytic amount of CuSO4 and Cu wire are then added to the reaction mixture. After the mixture is incubated (including but not limited to, about 4 hours at room temperature or 37° C., or overnight at 4° C.), H2O is added and the mixture is filtered through a dialysis membrane. The sample can be analyzed for the addition, including but not limited to, by similar procedures described in Example 3. In this Example, the PEG will have the following structure:

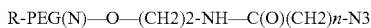
R-PEG(N)—O—(CH2)2-NH—C(O)(CH2)n-N3 where R is methyl, n is 4 and N=5,000; 10,000, 20,000; 30,000; or 40,000 MW.

Example 17

This example details substitution of a large, hydrophobic amino acid in a relaxin polypeptide with propargyl tyrosine.

A Phe, Trp or Tyr residue present within one the following regions of relaxin: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 (i.e., at the carboxyl terminus of the protein of SEQ ID NO: 1 or the corresponding positions in SEQ ID NOs: 2 and 3), is substituted with the following non-naturally encoded amino acid as described above:

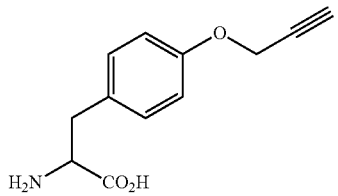 [SMILES: C#CCOc1ccc(CC(N)C(=O)O)cc1]

Once modified, a PEG is attached to the relaxin polypeptide variant comprising the alkyne-containing amino acid. The PEG will have the following structure:

Me-PEG(N)—O—(CH2)2-N3 and coupling procedures would follow those in examples above. This will generate a relaxin polypeptide variant comprising a non-naturally encoded amino acid that is approximately isosteric with one of the naturally-occurring, large hydrophobic amino acids and which is modified with a PEG derivative at a distinct site within the polypeptide.

Example 18

This example details generation of a relaxin polypeptide homodimer, heterodimer, homomultimer, or heteromultimer separated by one or more PEG linkers. Relaxin polypeptide multimers may be formed between proinsulins or between mature A and B chain relaxin polypeptides of the invention.

The alkyne-containing relaxin polypeptide variant produced in the example above is reacted with a bifunctional PEG derivative of the form:

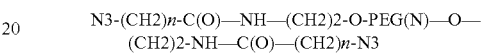
N3-(CH2)*n*-C(O)—NH—(CH2)2-O-PEG(N)—O—(CH2)2-NH—C(O)—(CH2)*n*-N3 where n is 4 and the PEG has an average MW of approximately 5,000; 10,000; 20,000; 30,000; or 40,000 MW to generate the corresponding relaxin polypeptide homodimer where the two relaxin molecules are physically separated by PEG. In an analogous manner a relaxin polypeptide may be coupled to one or more other polypeptides to form heterodimers, homomultimers, or heteromultimers. Coupling, purification, and analyses will be performed as in the examples above.

Example 19

This example details generation of a relaxin polypeptide homodimer, heterodimer, homomultimer, or heteromultimer separated by one or more PEG linkers. Relaxin polypeptide multimers may be formed between A chains and other A chains or B chains and other B chains.

The alkyne-containing relaxin polypeptide variant produced in the example above is reacted with a bifunctional PEG derivative of the form:

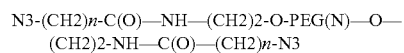
N3-(CH2)*n*-C(O)—NH—(CH2)2-O-PEG(N)—O—(CH2)2-NH—C(O)—(CH2)*n*-N3 where n is 4 and the PEG has an average MW of approximately 5,000; 10,000; 20,000; 30,000; or 40,000 MW to generate the corresponding relaxin polypeptide homodimer where the two relaxin molecules are physically separated by PEG. In an analogous manner a relaxin polypeptide may be coupled to one or more other polypeptides to form heterodimers, homomultimers, or heteromultimers. Coupling, purification, and analyses will be performed as in the examples above.

Example 20

This example details coupling of a saccharide moiety to a relaxin polypeptide.

One residue of the following is substituted with the non-naturally encoded amino acid below: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 (i.e., at the carboxyl terminus of the protein of SEQ ID NO: 1 or the corresponding positions in SEQ ID NOs: 2 and 3), as described above.

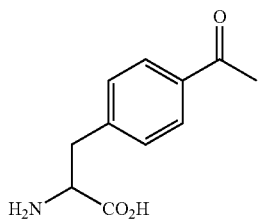

Once modified, the relaxin polypeptide variant comprising the carbonyl-containing amino acid is reacted with a β-linked aminooxy analogue of N-acetylglucosamine (GlcNAc). The relaxin polypeptide variant (10 mg/mL) and the aminooxy saccharide (21 mM) are mixed in aqueous 100 mM sodium acetate buffer (pH 5.5) and incubated at 37° C. for 7 to 26 hours. A second saccharide is coupled to the first enzymatically by incubating the saccharide-conjugated relaxin polypeptide (5 mg/mL) with UDP-galactose (16 mM) and β-1,4-galacytosyltransferase (0.4 units/mL) in 150 mM HEPES buffer (pH 7.4) for 48 hours at ambient temperature (Schanbacher et al. J. Biol. Chem. 1970, 245, 5057-5061).

Example 22

This example details generation of a PEGylated relaxin polypeptide antagonist.

A residue, including but not limited to, those involved in relaxin receptor binding is substituted with the following non-naturally encoded amino acid as described above. Once modified, the relaxin polypeptide variant comprising the carbonyl-containing amino acid will be reacted with an aminooxy-containing PEG derivative of the form:

R-PEG(N)—O—(CH2)n-O-NH2 where R is methyl, n is 4 and N is 5,000; 10,000; 20,000; 30,000; or 40,000 MW to generate a relaxin polypeptide antagonist comprising a non-naturally encoded amino acid that is modified with a PEG derivative at a single site within the polypeptide. Coupling, purification, and analyses are performed as described above.

Example 21

Generation of a relaxin polypeptide homodimer, heterodimer, homomultimer, or heteromultimer in which the relaxin molecules are linked directly A relaxin polypeptide variant comprising the alkyne-containing amino acid can be directly coupled to another relaxin polypeptide variant comprising the azido-containing amino acid. In an analogous manner a relaxin polypeptide may be coupled to one or more other polypeptides to form heterodimers, homomultimers, or heteromultimers. More description regarding multimers which may be formed is provided above in Examples 16 and 17 and coupling, purification, and analyses are performed as described above.

Example 22

$$\text{PEG—OH} + \text{Br—}(CH_2)_n\text{—C}\equiv\text{CR}' \longrightarrow$$

A

-continued $$\text{PEG—O—}(CH_2)_n\text{—C}\equiv\text{CR}'$$

B

The polyalkylene glycol (P—OH) is reacted with the alkyl halide (A) to form the ether (B). In these compounds, n is an integer from one to nine and R' can be a straight- or branched-chain, saturated or unsaturated C1, to C20 alkyl or heteroalkyl group. R' can also be a C3 to C7 saturated or unsaturated cyclic alkyl or cyclic heteroalkyl, a substituted or unsubstituted aryl or heteroaryl group, or a substituted or unsubstituted alkaryl (the alkyl is a C1 to C20 saturated or unsaturated alkyl) or heteroalkaryl group. Typically, PEG-OH is polyethylene glycol (PEG) or monomethoxy polyethylene glycol (mPEG) having a molecular weight of 800 to 40,000 Daltons (Da).

Example 23

$$\text{mPEG-OH+Br—}CH_2\text{—C}\equiv\text{CH}\rightarrow\text{mPEGO—}CH_2\text{—C}\equiv\text{CH}$$

mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). A solution of propargyl bromide, dissolved as an 80% weight solution in xylene (0.56 mL, 5 mmol, 50 equiv., Aldrich), and a catalytic amount of KI were then added to the solution and the resulting mixture was heated to reflux for 2 hours. Water (1 mL) was then added and the solvent was removed under vacuum. To the residue was added CH2Cl2 (25 mL) and the organic layer was separated, dried over anhydrous Na2SO4, and the volume was reduced to approximately 2 mL. This CH2Cl2 solution was added to diethyl ether (150 mL) drop-wise. The resulting precipitate was collected, washed with several portions of cold diethyl ether, and dried to afford propargyl-O-PEG.

Example 24

$$\text{mPEG-OH+Br—}(CH_2)_3\text{—C}\equiv\text{CH}\rightarrow\text{mPEG-O—}(CH_2)_3\text{—C}\equiv\text{CH}$$

The mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). Fifty equivalents of 5-bromo-1-pentyne (0.53 mL, 5 mmol, Aldrich) and a catalytic amount of KI were then added to the mixture. The resulting mixture was heated to reflux for 16 hours. Water (1 mL) was then added and the solvent was removed under vacuum. To the residue was added CH2Cl2 (25 mL) and the organic layer was separated, dried over anhydrous Na2SO4, and the volume was reduced to approximately 2 mL. This CH2Cl2 solution was added to diethyl ether (150 mL) drop-wise. The resulting precipitate was collected, washed with several portions of cold diethyl ether, and dried to afford the corresponding alkyne. 5-chloro-1-pentyne may be used in a similar reaction.

Example 25

$$m\text{-HOCH}_2C_6H_4\text{OH+NaOH+Br—}CH_2\text{—C}\equiv\text{CH}\rightarrow m\text{-HOCH}_2C_6H_4\text{O—}CH_2\text{—C}\equiv\text{CH} \quad (1)$$

$$m\text{-HOCH}_2C_6H_4\text{O—}CH_2\text{—C}\equiv\text{CH+MsCl+N(Et)}_3\rightarrow m\text{-MsOCH}_2C_6H_4\text{O—}CH_2\text{—C}\equiv\text{CH} \quad (2)$$

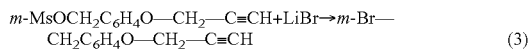

(3)

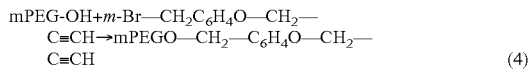

(4)

To a solution of 3-hydroxybenzylalcohol (2.4 g, 20 mmol) in THF (50 mL) and water (2.5 mL) was first added powdered sodium hydroxide (1.5 g, 37.5 mmol) and then a solution of propargyl bromide, dissolved as an 80% weight solution in xylene (3.36 mL, 30 mmol). The reaction mixture was heated at reflux for 6 hours. To the mixture was added 10% citric acid (2.5 mL) and the solvent was removed under vacuum. The residue was extracted with ethyl acetate (3×15 mL) and the combined organic layers were washed with saturated NaCl solution (10 mL), dried over MgSO4 and concentrated to give the 3-propargyloxybenzyl alcohol.

Methanesulfonyl chloride (2.5 g, 15.7 mmol) and triethylamine (2.8 mL, 20 mmol) were added to a solution of compound 3 (2.0 g, 11.0 mmol) in CH2Cl2 at 0° C. and the reaction was placed in the refrigerator for 16 hours. A usual work-up afforded the mesylate as a pale yellow oil. This oil (2.4 g, 9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous Na2SO4, and concentrated to give the desired bromide.

mPEG-OH 20 kDa (1.0 g, 0.05 mmol, Sunbio) was dissolved in THF (20 mL) and the solution was cooled in an ice bath. NaH (6 mg, 0.25 mmol) was added with vigorous stirring over a period of several minutes followed by addition of the bromide obtained from above (2.55 g, 11.4 mmol) and a catalytic amount of KI. The cooling bath was removed and the resulting mixture was heated to reflux for 12 hours. Water (1.0 mL) was added to the mixture and the solvent was removed under vacuum. To the residue was added CH2Cl2 (25 mL) and the organic layer was separated, dried over anhydrous Na2SO4, and the volume was reduced to approximately 2 mL. Dropwise addition to an ether solution (150 mL) resulted in a white precipitate, which was collected to yield the PEG derivative.

Example 26

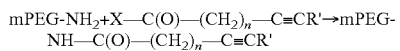

The terminal alkyne-containing poly(ethylene glycol) polymers can also be obtained by coupling a poly(ethylene glycol) polymer containing a terminal functional group to a reactive molecule containing the alkyne functionality as shown above. n is between 1 and 10. R' can be H or a small alkyl group from C1 to C4.

Example 27

HO₂C—(CH₂)₂—C≡CH+NHS+DCC→NHSO—C(O)—(CH₂)₂—C≡CH (1)

mPEG-NH₂+NHSO—C(O)—(CH₂)₂—C≡CH→mPEG-NH—C(O)—(CH₂)₂—C≡CH (2)

4-pentynoic acid (2.943 g, 3.0 mmol) was dissolved in CH2Cl2 (25 mL). N-hydroxysuccinimide (3.80 g, 3.3 mmol) and DCC (4.66 g, 3.0 mmol) were added and the solution was stirred overnight at room temperature. The resulting crude NHS ester 7 was used in the following reaction without further purification.

mPEG-NH2 with a molecular weight of 5,000 Da (mPEG-NH2, 1 g, Sunbio) was dissolved in THF (50 mL) and the mixture was cooled to 4° C. NHS ester 7 (400 mg, 0.4 mmol) was added portion-wise with vigorous stirring. The mixture was allowed to stir for 3 hours while warming to room temperature. Water (2 mL) was then added and the solvent was removed under vacuum. To the residue was added CH2Cl2 (50 mL) and the organic layer was separated, dried over anhydrous Na2SO4, and the volume was reduced to approximately 2 mL. This CH2Cl2 solution was added to ether (150 mL) drop-wise. The resulting precipitate was collected and dried in vacuo.

Example 28

This Example represents the preparation of the methane sulfonyl ester of poly(ethylene glycol), which can also be referred to as the methanesulfonate or mesylate of poly (ethylene glycol). The corresponding tosylate and the halides can be prepared by similar procedures.

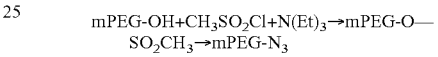

The mPEG-OH (MW=3,400, 25 g, 10 mmol) in 150 mL of toluene was azeotropically distilled for 2 hours under nitrogen and the solution was cooled to room temperature. 40 mL of dry CH2Cl2 and 2.1 mL of dry triethylamine (15 mmol) were added to the solution. The solution was cooled in an ice bath and 1.2 mL of distilled methanesulfonyl chloride (15 mmol) was added dropwise. The solution was stirred at room temperature under nitrogen overnight, and the reaction was quenched by adding 2 mL of absolute ethanol. The mixture was evaporated under vacuum to remove solvents, primarily those other than toluene, filtered, concentrated again under vacuum, and then precipitated into 100 mL of diethyl ether. The filtrate was washed with several portions of cold diethyl ether and dried in vacuo to afford the mesylate.

The mesylate (20 g, 8 mmol) was dissolved in 75 ml of THF and the solution was cooled to 4° C. To the cooled solution was added sodium azide (1.56 g, 24 mmol). The reaction was heated to reflux under nitrogen for 2 hours. The solvents were then evaporated and the residue diluted with CH2Cl2 (50 mL). The organic fraction was washed with NaCl solution and dried over anhydrous MgSO4. The volume was reduced to 20 ml and the product was precipitated by addition to 150 ml of cold dry ether.

Example 29

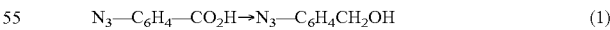 (1)

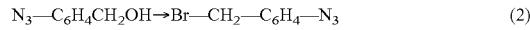 (2)

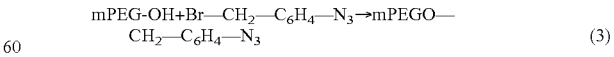 (3)

4-azidobenzyl alcohol can be produced using the method described in U.S. Pat. No. 5,998,595, which is incorporated by reference herein. Methanesulfonyl chloride (2.5 g, 15.7 mmol) and triethylamine (2.8 mL, 20 mmol) were added to a solution of 4-azidobenzyl alcohol (1.75 g, 11.0 mmol) in CH2Cl2 at 0° C. and the reaction was placed in the refrigerator for 16 hours. A usual work-up afforded the mesylate as a pale yellow oil. This oil (9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous Na2SO4, and concentrated to give the desired bromide.

mPEG-OH 20 kDa (2.0 g, 0.1 mmol, Sunbio) was treated with NaH (12 mg, 0.5 mmol) in THE (35 mL) and the bromide (3.32 g, 15 mmol) was added to the mixture along with a catalytic amount of KI. The resulting mixture was heated to reflux for 12 hours. Water (1.0 mL) was added to the mixture and the solvent was removed under vacuum. To the residue was added CH2Cl2 (25 mL) and the organic layer was separated, dried over anhydrous Na2SO4, and the volume was reduced to approximately 2 mL. Dropwise addition to an ether solution (150 mL) resulted in a precipitate, which was collected to yield mPEG-O—CH2-C6H4-N3.

Example 30

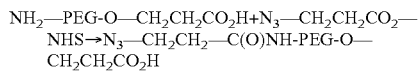

NH2-PEG-O—CH2CH2CO2H (MW 3,400 Da, 2.0 g) was dissolved in a saturated aqueous solution of NaHCO3 (10 mL) and the solution was cooled to 0° C. 3-azido-1-N-hydroxysuccinimido propionate (5 equiv.) was added with vigorous stirring. After 3 hours, 20 mL of H2O was added and the mixture was stirred for an additional 45 minutes at room temperature. The pH was adjusted to 3 with 0.5 N H2SO4 and NaCl was added to a concentration of approximately 15 wt %. The reaction mixture was extracted with CH2Cl2 (100 mL×3), dried over Na2SO4 and concentrated. After precipitation with cold diethyl ether, the product was collected by filtration and dried under vacuum to yield the omega-carboxy-azide PEG derivative.

Example 31

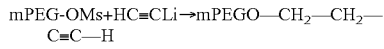

To a solution of lithium acetylide (4 equiv.), prepared as known in the art and cooled to −78° C. in THF, is added dropwise a solution of mPEG-OMs dissolved in THE with vigorous stirring. After 3 hours, the reaction is permitted to warm to room temperature and quenched with the addition of 1 mL of butanol. 20 mL of H2O is then added and the mixture was stirred for an additional 45 minutes at room temperature. The pH was adjusted to 3 with 0.5 N H2SO4 and NaCl was added to a concentration of approximately 15 wt %. The reaction mixture was extracted with CH2Cl2 (100 mL×3), dried over Na2SO4 and concentrated. After precipitation with cold diethyl ether, the product was collected by filtration and dried under vacuum to yield the 1-(but-3-ynyloxy)-methoxypolyethylene glycol (mPEG).

Example 32

Azide- and acetylene-containing amino acids can be incorporated site-selectively into proteins using the methods described in L. Wang, et al., (2001), Science 292:498-500, J. W. Chin et al., Science 301:964-7 (2003)), J. W. Chin et al., (2002), Journal of the American Chemical Society 124: 9026-9027; J. W. Chin, & P. G. Schultz, (2002), Chem Bio Chem 3(11):1135-1137; J. W. Chin, et al., (2002), PNAS United States of America 99:11020-11024: and, L. Wang, & P. G. Schultz, (2002), Chem. Comm., 1:1-11. Once the amino acids were incorporated, the cycloaddition reaction is carried out with 0.01 mM protein in phosphate buffer (PB), pH 8, in the presence of 2 mM PEG derivative, 1 mM CuSO4, and ~1 mg Cu-wire for 4 hours at 37° C.

Example 33

This example describes the synthesis of p-Acetyl-D,L-phenylalanine (pAF) and m-PEG-hydroxylamine derivatives.

The racemic pAF is synthesized using the previously described procedure in Zhang, Z., Smith, B. A. C., Wang, L., Brock, A., Cho, C. & Schultz, P. G., Biochemistry, (2003) 42, 6735-6746.

To synthesize the m-PEG-hydroxylamine derivative, the following procedures are completed. To a solution of (N-t-Boc-aminooxy)acetic acid (0.382 g, 2.0 mmol) and 1,3-Diisopropylcarbodiimide (0.16 mL, 1.0 mmol) in dichloromethane (DCM, 70 mL), which is stirred at room temperature (RT) for 1 hour, methoxy-polyethylene glycol amine (m-PEG-NH2, 7.5 g, 0.25 mmol, Mt. 30 K, from BioVectra) and Diisopropylethylamine (0.1 mL, 0.5 mmol) is added. The reaction is stirred at RT for 48 hours, and then is concentrated to about 100 mL. The mixture is added dropwise to cold ether (800 mL). The t-Boc-protected product precipitated out and is collected by filtering, washed by ether 3×100 mL. It is further purified by re-dissolving in DCM (100 mL) and precipitating in ether (800 mL) twice. The product is dried in vacuum yielding 7.2 g (96%), confirmed by NMR and Nihydrin test.

The deBoc of the protected product (7.0 g) obtained above is carried out in 50% TFA/DCM (40 mL) at 0° C. for 1 hour and then at RT for 1.5 hour. After removing most of TFA in vacuum, the TFA salt of the hydroxylamine derivative is converted to the HCl salt by adding 4N HCl in dioxane (1 mL) to the residue. The precipitate is dissolved in DCM (50 mL) and re-precipitated in ether (800 mL). The final product (6.8 g, 97%) is collected by filtering, washed with ether 3×100 mL, dried in vacuum, stored under nitrogen. Other PEG (5K, 20K) hydroxylamine derivatives are synthesized using the same procedure.

Example 34

In Vivo Studies of PEGylated Relaxin

PEG-Relaxin, unmodified relaxin and buffer solution are administered to mice or rats. The results will show superior activity and prolonged half life of the PEGylated relaxin of the present invention compared to unmodified relaxin. Similarly, modified relaxin, unmodified relaxin, and buffer solution are administered to mice or rats.

Pharmacokinetic Analysis

A relaxin polypeptide of the invention is administered by intravenous or subcutaneous routes to mice. The animals are bled prior to and at time points after dosing. Plasma is collected from each sample and analyzed by radioimmunoassay. Elimination half-life can be calculated and compared between relaxin polypeptides comprising a non-naturally encoded amino acid and wild-type relaxin or various relaxin analog polypeptides of the invention. Similarly, relaxin polypeptides of the invention may be administered to cynomolgus monkeys. The animals are bled prior to and at time points after dosing. Plasma is collected from each sample and analyzed by radioimmunoassay.

The polypeptide may be administered the mice via multiple doses, continuous infusion, or a single dose, etc.

Example 35

Relaxin is expressed using Novagen expression system (inducible T7 promoter; described in detail in the pET System Manual, version 9, hereby incorporated by reference), expression vector pET30a and expression strain BL21 (DE3).

2 mL of LB/Kanamycin (10 μg/ml) culture are inoculated with a sweep from BL21 (DE3) plate transformed with the desired analog. This decreases effects caused by colony to colony variability in expression levels. This culture is grown overnight at 37° C. with vigorous shaking and the following day, 10 ml LB/Kanamycin culture is inoculated with 1 ml from the overnight culture (OD600 0.4-0.5). The remaining mL of the overnight culture may be frozen as glycerol stock.

10 mL of the grown culture is put at 37° C. and 250 rpm for 30-45 min until OD600 reaches 0.8-0.9. This is then induced with 1 mM IPTG (with 1 mL that may be set aside as non-induced culture control) and harvested usually 3-4 hours post-induction and analyzed on SDS-PAGE.

It is also possible to do a time-course of expression (e.g. points 1, 2, 4, 6 hours post-induction and O/N) to determine the rate of accumulation, protein stability, etc.

Gel Analysis: at a desired time point post-induction 1 mL is harvested from the culture, the cells alre spun down, resuspended in 100 μl of 2×SDS-PAGE, sonicated to reduce viscosity and 10 μl are run on SDS-PAGE. If desired, this can be compared to non-induced control or controls and/or known positive control or standard and expression level may be estimated (e.g. good expression could be at >100 μg/ml). Western blot analysis may also be used. It is also possible to set aside 4 ml of the cultures, prepare inclusion bodies (if expressing insoluble analogs) and obtain mass spec analysis on these to confirm the identity of the over-expressed protein.

For larger scale protein expression, >250 mL of LB/Kanamycin (10 μg/ml) are inoculated with 250 μL of frozen glycerol stock and grown overnight. The following day, 10×1 L LB/Kanamycin cultures are inoculated with 25 mL from the overnight culture (OD600 0.1).

1 L cultures are grown at 37° C. and 250 rpm 2 h until OD600 reaches 0.8-0.9. This is then induced with 1 mM IPTG and harvested 4 h post-induction or the following morning (harvest may use centrifugation for 15 min at 4,000 rpm). The pellets are rinsed with 50 mM Tris-HCl, pH 8.0 (50 ml per pellet+50 ml to rinse the bottle) if it is desired to reduce endotoxin and facilitate purification. Pellets are pooled together and spun again.

Example 36

*Pichia* Expression Study—DNA Prep, Electroporation, Expression Protocols

This example provides a protocol for the preparation of relaxin polypeptides of the present invention in *Pichia*. SEQ ID NOs: 34, 35, 36, and 37 are used, and a plasmid can be used for cloning into *Pichia* and this or other modified plasmids may be used to obtain protein expression of relaxin polypeptides in *Pichia*, modifications made to the plasmid using methods known in the art.

On day 1 of the protocol, there is an overnight digestion, typically using 2 U enzyme per μg DNA to be digested and 10 mL YPhyD culture is inoculated overnight in a 50 mL flask, shaking at 260 rpm at 30° C. from the glycerol stock.

DNA Preparation

DNA is precipitated by the addition first of $\frac{1}{10}^{th}$ volume sterile 3M NaOAc and then of 0.7 volumes sterile IPA and then the sample is vigorously mixed and the precipitation is continued overnight at −20° C. or at −70° C. until frozen. The DNA is then pelleted by centrifugation (benchtop centrifuge 14,000 rpm/10 minutes), supernatant removed, and the pellet is washed using 500 μL of sterile 70% ETOH. Spin (bench-top centrifuge 14,000 rpm/10 minutes) and decant supernatant and air dry pellet for 15-20 minutes. Resuspend DNA pellet with sterile water to 1 g/l and transform *Pichia* with 10 μg DNA.

Electroporation

Using overnight culture with $OD_{600}$, dilute in YPhyD to $OD_{600}=0.2$. Shake culture at 260 rpm at 30° C. until $OD_{600}$ reaches 0.8-1.0. Collect cells by centrifugation (4000 rpm/5 minutes). Decant medium, wash cells in 20 mL ice cold sterile water, decant again and repeat. After water wash, wash pellet in 20 mL of ice-cold sterile 1 M sorbitol, decant, and resuspend washed cell pellet in 600 μL of 1 M cold sorbitol, then this may be stored on ice.

From the washed cells, mix 50 μL with 10 μg linearized DNA in sterile 1.5 mL eppendorf tube, mix gently and incubate on ice for 25 minutes. Transfer cell/DNA mixture to prechilled 0.2 cm cuvette using long pipette tips. Electroporate cells using BioRad GenePulsar II unit with the following settings: 2000 V, 200 Ohms, 25 μFd (use single pulse) and immediately add 0.5 mL YPhyD medium to the cuvette and mix by pipetting. Transfer entire contents to sterile round bottom tube and shake gently (200 rpm) for 30 minutes at 30° C. Plate and spread cells evenly and incubate plates, inverted, for 3 days at 30° C.

After three day incubation, pick colonies with a loop and inoculate 10 ml BYPhyD media in a 50 ml flask and incubate for 3 days at 30° C. Count the colonies on the 20 μl plates and record the average number and then harvest cells, first by preparing 2 sets of cryovials labeled with strain name and clone number, relaxin (i.e. protein expressed), and date. Transfer culture to 15 ml conical tube, take $OD_{600}$ of each culture, dilute culture 1:50 or 1:20 in YPhyD medium. Save an alquot of culture for glycerol stock. Then pellet yeast at 4000 rpm for 5 min at RT, transfer the supernatant to a new, labeled 15 mL conical tube, and store at −20 or −80° C. until needed for analytical data.

Protein Expression Analysis

Run samples on 4-12% NuPAGE TB gel (Novex). SDS-PAGE reagents used from Invitrogen, analyze by Western blot or Stained-gel analysis Media Formulations

| Buffered Yeast Phytone Dextrose (BYPhyD) | |
| --- | --- |
| Yeast Extract | 10 g/L |
| Phytone Peptone | 20 g/L |
| 1 M potassium phosphate buffer (pH 6) | 100 ml/L |
| 10X YNB | 100 mL/L |
| 20% Dextrose | 100 mL/L |

-continued

Yeast Phytone Dextrose (YPhyD)

| Yeast Extract | 10 g/L |
|---|---|
| Phytone Peptone | 20 g/L |
| 20% Dextrose | 100 ml/L |

10X YNB (13.4% Yeast Nitrogen Base with Ammonium Sulfate without amino acids)

| Yeast Nitrogen Base | 134 g/L |
|---|---|

Example 37

Relaxin A21G Production

In this example, 4.0 L culture were fermented to produce 13.4 g wet cell paste and an inclusion body preparation was performed with and without Triton-X100. 2.07 g wet inclusion bodies were produced in this manner, and solubilization and refolding followed. The inclusion bodies were resuspended with 200 mL $H_2O$ per gram of wet inclusion bodies (IBs) to a final concentration of 3 mM and cysteine is added to the resuspension. IB's are then solubilized by pH increase to 11.5 for 1 hour at RT. Refolding was then allowed to occur by dropping the pH of the solubilized material to 10.6±0.1 and stored at 2-8° C. for ~72 hours. The refold reaction was stopped by addition of HCl to a final pH of 3.0, 0.45 µM filtered and stored at 2-8° C. until further processing.

The refolded protein was purified by increasing the pH of quenched refold to 8.0 with Tris base and directly loading onto a Q HP column. Conductivity of load in the instance shown was >3.5 mS/cm. Run conditions were (A) 20 mM Tris, 8.0; (B) 20 mM Tris, 8.0; 200 mM NaCl and there was 0-100% B over 30 CV. The correctly refolded proinsulin was pooled and 79 mg proinsulin was recovered.

Ultrafiltration/diafiltration (UF/DF) was done and precipitation was performed with 25 mM zinc, precipitated protein was resuspended to concentration of 2 mg/mL with 20 mM NaOAc, 4.0, 30% ACN, 5 mM EDTA and 20K PEG was added to a final molar ratio of 10:1 PEG to protein and allowed to incubate for 48-72 hours at 28° C.

Figure 12A:
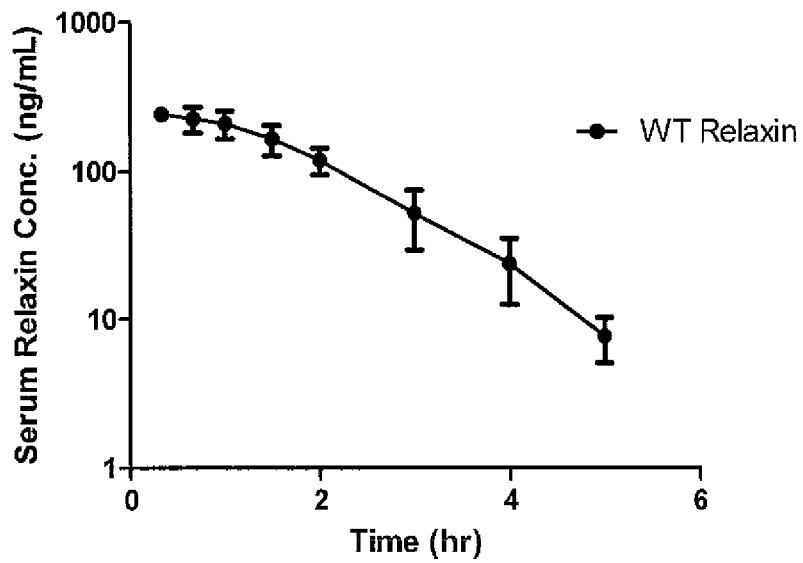
FIG. 12A shows a graph of a comparison of group mean serum concentration versus time for wt rhRelaxin dosed subcutaneously. A single dose injection was administered to each animal. N=5 animals per group.
Figure 12B:
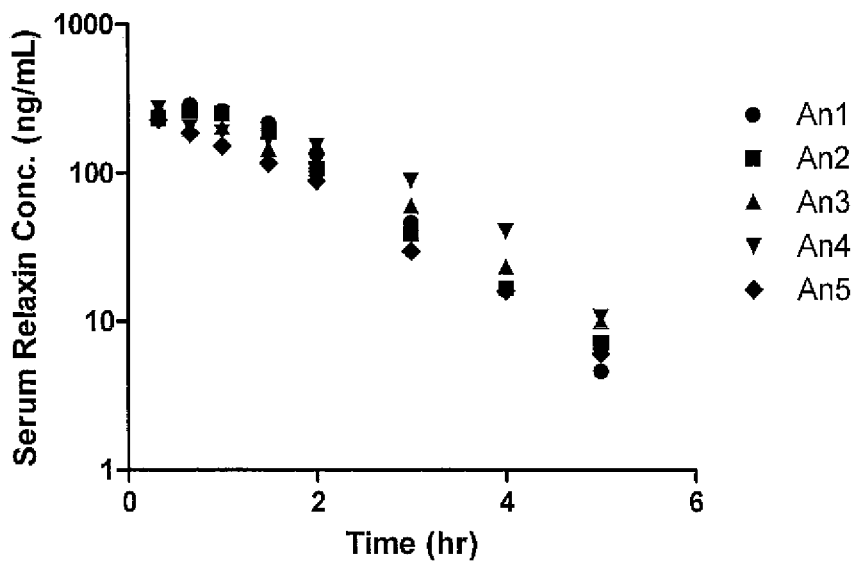
FIG. 12B shows a graph of individual animal serum concentration time curves for SD rats dosed intravenously with 0.5 mg/kg of wt rhRelaxin. A single, intravenous dose was administered to each animal. N=5 animals per group.
Figure 13A:
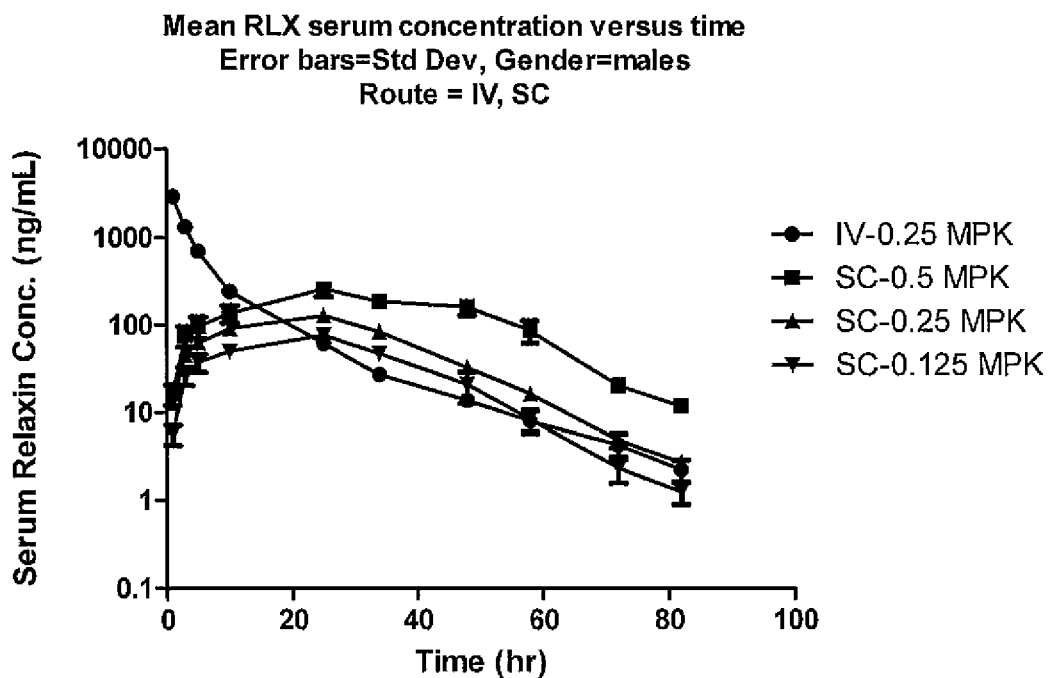
FIG. 13A shows a comparison of group mean serum concentration versus time for all PEG-RLX groups dosed subcutaneously or intravenously. A single dose injection was administered to each animal. N=3-5 animals per group.
Figure 13B:
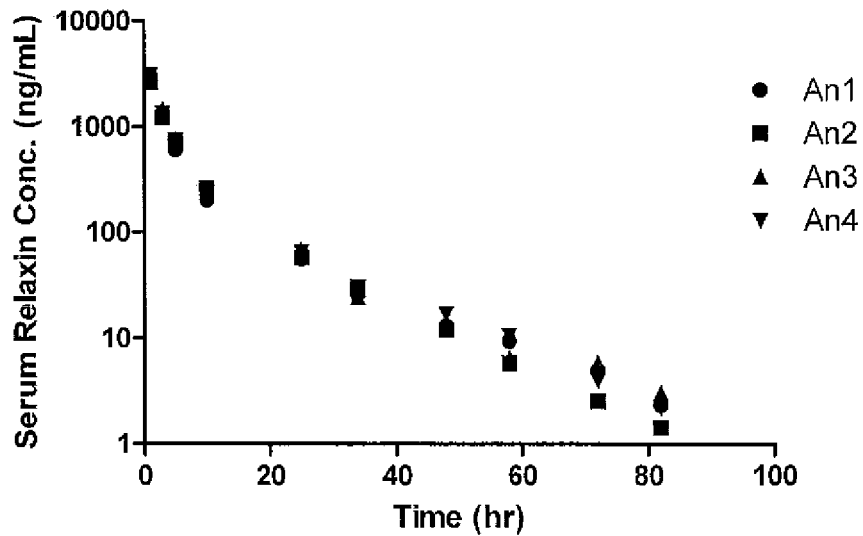
FIG. 13B shows a graph of individual animal serum concentration time curves for SD rats dosed intravenously with 0.25 mg/kg of 20KPEG-AQ1-RLX. A single, intravenous dose was administered to each animal. N=4 animals per group.
Figure 14A:
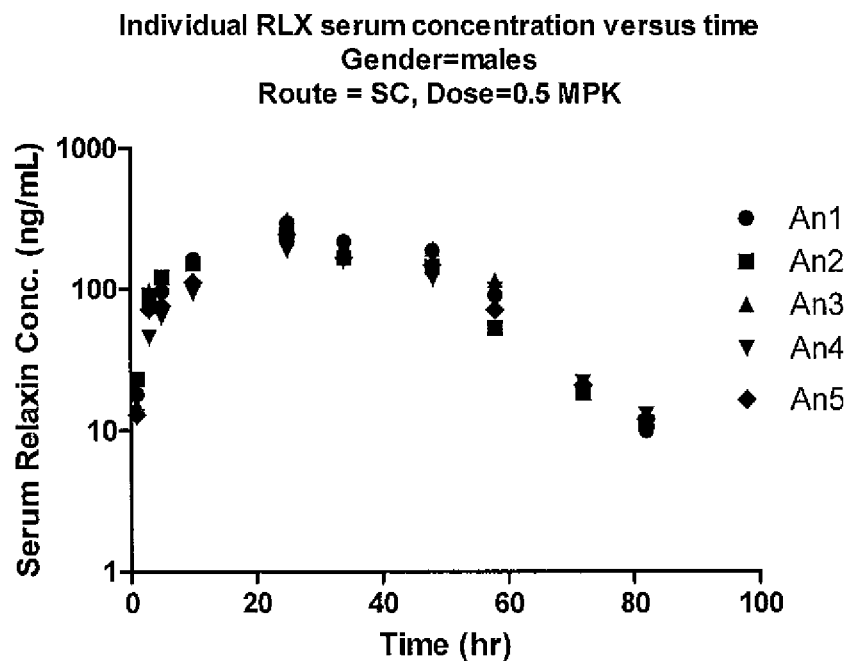
FIG. 14A shows a graph of individual animal serum concentration time curves for SD rats dosed subcutaneously with 0.5 mg/kg of PEG20-AQ1-RLX. A single, subcutaneous dose was administered to each animal. N=5 animals per group.
Figure 14B:
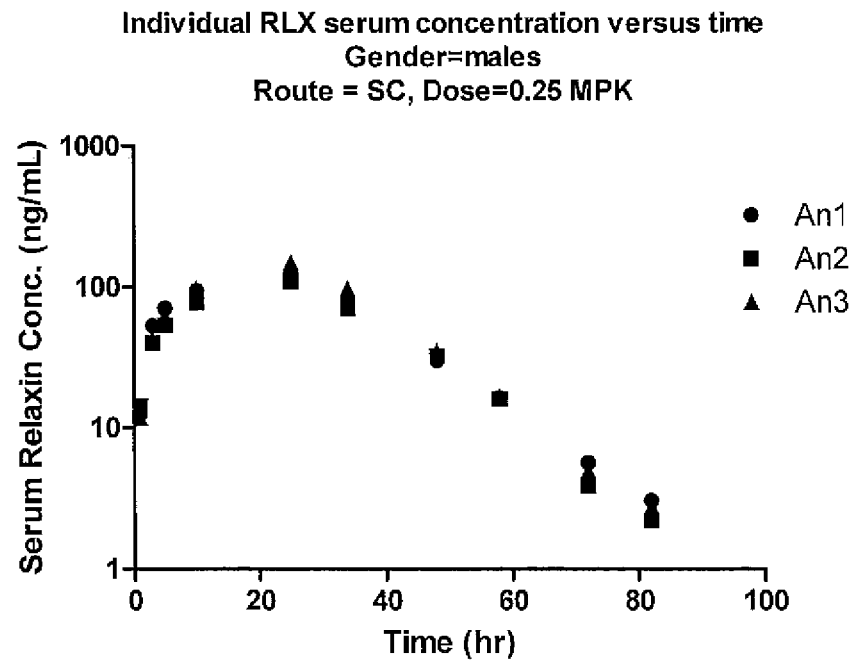
FIG. 14B shows a graph of individual animal serum concentration time curves for SD rats dosed subcutaneously with 0.25 mg/kg of PEG20-AQ1-RLX. A single, subcutaneous dose was administered to each animal. N=3 animals per group.
Figure 15:
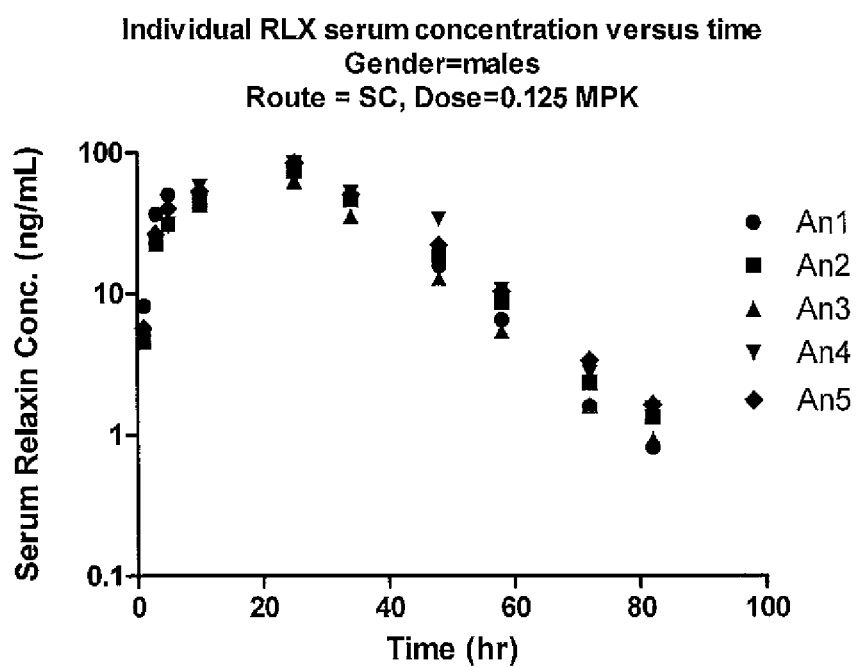
FIG. 15 shows a graph of individual animal serum concentration time curves for SD rats dosed intravenously with 0.125 mg/kg of PEG20-AQ1-RLX. A single, intravenous dose was administered to each animal. N=5 animals per group.
Figure 16A:
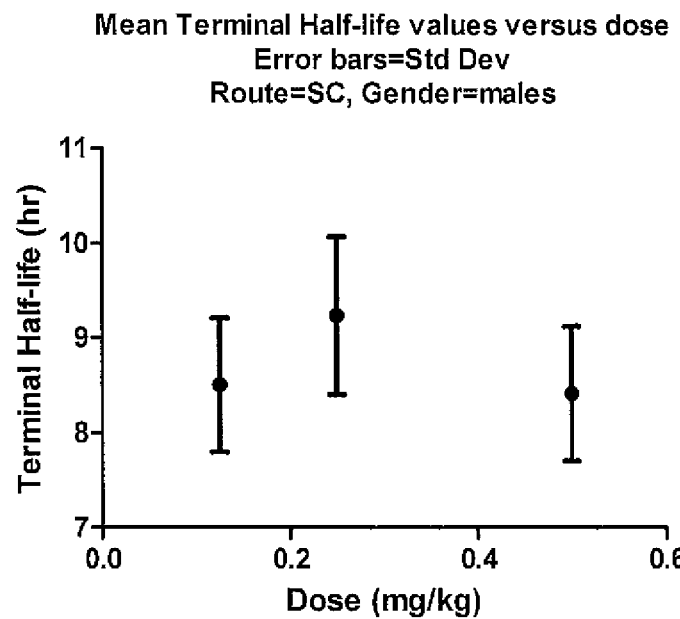
FIG. 16A shows a graph of the mean PEG-Relaxin Terminal Half-life versus dose; error bars=SD.
Figure 16B:
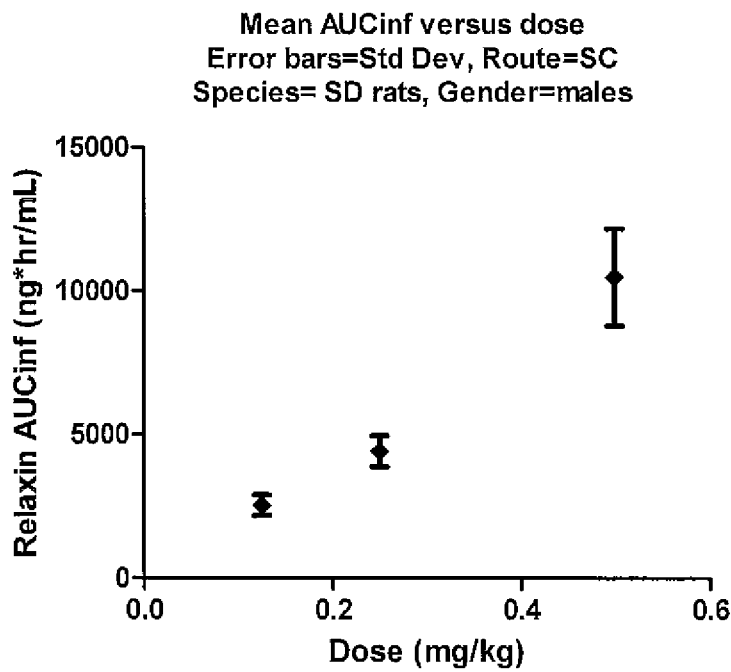
FIG. 16B shows a graph of mean PEG-Relaxin $AUC_{inf}$ versus dose; error bars=SD.
Figure 17A:
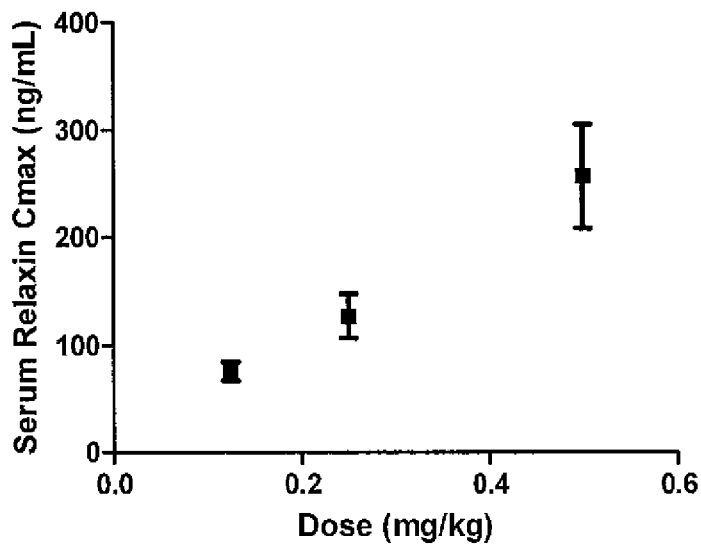
FIG. 17A shows a graph of the mean PEG-Relaxin Cmax versus dose; error bars=SD.
Figure 17B:
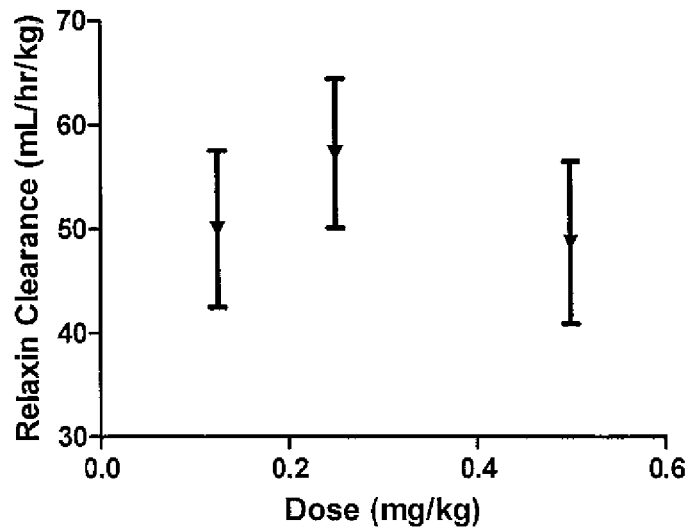
FIG. 17B shows a graph of the mean PEG-Relaxin Clearance versus dose; error bars=SD.
Figure 18A:
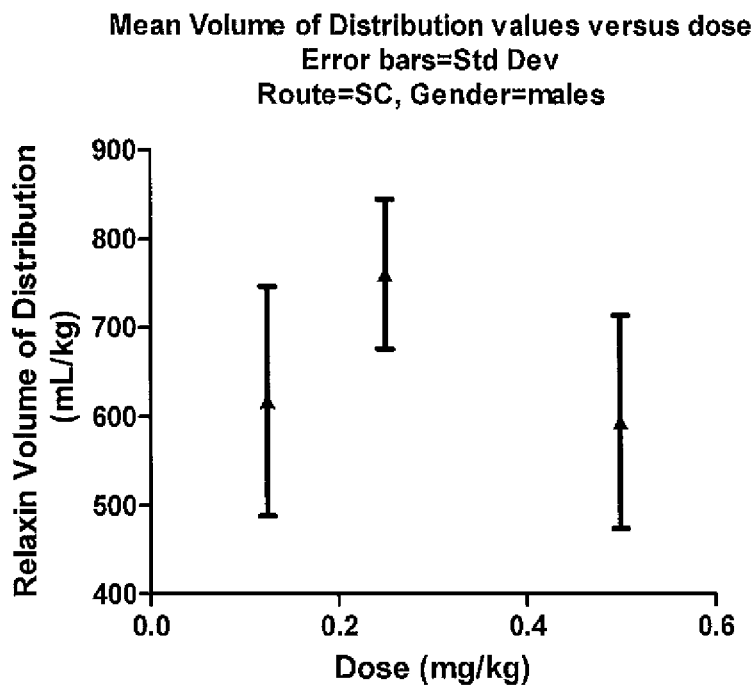
FIG. 18A shows a graph of the mean PEG-Relaxin Volume of distribution versus Dose; error bars=SD.
Figure 18B:
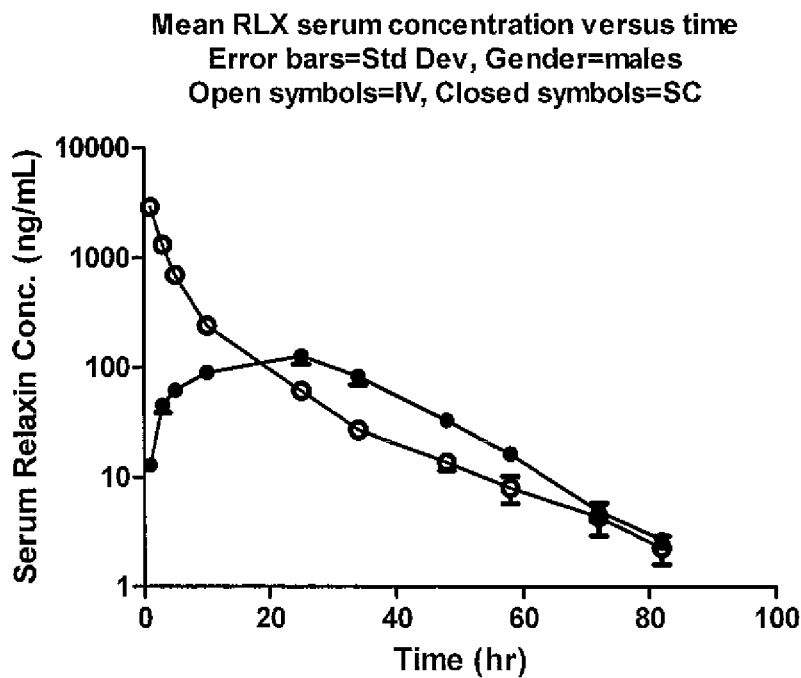
FIG. 18B shows a graph of a comparison of Serum-time concentration after a single intravenous or subcutaneous injection of 0.25 mg/kg of 20KPEG-AQ1 Relaxin.
Figure 19A:
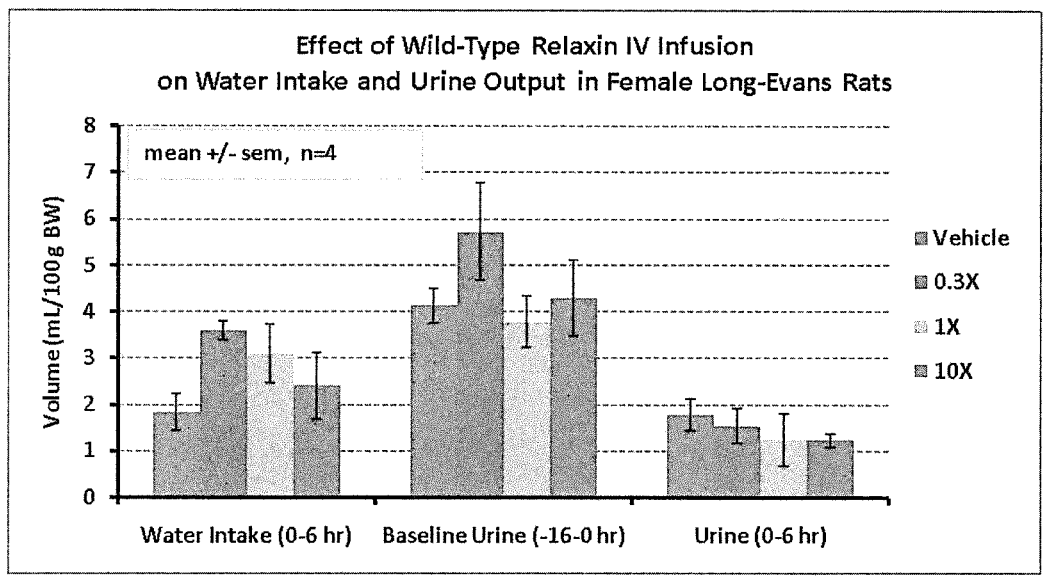
FIGS. 19A-F show data from Phase I of Example 43.
Figure 19B:
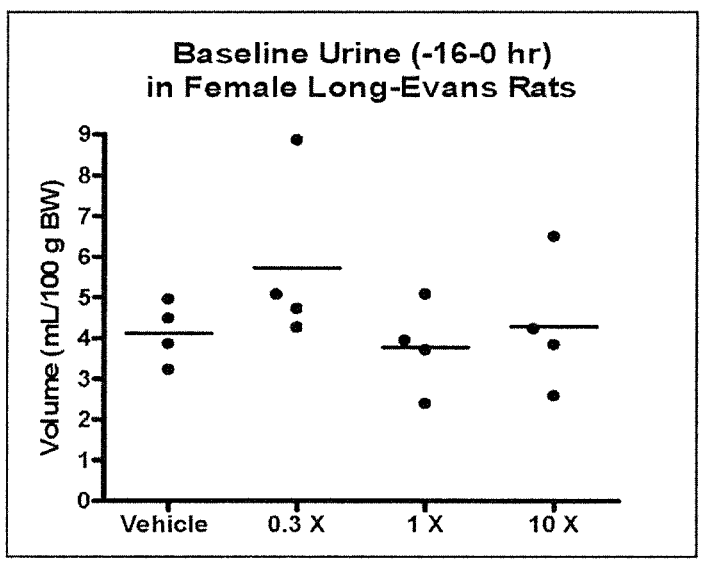
Figure 19C:
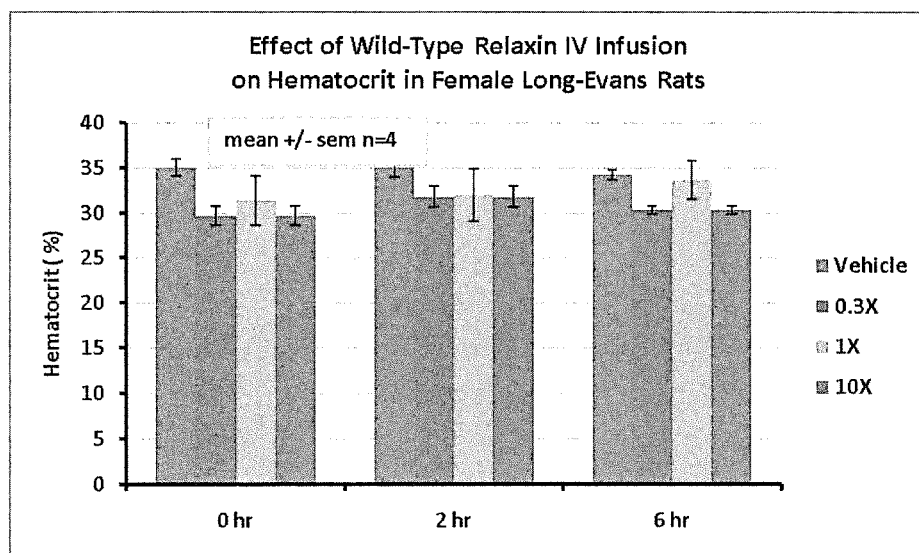
Figure 19D:
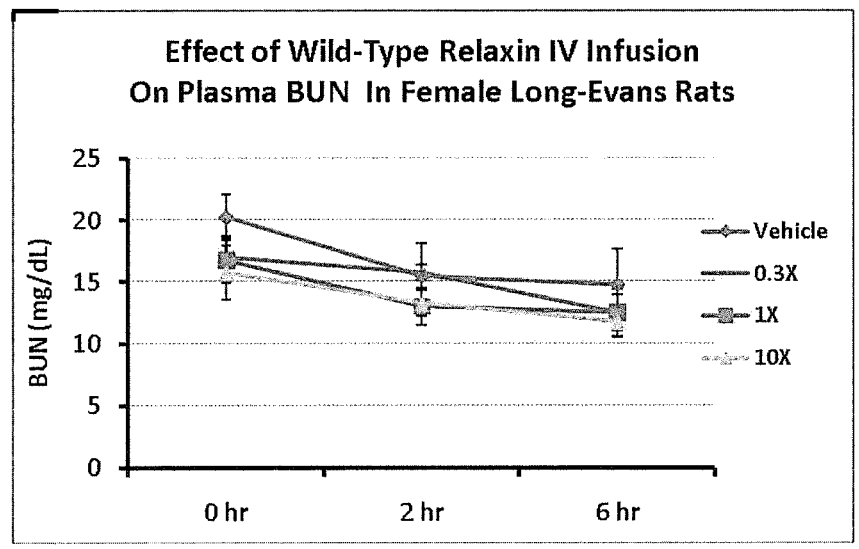
Figure 19E:
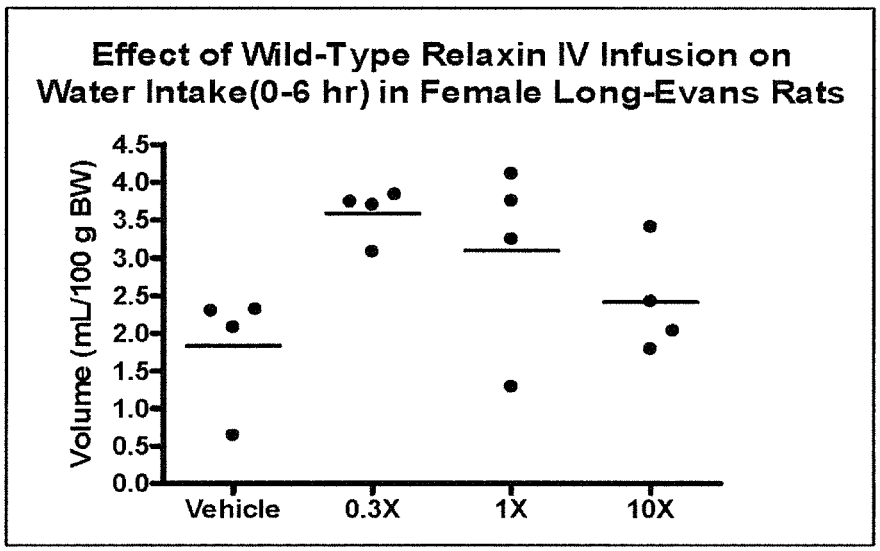
Figure 19F:
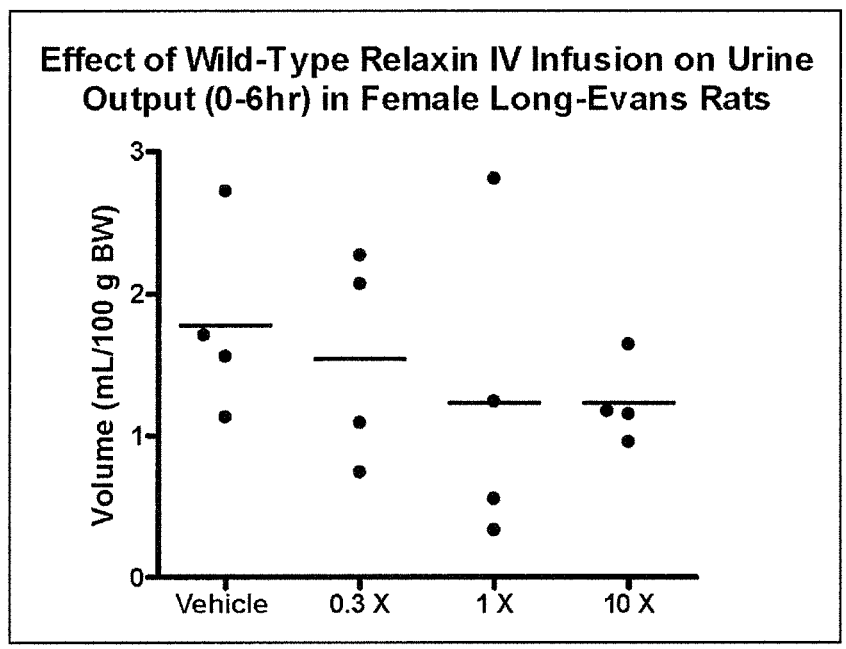
Figure 20A:
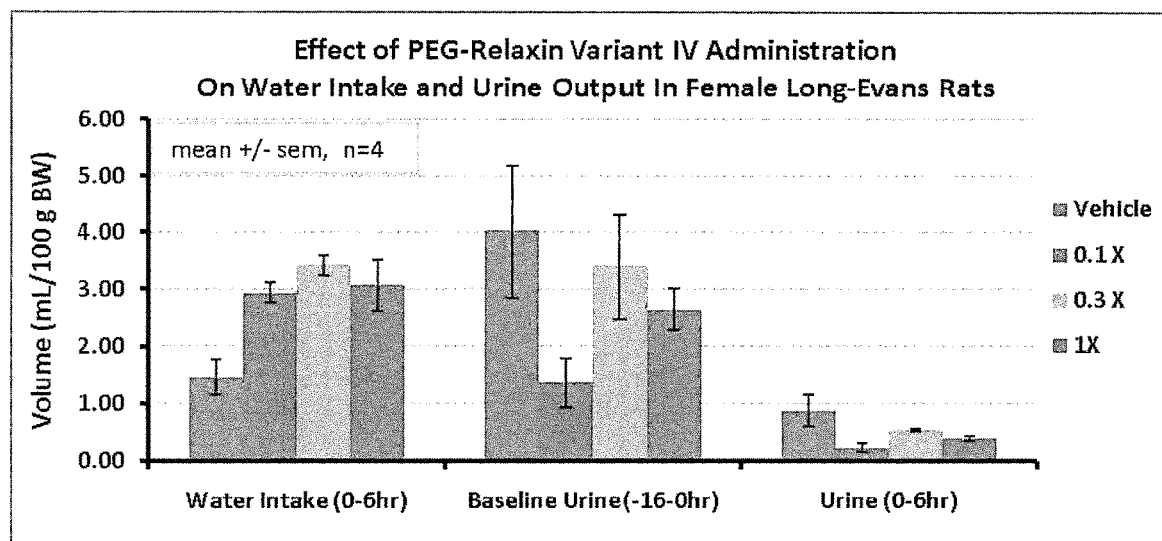
FIGS. 20A-I show data from Phase II following administration of vehicle (control group) and test groups with 0.1×, 0.3× and 1× administration of a 20K PEG-Relaxin variant with A chain substitution in position 1 with pAF bound to PEG from Example 43.
Figure 20B:
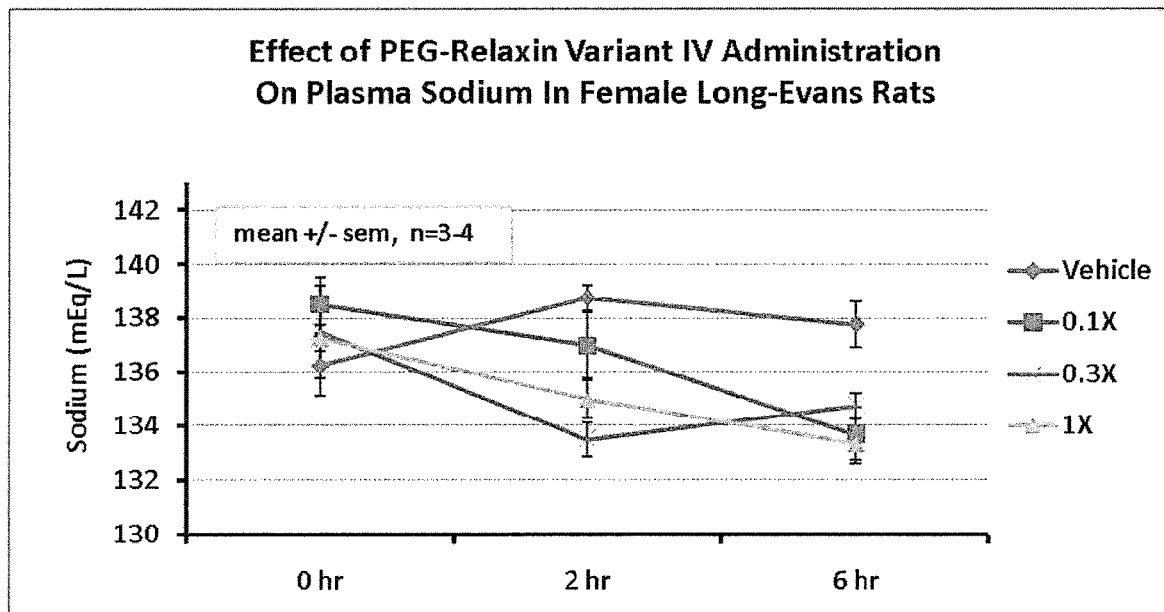
Figure 20C:
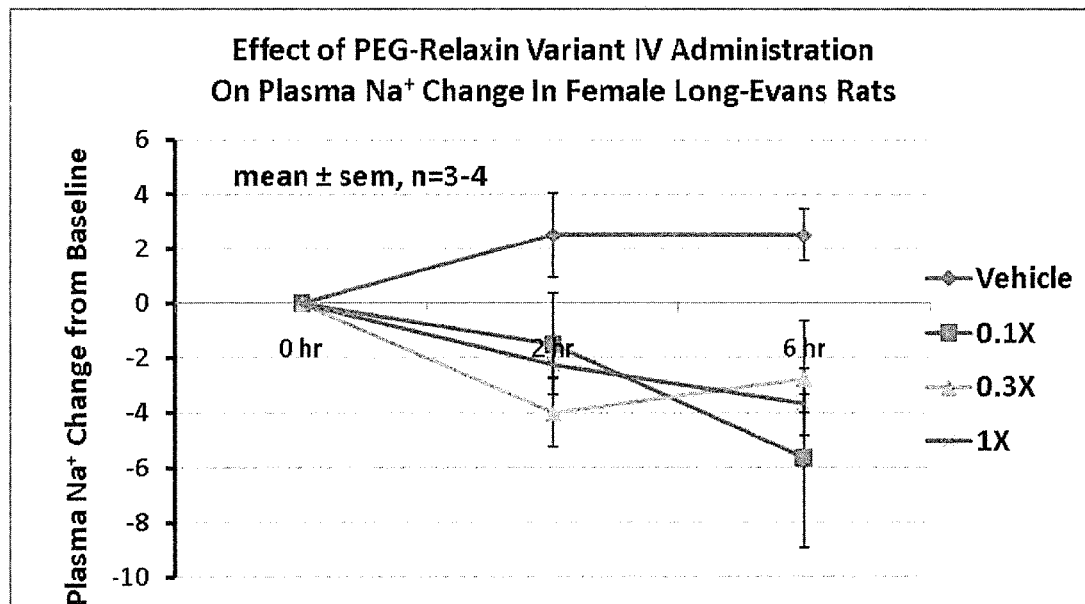
Figure 20D:
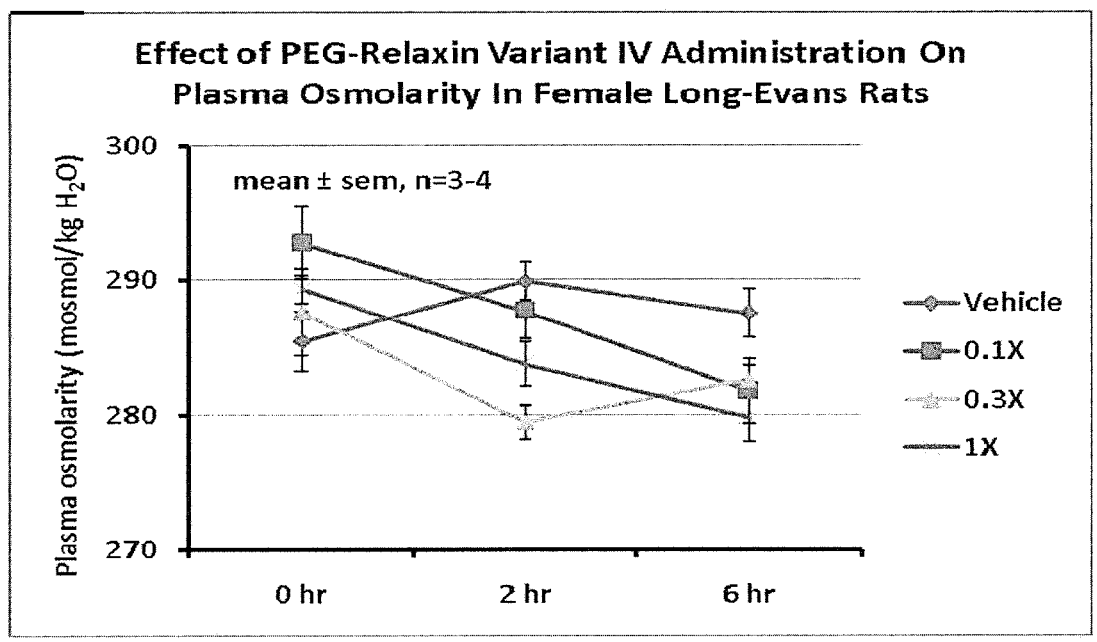
Figure 20E:
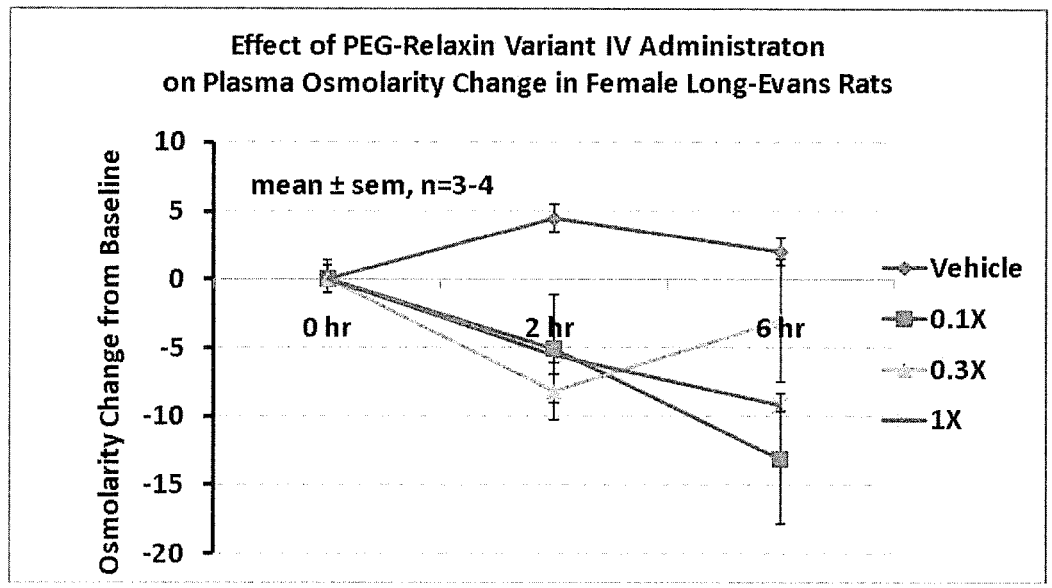
Figure 20F:
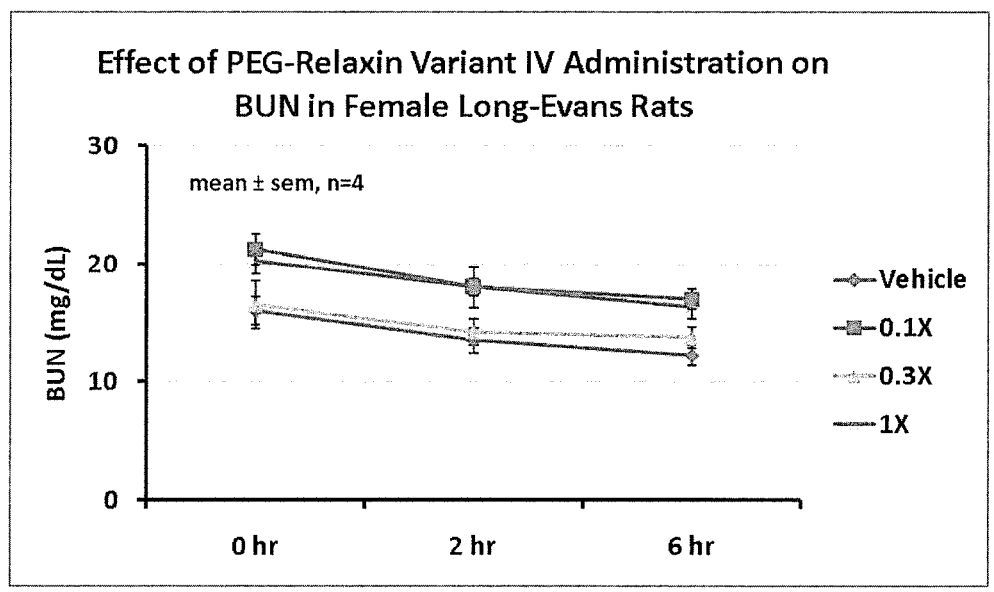
Figure 20G:
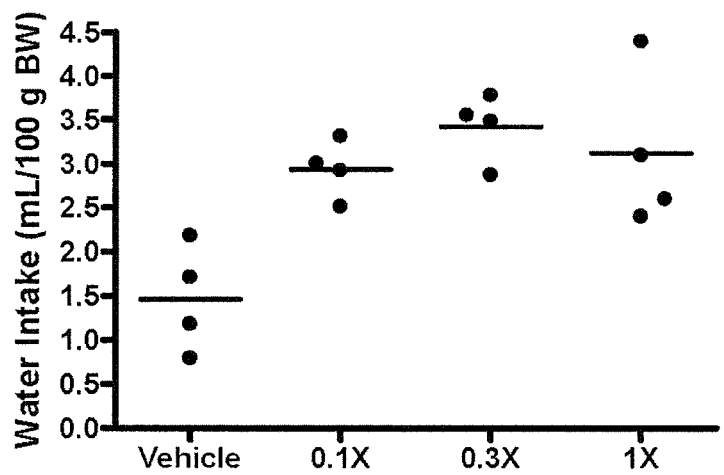
Figure 20H:
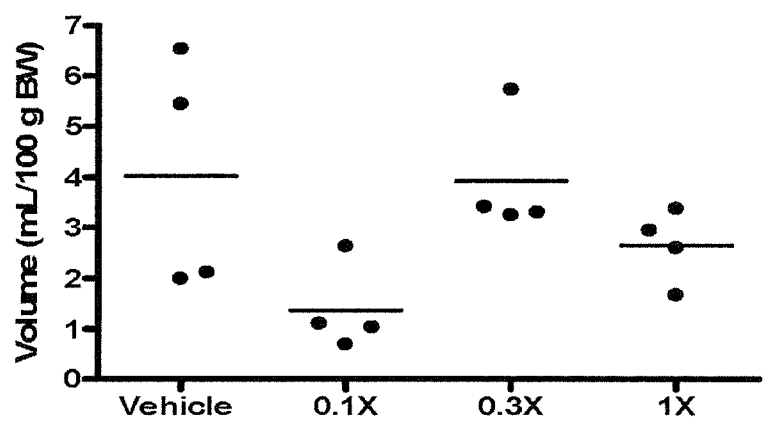
Figure 20I:
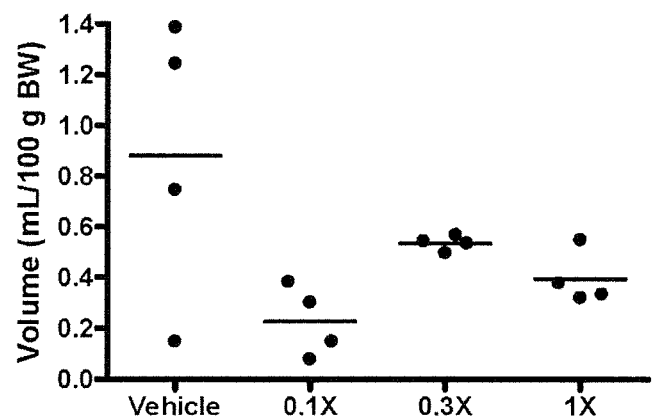

PEG reaction was diluted 1:10 in 0.5×PEG buffer A, 0.22 µM filtered and run over an SP 650S column. The run conditions were (A) 10 mM NaOAc, 4.0, 1 mM EDTA; (B) 10 mM NaOAc, 4.0, 1 mM EDTA, 0.4M NaCl; 0-50% B over 20 CV and PEG samples formulated in 10 mM NaCitrate, 6.5; 150 mM NaCl and this is shown in FIGS. 12A-B.

These methods were used to produce a variety of relaxin polypeptides with non-natural amino acids and a range of 0.1-22 mg for the end protein amounts of the purified and PEGylated variants. ACN was found to help solubilize PEG/protein mixture in PEG reaction and zinc precipitation at pI facilitated concentrating in the presence of CAN.

Example 38

Human Clinical Trial of the Safety and/or Efficacy of PEGylated Relaxin Comprising a Non-Naturally Encoded Amino Acid.

Objective: To observe the safety and pharmacokinetics of subcutaneously administered PEGylated recombinant human relaxin comprising a non-naturally encoded amino acid.

Patients Eighteen healthy volunteers ranging between 20-40 years of age and weighing between 60-90 kg are enrolled in the study. The subjects will have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to relaxin within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design: This will be a Phase I, single-center, open-label, randomized, two-period crossover study in healthy male volunteers. Eighteen subjects are randomly assigned to one of two treatment sequence groups (nine subjects/group). Relaxin is administered over two separate dosing periods as a bolus s.c. injection in the upper thigh using equivalent doses of the PEGylated relaxin comprising a non-naturally encoded amino acid and the commercially available product chosen. The dose and frequency of administration of the commercially available product is as instructed in the package label. Additional dosing, dosing frequency, or other parameter as desired, using the commercially available products may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the PEGylated relaxin as well. The experimental formulation of relaxin is the PEGylated relaxin comprising a non-naturally encoded amino acid.

Blood Sampling: Serial blood is drawn by direct vein puncture before and after administration of relaxin. Venous blood samples (5 mL) for determination of serum relaxin concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods: An ELISA kit is used for the determination of serum relaxin concentrations.

Safety Determinations: Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis Post-dose serum concentration values are corrected for pre-dose baseline relaxin concentrations by subtracting from each of the post-dose values the mean baseline relaxin concentration determined from averaging the relaxin levels from the three samples collected at 30, 20, and 10 minutes before dosing. Pre-dose serum relaxin concentrations are not included in the calculation of the mean value if they are below the quantification level of the assay. Pharmacokinetic parameters are determined from serum concentration data corrected for baseline relaxin concentrations. Pharmacokinetic parameters are calculated by model independent methods on a Digital Equipment Corporation VAX 8600 computer system using the latest version of the BIOAVL software. The following pharmacokinetics parameters are determined: peak serum concentration (Cmax); time to peak serum concentration (tmax); area under the concentration-time curve (AUC) from time zero to the last blood sampling time (AUC-72) calculated with the use of the linear trapezoidal rule; and terminal elimination half-life (t½), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results: The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appear similar.

Pharmacokinetic Results: Mean serum relaxin concentration-time profiles (uncorrected for baseline relaxin levels) in all 18 subjects after receiving PEGylated relaxin comprising a non-naturally encoded amino acid at each time point measured. All subjects should have pre-dose baseline relaxin concentrations within the normal physiologic range. Pharmacokinetic parameters are determined from serum data corrected for pre-dose mean baseline relaxin concentrations and the Cmax and tmax are determined. The mean tmax for the any clinical comparator(s) chosen is significantly shorter than the tmax for the PEGylated relaxin comprising the non-naturally encoded amino acid. Terminal half-life values are significantly shorter for the preclinical comparator(s) tested compared with the terminal half-life for the PEGylated relaxin comprising a non-naturally encoded amino acid.

Although the present study is conducted in healthy male subjects, similar absorption characteristics and safety profiles would be anticipated in other patient populations; such as male or female patients with diabetes, male or female patients with cancer or chronic renal failure, pediatric renal failure patients, patients in autologous predeposit programs, or patients scheduled for elective surgery.

In conclusion, subcutaneously administered single doses of PEGylated relaxin comprising non-naturally encoded amino acid will be safe and well tolerated by healthy male subjects. Based on a comparative incidence of adverse events, clinical laboratory values, vital signs, and physical examination results, the safety profiles of the commercially available forms of relaxin and PEGylated relaxin comprising non-naturally encoded amino acid will be equivalent. The PEGylated relaxin comprising non-naturally encoded amino acid potentially provides large clinical utility to patients and health care providers.

Example 39

Relaxin Functional Assay Development

This example provides the details of the relaxin functional assay. Human peripheral blood monocytes, THP-1 cells, were used to demonstrate measureable cAMP increase alongside positive controls Isoproterenol and Forskolin. THP-1 cells were preincubated in 500 uM IBMX for 30 minutes, RLX co-stimulation with 2 uM Forskolin for 20 min. Isoproterenol, Forskolin, and relaxin polypeptides, including wild-type A (with Alanine in the $1^{st}$ amino acid position of the B chain) and the variant RLX-BA1-AV13pAF (relaxin variant with the backbone amino acid sequence of the Alanine in the $1^{st}$ amino acid position of the B chain with a pAF substituted for position 13 (a valine) in the A chain, with four (4) different size PEG's attached; 5K, 10K, 20K, and 30K. TABLE 5

TABLE 5

| | Functional Assay Raw EC50 Values [ng/mL] | | |
|---|---|---|---|
| Sample | Nov. 4, 2010 | Nov. 5, 2010 | Nov. 5, 2010 |
| RLX-D-WT | 1.5 | 1.5 | 1.0 |
| RLX-A-WT-001 | 3.6 | 3.3 | 2.6 |
| RLX-A-AQ1-20KPEG-001 | | 38 | |
| RLX-A-AA5-20KPEG-001 | | 41 | |
| RLX-A-AV13-20KPEG-001 | | 56 | |
| RLX-A-AR18-20KPEG-001 | | 68 | |
| RLX-A-BV7-20KPEG-001 | 54 | | |
| RLX-A-BA18-20KPEG-001 | 172 | | |
| RLX-A-BW28-20KPEG-001 | 172 | | |
| RLX-A-BE5-20KPEG-001 | | | 45 |
| RLX-D-BE5-20KPEG-001 | | | 58 |
| RLX-D-AL2-20KPEG-001 | | | 43 |

Example 40

This example evaluates the pharmacokinetic properties of 20 kDa PEGylated relaxin polypeptides following a single subcutaneous injection in SD rats.

Sprague-Dawley (SD) Rats were received from Charles River Laboratories (CRL) at approximately 7-8 weeks of age (approximately 280 g at study start). The animals were received having been jugular vein catheterized at CRL. Animals then acclimated for 3 days prior to being placed on study.

Animals received a single subcutaneous injection on day 1 and PK samples were collected over the subsequent 80 hours. Blood samples were taken from animals treated with PEG-relaxin for analysis of serum concentration according to the following sampling schedule (sampling times are approximate):

Day 1: pre-dose, 1, 2, 4, 8, 12, 25, 34, 50, 58, 73 and 80 hours post-dose

Figure 8A:
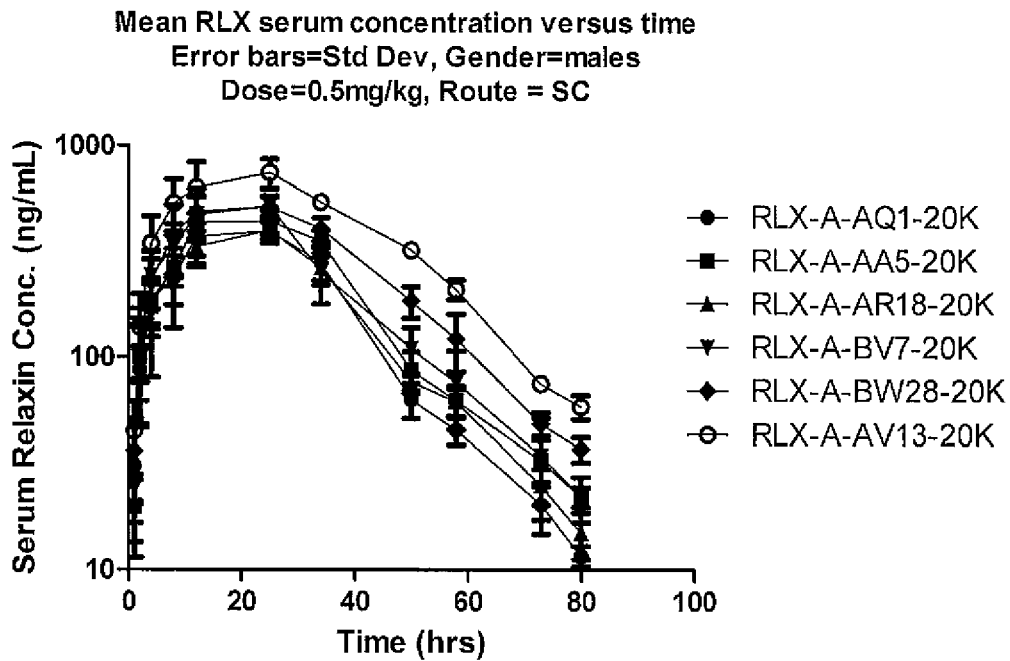
FIG. 8A shows a graph of the comparison of group mean serum concentration versus time for all PEG-RLX groups dosed subcutaneously in Example 40. A single dose injection was administered to each animal. N=5 animals per group. Symbols indicate mean SD of grouped serum concentrations versus time.

Compound concentrations were measured using a bridging ECLA based on an assay which was developed at Ambrx. Concentrations were calculated using a standard curve generated from the corresponding dosed compound and reported in an excel spreadsheet format (see appendix). Pharmacokinetic parameters were estimated using the modeling program WinNonlin (Pharsight, version 5.1). Noncompartmental analysis for individual animal data with linear-up/log-down trapezoidal integration was used, and concentration data was uniformly weighted. Compartmental analysis was performed using two compartment, 1st order elimination model and Gauss-Newton (Levenberg-Hartley) model fit equation. Table 6 shows group mean PEG-Relaxin serum concentration values versus time. FIG. 8A compares group mean serum concentration versus time for all PEG-Relaxin compounds dosed. All dose groups had measurable serum PEG-Relaxin levels.

Figure 8B:
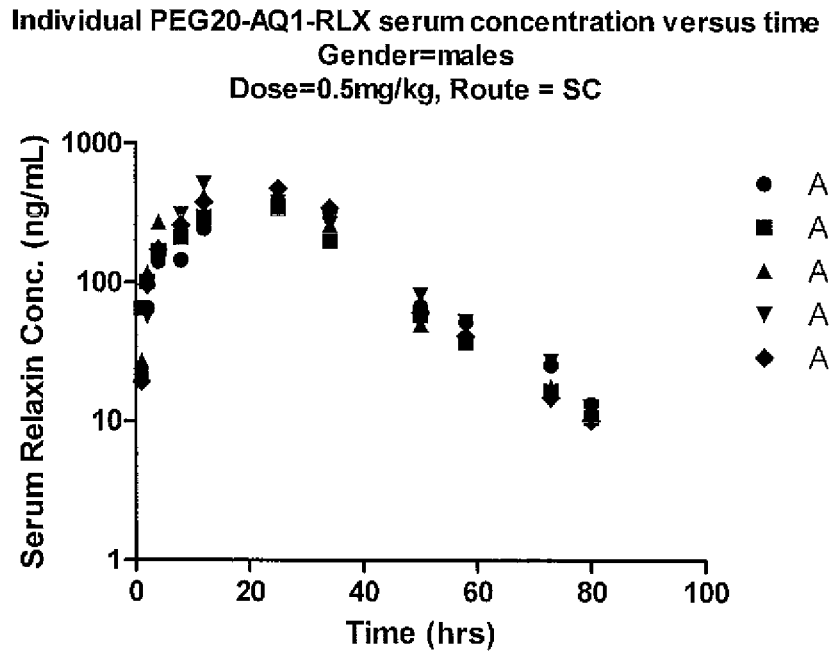
FIG. 8B shows a graph of the individual animal serum concentration time curves for SD rats dosed subcutaneously with 0.5 mg/kg of 20KPEG-AQ1-RLX. A single, subcutaneous dose was administered to each animal. N=5 animals per group.
Figure 9A:
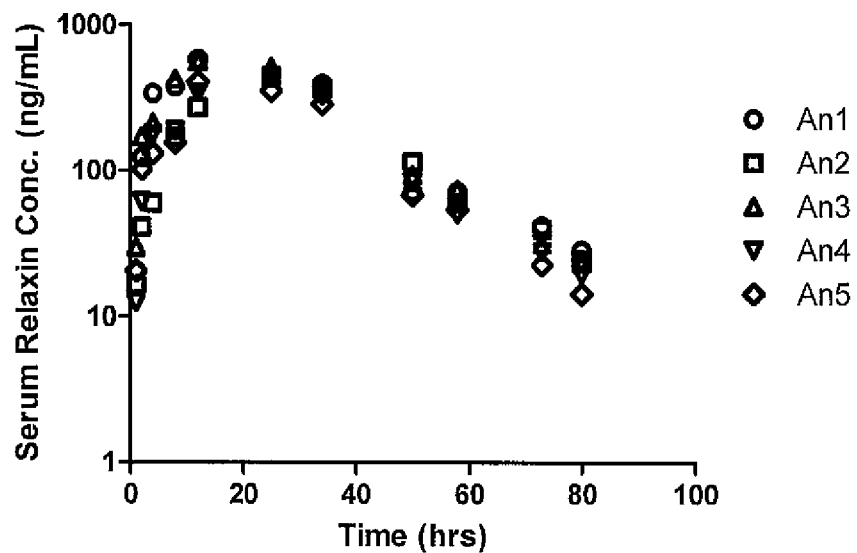
FIG. 9A shows a graph of the individual animal serum concentration time curves for SD rats dosed subcutaneously with 0.5 mg/kg of PEG20-AA5-RLX. A single, subcutaneous dose was administered to each animal. N=5 animals per group.
Figure 9B:
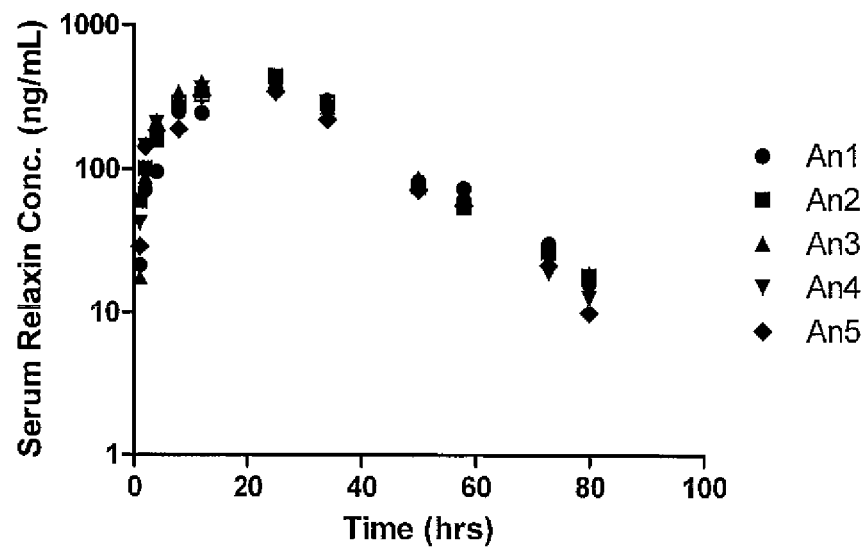
FIG. 9B shows a graph of the individual animal serum concentration time curves for SD rats dosed subcutaneously with 0.5 mg/kg of PEG20-AR18-RLX. A single, subcutaneous dose was administered to each animal. N=5 animals per group.
Figure 10A:
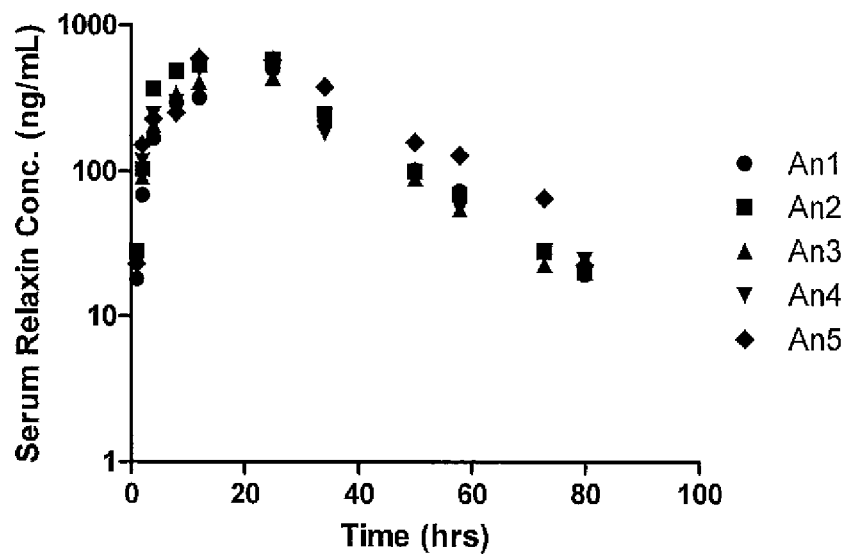
FIG. 10A shows a graph of the individual animal serum concentration time curves for SD rats dosed intravenously with 0.5 mg/kg of PEG20-BV7-RLX. A single, intravenous dose was administered to each animal. N=5 animals per group.
Figure 10B:
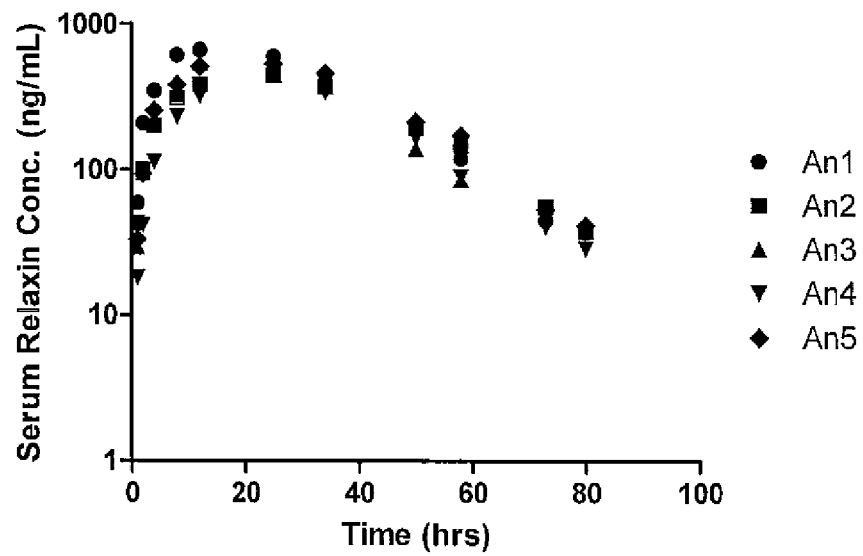
FIG. 10B shows a graph of the individual animal serum concentration time curves for SD rats dosed intravenously with 0.5 mg/kg of PEG20-BW28-RLX. A single, intravenous dose was administered to each animal. N=5 animals per group.
Figure 11:
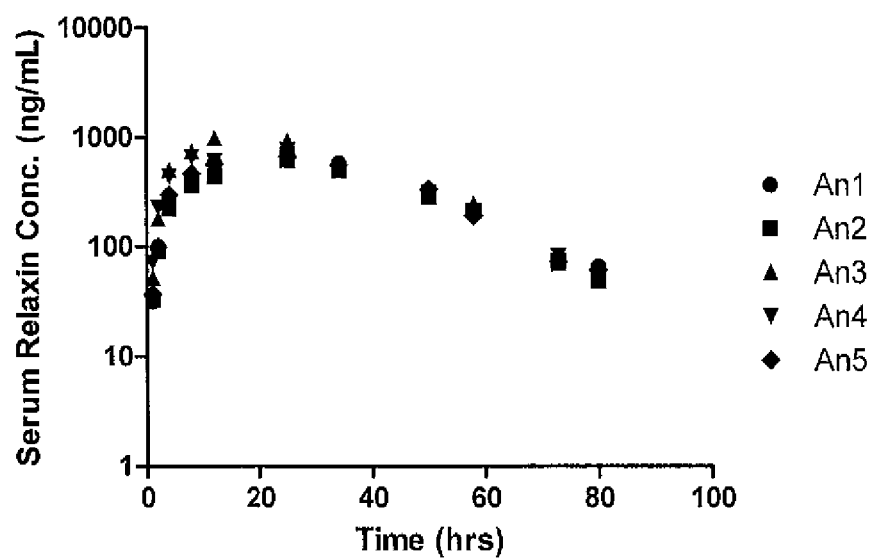
FIG. 11 shows a graph of the individual animal serum concentration time curves for SD rats dosed intravenously with 0.5 mg/kg of PEG20-AV13-RLX. A single, intravenous dose was administered to each animal. N=5 animals per group.

Individual serum concentration versus time was plotted in FIG. 8B from animals dosed SC with 0.5 mg/kg PEG20K-AQ-RLX. Individual serum concentration versus time was plotted in FIG. 9A from animals dosed SC with 0.5 mg/kg PEG20K-AA5-RLX. Individual serum concentration versus time was plotted in FIG. 9B from animals dosed SC with 0.5 mg/kg PEG20K-AR18-RLX. Individual serum concentration versus time was plotted in FIG. 10A from animals dosed SC with 0.5 mg/kg PEG20K-BV7-RLX. Individual serum concentration versus time was plotted in FIG. 10B from animals dosed SC with 0.5 mg/kg PEG20K-BW28-RLX. Individual serum concentration versus time was plotted in FIG. 11 from animals dosed SC with 0.5 mg/kg PEG20K-AV13.

Non-compartmental analysis of serum concentration versus time data from subcutaneously dosed animals is summarized in Table 6.

TABLE 6

Mean serum concentrations for SD rats following a single dose of PEG-Relaxin.

| Group | Test Article | Dose (mg/kg) | Route | Gender | Time (hr) | Mean Conc. (ng/mL) | SD (ng/mL) | N |
|---|---|---|---|---|---|---|---|---|
| 1 | 20KPEG-AQ1 | 0.5 | SC | Male | PD | BQL | NE | 5 |
| 1 | 20KPEG-AQ1 | 0.5 | SC | Male | 1 | 30.8 | 19.4 | 5 |
| 1 | 20KPEG-AQ1 | 0.5 | SC | Male | 2 | 87.4 | 25.2 | 5 |
| 1 | 20KPEG-AQ1 | 0.5 | SC | Male | 4 | 184.8 | 50.2 | 5 |
| 1 | 20KPEG-AQ1 | 0.5 | SC | Male | 8 | 237.6 | 61.9 | 5 |
| 1 | 20KPEG-AQ1 | 0.5 | SC | Male | 12 | 371.2 | 106.1 | 5 |
| 1 | 20KPEG-AQ1 | 0.5 | Sc | Male | 25 | 394.0 | 50.1 | 5 |
| 1 | 20KPEG-AQ1 | 0.5 | SC | Male | 34 | 278.7 | 59.1 | 5 |
| 1 | 20KPEG-AQ1 | 0.5 | SC | Male | 50 | 63.4 | 11.9 | 5 |
| 1 | 20KPEG-AQ1 | 0.5 | SC | Male | 58 | 45.6 | 6.8 | 5 |
| 1 | 20KPEG-AQ1 | 0.5 | SC | Male | 73 | 20.3 | 5.6 | 5 |
| 1 | 20KPEG-AQ1 | 0.5 | SC | Male | 80 | 11.6 | 1.3 | 5 |
| 2 | 20KPEG-AA5 | 0.5 | SC | Male | PD | BQL | NE | 5 |
| 2 | 20KPEG-AA5 | 0.5 | SC | Male | 1 | 19.9 | 6.4 | 5 |
| 2 | 20KPEG-AA5 | 0.5 | SC | Male | 2 | 100.1 | 51.8 | 5 |
| 2 | 20KPEG-AA5 | 0.5 | SC | Male | 4 | 185.0 | 104.8 | 5 |
| 2 | 20KPEG-AA5 | 0.5 | SC | Male | 8 | 264.7 | 128.0 | 5 |
| 2 | 20KPEG-AA5 | 0.5 | SC | Male | 12 | 434.3 | 135.0 | 5 |
| 2 | 20KPEG-AA5 | 0.5 | SC | Male | 25 | 438.0 | 55.2 | 5 |
| 2 | 20KPEG-AA5 | 0.5 | SC | Male | 34 | 353.5 | 44.2 | 5 |
| 2 | 20KPEG-AA5 | 0.5 | SC | Male | 50 | 86.9 | 19.1 | 5 |
| 2 | 20KPEG-AA5 | 0.5 | SC | Male | 58 | 62.4 | 10.6 | 5 |
| 2 | 20KPEG-AA5 | 0.5 | SC | Male | 73 | 32.8 | 8.1 | 5 |
| 2 | 20KPEG-AA5 | 0.5 | SC | Male | 80 | 22.1 | 5.4 | 5 |
| 3 | 20KPEG-AR18 | 0.5 | SC | Male | PD | BQL | NE | 5 |
| 3 | 20KPEG-AR18 | 0.5 | SC | Male | 1 | 33.9 | 17.3 | 5 |
| 3 | 20KPEG-AR18 | 0.5 | SC | Male | 2 | 109.7 | 32.9 | 5 |
| 3 | 20KPEG-AR18 | 0.5 | SC | Male | 4 | 172.7 | 48.2 | 5 |
| 3 | 20KPEG-AR18 | 0.5 | SC | Male | 8 | 270.5 | 55.3 | 5 |
| 3 | 20KPEG-AR18 | 0.5 | SC | Male | 12 | 332.5 | 57.7 | 5 |
| 3 | 20KPEG-AR18 | 0.5 | SC | Male | 25 | 398.6 | 37.6 | 5 |
| 3 | 20KPEG-AR18 | 0.5 | SC | Male | 34 | 264.3 | 33.8 | 5 |
| 3 | 20KPEG-AR18 | 0.5 | SC | Male | 50 | 76.7 | 6.9 | 5 |
| 3 | 20KPEG-AR18 | 0.5 | Sc | Male | 58 | 61.8 | 9.0 | 5 |
| 3 | 20KPEG-AR18 | 0.5 | SC | Male | 73 | 25.0 | 4.8 | 5 |
| 3 | 20KPEG-AR18 | 0.5 | SC | Male | 80 | 14.9 | 3.7 | 5 |
| 4 | 20KPEG-BV7 | 0.5 | SC | Male | PD | BQL | NE | 5 |
| 4 | 20KPEG-BV7 | 0.5 | SC | Male | 1 | 25.7 | 4.6 | 5 |
| 4 | 20KPEG-BV7 | 0.5 | SC | Male | 2 | 98.9 | 20.1 | 5 |
| 4 | 20KPEG-BV7 | 0.5 | SC | Male | 4 | 248.5 | 75.5 | 5 |
| 4 | 20KPEG-BV7 | 0.5 | SC | Male | 8 | 343.5 | 81.8 | 5 |
| 4 | 20KPEG-BV7 | 0.5 | SC | Male | 12 | 457.3 | 91.0 | 5 |
| 4 | 20KPEG-BV7 | 0.5 | SC | Male | 25 | 518.5 | 57.7 | 5 |
| 4 | 20KPEG-BV7 | 0.5 | SC | Male | 34 | 270.4 | 64.5 | 5 |
| 4 | 20KPEG-BV7 | 0.5 | SC | Male | 50 | 104.0 | 14.8 | 5 |
| 4 | 20KPEG-BV7 | 0.5 | SC | Male | 58 | 63.5 | 8.1 | 5 |
| 4 | 20KPEG-BV7 | 0.5 | SC | Male | 73 | 26.0 | 3.1 | 5 |
| 4 | 20KPEG-BV7 | 0.5 | SC | Male | 80 | 22.6 | 2.6 | 5 |
| 5 | 20KPEG-BW28 | 0.5 | SC | Male | PD | BQL | NE | 5 |
| 5 | 20KPEG-BW28 | 0.5 | SC | Male | 1 | 36.4 | 15.4 | 5 |
| 5 | 20KPEG-BW28 | 0.5 | SC | Male | 2 | 107.9 | 61.5 | 5 |
| 5 | 20KPEG-BW28 | 0.5 | SC | Male | 4 | 228.5 | 86.0 | 5 |
| 5 | 20KPEG-BW28 | 0.5 | SC | Male | 8 | 380.9 | 144.0 | 5 |
| 5 | 20KPEG-BW28 | 0.5 | SC | Male | 12 | 486.6 | 135.4 | 5 |
| 5 | 20KPEG-BW28 | 0.5 | SC | Male | 25 | 511.0 | 60.3 | 5 |
| 5 | 20KPEG-BW28 | 0.5 | SC | Male | 34 | 404.8 | 51.2 | 5 |
| 5 | 20KPEG-BW28 | 0.5 | SC | Male | 50 | 184.2 | 31.3 | 5 |
| 5 | 20KPEG-BW28 | 0.5 | SC | Male | 58 | 122.3 | 37.2 | 5 |
| 5 | 20KPEG-BW28 | 0.5 | SC | Male | 73 | 48.8 | 6.1 | 5 |
| 5 | 20KPEG-BW28 | 0.5 | SC | Male | 80 | 37.1 | 5.1 | 5 |
| 6 | 20KPEG-AV13 | 0.5 | Sc | Male | PD | BQL | NE | 5 |
| 6 | 20KPEG-AV13 | 0.5 | SC | Male | 1 | 44.9 | 16.8 | 5 |
| 6 | 20KPEG-AV13 | 0.5 | SC | Male | 2 | 138.9 | 60.1 | 5 |
| 6 | 20KPEG-AV13 | 0.5 | Sc | Male | 4 | 345.7 | 117.1 | 5 |
| 6 | 20KPEG-AV13 | 0.5 | SC | Male | 8 | 533.6 | 157.4 | 5 |
| 6 | 20KPEG-AV13 | 0.5 | SC | Male | 12 | 630.1 | 201.2 | 5 |
| 6 | 20KPEG-AV13 | 0.5 | SC | Male | 25 | 742.5 | 117.4 | 5 |
| 6 | 20KPEG-AV13 | 0.5 | SC | Male | 34 | 540.7 | 31.0 | 5 |
| 6 | 20KPEG-AV13 | 0.5 | SC | Male | 50 | 320.9 | 21.3 | 5 |
| 6 | 20KPEG-AV13 | 0.5 | SC | Male | 58 | 209.4 | 22.5 | 5 |
| 6 | 20KPEG-AV13 | 0.5 | SC | Male | 73 | 75.0 | 4.8 | 5 |
| 6 | 20KPEG-AV13 | 0.5 | SC | Male | 80 | 58.7 | 7.7 | 5 |

NE, not evaluated; BQL, below quantifiable limit; PD, Pre-dose

TABLE 7

| | AQ1-RLX | AA5-RLX | AR18-RLX | BV7-RLX | BW28-RLX | AV13-RLX |
|---|---|---|---|---|---|---|
| Terminal HL (hr) | 10.7 | 12.2 | 12.5 | 13.1 | 13.9 | 14.6 |
| $C_{max}$ (ng/mL) | 394.0 | 438.0 | 345.9 | 471.6 | 511.0 | 742.5 |
| $T_{max}$ (hr) | 25.0 | 25.0 | 25.0 | 12.0 | 25.0 | 25.0 |
| $AUC_{inf}$ (ng*hr/mL) | 14237.9 | 16095.9 | 12985.5 | 17260.9 | 22191.2 | 32230.5 |
| Vz (mL/kg) | 540.7 | 547.4 | 694.7 | 546.9 | 452.6 | 325.4 |
| CL (mL/hr) | 35.1 | 31.1 | 38.4 | 28.9 | 22.5 | 15.5 |
| MRT (hr) | 26.7 | 29.4 | 27.7 | 27.9 | 31.1 | 32.7 |

Concentration versus time curves were evaluated by non-compartmental analysis (Pharsight, version 4.1). N=5 rats per group. terminal HL, terminal half-life; Cmax, maximum serum concentration measured; Tmax, time at which Cmax occurred; $AUC_{inf}$, area under the concentration-time curve for all serum sample/timepoints extrapolated to infinity; Cl, apparent total serum clearance; Vz, apparent volume of distribution during terminal phase.

Dose solutions were measured with the ECLIA methods used for the serum concentration measurements. Dosing solutions were diluted so as to be within the range of the assay. All 20KPEG-RLX dose solutions fell within the specified 30 percent difference from theoretical (PDT). Table 8 below summarizes the results of the dose solution analyses for this study.

TABLE 8

| Pre-Dose in Buffer (DSA1) | Nominal Conc. (ng/mL) | Dilution Factor | Conc. (ng/mL) | % PDT |
|---|---|---|---|---|
| RLX A-AQ1-20K PEG | 500000 | 20000 | 495012 | −1 |
| RLX-A-AA5-20K PEG | 500000 | 20000 | 474478 | −5 |
| RLX-A-AR18-20K PEG | 500000 | 20000 | 432033 | −14 |
| RLX-A-BV7-20K PEG | 500000 | 20000 | 377302 | −25 |
| RLX-A-BV7-20K PEG | 500000 | 20000 | 475452 | −5 |
| RLX-A-AV13-20K PEG | 500000 | 20000 | 571645 | 14 |

Example 41

This example evaluates the pharmacokinetic properties of wild-type (WT) Relaxin compound following a single subcutaneous injection in SD rats.

SD Rats were received from Charles River Laboratories (CRL) at approximately 5 weeks of age (approximately 280 g at study start). The animals were received having been jugular vein catheterized at CRL. Animals then acclimated for 3 days prior to being placed on study.

Animals received a single subcutaneous injection on day 1 and PK samples were collected over the subsequent 12 hours. Blood samples were taken from animals treated with WT rhRelaxin for analysis of serum concentration according to the following sampling schedule (sampling times are approximate): Day 1: pre-dose, 0.33, 0.66, 1, 1.5, 2, 3, 4, 5, 6, 9 and 12 hours post-dose.

Compound concentrations were measured using a bridging ECLA based on an assay which was developed at Ambrx. Concentrations were calculated using a standard curve generated from the corresponding dosed compound and reported in an excel spreadsheet format (see appendix). Pharmacokinetic parameters were estimated using the modeling program WinNonlin (Pharsight, version 5.1). Noncompartmental analysis for individual animal data with linear-up/log-down trapezoidal integration was used, and concentration data was uniformly weighted.

Table 9 shows group mean wt rhRelaxin serum concentration values versus time. FIG. 12A compares group mean serum concentration versus time for wt rhRelaxin. All animals had measurable serum Relaxin levels.

Individual serum concentration versus time is plotted in FIG. 12B from animals dosed SC with 0.5 mg/kg wt Relaxin. Non-compartmental analysis of serum concentration versus time data from subcutaneously dosed animals is summarized in Table 10. Table 11 is a summary of the dose solution analyses. The dosing solutions met the acceptable criteria of less than or equal to 30% PDT.

TABLE 9

| Group | Test Article | Dose (mg/kg) | Route | Gender | Time (hr) | Mean Conc. (ng/mL) | SD (ng/mL) | N |
|---|---|---|---|---|---|---|---|---|
| 1 | wt rhRelaxin | 0.5 | SC | Male | PD | BQL | NE | 5 |
| 1 | wt rhRelaxin | 0.5 | SC | Male | 0.33 | 244.0 | 18.7 | 5 |
| 1 | wt rhRelaxin | 0.5 | SC | Male | 0.66 | 227.9 | 45.6 | 5 |
| 1 | wt rhRelaxin | 0.5 | SC | Male | 1 | 211.7 | 45.9 | 5 |
| 1 | wt rhRelaxin | 0.5 | SC | Male | 1.5 | 166.7 | 38.7 | 5 |
| 1 | wt rhRelaxin | 0.5 | SC | Male | 2 | 119.9 | 24.5 | 5 |
| 1 | wt rhRelaxin | 0.5 | SC | Male | 3 | 52.5 | 23.0 | 5 |
| 1 | wt rhRelaxin | 0.5 | SC | Male | 4 | 24.1 | 11.4 | 5 |
| 1 | wt rhRelaxin | 0.5 | SC | Male | 5 | 7.7 | 2.6 | 5 |
| 1 | wt rhRelaxin | 0.5 | SC | Male | 6 | BQL | NE | 5 |
| 1 | wt rhRelaxin | 0.5 | SC | Male | 9 | BQL | NE | 5 |
| 1 | wt rhRelaxin | 0.5 | SC | Male | 12 | BQL | NE | 5 |

NE, not evaluated; BQL, below quantifiable limit; PD, Pre-dose

TABLE 10

Pharmacokinetic parameter values for wt rhRelaxin dosed in SD rats.

| | wt rh Relaxin |
|---|---|
| Terminal HL (hr) | 0.8 (0.1) |
| $C_{max}$ (ng/mL) | 258.1 (26.1) |
| $T_{max}$ (hr) | 0.5 (0.2) |
| $AUC_{inf}$ (ng * hr/mL) | 508.9 (81.8) |
| Vz (mL/kg) | 1159 (284) |
| CL (mL/hr) | 1006 (185) |
| MRT (hr) | 1.56 (0.16) |

Concentration versus time curves were evaluated by non-compartmental analysis (Pharsight, version 4.1). N=5 rats per group. terminal HL, terminal half-life; Cmax, maximum serum concentration measured; Tmax, time at which Cmax occurred; $AUC_{inf}$, area under the concentration-time curve for all serum sample/timepoints extrapolated to infinity; Cl, apparent total serum clearance; Vz, apparent volume of distribution during terminal phase. Numbers are mean with SD in parentheses.

TABLE 11

Dose solution analyses of test article.

| Dose Solution Analysis | Nominal Conc. (ng/mL) | Dilution Factor | Conc. (ng/mL) | % PDT |
|---|---|---|---|---|
| 0.5 mg/mL Pre-Dose in formulation buffer (DSA1) | 250000 | 10000 | 208830 | −16 |
| 0.5 mg/mL Pre-Dose in serum (DSA2) | 250000 | 10000 | 225898 | −10 |

Dose solutions were measured with the ECLA methods used for the serum concentration measurements. Dosing solutions were diluted so as to be within the range of the assay. All wt rhRelaxin dose solutions fell within the specified 30 percent difference from theoretical (PDT). Table 3 below summarizes the results of the dose solution analyses for this study.

Example 42

This example evaluated the pharmacokinetic properties of a 20 kDa PEGylated Relaxin compound following a single subcutaneous or intravenous injection in SD rats.

SD Rats were received from Charles River Laboratories (CRL) at approximately 7-8 weeks of age (approximately 280 g at study start). The animals were received having been jugular vein catheterized at CRL. Animals then acclimated for 3 days prior to being placed on study. Animals received a single subcutaneous injection on day 1 and PK samples were collected over the subsequent 82 hours. Blood samples were taken from animals treated with PEG-Relaxin for analysis of serum concentration according to the following sampling schedule (sampling times are approximate): Day 1: pre-dose, 1, 3, 5, 10, 25, 34, 48, 58, 72 and 82 hours post-dose.

Compound concentrations were measured using a bridging ECLA based on an assay which was developed at Ambrx. Concentrations were calculated using a standard curve generated from the corresponding dosed compound and reported in an excel spreadsheet format (see appendix). Pharmacokinetic parameters were estimated using the modeling program WinNonlin (Pharsight, version 5.1). Noncompartmental analysis for individual animal data with linear-up/log-down trapezoidal integration was used, and concentration data was uniformly weighted. Compartmental analysis was performed using two compartment, $1^{st}$ order elimination model and Gauss-Newton (Levenberg-Hartley) model fit equation.

Table 12 shows group mean PEG-Relaxin serum concentration values versus time.

TABLE 12

| Group | Test Article | Dose (mg/kg) | Route | Gender | Time (hr) | Mean Conc. (ng/mL) | SD (ng/mL) | N |
|---|---|---|---|---|---|---|---|---|
| 1 | 20KPEG-AQ1 | 0.25 | IV | Male | PD | BQL | NE | 4 |
| 1 | 20KPEG-AQ1 | 0.25 | IV | Male | 1 | 2912.8 | 203.7 | 4 |
| 1 | 20KPEG-AQ1 | 0.25 | IV | Male | 3 | 1310.8 | 115.2 | 4 |
| 1 | 20KPEG-AQ1 | 0.25 | IV | Male | 5 | 700.7 | 68.3 | 4 |
| 1 | 20KPEG-AQ1 | 0.25 | IV | Male | 10 | 241.6 | 27.2 | 4 |
| 1 | 20KPEG-AQ1 | 0.25 | IV | Male | 25 | 61.2 | 5.4 | 4 |
| 1 | 20KPEG-AQ1 | 0.25 | IV | Male | 34 | 27.0 | 2.6 | 4 |
| 1 | 20KPEG-AQ1 | 0.25 | IV | Male | 48 | 13.7 | 2.2 | 4 |
| 1 | 20KPEG-AQ1 | 0.25 | IV | Male | 58 | 8.0 | 2.2 | 4 |
| 1 | 20KPEG-AQ1 | 0.25 | IV | Male | 72 | 4.3 | 1.4 | 4 |
| 1 | 20KPEG-AQ1 | 0.25 | IV | Male | 82 | 2.2 | 0.6 | 4 |
| 2 | 20KPEG-AQ1 | 0.5 | SC | Male | PD | BQL | NE | 5 |
| 2 | 20KPEG-AQ1 | 0.5 | SC | Male | 1 | 16.3 | 4.4 | 5 |
| 2 | 20KPEG-AQ1 | 0.5 | SC | Male | 3 | 75.8 | 20.2 | 5 |
| 2 | 20KPEG-AQ1 | 0.5 | SC | Male | 5 | 96.3 | 26.7 | 5 |
| 2 | 20KPEG-AQ1 | 0.5 | SC | Male | 10 | 135.1 | 30.1 | 5 |
| 2 | 20KPEG-AQ1 | 0.5 | SC | Male | 25 | 257.4 | 48.5 | 5 |
| 2 | 20KPEG-AQ1 | 0.5 | SC | Male | 34 | 184.9 | 26.8 | 5 |
| 2 | 20KPEG-AQ1 | 0.5 | SC | Male | 48 | 159.9 | 31.7 | 5 |
| 2 | 20KPEG-AQ1 | 0.5 | Sc | Male | 58 | 86.5 | 24.6 | 5 |
| 2 | 20KPEG-AQ1 | 0.5 | SC | Male | 72 | 20.3 | 1.4 | 5 |
| 2 | 20KPEG-AQ1 | 0.5 | SC | Male | 82 | 11.8 | 1.1 | 5 |
| 3 | 20KPEG-AQ1 | 0.25 | SC | Male | PD | BQL | NE | 3 |
| 3 | 20KPEG-AQ1 | 0.25 | SC | Male | 1 | 12.8 | 1.3 | 3 |
| 3 | 20KPEG-AQ1 | 0.25 | SC | Male | 3 | 45.3 | 6.9 | 3 |
| 3 | 20KPEG-AQ1 | 0.25 | SC | Male | 5 | 62.2 | 8.6 | 3 |
| 3 | 20KPEG-AQ1 | 0.25 | SC | Male | 10 | 90.1 | 10.9 | 3 |
| 3 | 20KPEG-AQ1 | 0.25 | SC | Male | 25 | 127.4 | 20.2 | 3 |
| 3 | 20KPEG-AQ1 | 0.25 | SC | Male | 34 | 83.2 | 13.8 | 3 |
| 3 | 20KPEG-AQ1 | 0.25 | SC | Male | 48 | 32.6 | 2.6 | 3 |
| 3 | 20KPEG-AQ1 | 0.25 | SC | Male | 58 | 16.3 | 0.3 | 3 |
| 3 | 20KPEG-AQ1 | 0.25 | SC | Male | 72 | 4.9 | 0.9 | 3 |
| 3 | 20KPEG-AQ1 | 0.25 | SC | Male | 82 | 2.7 | 0.4 | 3 |
| 4 | 20KPEG-AQ1 | 0.125 | SC | Male | PD | BQL | NE | 5 |
| 4 | 20KPEG-AQ1 | 0.125 | SC | Male | 1 | 5.7 | 1.5 | 5 |
| 4 | 20KPEG-AQ1 | 0.125 | SC | Male | 3 | 26.4 | 6.2 | 5 |
| 4 | 20KPEG-AQ1 | 0.125 | SC | Male | 5 | 37.2 | 8.6 | 5 |
| 4 | 20KPEG-AQ1 | 0.125 | SC | Male | 10 | 50.1 | 6.1 | 5 |
| 4 | 20KPEG-AQ1 | 0.125 | SC | Male | 25 | 75.9 | 8.8 | 5 |
| 4 | 20KPEG-AQ1 | 0.125 | SC | Male | 34 | 46.9 | 6.7 | 5 |
| 4 | 20KPEG-AQ1 | 0.125 | SC | Male | 48 | 20.8 | 8.2 | 5 |
| 4 | 20KPEG-AQ1 | 0.125 | SC | Male | 58 | 8.4 | 2.4 | 5 |
| 4 | 20KPEG-AQ1 | 0.125 | SC | Male | 72 | 2.3 | 0.8 | 5 |
| 4 | 20KPEG-AQ1 | 0.125 | SC | Male | 82 | 1.3 | 0.4 | 5 |

NE, not evaluated; BQL, below quantifiable limit; PD, Pre-dose

Example 43

This example evaluated the pharmacologically active dose and systemic exposure of wild-type relaxin and a PEG-relaxin variant in female Long-Evans rats.

The objective of these signal generation studies was to establish in vivo activity and define a pharmacologically active dose of the PEG-relaxin variant. To accomplish these objectives, physiologically relevant endpoints responsive to relaxin were evaluated in female Long-Evans rats including water intake, urine output, and select urine and blood clinical chemistry. To enable identification of candidate endpoints, wild-type relaxin was tested first (Phase 1), at doses calculated to achieve plasma concentrations of 0.3×, 1× and 10× of an in vitro target inhibition. Target doses were delivered by bolus intravenous (IV) dosing followed by 6-hour continuous infusion. Doses of 0.3×, 1×, and 10× wild-type relaxin induced increases of 95%, 68%, and 32%, respectively, in water intake compared to vehicle. Changes in mean plasma sodium concentrations from baseline to 2 and 6 hours were −9.5 and 1.2 mEq/L for vehicle (0×); −5.8 and −9.0 mEq/L at 0.3×; 1.0 and −1.5 mEq/L at 1×; −4.7 and −1.4 mEq/L at 10×. The changes in plasma osmolarity from baseline to 2 and 6 hours were −20.7 and 1.0 mosmol/kg water for vehicle (0×); −11.0 and −19.1 mosmol/kg water at 0.3×; 0.3 and −4.4 mosmol/kg water for 1×; −10.3 and −3.8 mosmol/kg water for 10×.

PEG-relaxin (Phase 2) was administered at a bolus volume of 1 μL per gram of body weight with blood collected 2 and 6 hours after dosing and urine was collected for the 6 hour period following dosing. Treatment with PEG-relaxin at 0.1×, 0.3× and 1× doses resulted in 93%, 128% and 105% increases, respectively, in water intake compared to the vehicle group. Changes in mean plasma sodium concentration from baseline to 2 and 6 hours were 2.5 and 1.5 mEq/L for vehicle (0×); −1.5 and −4.8 mEq/L at 0.1×; −4.0 and −2.9 mEq/L at 0.3×; −2.3 and −4.0 mEq/L at 1×. Changes in plasma osmolarity from baseline to 2 and 6 hours were 4.5 and 2.1 mosmol/kg water for vehicle (0×); −5.1 and −11.0 mosmol/kg water at 0.1×; −8.2 and −5.0 mosmol/kg water at 0.3×; −5.6 and −9.5 mosmol/kg water at 1×. There were no clear changes in urine clinical chemistry values following treatment with wild-type or PEG-relaxin. These data establish in vivo activity and enable rationale dose selection for subsequent in vivo disease model studies with PEG-relaxin.

TABLE 13

Animal Group Design

| Group | Test Article | Animal IDs | Plasma Concentration (Fold Increase Over Target) | IV Bolus Dose Concentration (mg/mL) | IV Infusion Concentration (mg/mL)[c] | # Animals per Group |
|---|---|---|---|---|---|---|
| Phase 1 Wild-Type Relaxin Dosing[a] | | | | | | |
| 1 | Wild type-relaxin | 1F001-1F004 | 1X | 0.003 | 0.08 | 4 |
| 2 | Wild type-relaxin | 2F001-2F004 | 10X | 0.03 | 0.8 | 4 |
| 3[b] | Wild type-relaxin | 3F001-3F004 | vehicle | vehicle | vehicle | 4 |
| 4[b] | Wild type-relaxin | 4F001-4F004 | 0.3X | 0.001 | 0.026 | 4 |

[a]Groups 1 and 2 (1x and 10x) were evaluated first, and because test article-related effects on drinking water consumption, hematocrit, and urine output were apparent, doses for the second set of rats were revised to vehicle and 0.3X in Groups 3 and 4, respectively. There was a washout period of at least 36 hours between the Groups 1 and 2. A washout period of at least 36 hours also occurred between Groups 3 and 4.
[b]Rats in Group 1 were subjected to a second randomization and assigned to Group 2 following the washout period. Rats in Group 3 were subjected to a second randomization and assigned to Group 4. Animal numbers, 001-004 remained the same in Groups 2 and 4 as they were in Groups 1 and 3; however, the group number designations, Group 2 and Group 4, were used to enable tube labeling and sample identification clarity.
[c]Wild-type relaxin was injected intravenously in a bolus volume of 100 µL followed by an infusion rate of 50 µL/hour.

TABLE 14

| Group | Test Article | Animal IDs | Plasma Concentration (Fold Increase Over Target) | IV Bolus Dose Concentration (mg/mL)[a] | #Animals per Group |
|---|---|---|---|---|---|
| Phase 2 PEG-Relaxin Dosing | | | | | |
| 5 | PEG-Relaxin | 5F001-5F004 | Vehicle | NA | 4 |
| 6 | PEG-Relaxin | 6F001-6F004 | 0.3× | 0.03 | 4 |
| 7 | PEG-Relaxin | 7F001-7F004 | 0.1× | 0.01 | 4 |
| 8 | PEG-Relaxin | 8F001-8F004 | 1.0× | 0.1 | 4 |

[a]Bolus dose was administered at a volume of 1 µL/g body weight.

Phase 1 Wild-Type Relaxin

Female Long-Evans rats 12-14 weeks of age with bi-lateral jugular vein catheters surgically placed by the vendor were obtained from Charles River Laboratories. Two sets of four rats were used. Each set was used to evaluate two doses of wild-type relaxin. There was a washout period of 36 hours or more between Groups 1 and 2 and Groups 3 and 4 as rats from Groups 1 and 3 were reused in Groups 2 and 4, respectively. Rats had ad libitum access to food and water and were housed in the Culex ABS metabolic caging system (Culex Automated Blood Sampler, Bioanalytical System Inc) the night prior to the initiation of dosing and for the 6 hours after the IV bolus dose and initiation of infusion dosing.

Phase 1 Wild-Type Relaxin Dose Administration

In phase 1 each rat was given a one-time IV bolus and a 6 hour IV infusion. The IV bolus injection via surgically implanted jugular catheters followed by IV infusion via surgically implanted jugular catheters. At least 36 hours between the Groups 1 and 2 in the first set of rats and Groups 3 and 4 in the second set of rats was allows for washout.

Phase 2 PEG-Relaxin

Female Long-Evans rats 12-14 weeks of age with bi-lateral jugular vein catheters surgically placed by the vendor were obtained from Charles River Laboratories. Four sets of four rats were used, with each set used to evaluate one dose of PEG-Relaxin. Rats receiving PEG-Relaxin were not reused following a washout period due to the extended plasma exposure of PEGylated compounds. Rats had ad libitum access to food and water and were housed in the Culex ABS metabolic cages.

Phase 2 PEG-Relaxin Dose Administration

In Phase 2, the rats received a one-time IV injection via surgically implanted jugular catheters.

All bolus and IV dosing solutions were formulated according to these thawing and mixing instructions for all dose solutions:

The frozen sample bottle for each dosing formulation was allowed to thaw at 4° C. for 3 to 4 hours, with hourly inspections of the thawing process. Once thawing was complete, the formulation was mixed with a gentle inversion taking care not to create bubbles. Care was taken to gently and thoroughly mix each formulation just prior to intravenous dosing. Each dosing formulation was maintained at 4° C. until used for dosing.

The doses were prepared immediately prior to preparation and each group received dose concentrations of the following:

| Phase 1 (Groups 1-4) |
|---|
| Group 1: (1×) IV Bolus 0.003 mg/mL |
| IV Infusion 0.08 mg/mL |
| Group 2: (10×) IV Bolus 0.03 mg/mL |
| IV Infusion 0.8 mg/mL |
| Group 3: (vehicle) Bolus and infusion |
| Group 4: (0.3×) IV Bolus 0.001 mg/mL |
| IV Infusion 0.026 mg/mL |

| Phase 2 (Groups 5-8) |
|---|
| Group 5: Vehicle IV Bolus NA |
| Group 6: (0.3×) IV Bolus 0.03 mg/mL |
| Group 7: (0.1×) IV Bolus 0.01 mg/mL |
| Group 8: (1.0×) IV Bolus 0.1 mg/mL |

Animals used on this study were selected on the basis of acceptable findings from body weight measurements, jugular catheter patency, and functionality. Animals identified with catheters unsuitable for dosing or blood collection prior to study start or during the blood collection period following initiation of dosing were removed from the study and replaced by rats with suitable catheters. Replacement of catheterized rats and compound dosing occurred at the earliest time possible relative to the dosing schedule, staffing availability, and receipt of rats from the vendor.

Phase 1: The animals were randomized according to pre-study body weight and assigned to Group 1. Following completion of dosing, rats in Group 1 were subjected to a second randomization following the washout period and reassigned to Group 2. Following completion of dosing, rats in Group 3 were subjected to a second randomization following the washout period and reassigned to Group 4.

Phase 2: The animals were randomized according to pre-study body weight and assigned to Groups 5 through 8.

Daily at approximately 30 minutes and 1, 2, 4, and 6 hours after initiation of dosing. Visual inspections of physical and behavioral changes were performed and animals were examined for changes in body posture, hair coat, activity, excreta, etc. Routine body weights were taken and recorded prior to dosing.

Blood and Urine Sample, Collection, Handling, and Analysis

Phase 1 Study Protocol

Baseline urine collection were started the night prior to dose administrations, continued for a period of 15-18 hours, and were collected into a chilled (wet ice) vial. Baseline blood samples (~400 µL whole blood) were collected at the end of baseline urine collection. On the day of the experiment, rats were given an IV bolus injection of the test article followed by continuous infusion with wild-type relaxin at a constant infusion rate delivered by a syringe pump (Harvard 11 plus) for 6 hours via left jugular vein catheter at volumes of 50 µL/hour. Two additional blood samples (~400 µL whole blood each) were collected at 2 and 6 hours post-relaxin infusion. All blood samples were collected via right jugular catheter into sample tubes containing K3EDTA anticoagulant using Culex ABS programmed sampling method and samples were stored in a refrigerated environment until sample processing. Urine was continuously collected into a chilled vial throughout the duration of the relaxin infusion period. The total urine volume from each collection was recorded, and 2-5 mL of each urine sample was stored in a Seventh Wave Labs freezer set to maintain approximately −80°. Water intake during the 6-hour infusion period was recorded by comparing pre- and post-infusion weight of bottle+water. The infusion pump was stopped after 6 hours of continuous infusion, and rats underwent a washout period of at least 36 hours before they were subjected to the second dose evaluation.

Continuous IV infusion was required to maintain targeted, stable plasma drug concentration.

Phase 2 Study Protocol

Baseline urine collection started the night prior to dose administrations for a period of 15-18 hours, and samples were collected into a chilled vial. Baseline blood samples (~400 µL whole blood) were collected at the end of the baseline urine collection period. On the day of the experiment, rats were administered a single dose of PEG-Relaxin intravenously at a volume not to exceed 10 mL/kg/day (one time dose). Two additional blood samples (~400 µL whole blood) were collected at 2 and 6 hours post-relaxin administration. All blood samples were collected via right jugular catheter into sample tubes containing K3EDTA anticoagulant using Culex ABS programmed sampling method and stored in a refrigerated environment until processing. Urine samples were continuously collected from time 0 to 6 hours post administration of PEG-Relaxin into a chilled vial during sampling. The total urine volume from each collection was recorded, and 2-5 mL of each urine sample was stored in a Seventh Wave Labs freezer set to maintain approximately −80° C. Rats were euthanized 6 hours after dosing. Water intake during the 6-hour infusion period was recorded by comparing weight of the bottle+water at the beginning and the end of drug infusion period.

Pathology

Urine samples were collected as already described in this example. Two to 5 mL of chilled urine samples were frozen on dry ice and stored in a freezer set to maintain approximately −80° C. until shipped on dry ice to AVL for analysis of urine creatinine and BUN for determination of creatinine clearance.

A blood sample was collected using the Culex ABS using $K_3EDTA$ as an anticoagulant. Fifteen microliters of whole blood samples were filled into untreated capillary tubes, sealed with clay on one end, and centrifuged in a hematocrit centrifuge (International Equipment Company, IEC MB centrifuge) for five minutes. Hematocrit results were obtained using a microhematocrit reading device provided by the manufacturer.

Blood was collected for potential determination of systemic exposure of wild-type and PEG-Relaxin in accordance with the collection schedule and procedures listed below. There were three collection intervals. Collection time points were 0, 2, and 6 hours post-dose for Phase 1 and Phase 2 rats. Phase 1: 8 animals per time point. Phase 2: 16 animals per time point. Collection volume was nearly 400 micro liters of whole blood. All animals in Groups 1 through 8 were bled at three time points: baseline (pre-dose t=0) and 2 and 6 hours post-initiation of infusion for wild-type relaxin IV dosing and post IV dosing for PEG-Relaxin dosing groups, respectively. The time of initiation of IV infusion dosing and the actual time of each bleed were recorded in the raw data for each animal. Per Sponsor decision, blood was not sent to Ambrx for systemic exposure determinations during the study conduct. Samples have been stored frozen at in a Seventh Wave Labs freezer set to maintain approximately −80° C. and will be returned to Sponsor.

Phase I Wildtype Relaxin RESULTS

The average water intake during the 6 hour infusion in vehicle (0×) treated rats was 1.8 mL per 100 grams of body weight, which increased to 3.6, 3.1, and 2.4 mL per 100 grams of body weight in the 0.3×, 1× and 10× wild-type relaxin treated rats, respectively. These are 95%, 68%, 32% increases over vehicle for the 0.3×, 1× and 10× dosing groups respectively.

Average hematocrit at baseline, 2 and 6 hours after initiation of dosing was 35.1%, 35.0%, and 34.3% in vehicle treated rats, respectively; 33.1%, 33.7%, and 32.3% in the 0.3× group; 31.4 T, 32.0% and 33.7% in the 1× group; 29.7%, 31.9% and 30.4% in the 10× group.

The average urine output during the 6 hour infusion was 1.8, 1.5, 1.2 and 1.2 mL per 100 grams of body weight for the vehicle (0×), 0.3×, 1× and 10× groups respectively.

The mean plasma sodium concentration at baseline, 2 and 6 hours after initiation of dosing was 139.3, 129.8, 140.5 mEq/L in vehicle (0×) group; 141.8, 136.0 and 132.8 mEq/L in the 0.3× group; 138.8, 139.8 and 137.3 mEq/L in 1× group; 137.0, 132.3 and 135.6 mEq/L in 10× group. The change from baseline at 2 and 6 hours was −9.5 and 1.2 mEq/L for vehicle (0×); −5.8 and −9.5 mEq/L at 0.3×; 1.0 and −1.5 mEq/L at 1×; −4.7 and −1.4 mEq/L at 10×.

Plasma osmolarity was calculated using the following equation: osmolarity $(OSM)=(2*na)+(Glu/18)+(BUN/2.8)$. The mean plasma osmolarity at baseline, 2 and 6 hours after initiation of 277.3 mosmol/kg water in the 0.3× group; 291.0, 291.3 and 286.6 mosmol/kg water in 1× group; 286.4, 276.1 and 282.6 mosmol/kg water in the 10× group. The change from baseline at 2 and 6 hours was −10.7 and 1.0 mosmol/kg water for vehicle (0×); =11.0 and =19.1 mosmol/ kg water at 0.3×; 0.3 and −4.4 mosmol/kg water for 1×; −10.3 and −3.8 mosmol/kg water for 10×. Urine clinical chemistry data of BUN/Cr, Na excretion are summarized in the tables below:

TABLE 3

Urine Clinical Chemistry Data Summary of Wild-Type Relaxin (Phase 1 Study)

| Groups | BUN/Cr | sem | Na Excretion (mEq/hr) | sem | BUN Excretion (mg/hr) | sem | Cr Cl (mL/min/100 g) | sem |
|---|---|---|---|---|---|---|---|---|
| Vehicle (baseline) | 36 | 12 | 0.083 | 0.010 | 13.5 | 4.4 | 0.65 | 0.04 |
| Vehicle (6 hr study) | 26 | 3 | 0.079 | 0.018 | 9.4 | 2.3 | 0.60 | 0.15 |
| 0.3X (baseline) | 66 | 9 | 0.055 | 0.005 | 17.3 | 3.9 | 0.38 | 0.06 |
| 0.3X (6 hr study) | 43 | 6 | 0.071 | 0.015 | 12.1 | 1.3 | 0.45 | 0.07 |
| 1X (baseline) | 18 | 2 | 0.046 | 0.010 | 7.6 | 1.5 | 0.62 | 0.09 |
| 1X (6 hr study) | 19 | 4 | 0.030 | 0.003 | 4.6 | 1.5 | 0.36 | 0.05 |
| 10X (baseline) | 21 | 2 | 0.063 | 0.001 | 8.5 | 1.1 | 0.69 | 0.04 |
| 10X (6 hr study) | 17 | 4 | 0.055 | 0.005 | 4.9 | 0.7 | 0.81 | 0.11 |

TABLE 4

Urine Clinical Chemistry Raw Data of Wild-Type Relaxin (Phase 1 Study)

| DOSE | Group | ID | K | Na | Creat | BUN | CrCl (ml/min/100 g) |
|---|---|---|---|---|---|---|---|
| Vehicle | 3F001 T0 | 68232 | 136 | 119 | 84 | 1080 | 0.702 |
| Vehicle | 3F001 T6 | 68233 | 74 | 67 | 33 | 850 | 0.257 |
| Vehicle | 3F002 T0 | 68234 | 122 | 130 | 59 | 980 | 0.692 |
| Vehicle | 3F002 T6 | 68235 | 99 | 66 | 39 | 920 | 0.979 |
| Vehicle | 3F003 T0 | 68236 | 276 | 130 | 54 | 2950 | 0.694 |
| Vehicle | 3F003 T6 | 68237 | 110 | 154 | 58 | 1980 | 0.552 |
| Vehicle | 3F004 T0 | 68238 | 355 | 126 | 52 | 3000 | 0.522 |
| Vehicle | 3F004 T6 | 68239 | 176 | 152 | 71 | 1320 | 0.614 |
| 0.3X | 4F001 T0 | 68791 | 272 | 47 | 22 | 1950 | 0.413 |
| 0.3X | 4F001 T6 | 68792 | 174 | 112 | 25 | 1500 | 0.356 |
| 0.3X | 4F002 T0 | 68793 | 274 | 68 | 42 | 1860 | 0.522 |
| 0.3X | 4F002 T6 | 68794 | 180 | 88 | 42 | 1500 | 0.657 |
| 0.3X | 4F003 T0 | 68795 | 230 | 54 | 25 | 1800 | 0.329 |
| 0.3X | 4F003 T6 | 68796 | 180 | 82 | 60 | 1880 | 0.449 |
| 0.3X | 4F004 T0 | 68797 | 225 | 68 | 23 | 1440 | 0.260 |
| 0.3X | 4F004 T6 | 68798 | 365 | 152 | 68 | 3100 | 0.352 |
| 1x | 1F001-T0 | 67488 | 194 | <40 | 64 | 1480 | 0.526 |
| 1x | 1F001-T6 | 67489 | 138 | 62 | 57 | 960 | 0.394 |
| 1x | 1F002-T0 | 67487 | 203 | 74 | 93 | 1540 | 0.579 |
| 1x | 1F002-T6 | 67496 | 296 | 161 | 88 | 1300 | 0.337 |
| 1x | 1F003-T0 | 67490 | 110 | 85 | 64 | 820 | 0.495 |
| 1x | 1F003-T6 | 67495 | 176 | 167 | 104 | 1440 | 0.236 |
| 1x | 1F004-T0 | 67483 | 224 | 74 | 67 | 1420 | 0.882 |
| 1x | 1F004-T6 | 67492 | 94 | <40 | 24 | 740 | 0.476 |
| 10X | 2F001-T0 | 67497 | 140 | 64 | 40 | 900 | 0.670 |
| 10X | 2F001-T6 | 67498 | 54 | 68 | 64 | 500 | 0.729 |
| 10X | 2F002-T0 | 67484 | 166 | 101 | 75 | 1120 | 0.598 |
| 10X | 2F002-T6 | 67485 | 214 | 126 | 57 | 1260 | 0.618 |
| 10X | 2F003-T0 | 67491 | 254 | <40 | 103 | 1650 | 0.696 |
| 10X | 2F003-T6 | 67486 | 60 | <40 | 106 | 800 | 1.129 |
| 10X | 2F004-T0 | 67494 | 294 | 88 | 74 | 1600 | 0.809 |
| 10X | 2F004-T6 | 67493 | 212 | 125 | 85 | 1400 | 0.756 |

Units: Na (mEq/L); Creatinine (mg/dL); BUN (mg/dL), glucose (mg/dL), K (mmol/L), CrCl: mL/min/100 g BW
Creatinine Clearance (Crcl) = (U creat. * U vol)/(P creat.* U time)

TABLE 5

Physiology Data Summary of Wild-Type Relaxin (Phase 1 Study)

| | Water Intake (0-6hr) mL/100 g BW | | Baseline Urine (-16-0 hr) mL/100 g BW | | Urine (0-6 hr) mL/100 g BW | |
|---|---|---|---|---|---|---|
| Dose | mean | sem | mean | sem | mean | sem |
| Vehicle | 1.8 | 0.4 | 4.1 | 0.4 | 1.8 | 0.3 |
| 0.3X | 3.6 | 0.2 | 5.7 | 1.1 | 1.5 | 0.4 |
| 1X | 3.1 | 0.6 | 3.8 | 0.6 | 1.2 | 0.6 |
| 10X | 2.4 | 0.7 | 4.3 | 0.8 | 1.2 | 0.1 |

| | Hematocrit (%) | | | | | |
|---|---|---|---|---|---|---|
| | 0 hr | | 2 hr | | 6 hr | |
| Dose | mean | sem | mean | sem | mean | sem |
| Vehicle | 35.1 | 1.0 | 35.0 | 0.9 | 34.3 | 0.5 |
| 0.3X | 29.7 | 1.1 | 31.9 | 1.2 | 30.4 | 0.4 |
| 1X | 31.4 | 2.7 | 32.0 | 2.9 | 33.7 | 2.1 |
| 10X | 29.7 | 1.1 | 31.9 | 1.2 | 30.4 | 0.4 |

Phase 2 PEG-Relaxin Variant RESULTS

The average water intake during the 6 hour post-dose period in vehicle (0×) treated rats was 1.5 mL per 100 grams of body weight, which increased to 2.9, 3.4, and 3.1 mL per 100 grams of body weight in 0.1×, 0.3× and 1×PEG-relaxin variant treated rats, respectively. These represent 93%, 128% and 105% increases over the mean of vehicle groups for the 0.1×, 0.3× and 1× groups respectively.

The average urine output during the 6 hour post-dose period was 0.9, 0.2, 0.5 and 0.4 mL per 100 grams of body weight for vehicle (0×, 0.3× and 1× groups respectively). The mean plasma sodium concentrations at baseline, 2 and 6 hours after dosing were 136.3, 138.8 and 137.8 mEq/L in the vehicle (0×) group, respectively; 138.5, 137.0 and 133.7 mEq/L in the 0.1× group, respectively; 137.5, 133.5 and 134.6 mEq/L in the 0.3× group, respectively; 137.3, 135.0 and 133.3 mEq/L in the 1× group, respectively. The change from baseline at 2 and 6 hours was 2.5 and 1.5 mEq/L for vehicle (0×); −1.5 and −4.8 mEq/L at 0.1×; −4.0 and −2.9 mEq/L at 0.3×; −2.3 and −4.0 mEq/L at 1×.

The mean plasma osmolarity at baseline, 2 and 6 hours after dosing was 285.4, 289.9, and 287.5 mosmol/kg water in the vehicle (0×) group, respectively; 292.7, 287.6 and 281.7 mosmol/kg water in the 0.1× group, respectively; 287.6, 279.4 and 282.6 mosmol/kg water in the 0.3× group, respectively; 289.3, 283.7 and 279.4 mosmol/kg water in the 1× group, respectively. The change from baseline at 2 and 6 hours was 4.5 and 2.1 mosmol/kg water for vehicle (0×); −5.1 and −11.0 mosmol/kg water at 0.1×; −8.2 and −5.0 mosmol/kg water for 0.3×; −5.6 and −9.9 mosmol kg water for IX.

It is understood that the examples and embodiments described herein are for illustrative purposes only and that various modifications or changes in light thereof will be suggested to those of ordinary skill in the art and are to be included within the spirit and purview of this application and scope of the appended claims. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An isolated nucleic acid encoding a modified relaxin polypeptide chain comprising a non-naturally encoded amino acid, wherein:
   (a) said isolated nucleic acid comprises a selector codon that encodes said non-naturally encoded amino acid and said selector codon comprises an amber codon, an ochre codon, an opal codon, or a four base codon;
   (b) the encoded modified relaxin polypeptide comprises a relaxin A chain polypeptide having a sequence at least 95% identical to SEQ ID NO: 4; and
   (c) said non-naturally encoded amino acid occurs at residue 1 of the A chain of SEQ ID NO:4 or the corresponding position of said modified relaxin polypeptide.

2. The isolated nucleic acid of claim 1, wherein said nucleic acid encodes a relaxin A chain polypeptide having the sequence of SEQ ID NO: 4 containing said non-naturally occurring amino acid.

3. The isolated nucleic acid of claim 2, wherein said nucleic acid further encodes a relaxin B chain polypeptide of SEQ ID NO: 5 or SEQ ID NO: 6.

4. The isolated nucleic acid of claim 1, wherein said nucleic acid further encodes a relaxin B chain polypeptide having a sequence at least 95% identical to SEQ ID NO: 5 or SEQ ID NO: 6.

5. The isolated nucleic acid of claim 1, wherein said selector codon comprises an amber codon, an ochre codon, or an opal codon.

6. An isolated host cell comprising the isolated nucleic acid of claim 1.

7. The isolated host cell of claim 6, wherein said host cell further comprises an orthogonal tRNA that recognizes said selector codon and inserts said non-naturally encoded amino acid during translation of said isolated nucleic acid.

8. The isolated host cell of claim 7, wherein said host cell further comprises an orthogonal tRNA synthetase that synthesizes said orthogonal tRNA.

9. The isolated host cell of claim 6, wherein said non-naturally encoded amino acid comprises a functional group selected from a carbonyl group, an aminooxy group, a hydrazide group, a hydrazine group, a semicarbazide group, an azide group, or an alkyne group.

10. The isolated host cell of claim 6, wherein said non-naturally encoded amino acid comprises a phenylalanine analog or derivative.

11. The isolated host cell of claim 6, wherein said non-naturally encoded amino acid has the structure:

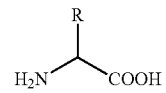

wherein the R group is any substituent other than the side chain found in alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine.

12. The isolated host cell of claim 6, wherein said non-naturally encoded amino acid comprises para-acetyl-L-phenylalanine.

13. The isolated host cell of claim 6, wherein said host cell a bacterial cell.

14. The isolated host cell of claim 13, wherein said host cell an *Escherichia coli* cell.

15. An in vitro translation system comprising the isolated nucleic acid of claim 1 and components that provide for the in vitro translation of said isolated nucleic acid.

16. The isolated nucleic acid of claim 1, wherein said isolated nucleic acid further comprises a nucleic acid encoding a secretion signal sequence.

17. An isolated nucleic acid encoding a modified relaxin polypeptide chain comprising a non-naturally encoded amino acid, wherein:
   (a) said isolated nucleic acid comprises a selector codon that encodes said non-naturally encoded amino acid and said selector codon comprises an amber codon, an ochre codon, an opal codon, or a four base codon;
   (b) the encoded modified relaxin polypeptide comprises the relaxin A chain polypeptide of SEQ ID NO: 4 containing one non-naturally encoded amino acid substitution; and
   (c) said non-naturally encoded amino acid occurs at residue 1 of the A chain of SEQ ID NO:4.

18. An isolated host cell comprising the isolated nucleic acid of claim 17.

19. The isolated host cell of claim 18, wherein said host cell an *Escherichia coli* cell.

20. A method of making a modified relaxin polypeptide chain comprising a non-naturally encoded amino acid, the method comprising, culturing cells comprising a polynucleotide according to claim 1 and an orthogonal tRNA under conditions to permit expression of the relaxin polypeptide comprising a non-naturally encoded amino acid.

* * * * *

SEQUENCE LISTING

<160> NUMBER OF SEQ ID NOS: 34

<210> SEQ ID NO 1
<211> LENGTH: 53
<212> TYPE: PRT
<213> ORGANISM: Homo sapiens
<220> FEATURE:
<221> NAME/KEY: CHAIN
<222> LOCATION: (1)..(24)
<223> OTHER INFORMATION: Relaxin A chain
<220> FEATURE:
<221> NAME/KEY: CHAIN
<222> LOCATION: (25)..(53)
<223> OTHER INFORMATION: Relaxin B chain
<220> FEATURE:
<221> NAME/KEY: VARIANT
<222> LOCATION: (1)..(1)
<223> OTHER INFORMATION: Optionally glutamine or pyroglutamate (Pe)
<220> FEATURE:
<221> NAME/KEY: DISULFID
<222> LOCATION: (10)..(15)
<223> OTHER INFORMATION: Intrachain (A chain)
<220> FEATURE:
<221> NAME/KEY: DISULFID
<222> LOCATION: (11)..(35)
<223> OTHER INFORMATION: Interchain (between A and B chains)
<220> FEATURE:
<221> NAME/KEY: DISULFID
<222> LOCATION: (24)..(47)
<223> OTHER INFORMATION: Interchain (between A and B chains)

<400> SEQUENCE: 1

Gln Leu Tyr Ser Ala Leu Ala Asn Lys Cys Cys His Val Gly Cys Thr
1               5                   10                  15

Lys Arg Ser Leu Ala Arg Phe Cys Asp Ser Trp Met Glu Glu Val Ile
            20                  25                  30

Lys Leu Cys Gly Arg Glu Leu Val Arg Ala Gln Ile Ala Ile Cys Gly
        35                  40                  45

Met Ser Thr Trp Ser
    50

<210> SEQ ID NO 2
<211> LENGTH: 53
<212> TYPE: PRT
<213> ORGANISM: Homo sapiens
<220> FEATURE:
<221> NAME/KEY: CHAIN
<222> LOCATION: (1)..(24)
<223> OTHER INFORMATION: Relaxin A chain
<220> FEATURE:
<221> NAME/KEY: CHAIN
<222> LOCATION: (25)..(53)
<223> OTHER INFORMATION: Relaxin B chain
<220> FEATURE:
<221> NAME/KEY: VARIANT
<222> LOCATION: (1)..(1)
<223> OTHER INFORMATION: Optionally glutamine or pyroglutamate (Pe)
<220> FEATURE:
<221> NAME/KEY: DISULFID
<222> LOCATION: (10)..(15)
<223> OTHER INFORMATION: Intrachain (A chain)
<220> FEATURE:
<221> NAME/KEY: DISULFID
<222> LOCATION: (11)..(35)
<223> OTHER INFORMATION: Interchain (between A and B chains)
<220> FEATURE:
<221> NAME/KEY: DISULFID
<222> LOCATION: (24)..(47)
<223> OTHER INFORMATION: Interchain (between A and B chains)

<400> SEQUENCE: 2

Gln Leu Tyr Ser Ala Leu Ala Asn Lys Cys Cys His Val Gly Cys Thr

```
                1               5                  10                 15
         Lys Arg Ser Leu Ala Arg Phe Cys Ala Ser Trp Met Glu Glu Val Ile
                         20                  25                 30
         Lys Leu Cys Gly Arg Glu Leu Val Arg Ala Gln Ile Ala Ile Cys Gly
                    35                  40                 45

Met Ser Thr Trp Ser
              50

<210> SEQ ID NO 3
<211> LENGTH: 88
<212> TYPE: PRT
<213> ORGANISM: Homo sapiens
<220> FEATURE:
<221> NAME/KEY: CHAIN
<222> LOCATION: (1)..(29)
<223> OTHER INFORMATION: Relaxin B Chain
<220> FEATURE:
<221> NAME/KEY: SITE
<222> LOCATION: (30)..(64)
<223> OTHER INFORMATION: Removed in mature form
<220> FEATURE:
<221> NAME/KEY: CHAIN
<222> LOCATION: (65)..(88)
<223> OTHER INFORMATION: Relaxin A Chain
<220> FEATURE:
<221> NAME/KEY: VARIANT
<222> LOCATION: (65)..(65)
<223> OTHER INFORMATION: Optionally glutamine or pyroglutamate (Pe)

<400> SEQUENCE: 3

Asp Ser Trp Met Glu Glu Val Ile Lys Leu Cys Gly Arg Glu Leu Val
1               5                  10                 15

Arg Ala Gln Ile Ala Ile Cys Gly Met Ser Thr Trp Ser Arg Arg Glu
             20                  25                 30

Ala Glu Asp Leu Gln Val Gly Gln Val Glu Leu Gly Gly Gly Pro Gly
        35                  40                 45

Ala Gly Ser Leu Gln Pro Leu Ala Leu Glu Gly Ser Leu Gln Lys Arg
     50                  55                 60

Gln Leu Tyr Ser Ala Leu Ala Asn Lys Cys Cys His Val Gly Cys Thr
65                  70                 75                 80

Lys Arg Ser Leu Ala Arg Phe Cys
                 85

<210> SEQ ID NO 4
<211> LENGTH: 24
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Optionally glutamine or pyroglutamate (Pe)

<400> SEQUENCE: 4

Gln Leu Tyr Ser Ala Leu Ala Asn Lys Cys Cys His Val Gly Cys Thr
1               5                  10                 15

Lys Arg Ser Leu Ala Arg Phe Cys
             20

<210> SEQ ID NO 5
<211> LENGTH: 29
<212> TYPE: PRT
<213> ORGANISM: Homo sapiens

<400> SEQUENCE: 5
```

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 6
<211> LENGTH: 29
<212> TYPE: PRT
<213> ORGANISM: Homo sapiens

<400> SEQUENCE: 6

Ala Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 7
<211> LENGTH: 35
<212> TYPE: PRT
<213> ORGANISM: Homo sapiens

<400> SEQUENCE: 7

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35

<210> SEQ ID NO 8
<211> LENGTH: 11
<212> TYPE: PRT
<213> ORGANISM: Homo sapiens

<400> SEQUENCE: 8

Met Lys Lys Asn Ile Ala Phe Leu Leu Lys Arg
1               5                   10

<210> SEQ ID NO 9
<211> LENGTH: 6
<212> TYPE: PRT
<213> ORGANISM: Homo sapiens

<400> SEQUENCE: 9

Met Ile Glu Gly Gly Arg
1               5

<210> SEQ ID NO 10
<211> LENGTH: 72
<212> TYPE: DNA
<213> ORGANISM: Homo sapiens

<400> SEQUENCE: 10
caactctaca gtgcattggc taataaatgt tgccatgttg gttgtaccaa aagatctctt    60
gctagatttt gc                                                       72

<210> SEQ ID NO 11
<211> LENGTH: 87
<212> TYPE: DNA
<213> ORGANISM: Homo sapiens

<400> SEQUENCE: 11

```
gactcatgga tggaggaagt tattaaatta tgcggccgcg aattagttcg cgcgcagatt    60
gccatttgcg gcatgagcac ctggagc                                       87
```

<210> SEQ ID NO 12
<211> LENGTH: 159
<212> TYPE: DNA
<213> ORGANISM: Homo sapiens

<400> SEQUENCE: 12

```
caactctaca gtgcattggc taataaatgt tgccatgttg gttgtaccaa aagatctctt    60
gctagatttt gcgactcatg gatggaggaa gttattaaat tatgcggccg cgaattagtt   120
cgcgcgcaga ttgccatttg cggcatgagc acctggagc                          159
```

<210> SEQ ID NO 13
<211> LENGTH: 33
<212> TYPE: DNA
<213> ORGANISM: Homo sapiens

<400> SEQUENCE: 13

```
atgaaaaaga atatcgcatt tcttcttaaa cgg                                33
```

<210> SEQ ID NO 14
<211> LENGTH: 18
<212> TYPE: DNA
<213> ORGANISM: Homo sapiens

<400> SEQUENCE: 14

```
atgattgaag gtggtcgt                                                 18
```

<210> SEQ ID NO 15
<211> LENGTH: 94
<212> TYPE: PRT
<213> ORGANISM: Homo sapiens
<220> FEATURE:
<221> NAME/KEY: SITE
<222> LOCATION: (1)..(6)
<223> OTHER INFORMATION: Removed in mature form
<220> FEATURE:
<221> NAME/KEY: CHAIN
<222> LOCATION: (7)..(35)
<223> OTHER INFORMATION: Relaxin B Chain
<220> FEATURE:
<221> NAME/KEY: SITE
<222> LOCATION: (36)..(70)
<223> OTHER INFORMATION: Removed in mature form
<220> FEATURE:
<221> NAME/KEY: CHAIN
<222> LOCATION: (71)..(94)
<223> OTHER INFORMATION: Relaxin A Chain
<220> FEATURE:
<221> NAME/KEY: VARIANT
<222> LOCATION: (71)..(71)
<223> OTHER INFORMATION: Optionally glutamine or pyroglutamate (Pe)

<400> SEQUENCE: 15

```
Met Ile Glu Gly Gly Arg Asp Ser Trp Met Glu Glu Val Ile Lys Leu
1               5                   10                  15

Cys Gly Arg Glu Leu Val Arg Ala Gln Ile Ala Ile Cys Gly Met Ser
            20                  25                  30

Thr Trp Ser Arg Arg Glu Ala Glu Asp Leu Gln Val Gly Gln Val Glu
        35                  40                  45

Leu Gly Gly Gly Pro Gly Ala Gly Ser Leu Gln Pro Leu Ala Leu Glu
    50                  55                  60

Gly Ser Leu Gln Lys Arg Gln Leu Tyr Ser Ala Leu Ala Asn Lys Cys
```

```
                65                  70                  75                  80
Cys His Val Gly Cys Thr Lys Arg Ser Leu Ala Arg Phe Cys
                85                  90

<210> SEQ ID NO 16
<211> LENGTH: 306
<212> TYPE: PRT
<213> ORGANISM: Artificial
<220> FEATURE:
<223> OTHER INFORMATION: Mutant synthetase derived from Methanococcus
      jannaschii synthetase

<400> SEQUENCE: 16

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Val
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Tyr Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu His Gly Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Ile His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 17
<211> LENGTH: 77
```

```
<212> TYPE: DNA
<213> ORGANISM: Artificial
<220> FEATURE:
<223> OTHER INFORMATION: Mutant tRNA derived from Methanococcus
      jannaschii tRNA

<400> SEQUENCE: 17
ccggcggtag ttcagcaggg cagaacggcg gactctaaat ccgcatggcg ctggttcaaa    60
tccagcccgc cggacca                                                   77

<210> SEQ ID NO 18
<211> LENGTH: 77
<212> TYPE: DNA
<213> ORGANISM: Methanococcus jannaschii

<400> SEQUENCE: 18
ccggcggtag ttcagcaggg cagaacggcg gactctaaat ccgcatggcg ctggttcaaa    60
tccggcccgc cggacca                                                   77

<210> SEQ ID NO 19
<211> LENGTH: 88
<212> TYPE: DNA
<213> ORGANISM: Artificial
<220> FEATURE:
<223> OTHER INFORMATION: An optimized amber supressor tRNA

<400> SEQUENCE: 19
cccagggtag ccaagctcgg ccaacggcga cggactctaa atccgttctc gtaggagttc    60
gagggttcga atcccttccc tgggacca                                       88

<210> SEQ ID NO 20
<211> LENGTH: 89
<212> TYPE: DNA
<213> ORGANISM: Artificial
<220> FEATURE:
<223> OTHER INFORMATION: An optimized AGGA frameshift supressor tRNA

<400> SEQUENCE: 20
gcgagggtag ccaagctcgg ccaacggcga cggacttcct aatccgttct cgtaggagtt    60
cgagggttcg aatccctccc ctcgcacca                                      89

<210> SEQ ID NO 21
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-L-phenylalanine

<400> SEQUENCE: 21
```

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met

```
                85                  90                  95
Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 22
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-benzoyl-L-phenylalanine

<400> SEQUENCE: 22

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125
```

```
Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
                195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
                275                 280                 285

Asn Ala Val Ala Glu Glu Leu Ile Lys Ile Leu Glu Pro Ile Arg Lys
290                 295                 300

Arg Leu
305

<210> SEQ ID NO 23
<211> LENGTH: 305
<212> TYPE: PRT
<213> ORGANISM: Artificial
<220> FEATURE:
<223> OTHER INFORMATION: Aminoacyl tRNA synthetase for the incorporation
      of propargyl-phenylalanine

<400> SEQUENCE: 23

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
                35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
                100                 105                 110

Asp Tyr Thr Leu Asn Val Tyr Arg Leu Ala Leu Lys Thr Thr Leu Lys
                115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175
```

```
Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
    210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Leu
        260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
    290                 295                 300

Leu
305
```

<210> SEQ ID NO 24
<211> LENGTH: 305
<212> TYPE: PRT
<213> ORGANISM: Artificial
<220> FEATURE:
<223> OTHER INFORMATION: Aminoacyl tRNA synthetase for the incorporation of propargyl-phenylalanine

<400> SEQUENCE: 24

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ile Pro Tyr
145                 150                 155                 160

Leu Pro Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
```

```
            210                 215                 220
Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Leu
                260                 265                 270

Glu Ser Leu Phe Lys Asn Lys Glu Leu His Pro Met Asp Leu Lys Asn
                275                 280                 285

Ala Val Ala Glu Glu Leu Ile Lys Ile Leu Glu Pro Ile Arg Lys Arg
                290                 295                 300

Leu
305

<210> SEQ ID NO 25
<211> LENGTH: 305
<212> TYPE: PRT
<213> ORGANISM: Artificial
<220> FEATURE:
<223> OTHER INFORMATION: Aminoacyl tRNA synthetase for the incorporation
      of propargyl-phenylalanine

<400> SEQUENCE: 25

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
                35                  40                  45

Ile Lys Lys Met Ile Asp Leu Gln Asn Ala Gly Phe Asp Ile Ile Ile
            50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
                180                 185                 190

Pro Val Leu Thr Gly Leu Asp Gly Glu Gly Lys Met Ser Ser Ser Lys
            195                 200                 205

Gly Asn Phe Ile Ala Val Asp Asp Ser Pro Glu Glu Ile Arg Ala Lys
        210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255
```

Pro Glu Lys Phe Gly Gly Asp Leu Thr Val Asn Ser Tyr Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
    290                 295                 300

Leu
305

<210> SEQ ID NO 26
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-phenylalanine

<400> SEQUENCE: 26

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Asn Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 27
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-phenylalanine

<400> SEQUENCE: 27

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 28
<211> LENGTH: 306
<212> TYPE: PRT

-continued

```
<213> ORGANISM: Artificial
<220> FEATURE:
<223> OTHER INFORMATION: Aminoacyl tRNA synthetase for the incorporation
      of p-azido-phenylalanine

<400> SEQUENCE: 28

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 29
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-phenylalanine

<400> SEQUENCE: 29

Met Asp Glu Phe Glu Met Ile Lys Arg Asn Thr Ser Glu Ile Ile Ser
```

```
                1               5                  10                15
        Glu Glu Glu Leu Arg Glu Val Leu Lys Lys Asp Glu Lys Ser Ala Thr
                        20                  25                  30

Ile Gly Phe Glu Pro Ser Gly Lys Ile His Leu Gly His Tyr Leu Gln
                        35                  40                  45

Ile Lys Lys Met Ile Asp Leu Gln Asn Ala Gly Phe Asp Ile Ile Ile
                    50                  55                  60

Leu Leu Ala Asp Leu His Ala Tyr Leu Asn Gln Lys Gly Glu Leu Asp
        65                  70                  75                  80

Glu Ile Arg Lys Ile Gly Asp Tyr Asn Lys Lys Val Phe Glu Ala Met
                            85                  90                  95

Gly Leu Lys Ala Lys Tyr Val Tyr Gly Ser Ser Phe Gln Leu Asp Lys
                        100                 105                 110

Asp Tyr Thr Leu Asn Val Tyr Arg Leu Ala Leu Lys Thr Thr Leu Lys
                    115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Pro Ser His
        145                 150                 155                 160

Tyr Gln Gly Val Asp Val Ala Val Gly Gly Met Glu Gln Arg Lys Ile
                        165                 170                 175

His Met Leu Ala Arg Glu Leu Leu Pro Lys Lys Val Val Cys Ile His
                    180                 185                 190

Asn Pro Val Leu Thr Gly Leu Asp Gly Glu Gly Lys Met Ser Ser Ser
                    195                 200                 205

Lys Gly Asn Phe Ile Ala Val Asp Asp Ser Pro Glu Glu Ile Arg Ala
                210                 215                 220

Lys Ile Lys Lys Ala Tyr Cys Pro Ala Gly Val Val Glu Gly Asn Pro
        225                 230                 235                 240

Ile Met Glu Ile Ala Lys Tyr Phe Leu Glu Tyr Pro Leu Thr Ile Lys
                        245                 250                 255

Arg Pro Glu Lys Phe Gly Gly Asp Leu Thr Val Asn Ser Tyr Glu Glu
                    260                 265                 270

Leu Glu Ser Leu Phe Lys Asn Lys Glu Leu His Pro Met Asp Leu Lys
                    275                 280                 285

Asn Ala Val Ala Glu Glu Leu Ile Lys Ile Leu Glu Pro Ile Arg Lys
                290                 295                 300

Arg Leu
        305
```

<210> SEQ ID NO 30
<211> LENGTH: 306
<212> TYPE: PRT
<213> ORGANISM: Artificial
<220> FEATURE:
<223> OTHER INFORMATION: Aminoacyl tRNA synthetase for the incorporation of p-acetyl-phenylalanine

<400> SEQUENCE: 30

```
        Met Asp Glu Phe Glu Met Ile Lys Arg Asn Thr Ser Glu Ile Ile Ser
        1               5                   10                  15

Glu Glu Glu Leu Arg Glu Val Leu Lys Lys Asp Glu Lys Ser Ala Leu
                        20                  25                  30

Ile Gly Phe Glu Pro Ser Gly Lys Ile His Leu Gly His Tyr Leu Gln
                        35                  40                  45
```

Ile Lys Lys Met Ile Asp Leu Gln Asn Ala Gly Phe Asp Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Glu Phe Gln Leu Asp Lys
                100                 105                 110

Asp Tyr Thr Leu Asn Val Tyr Arg Leu Ala Leu Lys Thr Thr Leu Lys
                115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
                195                 200                 205

Lys Gly Asn Phe Ile Ala Val Asp Asp Ser Pro Glu Glu Ile Arg Ala
                210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
                275                 280                 285

Asn Ala Val Ala Glu Glu Leu Ile Lys Ile Leu Glu Pro Ile Arg Lys
                290                 295                 300

Arg Leu
305

<210> SEQ ID NO 31
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-acetyl-phenylalanine

<400> SEQUENCE: 31

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Leu
                 20                  25                  30

Ile Gly Phe Glu Pro Ser Gly Lys Ile His Leu Gly His Tyr Leu Gln
                 35                  40                  45

Ile Lys Lys Met Ile Asp Leu Gln Asn Ala Gly Phe Asp Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Thr His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 32
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-acetyl-phenylalanine

<400> SEQUENCE: 32

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro

Lys Val Ala Glu Val Ile Tyr Pro Ile Met Gln Val Asn Gly Gly His
145                 150                 155                 160

Tyr Leu Gly Val Asp Val Ile Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 33
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-phenylalanine

<400> SEQUENCE: 33

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Ile His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 34
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-phenylalanine

<400> SEQUENCE: 34

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

```
Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
            290                 295                 300

Arg Leu
305
```